(12) United States Patent
Sällberg et al.

(10) Patent No.: US 11,478,544 B2
(45) Date of Patent: *Oct. 25, 2022

(54) CHIMERIC HEPATITIS D VIRUS ANTIGEN AND HEPATITIS B VIRUS PRE S1 GENES FOR USE ALONE OR IN VACCINES CONTANING HEPATITIS B VIRUS GENES

(71) Applicant: Svenska Vaccinfabriken Produktion AB, Stockholm (SE)

(72) Inventors: Matti Sällberg, Stockholm (SE); Lars Frelin, Älvsjö (SE)

(73) Assignee: SVENSKA VACCINFABRIKEN PRODUKTION AB, Stockholm (SE)

( * ) Notice: Subject to any disclaimer, the term of this patent is extended or adjusted under 35 U.S.C. 154(b) by 3 days.

This patent is subject to a terminal disclaimer.

(21) Appl. No.: 17/112,055

(22) Filed: Dec. 4, 2020

(65) Prior Publication Data

US 2021/0236626 A1 Aug. 5, 2021

Related U.S. Application Data

(63) Continuation of application No. 16/069,372, filed as application No. PCT/US2017/015064 on Jan. 26, 2017, now Pat. No. 10,905,760.

(60) Provisional application No. 62/288,316, filed on Jan. 28, 2016.

(51) Int. Cl.
| | |
|---|---|
| *A61K 39/29* | (2006.01) |
| *A61K 39/12* | (2006.01) |
| *C07K 14/02* | (2006.01) |
| *C07K 14/005* | (2006.01) |
| *A61K 39/39* | (2006.01) |
| *A61K 39/00* | (2006.01) |

(52) U.S. Cl.
CPC ............ *A61K 39/29* (2013.01); *A61K 39/12* (2013.01); *A61K 39/39* (2013.01); *C07K 14/005* (2013.01); *C07K 14/02* (2013.01); *A61K 2039/55538* (2013.01); *A61K 2039/70* (2013.01); *C07K 2319/00* (2013.01); *C12N 2730/10122* (2013.01); *C12N 2730/10134* (2013.01); *C12N 2760/10122* (2013.01); *C12N 2760/10134* (2013.01)

(58) Field of Classification Search
CPC .... A61K 2300/00; A61K 39/29; A61K 39/42; A61P 31/20; A61P 31/14; C07K 14/02; C07K 16/082; C07K 16/10; C07K 2319/00; G01N 33/5765; G01N 33/5761
See application file for complete search history.

(56) References Cited

U.S. PATENT DOCUMENTS

| | | | |
|---|---|---|---|
| 10,905,760 B2 * | 2/2021 | Sällberg | ................. A61K 39/39 |
| 2003/0158149 A1 | 8/2003 | Casey et al. | |
| 2005/0170337 A1 | 8/2005 | Hogle et al. | |

OTHER PUBLICATIONS

Hsu el al., "Immunohistochemical differentiation of hepatitis D virus genotypes. Hepalology", Nov. 2000, vol. 32, No. 5. pp 1111 -1116. Especially p. 1111, col. 2, para 2; p. 11 14, col. 2, para 3.
Search Report and Written Opinion in International application No. PCT/US2017/015064, dated Apr. 4, 2017.

* cited by examiner

*Primary Examiner* — Bao Q Li
(74) *Attorney, Agent, or Firm* — Knobbe, Martens, Olson & Bear LLP

(57) ABSTRACT

Chimeric genes, compositions of chimeric genes, and compositions of polypeptides that are useful for the generation, enhancement, or improvement of an immune response to a target antigen. Some embodiments of the compositions include chimeric genes encoding hepatitis D antigen (HDAg) protein in combination with one or more self-cleavage 2A polypeptides and a preS1 polypeptide. In certain embodiments the self-cleavage polypeptide is P2A.

14 Claims, 24 Drawing Sheets

Specification includes a Sequence Listing.

Delta-1

Delta-2

Delta-3

Delta-4

Delta-5

Delta-6

Delta-7

| HDAg gt1 A/B | PreS1 A/B |

Delta-8

| HDAg gt2 A/B | PreS1 A/B |

Delta-9

| HDAg gt1 A/B |

Delta-10

| HDAg gt2 A/B |

FIG. 2 (continued)

Core-1

Core-2

Core-3

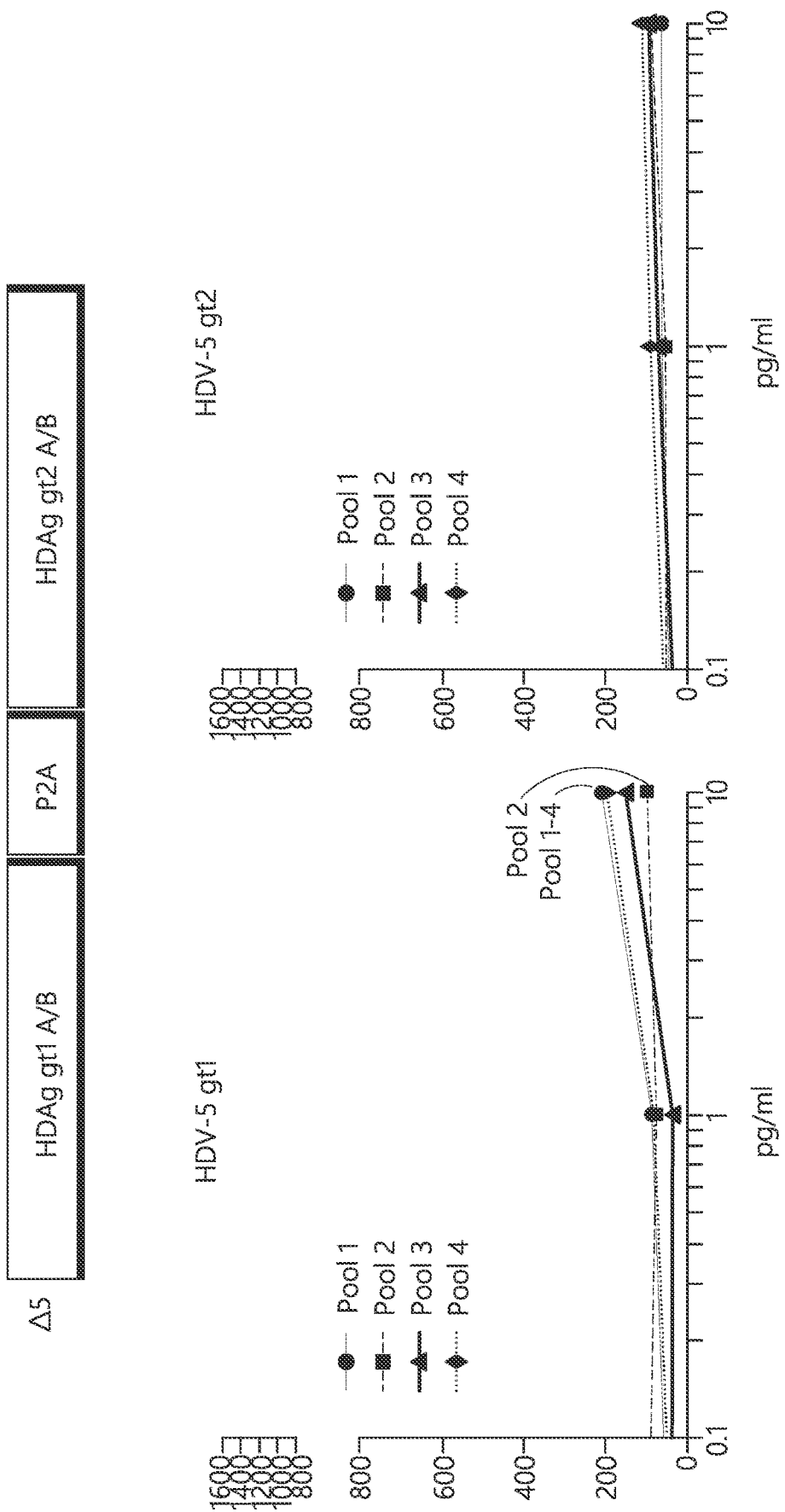

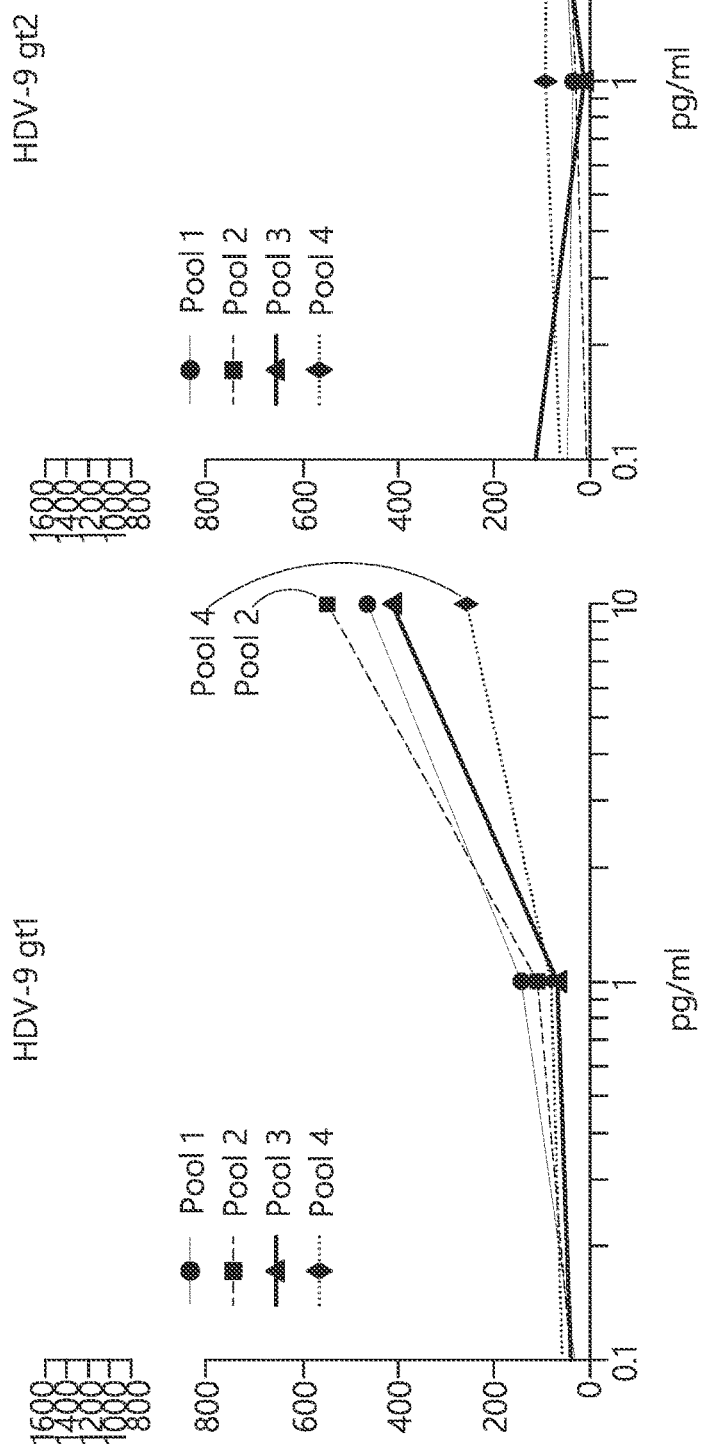

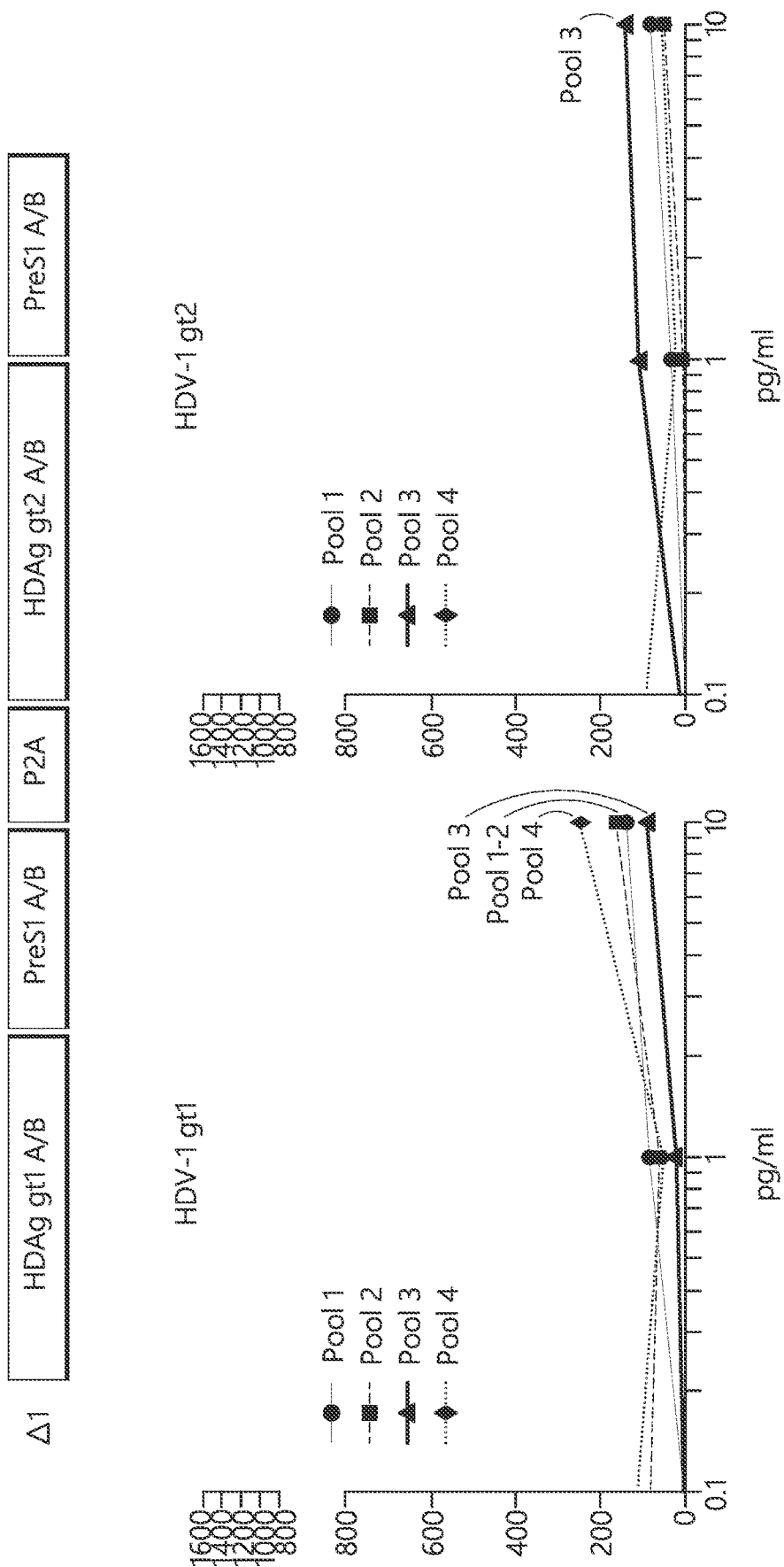

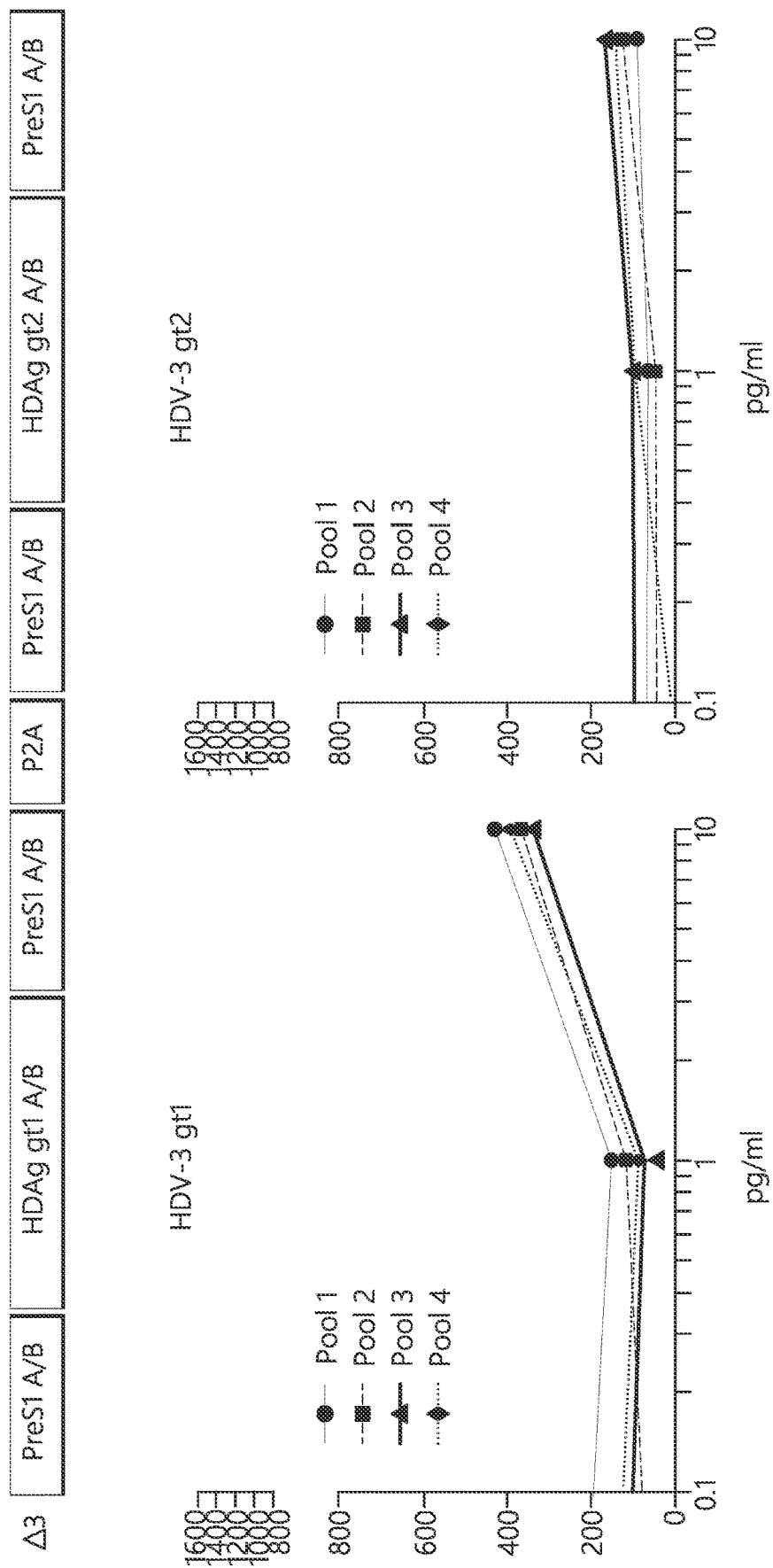

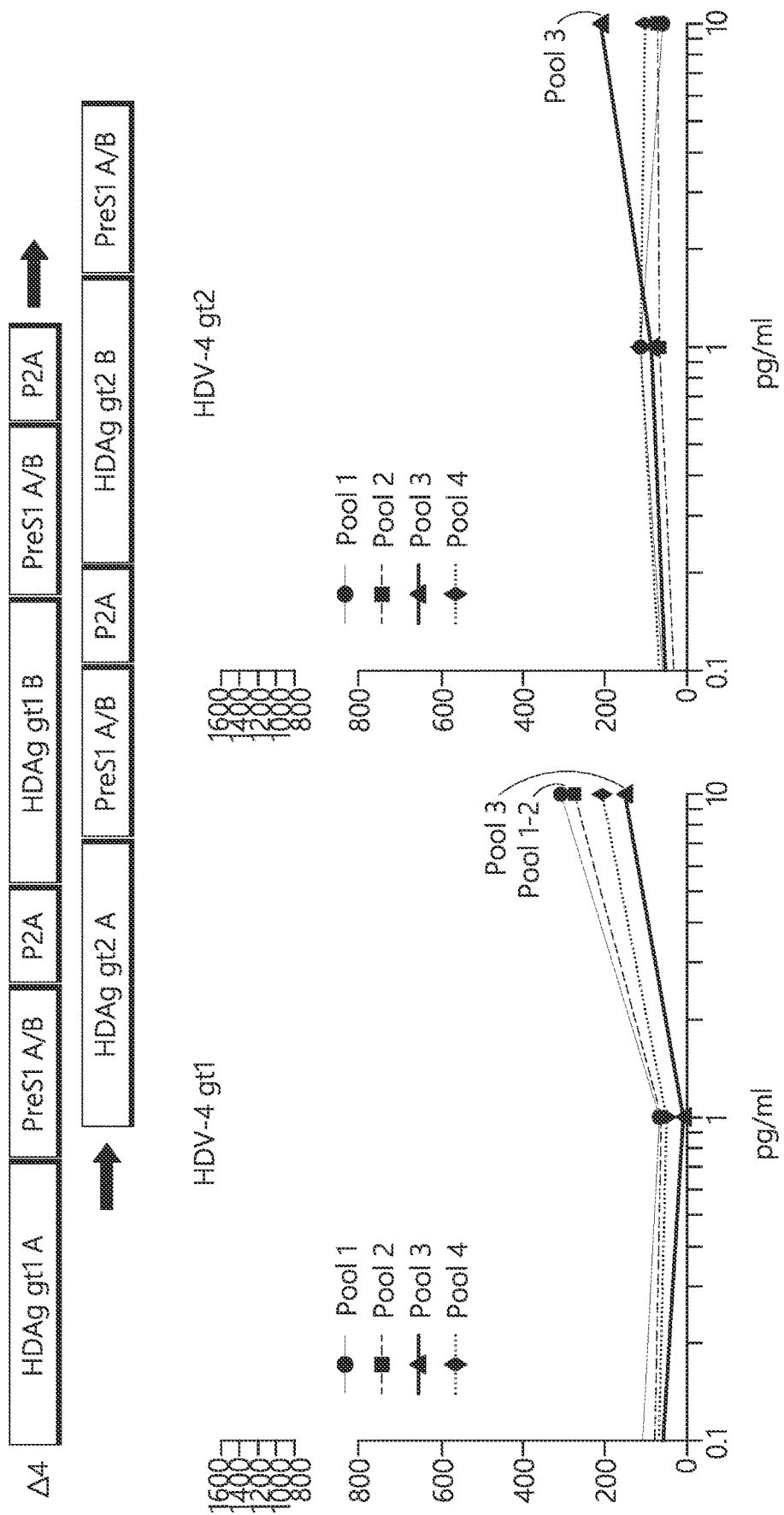

CHIMERIC HEPATITIS D VIRUS ANTIGEN AND HEPATITIS B VIRUS PRE S1 GENES FOR USE ALONE OR IN VACCINES CONTANING HEPATITIS B VIRUS GENES

RELATED APPLICATIONS

The present application is a continuation of U.S. patent application Ser. No. 16/069,372, filed Jul. 11, 2018, which is the U.S. national phase entry under 35 U.S.C. 371 of PCT/US2017/015064, filed Jan. 26, 2017, which claims priority to U.S. Provisional Application Ser. No. 62/288,316, entitled "Chimeric Hepatitis D Virus Antigen And Hepatitis B Virus PRE 51 Genes For Use Alone Or In Vaccines Containing Hepatitis B Virus Genes" filed Jan. 28, 2016, the contents of which are hereby expressly incorporated by reference in their entirety.

REFERENCE TO SEQUENCE LISTING, TABLE, OR COMPUTER PROGRAM LISTING

The present application is being filed along with a Sequence Listing in electronic format. The Sequence Listing is provided as a file entitled SEQLISTSVF002WO.TXT created Jan. 25, 2017, which is 233 kb in size. The information is the electronic format of the Sequence Listing is incorporated herein by reference in its entirety.

FIELD OF THE INVENTION

Described herein are chimeric genes that overcome genotype variability. Hepatitis D virus (HDV) genotype 1 sequences, which serve as an adjuvant in patients infected by genotype 2 HDV strains, are utilized. Moreover, the HDV genes are linked to a sequence encoding a part of the PreS1 region of the Hepatitis B virus (HBV). By this approach, neutralizing antibodies and T cells to HBV and HDV are generated. These can be used alone or be combined with genes or proteins expressing HBV proteins to raise both HBV and HDV specific immune responses in patients with HBV. These constructs are used as both genetic and protein-based vaccines or immunogenic compositions, which inhibit, ameliorate, treat and/or prevent HDV and/or HBV infections.

BACKGROUND

Hepatitis is a disease resulting in swelling and inflammation of the liver. This disorder is commonly caused by viruses, five types of which are currently known (Hepatitis A, B, C, D and E). The hepatitis D virus (HDV) causes severe liver disease and cancer in patients infected by the hepatitis B virus (HBV). HDV exist in three major genotypes world-wide. Hepatitis D virus (HDV), also referred to as Hepatitis delta virus, is a small, spherical single-stranded circular RNA virus. The entire virus was cloned and sequenced in 1986, and given the genus of Deltavirus. HDV is structurally unrelated to the other hepatitis viruses. Since HDV is an incomplete virus, it can only replicate in the presence of Hepatitis B (HBV) virus, which provides structural components for HDV. In particular, HDV has an outer coat that contains large, medium and small hepatitis B surface antigens, and host lipids surrounding an inner nucleocapsid, which contains about 200 molecules of hepatitis D antigen (HDAg) for each genome. The circular genome of HDV is unique to animal viruses because of its high GC content.

HDV produces a single protein, namely hepatitis D antigen (HDAg). HDAg exists in two isoforms: a 27 kDa large-HDAg (HDAg-L), and a 24 kDa small-HDAg (HDAg-S). The two sequences differ in that the C-terminus of the HDAg-L contains an additional 19 amino acids not found in HDAg-S, which are essential to virus assembly. Both isoforms are produced from the same open reading frame (ORF), which contains a UAG stop codon at codon 196, which normally produces only the HDAg-S. However, editing by the cellular enzyme adenosine deaminase-1 changes the stop codon to UCG, allowing HDAg-L to be produced. HDAg-S is produced in the early stages of infection, enters the nucleus and supports viral replication. In contrast, HDAg-L is produced during the later stages of infection, acts as an inhibitor of viral replication, and is required for assembly of viral particles. Both isoforms bind RNA, with a specificity for the rod-like folding of the HDV genome and antigenome (Chao et al., *J. Virol.* 65:4057-4062, 1991; Lee et al., *J. Virol.,* 67:2221-2227, 1993). HDAg contains a coiled-coil dimerization domain, nuclear localization signal, RNA-binding domain, and a putative assembly domain. Various epitopes of HDAg were determined to be exposed by PEPSCAN, immunoprecipitation analysis and ELISA, including those within amino acids 12-60, 58-78, 82-102, 123-143, 156-184, 167-184 and 197-211 (Bichko et al., (1996) *J. Virol.* 70:5807-5811). Epitope mapping of HDAg in patients with chronic Hepatitis D infection exhibited the following potential cytotoxic T-ligand epitopes: amino acids 43 to 51, 50 to 58 and 114 to 122 (Wang et al., *J. Virol.,* 81:4438-4444, 2007).

HDV is transmitted through percutaneous or mucosal contact with infected blood. HDV can be acquired by either simultaneous infection with HBV (coinfection), or by super-infection, in, which HDV is superimposed on chronic HBV infection or carrier state. Both types of infection result in more deleterious effects than infection solely with HBV, including enhanced possibility of liver failure and more rapid onset of cirrhosis and potentially liver cancer. The combination of HBV and HDV results in the highest mortality rate of all hepatitis infections at about 20%. There is no current vaccine for HDV, but it can be prevented in individuals who are not already infected with HBV by HBV vaccination.

HDV is structurally unrelated to the other hepatitis viruses. As HDV is an incomplete virus, it can only replicate in the presence of Hepatitis B (HBV) virus, which provides structural components for HDV. HDV is a defect virus, or a viroid, that lacks the ability to productively infect a liver cell on its own. In particular, HDV has an outer coat that contains large, medium and small hepatitis B surface antigens, and host lipids surrounding an inner nucleocapsid, which contains about 200 molecules of hepatitis D antigen (HDAg) for each genome. The circular genome of HDV is unique to animal viruses because of its high GC content. The 1700 base circular positive RNA genome encodes a single protein, the small (S) hepatitis D antigen (S-HDAg) that acts as the viral capsid. However, a posttranscriptional editing of the S-HDAg stop codon in the transcribed genome results in the production of a 19 amino acid longer large (L-HDAg), which acts as a regulator of transcription. The replication of the viral RNA genome takes place in the nucleus through a rolling circle mechanism using host cell RNA polymerases. The use of host RNA polymerase for genome synthesis makes it extremely difficult to develop non-toxic antiviral polymerase inhibitors. The rolling circle replication results in a more than full length genomic RNA than is trimmed to the genomic RNA by hammer-head ribozymes and then circularized. For assembly and release of viral particles HDV will steal the surface protein of HBV, HBsAg. Thus, the HDV virion leaving the cell is encompassed of HDAg enclosing the viral RNA genome with a lipid envelope containing HBsAg.

Since all cells infected by HBV express and secrete high levels of HBsAg particles, and importantly, HBsAg expression can be completely independent of the HBV replication, this means that HDV uses the same entry receptor as HBV, the sodium taurocholate co-transporting polypeptide (NTCP) and can only productively infect cells infected by HBV.

HDV can be prevented by HBV vaccination in a host naïve to both HBV and HDV. However, since the HBV vaccine is based on HBsAg this vaccine is useless in a person already infected with HBV. Thus, there is no strategy currently to prevent HDV infection in HBV carriers. In addition, since the production of HBsAg is independent of the HBV replication, the currently used polymerase inhibitors for HBV cannot be used to prevent or to treat the HDV coinfection.

Potent antiviral drugs inhibit HBV replication without affecting the HDV replication. Thus antiviral drugs affect neither the production of the HBV envelope (HBsAg) required for HDV assembly, nor the replication of the HDV genome mediated by the host cell RNA polymerase II. The latter significantly impairs the possibility to develop antiviral enzyme inhibitors for HDV. HBsAg-based HBV vaccines can prevent a non-infected subject from becoming infected by both HBV and HDV; however, the HBV vaccine cannot protect a subject already infected by HBV against HDV super-infection due to the inherent overproduction of HBsAg during the HBV infection. HDV RNA replication is mediated by host cell RNA polymerase II, which significantly impairs the possibility to develop antiviral enzyme inhibitors. The HBV infection can be treated with a life-long therapy using polymerase inhibitors that blocks HBV replication, but not protein synthesis, and reduces the risk of HBV-induced liver damage. However, HDV replication is completely unaffected by the HBV antivirals since these do not block HBsAg production. The only treatment available for HDV today is an expensive and cumbersome 48-month therapy of pegylated interferon (PEG-IFN), which cures 25% of HDV infections. Thus, new preventive and therapeutic strategies are desperately needed for the increasing problem of HBV-HDV coinfections.

SUMMARY OF THE INVENTION

In a first aspect, a chimeric gene comprising HDAg sequences is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof.

In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans.

In a second aspect, a chimeric protein comprising at least two HDAg protein domains, encoded by the chimeric gene of anyone of the alternatives described herein is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59 In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans.

In a third aspect, a composition comprising anyone or more of the chimeric genes of any one of the alternatives is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In a fourth aspect, the chimeric gene or composition of any one of the alternatives is for use in generating an immune response in a subject or for DNA vaccination so as to inhibit, ameliorate, treat, or prevent HBV and HDV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In a fifth aspect, the chimeric gene or composition of any one of the alternatives herein, is for use in generating an antibody, T-lymphocyte or CTL-specific response in a subject so as to inhibit, ameliorate, treat, or prevent an HBV and HDV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In a sixth aspect, the chimeric gene or composition of any one of the alternatives described herein is for DNA vaccination against HBV and HDV in a subject that has been identified as having and HDV or HBV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In a seventh aspect, a method of eliciting an immune response is provided, wherein the method comprises administering to a subject having HDV infection and/or HBV infection the nucleic acid or composition of any one of the alternatives herein. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or an antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21. In some alternatives, said administering comprises injecting said nucleic acid into a patient, such as using an IVIN needle with or without electroporation. In some alternatives, the method further comprising administering a second administration of a nucleic acid or composition of any one of the alternatives described herein. In some alternatives, the method further comprises providing an adjuvant. In some alternatives, said adjuvant is a nucleic acid encoding a polypeptide adjuvant, such as IL-12, IL-15, or IL-21. In some alternatives, said adjuvant is IL-12, IL-15, or IL-21. In some alternatives, said second administration is given after said first time. In some alternatives, said adjuvant is given before, during, or after administration of said nucleic acid or composition of any one of claims 1-45. In some alternatives, said second administration is given one week, two weeks, three weeks, four weeks, five weeks, or six weeks after the first administration of said nucleic acid or composition of any one of claims 1-45. In some alternatives, the subject has been identified as a person at risk of contracting HDV or that has HDV. In some alternatives, the method further comprises evaluating the subject for an immunoresponse after administering the compositions of anyone of the alternatives here. In some alternatives, the evaluating is performed by an ELISpot assay. In some alternatives, the ELISpot assay is performed using any one of the peptides comprising a sequence set forth in SEQ ID NO: 75-116.

In an eighth aspect, a method of increasing preS1 antibodies in a subject in need, the method comprising administering the compositions of anyone of the alternatives described herein to the subject in need. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21. In some alternatives, the method further comprises evaluating the subject for an immunoresponse after administering the compositions of anyone of the alternatives here. In some alternatives, the evaluating is performed by an ELISpot assay. In some alternatives, the ELISpot assay is performed using any one of the peptides comprising a sequence set forth in SEQ ID NO: 75-116.

DEFINITIONS

Figure 1:
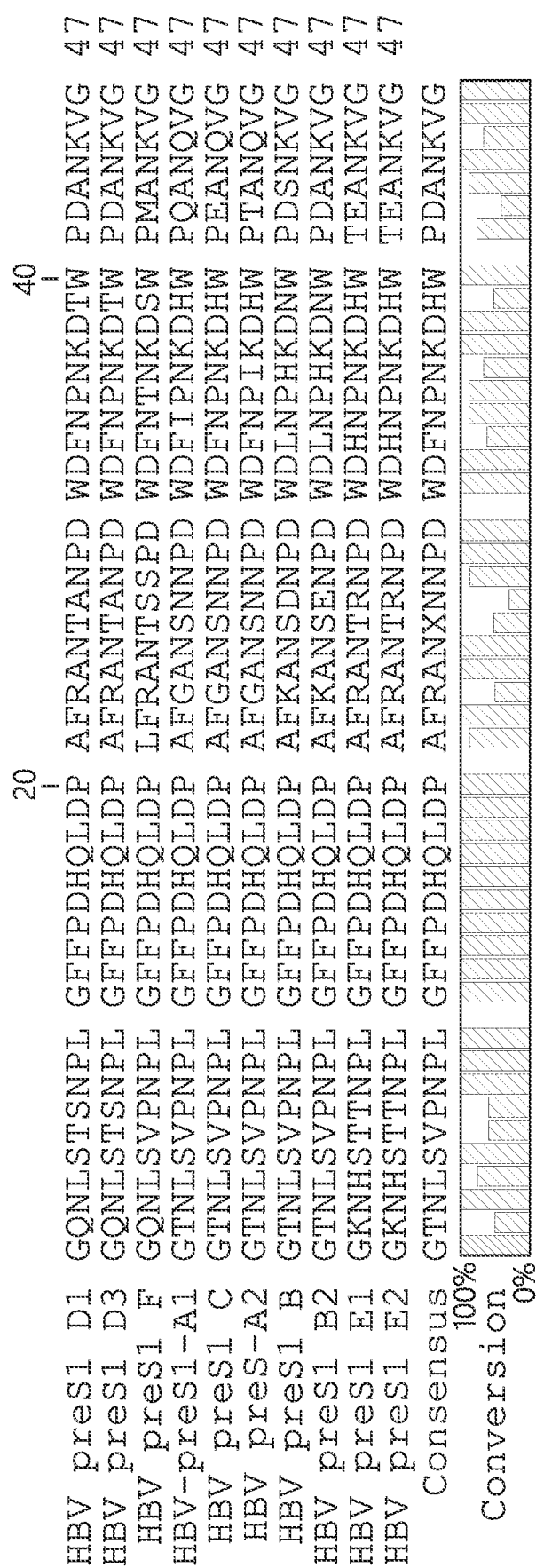
FIG. 1 shows the alignment of HBV preS1 peptides.

Unless defined otherwise, all technical and scientific terms used herein have the same meaning as commonly understood by one of ordinary skill in the art to which the invention pertains.

"About" as used herein when referring to a measurable value is meant to encompass variations of ±20% or ±10%, more preferably ±5%, even more preferably ±1%, and still more preferably ±0.1% from the specified value.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives described herein, a gene delivery polynucleotide for stable insertion of a nucleic acid into a gene is provided. "Oligonucleotide" can be used interchangeable with nucleic acid and can refer to DNA or RNA, either double stranded or a single stranded piece or DNA or RNA.

The nucleic acids described herein can have natural bases, modified bases and/or synthetic bases. Natural bases can include, for example, cytosine, guanine, adenine, thymine, uracil and pseudouracil. Modified bases can include, but are not limited to, xanthine and 2-deoxypseudoguanosine. Synthetic bases may include methyl-cytosine.

"Chimeric gene" as described herein refers to a combination of portions of one or more coding sequences to produce new genes. These mutations are distinct from fusion genes which merge whole gene sequences into a single reading frame and often retain their original functions. In some alternatives described herein, a chimeric gene comprising HDAg sequences is provided. The chimeric gene can have at least two sequences encoding hepatitis D antigen (HDAg), at least one cleavage sequence and at least one preS1 derived sequence. A chimeric gene can be DNA or RNA.

"Chimeric protein" is a hybrid protein that is encoded by a nucleotide sequence spliced together from two or more complete or partial genes produced by recombinant DNA technology. Methods for creating a chimeric protein through chimeric genes is well known to those skilled in the art and can be performed with basic molecular cloning in which fragments of genes are combined with vector DNA to create the chimeric gene for protein expression.

"HDag" as described herein is hepatitis D antigen. In some alternatives described herein a chimeric gene comprising HDAg sequences is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. A chimeric gene can be DNA or RNA. Shown in FIG. 2 are the combined HDV-PreS1 vaccine designs for Delta-1, Delta-2, Delta-3, Delta-4, Delta-5, Delta-6, Delta-7, Delta-8, Delta-9 and Delta-10 for the chimeric genes described in the alternatives herein. These constructs are used to encode the chimeric proteins described in the alternatives herein and are utilized for nucleic acid-based immunization by approaches described herein.

"Cleavage sequence" as described herein can refer to a self-cleaving 2A peptide. The chimeric genes can further encode at least one self-cleavage polypeptide sequence. Self-cleaving 2A polypeptide sequences, also referred to herein as self-cleavage sequences, sites or domains were first identified in the foot-and-mouth disease virus (Ryan, M D et al. (1991) "Cleavage of foot and mouth disease virus protein is mediated by residues located within a 19 amino acid sequence." J. Gen. Virol. 72(Pt 11):2727-2732). The 'cleavage' of a 2A peptide from its immediate downstream peptide is in fact affected by ribosomal skipping of the synthesis of the glycyl-prolyl peptide bond at the C-terminus of the 2A polypeptide (Lyan Lab Webpage; de Felipe P, Luke G A, Brown J D, Ryan M D (2010) Inhibition of 2A-mediated 'cleavage' of certain artificial polyproteins bearing N-terminal signal sequences. Biotechnol J 5: 213-223; Donnelly M L, Luke G, Mehrotra A, Li X, Hughes L E, et al. (2001) Analysis of the aphthovirus 2A/2B polyprotein 'cleavage' mechanism indicates not a proteolytic reaction, but a novel translational effect: a putative ribosomal 'skip'. J Gen Virol 82: 1013-1025). Several 2A self-cleavage polypeptides have been isolated (see, e.g., Szymczak A L, Vignali D A (2005) Development of 2A peptide-based strategies in the design of multicistronic vectors. Expert Opin Biol Ther 5: 627-638, the disclosure of which is hereby incorporated by reference in its entirety). Four of the 2A polypeptide sequences identified to date have seen substantial use in biomedical research: picornavirus 2A sequences FMDV 2A (abbreviated herein as F2A); equine rhinitis A virus (ERAV) 2A (E2A); porcine teschovirus-1 2A (P2A), and insect virus *Thosea asigna* virus 2A (T2A), (de Felipe P, Luke G A, Hughes L E, Gani D, Halpin C, et al. (2006) E unum pluribus: multiple proteins from a self-processing polyprotein. *Trends Biotechnol* 24: 68-75).

Self-cleaving 2A sequences are preferred over alternative methods of expressing multiple proteins from a single construct, such as Internal Ribosomal Entry Sequences (IRES), because of their short length and stoichiometric expression of multiple proteins flanking the 2A polypeptide (de Felipe P, Luke G A, Hughes L E, Gani D, Halpin C, et al. (2006) E unum pluribus: multiple proteins from a self-processing polyprotein. Trends Biotechnol 24: 68-75). In the alternatives described herein, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus.

The Pre-S1 derived sequence, as described herein encodes the Pre-S1 domain of the surface antigen of hepatitis B virus. Targeting of preS1 may be used to prevent both infections of HBV and HDV. It has been shown that a 48 amino acid stretch within the preS1 region is effective in generating preS1-specific antibodies. In some alternatives described herein, a chimeric gene comprising HDAg sequences is provided. The chimeric gene can have at least two sequences encoding hepatitis D antigen (HDAg), at least one cleavage sequence and at least one preS1 derived sequence. In some alternatives, the at least one preS1 derived sequence is preS1 A and/or preS1 B.

"Codon optimization" as described herein, refers to a method for maximal protein selection by adaptation of codons of the transcript gene to the typical codon usage of a host. Those skilled in the art will appreciate that gene expression levels are dependent on many factors, such as promoter sequences and regulatory elements. As noted for most bacteria, small subsets of codons are recognized by tRNA species leading to translational selection, which can be an important limit on protein expression. In this aspect, many synthetic genes can be designed to increase their protein expression level. The design process of codon optimization can be to alter rare codons to codons known to increase maximum protein expression efficiency. In some alternatives, codon selection is described, wherein codon selection is performed by using algorithms that are known to those skilled in the art to create synthetic genetic transcripts optimized for higher levels of transcription and protein yield. Programs containing algorithms for codon optimization are known to those skilled in the art. Programs can include, for example, OptimumGene™, GeneGPS® algorithms, etc. Additionally synthetic codon optimized sequences can be obtained commercially for example from Integrated DNA Technologies and other commercially available DNA sequencing services. In some alternatives, the chimeric gene comprises sequences, wherein at least one sequence is codon optimized. In some alternatives, the genes are codon optimized for expression in humans, which can include gene transcripts the core protein, HDAg, or at least one preS1 derived sequence. The 2A and/or P2A sequences may or may not be codon optimized for expression in humans.

"HBV core antigen" (HBcAg) or the nucleocapsid of HBV is an immunogenic particle composed of 180 subunits of a single protein chain. HBcAg has been disclosed as an immunogenic moiety that stimulates the T cell response of an immunized host animal. See, e.g, U.S. Pat. Nos. 4,818, 527, 4,882,145 and 5,143,726, each of which is hereby incorporated by reference in their entirety. It can be used as a carrier for several peptidic epitopes covalently linked by genetic engineering as well as for chemically coupled protein antigens. (See Sallberg et al. (1998) Human Gene Therapy 9:1719-29). In addition, HBcAg is non-cytotoxic in humans. Accordingly, it was contemplated that HBcAg is useful in genetic constructs for generating or enhancing an immune response to an accompanied target antigen (e.g., in constructs that encode a TCE derived from a pathogen).

Current listings of exemplary HBcAg sequences are publicly available at the National Center for Biotechnology Information (NCBI) world-wide web site. Several different HBcAg nucleic acid sequences (including novel HBcAg regions) can be utilized (e.g., humans, birds, such as stork or heron, or rodents such as ground squirrel or woodchuck). DNA obtained from a subject infected with HBV (e.g., humans, birds, such as stork or heron, or rodents such as ground squirrel or woodchuck) can also be isolated by PCR or another amplification technique.

For a review of PCR technology, see Molecular Cloning to Genetic Engineering White, B. A. Ed. in *Methods in Molecular Biology* 67: Humana Press, Totowa (1997) and the publication entitled "PCR Methods and Applications" (1991, Cold Spring Harbor Laboratory Press). For amplification of mRNAs, it is within the scope of the invention to reverse transcribe mRNA into cDNA followed by PCR (RT-PCR); or, to use a single enzyme for both steps as described in U.S. Pat. No. 5,322,770. Another technique involves the use of Reverse Transcriptase Asymmetric Gap Ligase Chain Reaction (RT-AGLCR), as described by Marshall R. L. et al. (*PCR Methods and Applications* 4:80-84, 1994).

The source of the HBcAg sequences that are included in the isolated nucleic acids described herein is not particularly limited. Accordingly, alternatives described herein may utilize an isolated nucleic acid that encodes an HBcAg derived from a hepatitis virus capable of infecting animals of any species, including but limited to, humans, non-human primates (e.g., baboons, monkeys, and chimpanzees), rodents, mice, reptiles, birds (e.g., stork and heron), pigs, micro-pigs, goats, dogs and cats. In some alternatives, the HBcAg is selected from a human hepatitis antigen or an avian hepatitis antigen. Particularly preferred are the stork hepatitis antigen and a heron hepatitis antigen.

In certain alternatives, the HBcAg sequences described herein have variations in nucleotide and/or amino acid sequences, compared to native HBcAg sequences and are referred to as HBcAg variants or mutants. As used herein, the term "native" refers to naturally occurring HBV sequences (e.g., available HBV isotypes). Variants may include a substitution, deletion, mutation or insertion of one or more nucleotides, amino acids, or codons encoding the HBcAg sequence, which may result in a change in the amino acid sequence of the HBcAg polypeptide, as compared with the native sequence. Variants or mutants can be engineered, for example, using any of the techniques and guidelines for conservative and non-conservative mutations set forth, for instance, in U.S. Pat. No. 5,364,934, which is hereby incorporated by reference in its entirety.

Accordingly, when the term "consisting essentially of" is used, in some contexts, variants or mutants of an HBcAg sequence or of a particular antigen sequence are intended to be encompassed. That is, in some contexts and in some alternatives, the variants or mutants of the sequences disclosed herein are equivalents because the variation or mutation in sequence does not change or materially affect the basic and novel characteristics of the claimed invention.

A codon-optimized HBcAg can, in some alternatives, be encoded within the isolated nucleic acid or chimeric gene. A codon-optimized sequence may, in some alternatives, be obtained by substituting codons in an existing sequence with codons more frequently used in the intended host subject (e.g., a human).

Some alternatives include, for example, one or more of the HBcAg nucleic acid or protein sequences disclosed in International Patent Application Publication Number WO 20091130588, published Dec. 7, 2011, which designated the United States and was published in English, the disclosure of which is hereby expressly incorporated by reference in its entirety. In some alternatives, a chimeric gene encoding HBV core (HBcAg) is provided. In some alternatives, the chimeric gene comprises a sequence set forth in SEQ ID NO's: 60, 62, 65, 67, 70 or 72.

DETAILED DESCRIPTION

Existing therapies with reversed transcriptase (RT) inhibitors effectively supress HBV replication but fails to induce off-therapy responses, and have no effect on HDV replication. The viroid-like virus HDV is a highly pathogenic virus and can only complete its replication cycle in cells infected by HBV. HDV lacks its own gene for a viral envelope protein and therefore "steals" the envelope of HBV, the hepatitis B surface antigen (HBsAg), when leaving the cell. Hence, the HBV vaccine can protect naive individuals from both HBV and HDV, but cannot protect a person infected by HBV against HDV superinfection due to the inherent overproduction of HBsAg during the HBV infection.

In some alternatives described herein, preS1 antibodies were shown to prevent HBV and HDV infection. Importantly, both HBV and HDV require the same preS1 sequence to enter hepatocytes. Thus, targeting preS1 is an excellent way to prevent both infections. It has been shown that a 48 amino acid stretch within the preS1 region is effective in generating preS1-specific antibodies. In some alternatives described herein, preS1 antibodies can be induced by a chimeric HBV core antigen (HBcAg) protein exposing a preS1 sequence (aa 1-42) on the surface. In addition, HDAg was shown to induce genotype-specific T cell responses in mice. This suggests that multiple genotypes must be contained in an HDAg-based vaccine.

Additionally, it has been discovered that hepatitis B core antigen (HBcAg) is a potent adjuvant that improves the immune response of a subject to a co-administered antigen (See, e.g., PCT Publication No. WO 2010/086743 A2, published Aug. 5, 2010, which is hereby incorporated by reference in its entirety). In the present disclosure, it is contemplated that a nucleic acid encoding HBcAg improves the immune response of a mammal to the second polypeptide antigen.

Accordingly, some alternatives include methods of enhancing or improving an immune response of a subject, wherein a nucleic acid encoding an HBcAg, preferably codon-optimized for expression in humans, is provided to a subject along with another chimeric gene comprises at least two HDAg sequences, which are also preferably codon-optimized for expression in humans. In some alternatives, a chimeric gene encoding a HDV polypeptide with a pre-S1 domain is provided. The pre-S1 domain, as described herein, can allow prevention of HBV and HDV infections. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, preS1 A is encoded by a nucleic acid sequence set forth in SEQ ID NO: 5. In some alternatives, preS1 B is encoded by a nucleic acid sequence set forth in SEQ ID NO: 6.

The HDV infection cannot be prevented in patients infected by HBV using the current HBsAg-based vaccines lacking both preS1 and preS2. Thus, a combined approach with vaccines containing both parts of preS1 that induces neutralising antibodies, and parts or the whole HDAg to induce HDV-specific T cells should be able to inhibit, ameliorate, treat or prevent HDV infection in HBV infected patients.

Several alternatives described herein concern isolated chimeric genes, expression constructs, DNA immunogenic compositions, DNA vaccines or nucleic acid immunogens, preferably, which are codon-optimized for expression in humans, and that encode a peptide that comprises, consists of, or consists essentially of at least two antigenic sequence, which is an HDV sequence. In some alternatives a chimeric gene is also contemplated, which can encode HBcAg, preferably from avian, stork or heron, which is codon optimized for expression in humans.

Chimeric Genes

Chimeric Genes for Expression of HDAg Protein Domains.

Provided herein are chimeric genes comprising HDAg sequences and chimeric genes encoding HBV core antigen (HBcAg). In some alternatives, a chimeric gene comprising HDAg sequences and a sequence encoding a preS1 domain is provided. The chimeric gene can comprise at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, preS1 A comprises an amino acid sequence set forth in SEQ ID NO: 1. In some alternatives, preS1 B comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO: 10. In some alternatives, the chimeric gene comprises a nucleic acid sequence set forth in SEQ ID NO: 12. In some alternatives, the chimeric gene encodes a protein comprises an amino acid sequence set forth in SEQ ID NO: 14. In some alternatives, the chimeric gene comprises a nucleic acid sequence set forth in SEQ ID NO: 15. In some alternatives, the chimeric gene comprises a nucleic acid sequence set forth in SEQ ID NO: 17. In some alternatives, the chimeric gene encodes a protein wherein the protein comprises an amino acid sequence set forth in SEQ ID NO: 19. In some alternatives, the chimeric gene comprises a nucleic acid sequence set forth in SEQ ID NO: 20. In some alternatives, the chimeric gene comprises a nucleic acid sequence set forth in SEQ ID NO: 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO: 25. In some alternatives, the chimeric gene comprises a nucleic acid sequence set forth in SEQ ID NO: 27. In some alternatives, the chimeric gene encodes a protein wherein the protein comprises an amino acid sequence set forth in SEQ ID NO: 21. In some alternatives, the chimeric gene comprises a nucleic acid sequence set forth in SEQ ID NO: 30. In some alternatives, the chimeric gene comprises a nucleic acid sequence set forth in SEQ ID NO: 32. In some alternatives, the chimeric gene encodes a protein wherein the protein comprises an amino acid sequence set forth in SEQ ID NO: 34. In some alternatives, the chimeric gene comprises a nucleic acid sequence set forth in SEQ ID NO: 35. In some alternatives, the chimeric gene comprises a nucleic acid sequence set forth in SEQ ID NO: 37. In some alternatives, the chimeric gene encodes a protein wherein the protein comprises an amino acid sequence set forth in SEQ ID NO: 39. In some alternatives, the chimeric gene comprises a nucleic acid sequence set forth in SEQ ID NO: 40. In some alternatives, the chimeric gene comprises a nucleic acid sequence set forth in SEQ ID NO: 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO: 45. In some alternatives, the chimeric gene comprises a nucleic acid sequence set forth in SEQ ID NO: 47. In some alternatives, the chimeric gene encodes a protein wherein the protein comprises an amino acid sequence set forth in SEQ ID NO: 49. In some alternatives, the chimeric gene comprises a nucleic acid sequence set forth in SEQ ID NO: 50. In some alternatives, the chimeric gene comprises a nucleic acid sequence set forth in SEQ ID NO: 52. In some alternatives, the chimeric gene encodes a protein wherein the protein comprises an amino acid sequence set forth in SEQ ID NO: 54. In some alternatives, the chimeric gene comprises a nucleic acid sequence set forth in SEQ ID NO: 55. In some alternatives, the chimeric gene comprises a nucleic acid sequence set forth in SEQ ID NO: 57. In some alternatives, the chimeric gene encodes a protein wherein the protein comprises an amino acid sequence set forth in SEQ ID NO: 59. In some alternatives, the chimeric gene is codon optimized. Preferably, this sequence is codon optimized for expression in humans.

Figure 2:
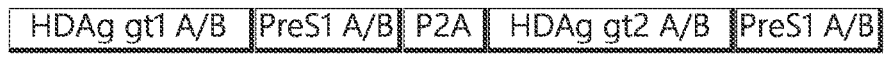
FIG. 2 is a schematic of several primary sequences of combined HDV-PreS1 vaccine design. As shown, the HDV-PreS1's can have domains from HDAg genotype 1 A/B, PreS1 A/B, P2A and HDAg gt2 A/B to make up the vaccines Delta-1, Delta-2, Delta-3, Delta-4, Delta-5, Delta-6, Delta-7, Delta-8, Delta-9 and Delta 10.
Figure 2:
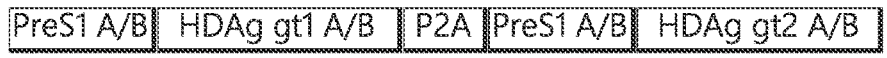
Figure 2:
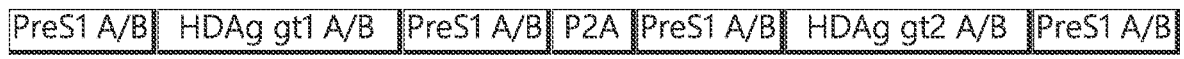
Figure 2:
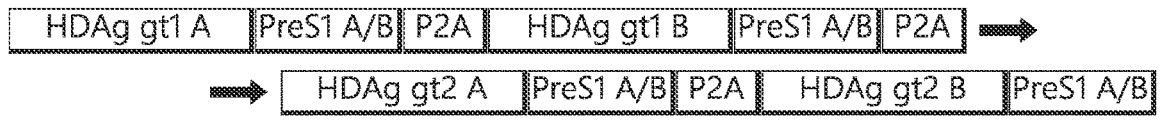
Figure 2:
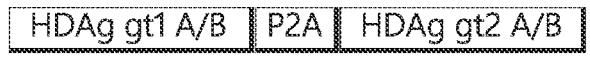
Figure 2:

The preS1 peptides that are used are shown in FIG. 1, which is an alignment of the preS1 peptides of HBV. As shown in FIG. 2 are the combined HDV-PreS1 vaccine designs for Delta-1, Delta-2, Delta-3, Delta-4, Delta-5, Delta-6, Delta-7, Delta-8, Delta-9 and Delta-10 for the chimeric genes described in the alternatives herein. These constructs are used to encode the chimeric proteins described herein.

Chimeric Genes for Expression of HBV Core Protein

Described herein are chimeric genes for the expression of HBV core. In some alternatives, a chimeric gene for expressing HBV core antigen is provided, wherein the chimeric gene comprises a sequence encoding an HBV core antigen. In some alternatives, the chimeric gene comprises a sequence set forth in SEQ ID NO's: 60, 62, 65, 67, 70 or 72. In some alternatives, the chimeric gene is codon optimized for expression in humans. In some alternatives, the chimeric gene encodes a protein, wherein the protein comprises an amino acid sequence set forth in SEQ ID NO's 64, 69 or 74. Preferably, this sequence is codon optimized for expression in humans.

Chimeric Proteins

Chimeric HDAg Proteins

Chimeric proteins encoded by the chimeric genes described herein are provided. In some alternatives a chimeric protein comprising at least two HDAg protein domains, encoded by the chimeric genes of anyone of the alternatives described herein is provided. The chimeric gene can comprise at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, preS1 A comprises an amino acid sequence set forth in SEQ ID NO: 1. In some alternatives, preS1 B comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO: 10. In some alternatives, the chimeric gene comprises a nucleic acid sequence set forth in SEQ ID NO: 12. In some alternatives, the chimeric gene encodes a protein comprises an amino acid sequence set forth in SEQ ID NO: 14. In some alternatives, the chimeric gene comprises a nucleic acid sequence set forth in SEQ ID NO: 15. In some alternatives, the chimeric gene comprises a nucleic acid sequence set forth in SEQ ID NO: 17. In some alternatives, the chimeric gene encodes a protein wherein the protein comprises an amino acid sequence set forth in SEQ ID NO: 19. In some alternatives, the chimeric gene comprises a nucleic acid sequence set forth in SEQ ID NO: 20. In some alternatives, the chimeric gene comprises a nucleic acid sequence set forth in SEQ ID NO: 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO: 25. In some alternatives, the chimeric gene comprises a nucleic acid sequence set forth in SEQ ID NO: 27. In some alternatives, the chimeric gene encodes a protein wherein the protein comprises an amino acid sequence set forth in SEQ ID NO: 21. In some alternatives, the chimeric gene comprises a nucleic acid sequence set forth in SEQ ID NO: 30. In some alternatives, the chimeric gene comprises a nucleic acid sequence set forth in SEQ ID NO: 32. In some alternatives, the chimeric gene encodes a protein wherein the protein comprises an amino acid sequence set forth in SEQ ID NO: 34. In some alternatives, the chimeric gene comprises a nucleic acid sequence set forth in SEQ ID NO: 35. In some alternatives, the chimeric gene comprises a nucleic acid sequence set forth in SEQ ID NO: 37. In some alternatives, the chimeric gene encodes a protein wherein the protein comprises an amino acid sequence set forth in SEQ ID NO: 39. In some alternatives, the chimeric gene comprises a nucleic acid sequence set forth in SEQ ID NO: 40. In some alternatives, the chimeric gene comprises a nucleic acid sequence set forth in SEQ ID NO: 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO: 45. In some alternatives, the chimeric gene comprises a nucleic acid sequence set forth in SEQ ID NO: 47. In some alternatives, the chimeric gene encodes a protein wherein the protein comprises an amino acid sequence set forth in SEQ ID NO: 49. In some alternatives, the chimeric gene comprises a nucleic acid sequence set forth in SEQ ID NO: 50. In some alternatives, the chimeric gene comprises a nucleic acid sequence set forth in SEQ ID NO: 52. In some alternatives, the chimeric gene encodes a protein wherein the protein comprises an amino acid sequence set forth in SEQ ID NO: 54. In some alternatives, the chimeric gene comprises a nucleic acid sequence set forth in SEQ ID NO: 55. In some alternatives, the chimeric gene comprises a nucleic acid sequence set forth in SEQ ID NO: 57. In some alternatives, the chimeric gene encodes a protein wherein the protein comprises an amino acid sequence set forth in SEQ ID NO: 59. In some alternatives, the chimeric gene is codon optimized for expression in humans.

Chimeric HBV Core (HBcAg)

In some alternatives described herein, a chimeric protein comprising HBV core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof is provided. The protein can be encoded by any one of the chimeric genes encoding HBV core or an antigenic portion thereof described herein. In some alternatives, the chimeric gene comprises a sequence encoding an HBV core antigen or an antigenic portion thereof. In some alternatives, the chimeric gene comprises a sequence set forth in SEQ ID NO's: 60, 62, 65, 67, 70 or 72 or an antigenic or immunogenic portion thereof. In some alternatives, the chimeric gene is codon optimized for expression in humans. In some alternatives, the chimeric gene encodes a protein, wherein the protein comprises an amino acid sequence set forth in SEQ ID NO's 64, 69 or 74 or an antigenic or immunogenic portion thereof.

Compositions

Accordingly, several aspects of the invention described herein concern compositions that comprise, consist essentially of, or that consist of chimeric genes that encode an HDAg which may be codon-optimized for expression in humans, and, which can be joined (e.g., in Cis) to a nucleic acid (preferably codon-optimized for expression in an animal or human) that encodes at least one preS1 derived sequence. The sequence can further comprise a self-cleavage sequence or domains (e.g., P2A, T2A, E2A, or F2A) that exist between the nucleic acid encoding the target antigen and the nucleic acid encoding the HDAg, and, which may optionally, exist within the nucleic acid sequence encoding the HDAg polypeptide such that the translated HDAg is self-cleaved into polypeptide fragments. Preferably, one or more or all of these sequences are codon optimized for expression in humans. Methods of using the foregoing immunogenic compositions to generate an immune response (e.g., a T cell and/or antibody specific immune response) or to inhibit, ameliorate, treat, or prevent HBV and HDV infection in a subject, preferably a human and, optionally a chronically infected human, are contemplated alternatives.

Optionally, a subject can be identified as one in need of an immune response to HBV and HDV prior to administration of the composition and/or said subject can be evaluated for the immune response or viral clearance after administration of said compositions and such identification and/or evaluation can be accomplished using readily available diagnostics and/or clinical approaches.

Compositions or mixtures that further comprise, consist essentially of, or that consist of one or more of nucleic acids (e.g., in Trans) that encode polypeptide adjuvants, such as nucleic acids encoding IL-12, IL-15, or IL-21, which may optionally be codon optimized for expression in humans, or that consist of polypeptide adjuvants IL-12, IL-15, or IL-21 or that consist of small molecule adjuvants such as ribavirin or CpG nucleic acids are also alternatives. Preferably, these nucleic acids are codon optimized for expression in humans and these nucleic acids can be used as an immunogen to inhibit, ameliorate, treat, or prevent HBV and HDV infection. Methods of using the aforementioned compositions to improve, enhance, or generate an immune response in a subject or to treat diseases such as HBV and HDV, especially in chronically infected individuals, are also contemplated.

Figure 3:
FIG. 3 shows the primary structures of the HBv-PreC/C vaccine designs, Core-1, Core-2 and Core-3.
Figure 3:
Figure 3:
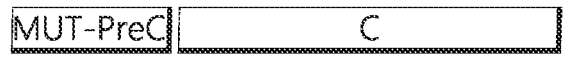
Figures 4A, 4B:
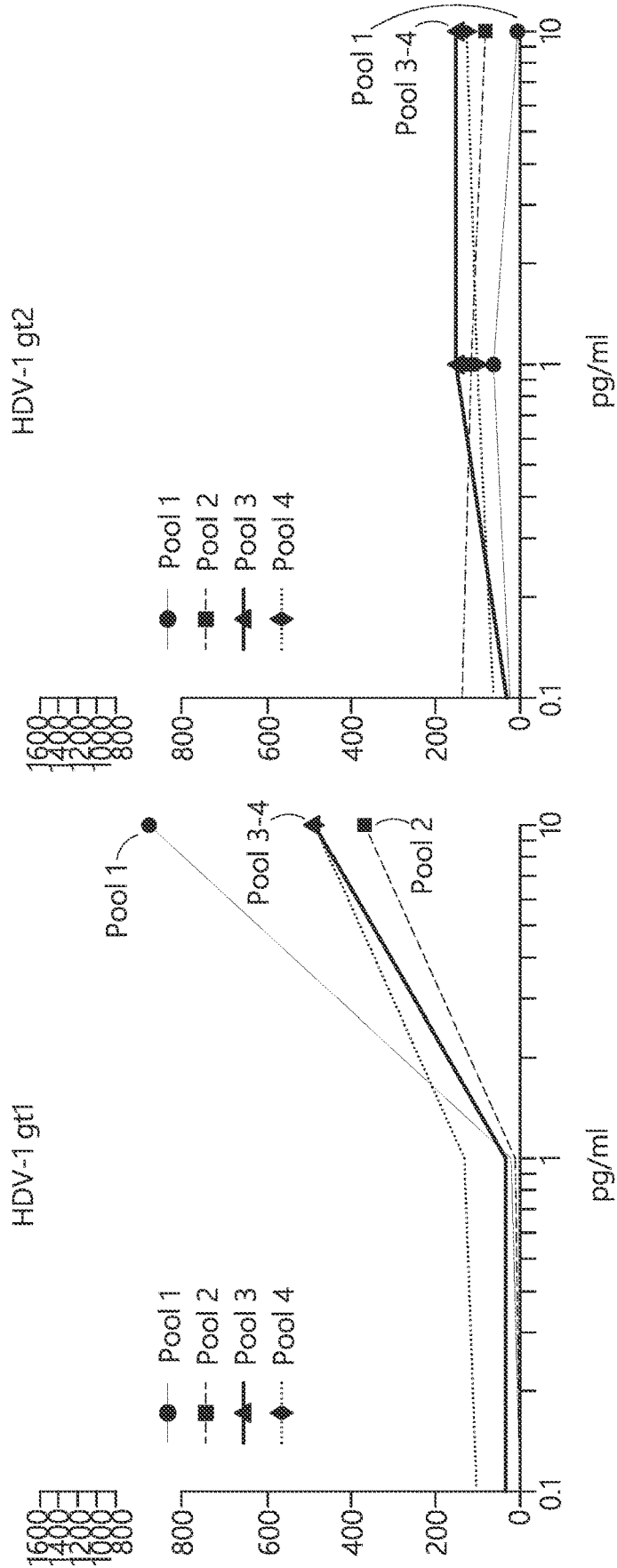
FIG. 4A-4T shows an in vitro recall of T cells primed after a single immunization using HDV constructs 1-10 towards gt1 (right panel) or gt2 (left panel) peptides (Peptides are shown in Table 1). The peptide constructs are also shown above the graphs.
Figures 4C, 4D:
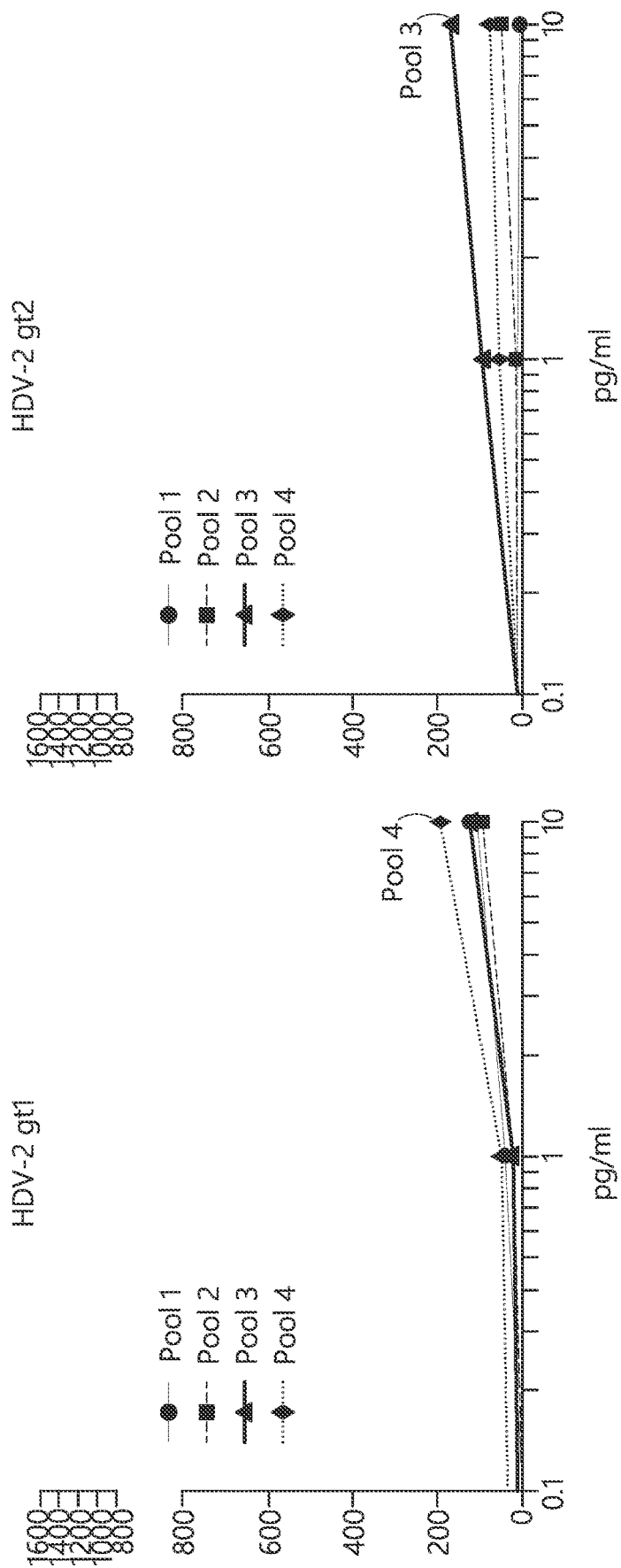
Figures 4E, 4F:
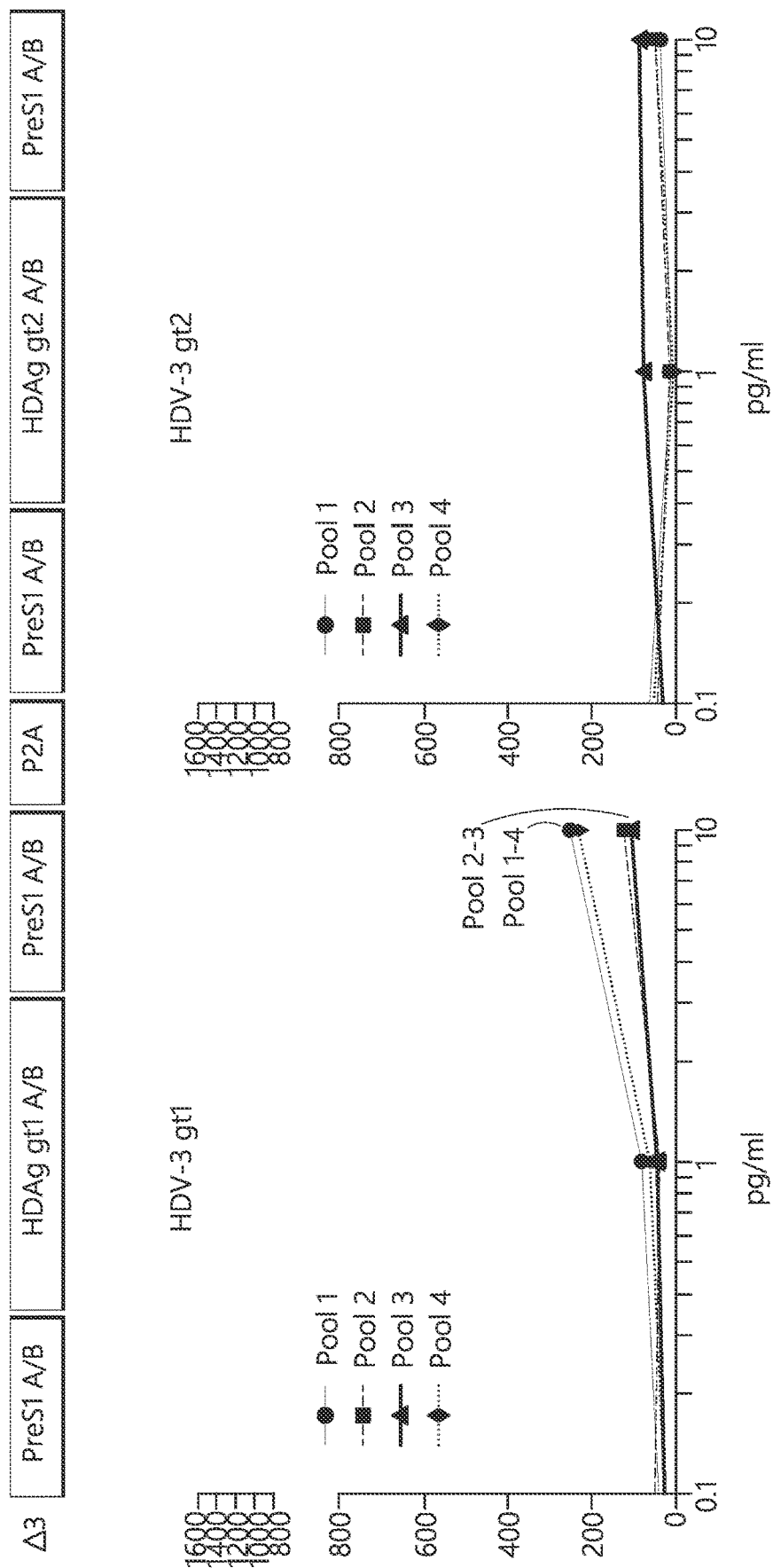
Figures 4G, 4H:
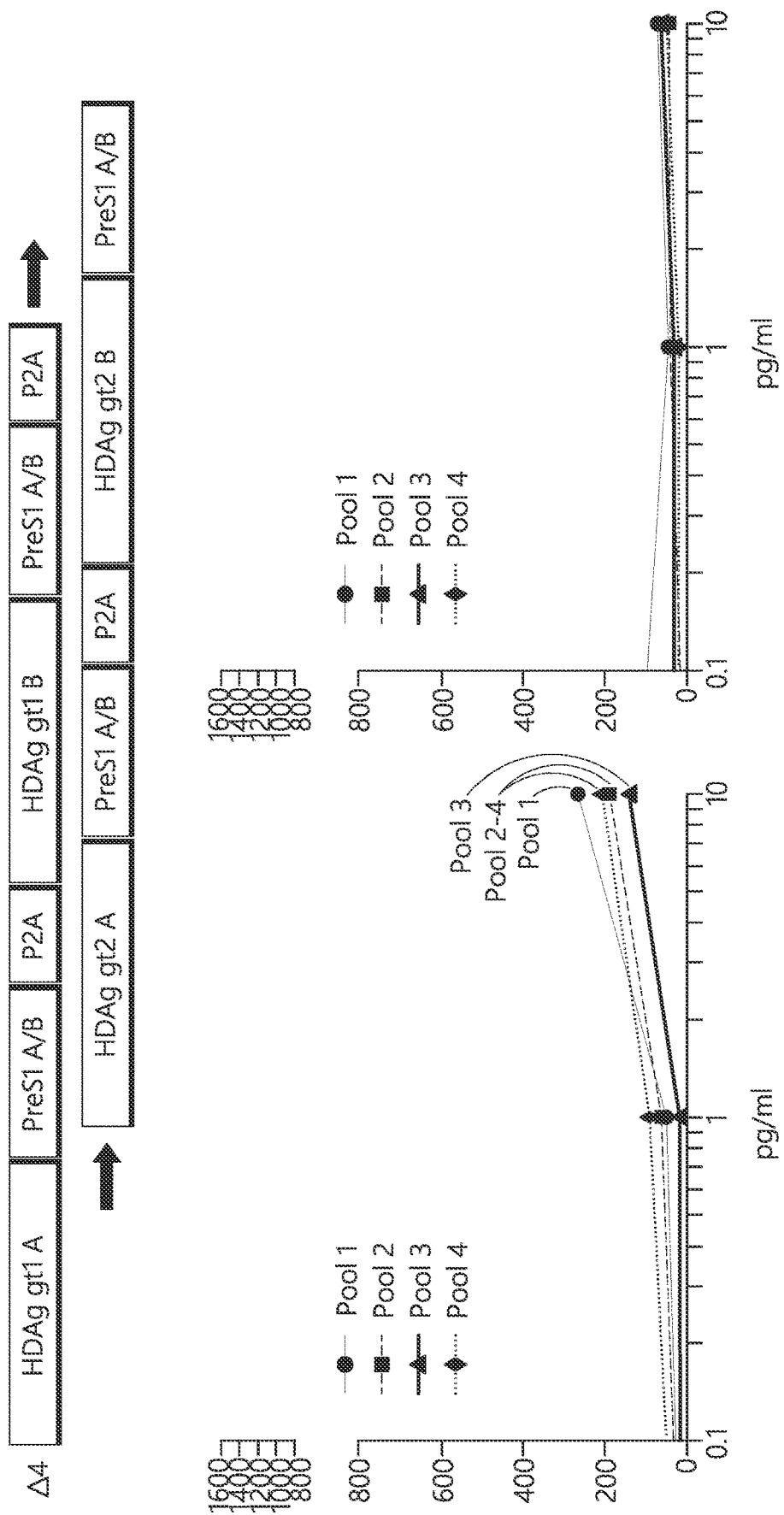
Figures 4K, 4L:
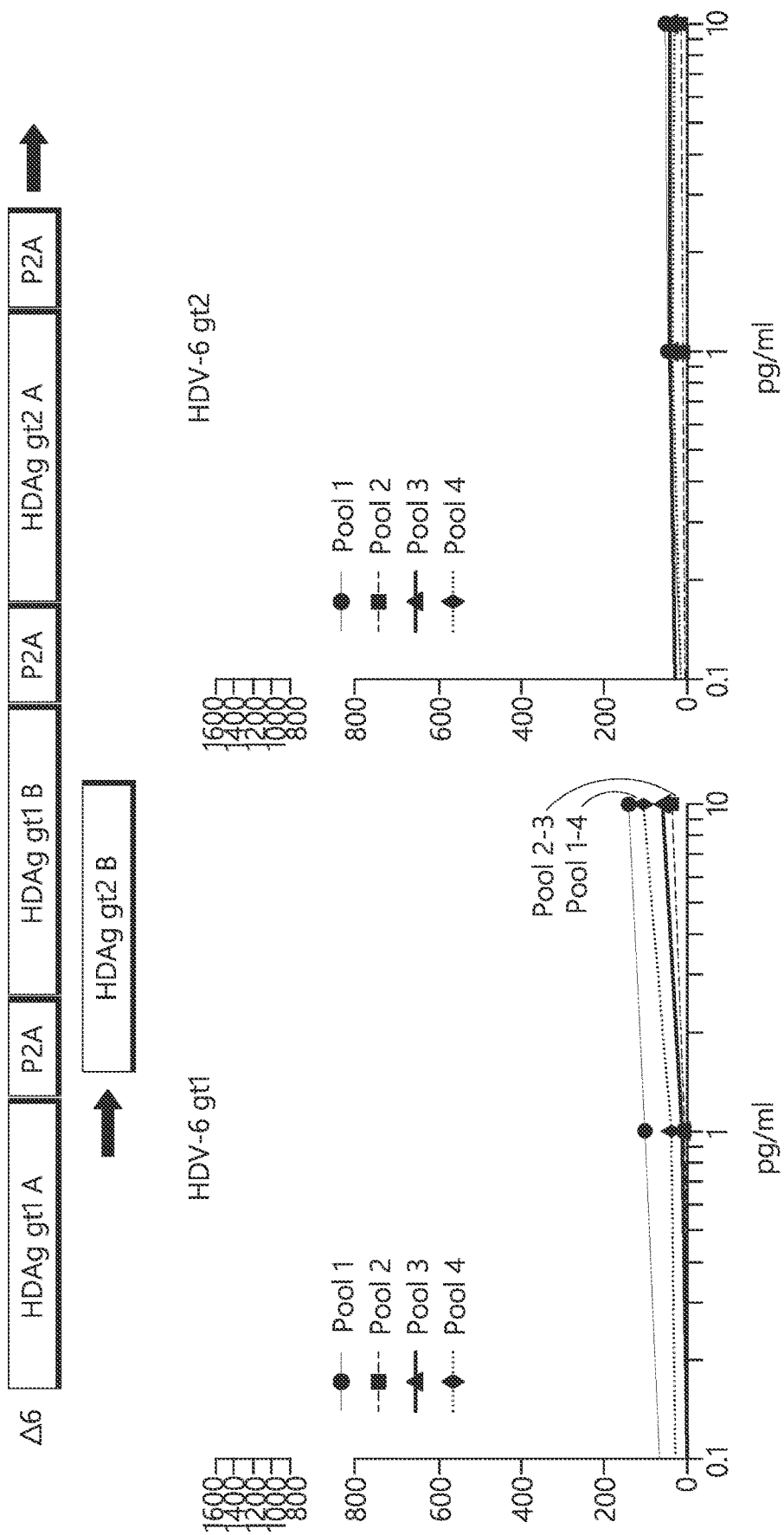
Figures 4M, 4N:
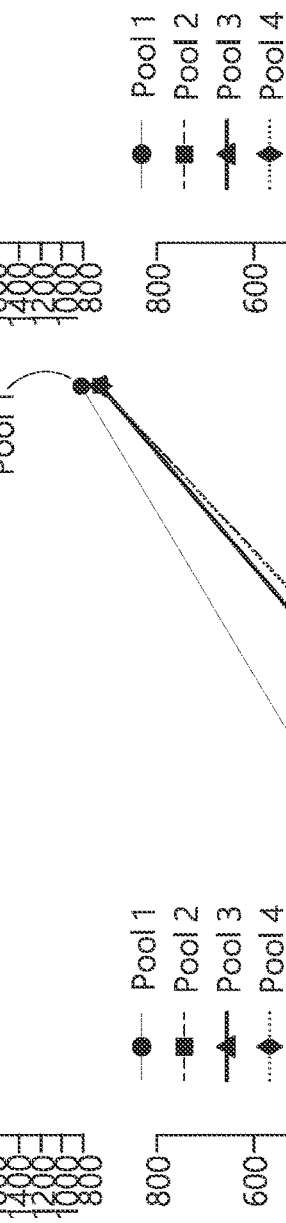
Figures 4O, 4P:
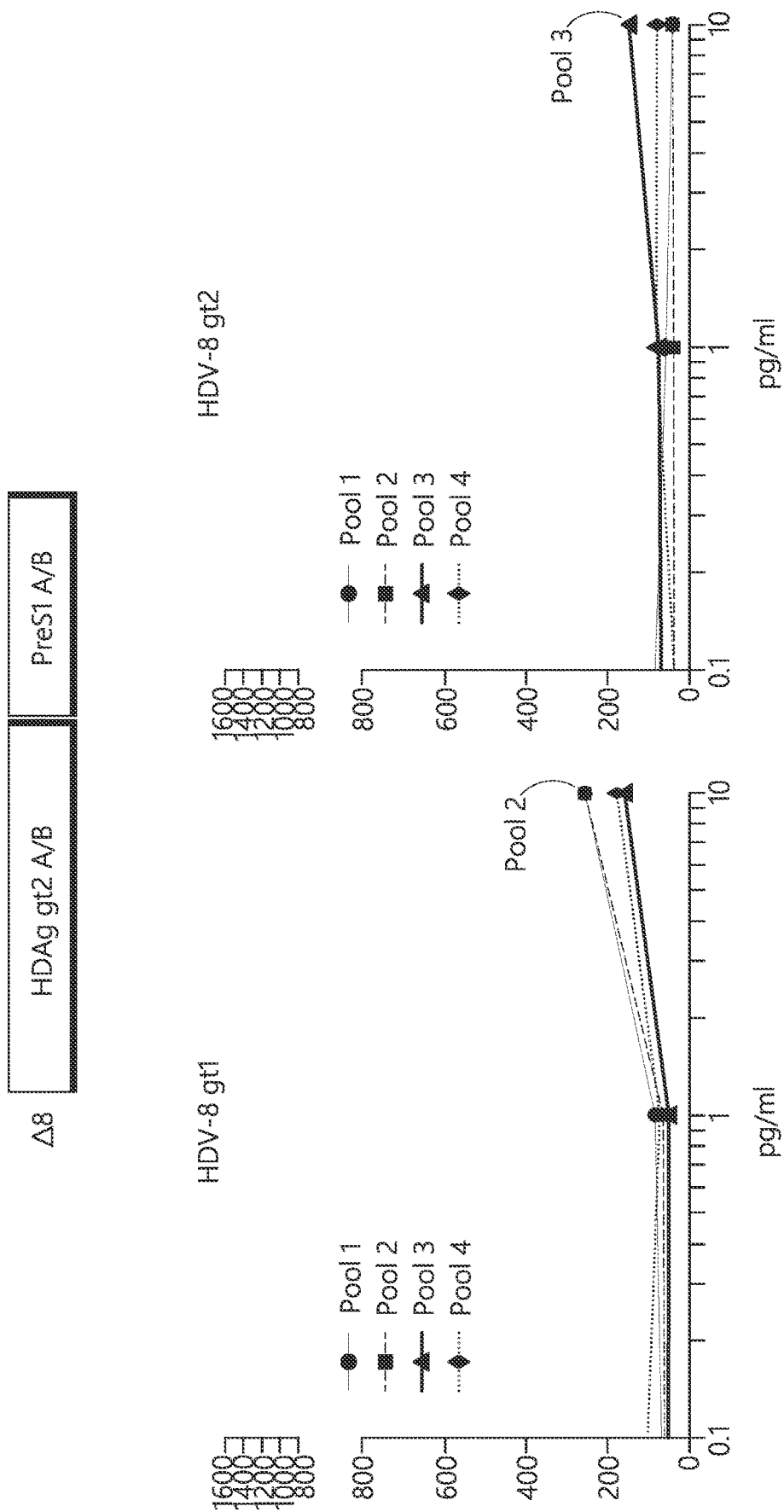
Figures 4S, 4T:
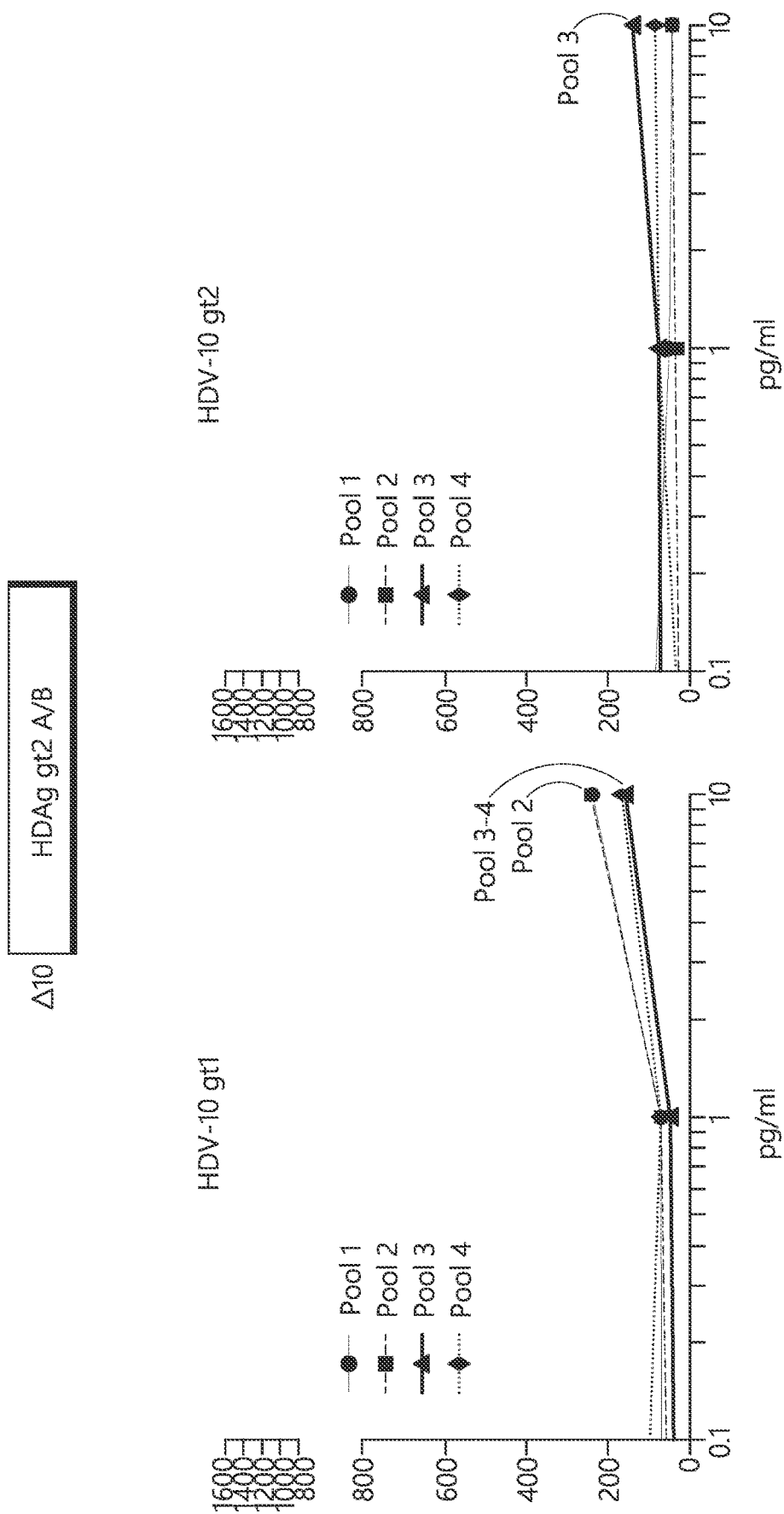
Figures 5C, 5D:
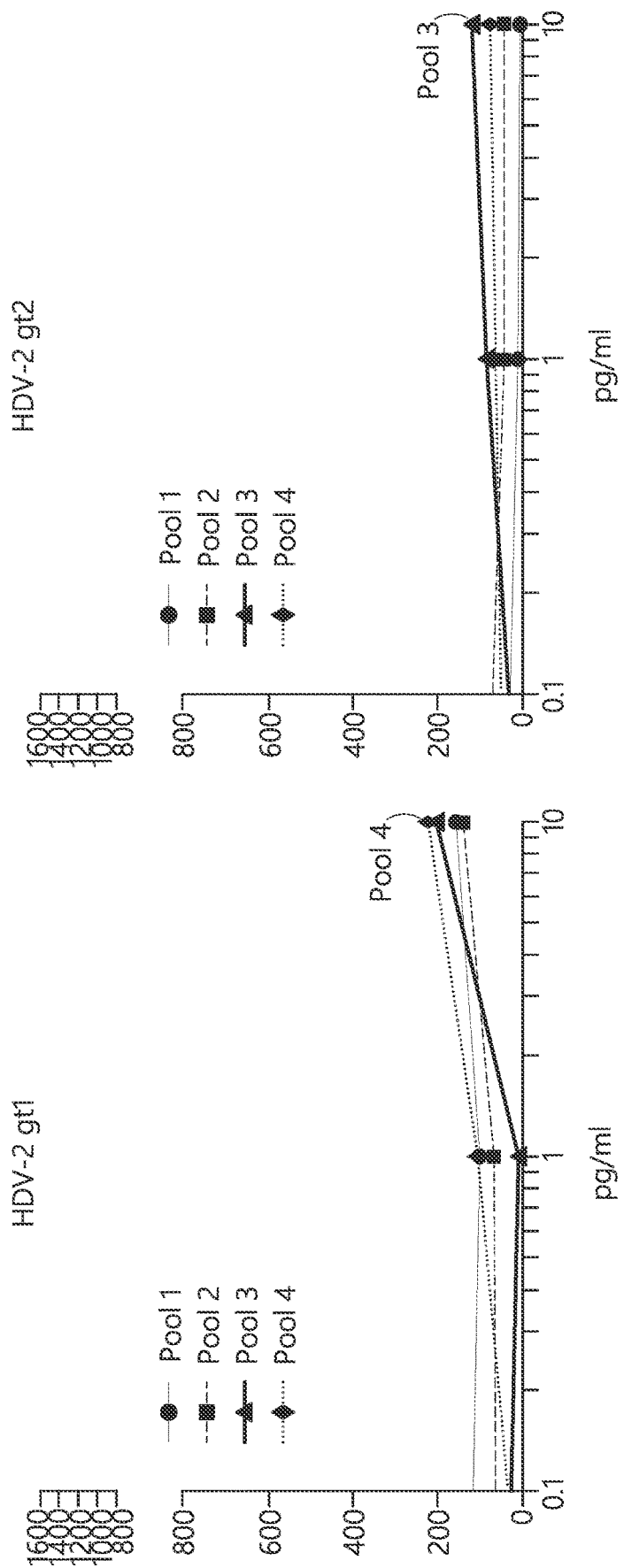
FIG. 5A-5T shows an in vitro recall of T cells primed after two monthly immunizations using HDV constructs 1-10 towards gt1 (right panel) or gt2 (left panel) peptides (Peptides are shown in Table 1).
Figures 5I, 5J:
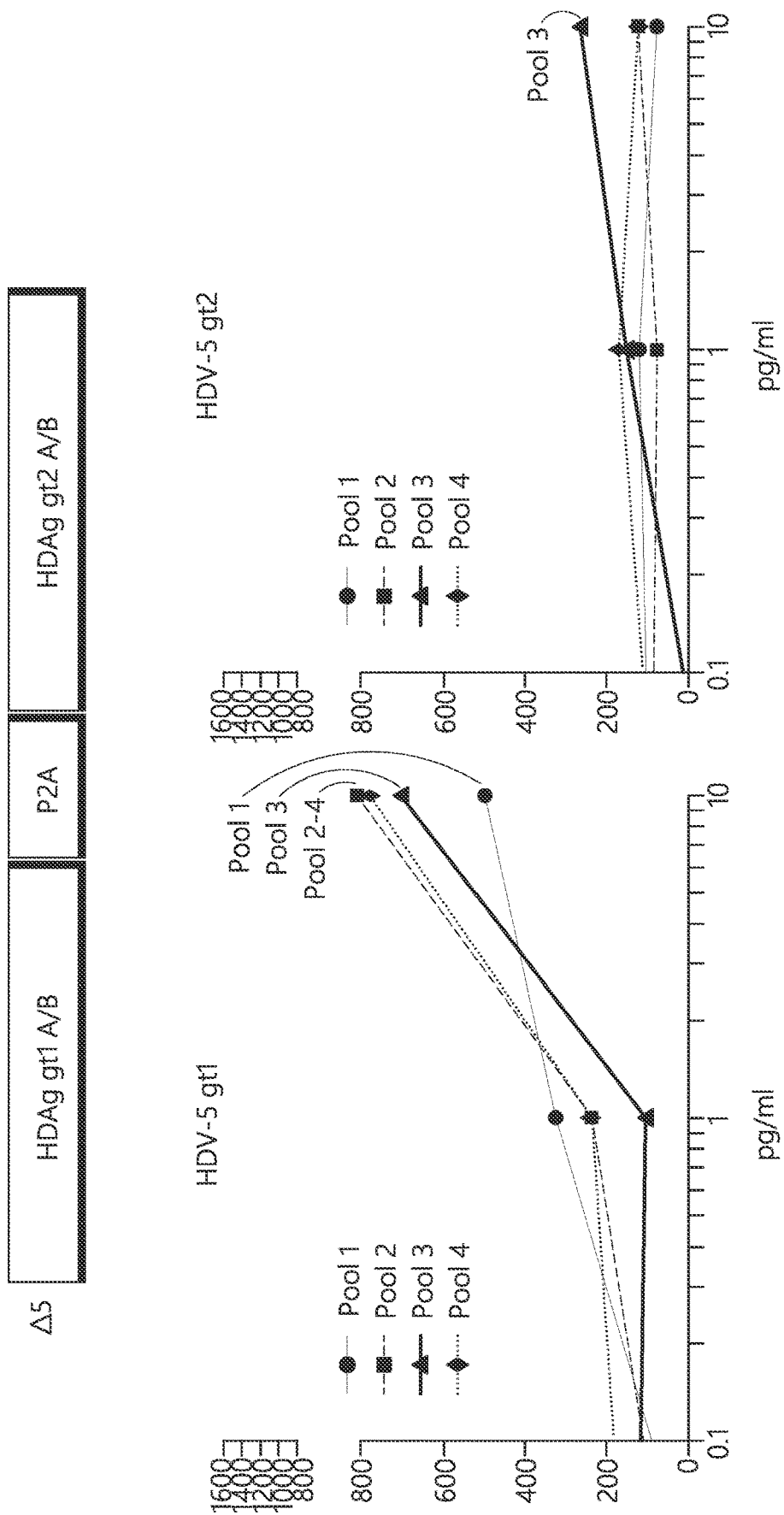
Figures 5K, 5L:
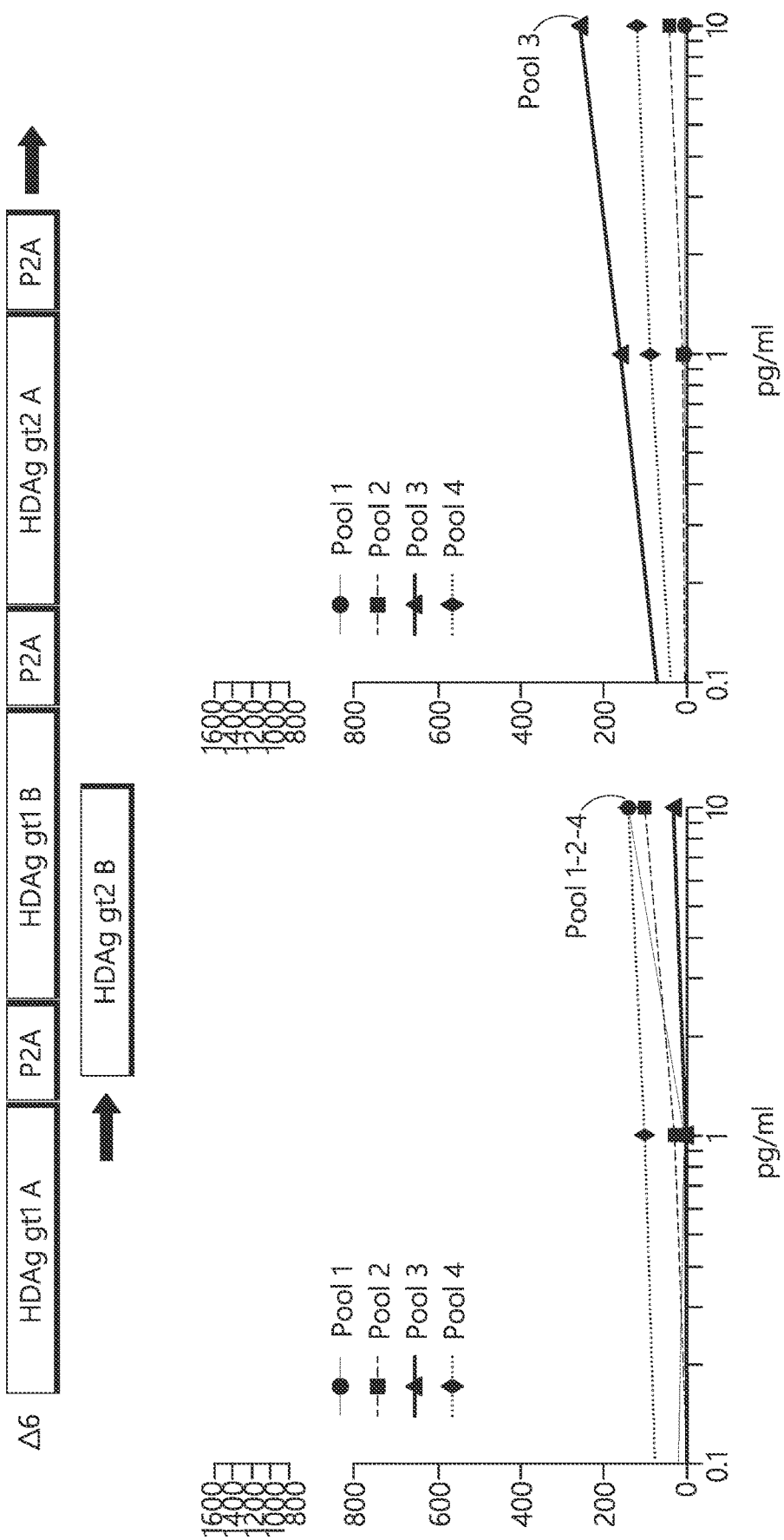
Figures 5M, 5N:
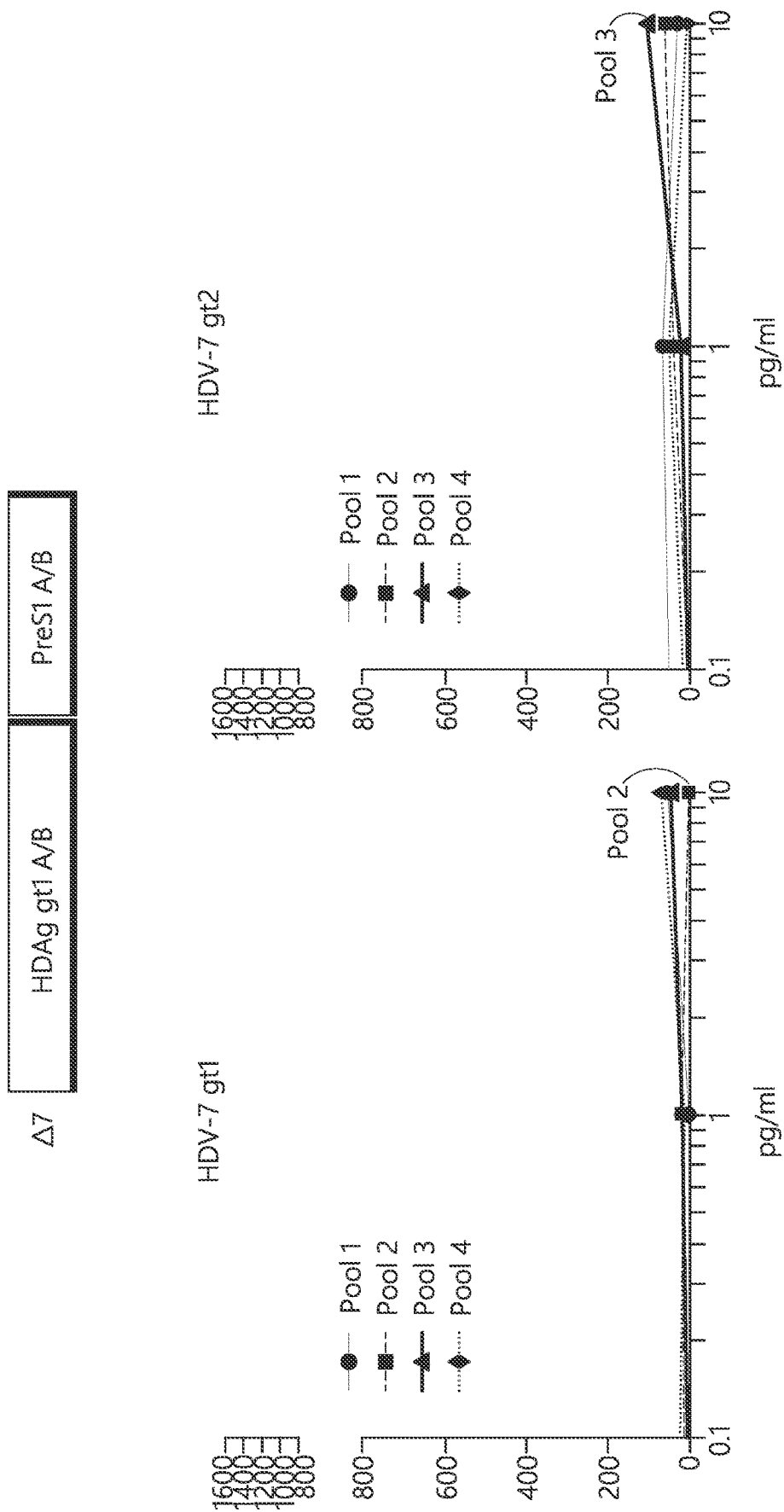
Figures 5O, 5P:
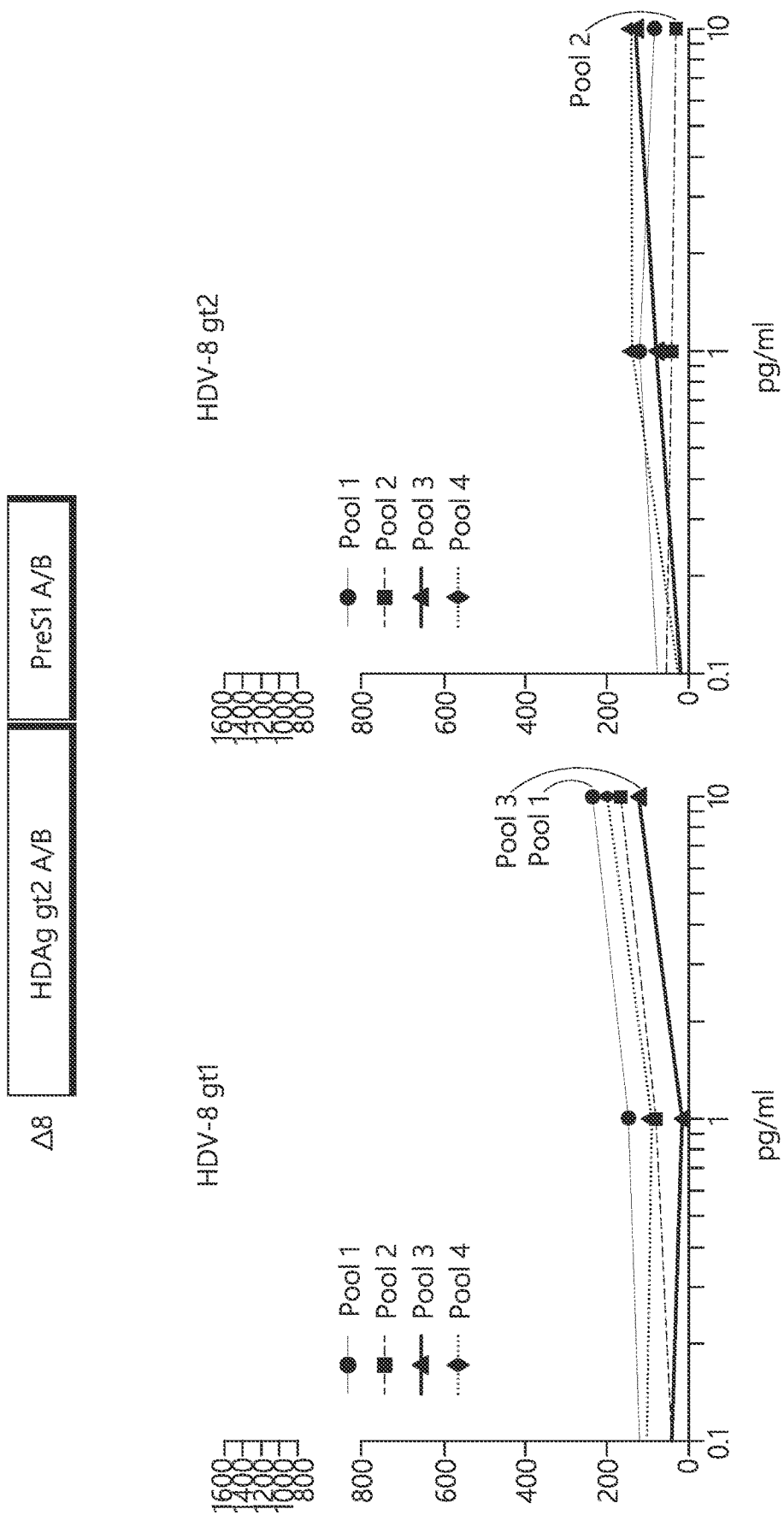
Figures 5Q, 5R:
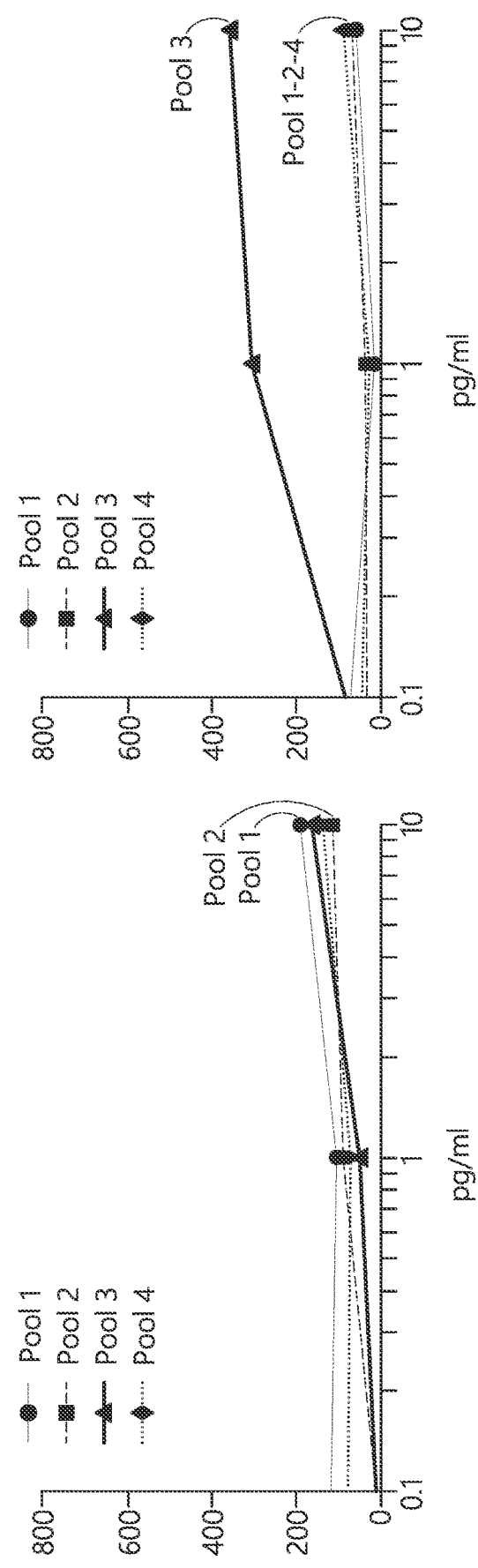
Figures 5S, 5T:
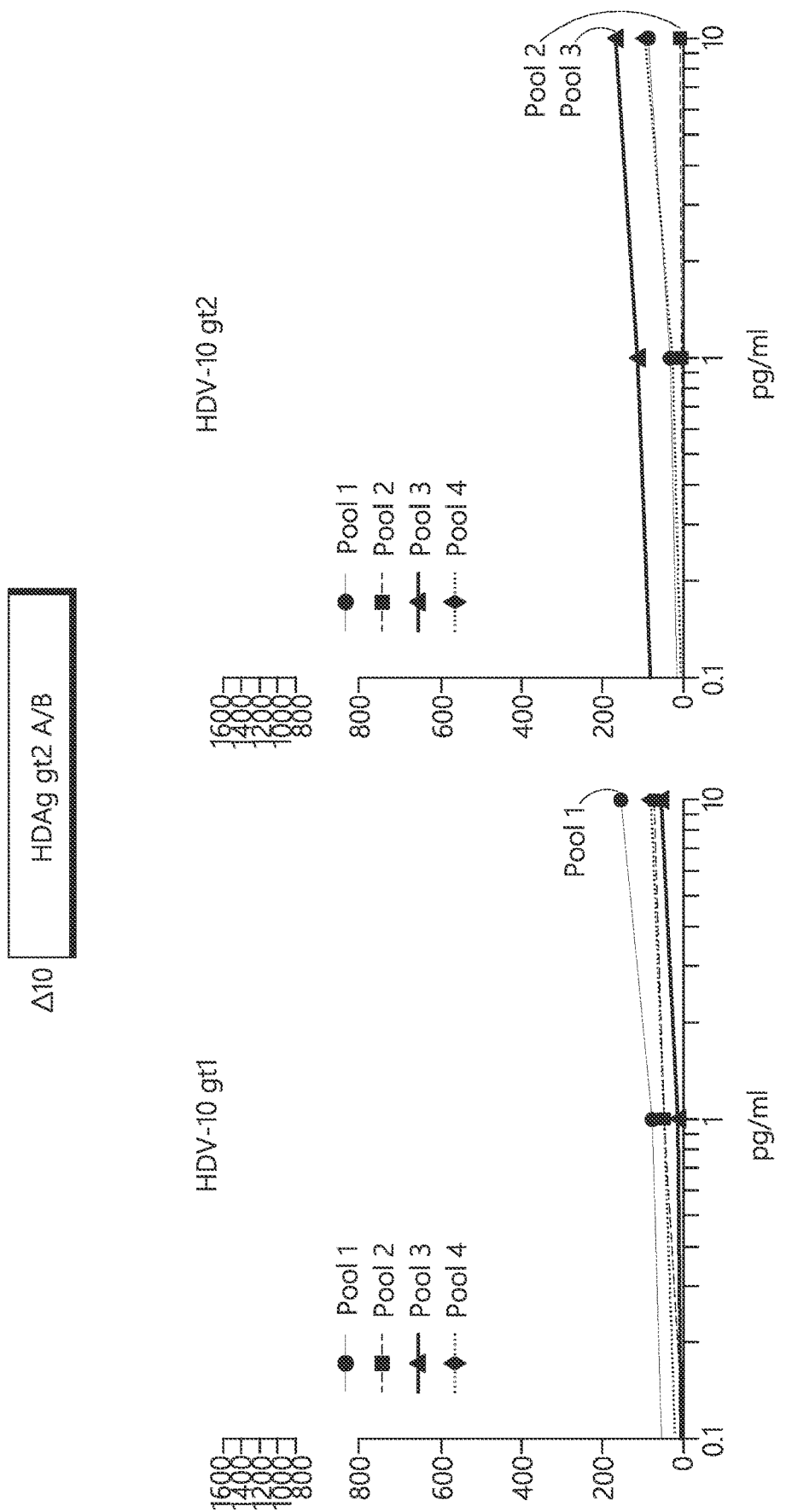

In some alternatives, the compositions can comprise proteins encoded by the chimeric genes. Furthermore compositions comprising chimeric genes and the chimeric proteins are also contemplated. The composition can comprise chimeric genes encoding at least one HDAg and/or chimeric genes encoding hepatitis B core. In some alternatives, the compositions comprise chimeric proteins. The chimeric proteins can comprise the Delta-1, Delta-2, Delta-3, Delta-4, Delta-5, Delta-6, Delta-7, Delta-8, Delta-9, Delta-10 and/or any of the Core constructs as described herein and/or in FIGS. 2 and 3.

In some alternatives, the HDAg sequence comprises a sequence set forth in SEQ ID NO's 3, 4, 8 or 9. In some alternatives, the sequences are codon optimized for expression in humans. In some alternatives, the nucleic acid sequence encodes greater than or equal to 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the HDAg polypeptide or an amount that is within a range defined by any two of the aforementioned percentages. Optionally, these sequences can be codon optimized for expression in humans. In some alternatives, the nucleic acid sequence encodes greater than or equal to or any number in between 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, or 195 amino acid residues of the HDAg polypeptide or an amount that is within a range defined by any two of the aforementioned percentages. In some alternatives, the nucleic acid encodes a full length HDAg polypeptide. Optionally, these sequences can be codon optimized for expression in humans Methods of using the foregoing compositions to generate an immune response (e.g., a T cell and/or antibody specific immune response) or to inhibit, ameliorate, treat, or prevent an HBV and HDV infection in a subject, preferably a human and, optionally a chronically infected human, are contemplated alternatives. Optionally, a subject can be identified as one in need of an immune response to HBV and HDV prior to administration of the composition and/or said subject can be evaluated for the immune response or viral clearance after administration of said compositions and such identification and/or evaluation can be accomplished using readily available diagnostics and/or clinical approaches.

In some alternatives, the self-cleavage polypeptide exists after amino acid residue number 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, or 195 of the HDAg polypeptide. Optionally, these sequences can be codon optimized for expression in humans. In some alternatives, the self-cleavage polypeptide exists before amino acid residue number 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, or 195 of the HDAg polypeptide. Optionally, these sequences can be codon optimized for expression in humans Methods of using the foregoing compositions to generate an immune response (e.g., a T cell and/or antibody specific immune response) or to inhibit, ameliorate, treat, or prevent HBV and HDV in a subject, preferably a human and, optionally a chronically infected human, are contemplated alternatives. Optionally, a subject can be identified as one in need of an immune response to HBV and HDV prior to administration of the composition and/or said subject can be evaluated for the immune response or viral clearance after administration of said compositions and such identification and/or evaluation can be accomplished using readily available diagnostics and/or clinical approaches.

In some alternatives a composition that comprises anyone or more of the chimeric genes described herein, wherein the chimeric genes encode at least at least two HDAg protein domains, is provided. In some alternatives, the chimeric gene comprises HDAg sequences, wherein the chimeric gene comprises at least two sequences encoding hepatitis D antigen (HDAg), at least one cleavage sequence and at least one preS1 derived sequence. In some alternatives, the composition comprises a protein encoded by anyone or more of the chimeric genes provided herein.

In some alternatives a composition comprising anyone or more of the chimeric genes encoding HBcAg is provided. In some alternatives, the chimeric gene comprises a sequence encoding an HBV core antigen. In some alternatives, the composition comprises a protein encoded by anyone or more of the chimeric genes provided herein.

In some alternatives a composition comprising a protein encoded by anyone or more of the chimeric genes is provided. In some alternatives, the composition further comprises a chimeric gene of any one or more of the alternatives provided herein.

In some alternatives, the composition further comprises the chimeric protein of anyone of the alternatives described herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In some alternatives, the composition is present or provided in an injection device or an injection device configured to be used in conjunction with an electroporation device.

Methods for Using the Chimeric Gene or Composition

In some alternatives, the chimeric gene or composition of any one of the alternatives is for use in providing an immunogenic composition, generating an immune response in a subject, or for DNA vaccination so as to inhibit, ameliorate, treat, or prevent HBV and HDV infection. In some alternatives, the chimeric gene, chimeric protein or composition is for use in generating an antibody, T-lymphocyte or CTL-specific response in a subject so as to prevent an HBV and HDV infection. In some alternatives, the chimeric gene, chimeric protein or composition of any one of the alternatives described herein is for immunogen delivery so as to inhibit, ameliorate, treat, or prevent HBV and HDV in a subject that has been identified as having and HDV or HBV infection.

In some alternatives, a method of eliciting an immune response is provided wherein the method comprises administering to a subject having HDV infection and/or HBV infection the nucleic acid or composition of any one of the alternatives at a first time. In some alternatives, said administering comprises injecting said nucleic acid into a patient, such as using an IVIN needle with or without electroporation. In some alternatives, the method further comprises administering a second administration of a nucleic acid or composition of any one of the alternatives described herein is provided. In some alternatives, the method further comprises providing an adjuvant. In some alternatives, said adjuvant is a nucleic acid encoding a polypeptide adjuvant, such as IL-12, IL-15, or IL-21. In some alternatives, said adjuvant is IL-12, IL-15, or IL-21. In some alternatives, said second administration is given after said first time. In some alternatives, said adjuvant is given before, during, or after administration of said nucleic acid or composition of any one of the alternatives described herein. In some alternatives, said second administration is given one week, two weeks, three weeks, four weeks, five weeks, or six weeks after the first administration of said nucleic acid or composition of any one of the alternatives described herein.

In some alternatives, a method of inhibiting, ameliorating, treating, or preventing hepatitis D virus in a subject in need is provided, wherein the method comprises administering the composition of anyone or more of the alternatives described herein to the subject in need. In some alternatives, the subject has been identified as a person at risk of contracting HDV or a person having HDV.

In some alternatives, a method of increasing preS1 antibodies in a subject in need is provided, wherein the method comprises administering the compositions of anyone of the alternatives to the subject in need. In some alternatives, the method further comprises administering the composition of anyone of the alternatives described herein to the subject in need.

Various routes of administration may be used for the methods described herein. In some alternatives, the immunogenic composition is administered parenterally (e.g., intramuscularly, intraperitoneally, subcutaneously, or intravenously to a mammal subject). In a preferred alternative, the immunogenic compositions are administered intramuscularly, dermally, or subcutaneously. The methods may also include applying electrical stimulation, which can enhance the administration of the immunogenic compositions. As an example, electroporation may be included in the present methods disclosed herein. Electroporation includes applying electrical stimulation to improve the permeability of cells to the administered composition. Examples of electroporation techniques are disclosed in U.S. Pat. Nos. 6,610,044 and 5,273,525, the disclosures of both of these references are hereby incorporated by reference in their entireties.

The concentration of the nucleic acid or protein in the immunogenic composition to be administered can vary from 0.1 ng/ml to 50 mg/ml. In some aspects, the concentration of the immunogenic composition administered (e.g., a suitable dose of nucleic acid or protein for administration) is between 10 ng/ml to 25 mg/ml. In still other aspects, the concentration is between 100 ng/ml to 10 mg/ml. In some aspects, the suitable dose of nucleic acid or protein for administration is greater than or equal to or less than 100 ng/ml, 150 ng/ml, 200 ng/ml, 250 ng/ml, 300 ng/ml, 350 ng/ml, 400 ng/ml, 450 ng/ml, 500 ng/ml, 550 ng/ml, 600 ng/ml, 650 ng/ml, 700 ng/ml, 750 ng/ml, 800 ng/ml, 850 ng/ml, 900 ng/ml, 950 ng/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 11 µg/ml, 12 µg/ml, 13 µg/ml, 14 µg/ml, 15 µg/ml, 16 µg/ml, 17 µg/ml, 18 µg/ml, 19 µg/ml, 20 µg/ml, 21 µg/ml, 22 µg/ml, 23 µg/ml, 24 µg/ml, 25 µg/ml, 26 µg/ml, 27 µg/ml, 28 µg/ml, 29 µg/ml, 30 µg/ml, 31 µg/ml, 32 µg/ml, 33 µg/ml, 34 µg/ml, 35 µg/ml, 36 µg/ml, 37 µg/ml, 38 µg/ml, 39 µg/ml, 40 µg/ml, 41 µg/ml, 42 µg/ml, 43 µg/ml, 44 µg/ml, 45 µg/ml, 46 µg/ml, 47 µg/ml, 48 µg/ml, 49 µg/ml, 50 µg/ml, 55 µg/ml, 60 µg/ml, 65 µg/ml, 70 µg/ml, 75 µg/ml, 80 µg/ml, 85 µg/ml, 90 µg/ml, 95 µg/ml, 100 µg/ml, 150 µg/ml, 200 µg/ml, 250 µg/ml, 300 µg/ml, 350 µg/ml, 400 µg/ml, 450 µg/ml, 500 µg/ml, 550 µg/ml, 600 µg/ml, 650 µg/ml, 700 µg/ml, 750 µg/ml, 800 µg/ml, 850 µg/ml, 900 µg/ml, 950 µg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml, 5.1 mg/ml, 5.2 mg/ml, 5.3 mg/ml, 5.4 mg/ml, 5.5 mg/ml, 5.6 mg/ml, 5.7 mg/ml, 5.8 mg/ml, 5.9 mg/ml, 6.0 mg/ml, 6.1 mg/ml, 6.2 mg/ml, 6.3 mg/ml, 6.4 mg/ml, 6.5 mg/ml, 6.6 mg/ml, 6.7 mg/ml, 6.8 mg/ml, 6.9 mg/ml, 7.0 mg/ml, 7.1 mg/ml, 7.2 mg/ml, 7.3 mg/ml, 7.4 mg/ml, 7.5 mg/ml, 7.6 mg/ml, 7.7 mg/ml, 7.8 mg/ml, 7.9 mg/ml, 8.0 mg/ml, 8.1 mg/ml, 8.2 mg/ml, 8.3 mg/ml, 8.4 mg/ml, 8.5 mg/ml, 8.6 mg/ml, 8.7 mg/ml, 8.8 mg/ml, 8.9 mg/ml, 9.0 mg/ml, 9.1 mg/ml, 9.2 mg/ml, 9.3 mg/ml, 9.4 mg/ml, 9.5 mg/ml, 9.6 mg/ml, 9.7 mg/ml, 9.8 mg/ml, 9.9 mg/ml, 10.0 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, or an amount within a range defined by, and including, any two of these values.

The amount of the chimeric gene or protein administered using the methods described herein can vary from 1 ng to 10 g. In some aspects, the amount of nucleic acid or protein contained administered is less than greater than or equal to 1 ng, 5 ng, 10 ng, 20 ng, 30 ng, 40 ng, 50 ng, 60 ng, 70 ng, 80 ng, 90 ng, 100 ng, 150 ng, 200 ng, 250 ng, 300 ng, 350 ng, 400 ng, 500 ng, 600 ng, 700 ng, 800 ng, 900 ng, 1 µg1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, 20 µg, 21 µg, 22 µg, 23 µg, 24 µg, 25 µg, 26 µg, 27 µg, 28 µg, 29 µg, 30 µg, 31 µg, 32 µg, 33 µg, 34 µg, 35 µg, 36 µg, 37 µg, 38 µg, 39 µg, 40 µg, 41 µg, 42 µg, 43 µg, 44 µg, 45 µg, 46 µg, 47 µg, 48 µg, 49 µg, 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg 150 µg, 155 µg, 160 µg, 165 µg, 170 µg, 175 µg, 180 µg, 185 µg, 190 µg, 195 µg 200 µg, 205 µg, 210 µg, 215 µg, 220 µg, 225 µg, 230 µg, 235 µg, 240 µg, 245 µg 250 µg, 255 µg, 260 µg, 265 µg, 270 µg, 275 µg, 280 µg, 285 µg, 290 µg, 295 µg, 300 µg, 305 µg, 310 µg, 315 µg, 320 µg, 325 µg, 330 µg, 335 µg, 340 µg, 345 µg 350 µg, 355 µg, 360 µg, 365 µg, 370 µg, 375 µg, 380 µg, 385 µg, 390 µg, 395 µg 400 µg, 405 µg, 410 µg, 415 µg, 420 µg, 425 µg, 430 µg, 435 µg, 440 µg, 445 µg 450 µg, 455 µg, 460 µg, 465 µg, 470 µg, 475 µg, 480 µg, 485 µg, 490 µg, 495 µg 500 µg, 505 µg, 510 µg, 515 µg, 520 µg, 525 µg, 530 µg, 535 µg, 540 µg, 545 µg 550 µg, 555 µg, 560 µg, 565 µg, 570 µg, 575 µg, 580 µg, 585 µg, 590 µg, 595 µg 600 µg, 605 µg, 610 µg, 615 µg, 620 µg, 625 µg, 630 µg, 635 µg, 640 µg, 645 µg 650 µg, 655 µg, 660 µg, 665 µg, 670 µg, 675 µg, 680 µg, 685 µg, 690 µg, 695 µg, 700 µg, 705 µg, 710 µg, 715 µg, 720 µg, 725 µg, 730 µg, 735 µg, 740 µg, 745 µg 750 µg, 755 µg, 760 µg, 765 µg, 770 µg, 775 µg, 780 µg, 785 µg, 790 µg, 795 µg, 800 µg, 805 µg, 810 µg, 815 µg, 820 µg, 825 µg, 830 µg, 835 µg, 840 µg, 845 µg 850 µg, 855 µg, 860 µg, 865 µg, 870 µg, 875 µg, 880 µg, 885 µg, 890 µg, 895 µg 900 µg, 905 µg, 910 µg, 915 µg, 920 µg, 925 µg, 930 µg, 935 µg, 940 µg, 945 µg 950 µg, 955 µg, 960 µg, 965 µg, 970 µg, 975 µg, 980 µg, 985 µg, 990 µg, 995 µg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, 10.0 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 2 g, 3 g, 4 g, 5 g, 6 g, 7 g, 8 g, 9 g, 10 g or within a range defined by, and including, any two of these values.

Materials and Methods.

In some alternatives, compositions are employed and methods performed according to the descriptions below. Other materials and methods are contemplated and consistent with the disclosure herein. Accordingly, the disclosure below should be read as enabling but not limiting to the claimed subject matter.

Materials and methods are drawn from Holmstrom et al., (2013) "A Synthetic Codon-Optimized Hepatitis C Polyfunctional CD8+T Cell Responses in Virus Nonstructural 5A DNA Vaccine Primes Wild-Type and NS5A-Transgenic Mice" J Immunol 190:1113-1124, prepublished online Jan. 2, 2013, which is hereby incorporated by reference in its entirety for all content from pages 1113-1124.

The following sections are provided to illustrate various alternatives of the present invention. It is to be understood that the following discussion is not comprehensive or exhaustive of the many types of alternatives, which can be prepared in accordance with the present invention.

Delivery of the Chimeric Genes, Chimeric Protein or Compositions

In some embodiments the methods described herein comprises delivering to an intracellular space, such as a plurality of muscle cells, of said subject the chimeric gene, chimeric protein or compositions of the alternatives herein. In some embodiments this method comprises delivering to an intracellular space such as a plurality of muscle cells or intradermally of said subject an HBcAg chimeric protein or HDag chimeric protein or a chimeric gene encoding HDag chimeric protein or HBCAg chimeric proteins as described herein. In some embodiments this method comprises HBcAg chimeric protein encoded by a chimeric gene, and the polynucleotide is delivered to an intracellular space such as a plurality of muscle cells or intradermally of an animal and translated into an HBcAg chimeric protein therein, thereby delivering said HBcAg chimeric protein to said subject. In some alternatives, this method comprises HDAg chimeric protein encoded by a chimeric gene, and the polynucleotide is delivered to an intracellular space such as a plurality of muscle cells or intradermally of an animal and translated into an HDAg chimeric protein therein, thereby delivering said HDAg chimeric protein to said subject. As the HDAg chimeric proteins described herein further comprise a PreS1 A/B domain, this can be used to inhibit, ameliorate, treat, or prevent HBV and/or HDV infections. In some embodiments the components of said immunogenic composition are delivered in a single injection. In some embodiments the components of said immunogenic composition are delivered in two or more injections. In some embodiments this method comprises providing ribavirin to said subject. In some embodiments this method comprises providing pegylated interferon to said subject. In some embodiments the pegylated interferon is pegylated interferon α2a. In some embodiments a boost vaccination is administered within 28 days of the administration of said chimeric gene.

Preferred Constructs and Evaluation for Immunogenicity

Preferred expression constructs comprising one or more of the genes described herein (see e.g., FIGS. 2 AND 3, and chimeric genes of or encoding proteins as set forth in SEQ ID NOs: 1-74) are tested in animals to confirm that the introduction of self-cleavage sites into the fusion proteins encoded by the administered nucleic acids improve the immunogenicity (e.g., T cell and/or antibody response of the subject) of the immunogenic compositions. The immunogenicity of several constructs are evaluated after introducing the constructs into animals using the IVIN injector with electroporation (see PCT/IB2012/001321, WO 2012/172424 A1), which was published in English on Dec. 20, 2012 and designated the United States, hereby expressly incorporated by reference in its entirety). In a first set of experiments, the following constructs are evaluated:

(1) expression constructs comprising a chimeric encoding a wild-type HDAg (i.e. HDAg gt 1 A/B, HDag gt 2 A/B, HDAg-L or HDAg-S) sequence or both, and at least one pre-S1 sequence;

(2) expression constructs comprising a nucleic acid encoding a HDAg (i.e. HDAg gt 1 A/B, HDag gt 2 A/B, HDAg-L or HDAg-S) sequence or both, and at least one pre-S1 sequence wherein said nucleic acid is codon optimized for expression in humans;

(3) expression constructs comprising a nucleic acid encoding a HDag (i.e. HDAg gt 1 A/B, HDag gt 2 A/B, HDAg-L or HDAg-S) sequence or both, and at least one pre-S1 sequence wherein said nucleic acid is codon optimized for expression in humans and wherein said nucleic acid additionally encodes a self-cleavage sequence, which may also be codon optimized for expression in humans (e.g., P2A, E2A, F2A, or T2A with or without GSG modification).

(4) expression constructs comprising a nucleic acid encoding a HDAg (i.e. HDAg gt 1 A/B, HDag gt 2 A/B, HDAg-L or HDAg-S) sequence or both, wherein said nucleic acid is codon optimized for expression in humans and wherein said nucleic acid, optionally encodes a self-cleavage sequence, which may also be codon optimized for expression in humans (e.g., P2A, E2A, F2A, or T2A with or without GSG modification) within said i.e. HDAg gt 1 A/B, HDag gt 2 A/B, HDAg-L or HDAg-S sequence or both or at the N or C terminus of said i.e. HDAg gt 1 A/B, HDag gt 2 A/B, HDAg-L or HDAg-S sequence or both. These expression construct can also be administered with an expression construct that comprises a nucleic acid sequence encoding an HBcAg, which may also be codon optimized for expression in humans (e.g., a codon optimized stork or heron HBcAg)

(5) expression constructs comprising a nucleic acid encoding a i.e. HDAg gt 1 A/B, HDag gt 2 A/B, HDAg-L or HDAg-S sequence or both, wherein said nucleic acid is codon optimized for expression in humans and, wherein said nucleic acid, optionally encodes a self-cleavage sequence, which may also be codon optimized for expression in humans (e.g., P2A, E2A, F2A, or T2A with or without GSG modification) within said e.g., HDAg gt 1 A/B, HDag gt 2 A/B, HDAg-L or HDAg-S sequence or both or at the N or C terminus of said HDAg-L or said HDAg-S sequence or both. Additionally the expression construct may be administered with another expression construct which comprises a nucleic acid sequence encoding an HBcAg, which may also be codon optimized for expression in humans (e.g., a codon optimized stork or heron HbcAg).

Assays are then performed to determine the relative impact of having self-cleavage polypeptide sequences in the constructs encoding the HBcAg and/or HDAg polypeptides. Methods are performed largely as described in Antony Chen, Gustaf Ahlen, Erwin D. Brenndörfer, Anette Brass, Fredrik Holmstrom, Margaret Chen, Jonas Söderholm, David R. Milich, Lars Frelin and Matti Sallberg (2011) Heterologous T Cells Can Help Restore Function in Dysfunctional Hepatitis C Virus Nonstructural 3/4A-Specific T Cells during Therapeutic Vaccination. J Immunol 186:5107-5118, the contents of which are hereby incorporated by reference in their entirety as to the entire disclosure of pages 5107 through 5118 inclusive. In sum, the immunogenicity of the constructs tested are evaluated after introducing the constructs into animals using the IVIN injector with electroporation (see PCT/IB2012/001321 (WO 2012/172424 A1, published Dec. 20, 2012), hereby expressly incorporated by reference in its entirety. After administration of the various constructs to the animals, with or without additional boosts, the immunogenicity of the constructs are evaluated (e.g., T helper and CTL-specific immune responses, cytokine responses, and/or antibody responses are evaluated and the efficacy of the various constructs tested are compared). It will be determined that the construct comprising the codon-optimized sequence encoding e.g., HDAg gt 1 A/B, HDag gt 2 A/B, HDAg-L or HDAg-S sequence or both will be more immunogenic (e.g., stronger T helper and CTL-specific immune responses, cytokine responses, and/or antibody responses) than the construct encoding wild-type i.e. HDAg gt 1 A/B, HDag gt 2 A/B, HDAg-L or HDAg-S sequence or both. It will also be determined that the construct encoding a fusion of HBcAg (e.g., a nucleic acid encoding an avian HBcAg that has been codon optimized for expression in humans) when administered with a construct comprising i.e. HDAg gt 1 A/B, HDag gt 2 A/B, HDAg-L or HDAg-S sequence or both will be more immunogenic (e.g., stronger T helper and CTL-specific immune responses, cytokine responses, and/or antibody responses).

Administration Regimen

Truncated Therapeutic administration of a preventative therapy for HBV and HDV persons of risk is performed in patients with or without an existing HBV infection. Some patients who receive a booster dose start treatment within 1-2 months after the booster dose. Treatment begins after a mean interval of 15 months (range 1-30) from last administration.

Patients are preferably HDV treatment naïve. Patients receive administrations of an HDV-containing immunogenic composition (e.g., one or more of the contructs depicted in FIGS. 2 and/or 3 in the deltoid muscles (e.g., four monthly administrations with 167 µg, 500 µg, or 1.500 µg codon-optimized HDV immunogen formulations delivered by in vivo electroporation (EP) in some approaches). Enrollment may be done with two weeks interval between patients for safety reasons. It is expected that the administration will significantly improve IFNγ producing responses to HDAg during the first six weeks of therapy. Patients are expected to experience 0.6 log 10–2.4 log 10 reduction in serum HDV RNA and some are expected to be effectively treated (e.g., HDV viral titer is reduced) or cured (e.g., HDV viral titer is reduced to undetectable amounts by a clinical assay).

Patients are administered the therapy and in one minute or less electroporation is performed, for example as described in PCT Publication No. WO 2012/172424 A1, published Dec. 20, 2012, which is hereby incorporated by reference in its entirety not only as it relates to electroporation but for all content disclosed therein.

By some approaches, a volume of 0.5 mL 0.9% sodium chloride containing the DNA is injected in the deltoid muscle (alternating left and right) using an IVIN needle at a depth of 1.2 cm. The injection site is marked prior to injection with a surgical pen and then sterilized by swiping with an alcohol pad Immediately after the injection or along with the injection an IVIN-based electroporator is used at the site of injection and electroporation is administered, as described, for example, in PCT Publication No. WO 2012/172424 A1, published Dec. 20, 2012, incorporated by reference in its entirety here and above. The administration is expected to be safe and well tolerated by recipients.

Patients will demonstrate an increase in relative antibody levels detected by a paired comparison of the samples obtained at week 0 and 2, an effect, which is most pronounced in the two lowest dose groups. Some patients will demonstrate de novo T cell activation. The presence of HBV and/or HDV specific T cell responses before, during and after the therapeutic administration is determined as the number of IFNγ-producing T cells, or spot forming cells (SFCs) by ELISpot, and the level of proliferation as determined by the level of $^3$H-thymidine incorporation. In the ELISpot assay, only the responses to nine peptide pools spanning the whole HDAg region are used for the statistical comparison to avoid repeated use of the same epitope and to overcome HLA-restriction. In some alternatives, the ELISpot assay is performed to assay for the relative antibody levels or the presence of HBV and/or HDV specific T cell responses before, during and after the therapeutic administration. The presence of HDAg-specific T cells can be detected by ELISpot using recombinant HDAG or peptides that can span the complete HDag corresponding to HDV genotypes 1 or 2. In some alternatives, the peptides comprise the amino acid sequences set for in any one of SEQ ID NO's: 75-116.

The number of the IFNγ-producing spots are expected to increase after the two first vaccinations when comparing the number of SFCs at week 0, and the same at weeks 2 and 6. Proliferative T cell responses to HDAg are detected in a substantial number of subjects prior to or after vaccination. de novo ELISpot responses are observed in a fraction of all groups observed. In some patients the activation, or reactivation, of HDV HDAg IFNγ-producing T cells coincides with the suppression of the HDV RNA levels in blood.

A rapid viral response, and complete early viral response and sustained viral response will be seen in a substantial number of patients.

Enzyme-Linked Immunospot (ELISpot) Assay

The Enzyme-linked immunospot (ELISpot) assay is used to determine immune responses. Without being limiting, this can include monitoring cell mediated immunity as this technique is sensitive and can be accurate for the detection of rare antigen specific T cells or B cells. This can be performed after an initial immunization or after a booster after the initial immunization, for example.

In an ELISPOT assay, the surfaces in the wells of microtiter plate are coated with a capture antibody that binds a specific epitope of a protein that is being assayed. During the cell incubation and stimulation step, PBMCs are seeded into the wells of the plate along with the antigen, and form a monolayer on the membrane surface of the well. As the antigen-specific cells are activated, they release the cytokine, which is captured directly on the membrane surface by the immobilized antibody. In the alternatives herein, the ELISpot is used to determine a specific protein using PBMCs that are isolated from the mice. The techniques for the ELISpot are described in Ahlen et al. 2016 (incorporated by reference herein). In some alternatives, Immunization with a Nucleic Acid Immunization can be performed with a nucleic acid, such as RNA or DNA, for example. An approach of reproducibly delivering genetic material in muscle tissue in is by hydrodynamic injection, which is a forced injection of a volume equaling the volume of the tissue to be transfected thereby causing an increased local pressure resulting in an improved uptake of genetic material. In some alternatives, a small injection volume can be delivered to a targeted tissue volume, termed in vivo intracellular injection (IVIN). In some alternatives, a device based on needle(s) with apertures along the needle shafts, where multiple needles can fix the tissue volume to be transfected, is used for immunization with a nucleic acid. In some alternatives, immunization is performed with in vivo electroporation. The technique of using IVIN is described in Ahlen et al. 2016 (incorporated by reference in its entirety). Additional nucleic acid delivery devices with and without electroporation are also contemplated for use in delivering any one or more of the constructs described herein including, without limitation, the Medpulsar®, e.g., as described in U.S. Pat. Nos. 6,748,265, 6,746,441, and 6,763,264; the IGEA device, e.g., as described in U.S. Pat. No. 9,314,621, or the ICHOR device, as described in U.S. Pat. No. 6,278,895, all of which are hereby expressly incorporated by reference in their entireties.

IVIN delivery has been shown to improve the immunogenicity and can be more effective with in vivo electrotransfer.

Experimental Design for Testing the HDV Vaccination
Animals for the Testing of the HDV Vaccination Groups of 5 mice were immunized with 50 µg of DNA using in vivo electroporation as described (Ahlen et al., 2016; incorporated by reference in its entirety). In brief, mice were immunized with 50 µl of saline containing 50 µg of DNA in the tibialis anterior muscle Immediately after immunization, the site was treated with in vivo electroporation as described (Ahlen et al., 2016; incorporated by reference in its entirety). Half of the mice were sacrificed after 2 weeks, whereas the other half was boosted exactly the same way at 4 weeks, and then sacrificed two weeks later. Spleens were harvested and the presence of HDAg-specific T cells was detected by ELISpot as described (Ahlen et al., 2016) using recombinant HDAg or peptides spanning the complete HDAg corresponding to HDV genotypes 1 and 2 (see Table 1).

Results. The ELISpot assays showed that 2 weeks after a single immunization HDV specific T cells were primed using the HDV constructs 1-5, and 7-10 towards gt1 peptides (FIGS. 4A-4T)(Table 1; peptides). At two weeks after a booster dose at 4 week the HDV DNA constructs 1-5 and 8-10 primed the HDV specific T cells. Thus, unexpectedly, most constructs were immunogenic in vivo and could therefore potentially be used in humans. As shown below is the sequences that were used that are shown in FIGS. 4A-T and 5A-5T (Table 1).

TABLE 1

Peptide pool design. A total of twenty-one 20-mer peptides (each having 10 amino acid (aa) overlap) covering the full-length HDV large antigen of genotype 1 and 2 were purchased from Sigma Aldrich (St. Louis, MO). The twenty-one peptides were divided into four peptide pools as outlined in the table.

| Peptide Name | Genotype | Sequence | SEQ ID NO: | Peptide pool |
| --- | --- | --- | --- | --- |
| L-HDAg-gt1-#1 | 1 | MGRSESKRNRDGREGILEQW | 75 | 1 |
| L-HDAg-gt1-#2 | 1 | DGREGILEQWVNGRKKLEDL | 76 | 1 |
| L-HDAg-gt1-#3 | 1 | VNGRKKLEDLEREARKIKKK | 77 | 1 |
| L-HDAg-gt1-#4 | 1 | EREARKIKKKIKKLEDENPW | 78 | 1 |
| L-HDAg-gt1-#5 | 1 | IKKLEDENPWLGNIKGILGK | 79 | 1 |
| L-HDAg-gt1-#6 | 1 | LGNIKGILGKRDKDGEGAPP | 80 | 2 |
| L-HDAg-gt1-#7 | 1 | RDKDGEGAPPAKRARTDQME | 81 | 2 |
| L-HDAg-gt1-#8 | 1 | AKRARTDQMEIDSGPGKRPL | 82 | 2 |
| L-HDAg-gt1-#9 | 1 | IDSGPGKRPLRGGFSDKERQ | 83 | 2 |
| L-HDAg-gt1-#10 | 1 | RGGFSDKERQDHRRRKALEN | 84 | 2 |
| L-HDAg-gt1-#11 | 1 | DHRRRKALENKRKQLAAGGK | 85 | 3 |
| L-HDAg-gt1-#12 | 1 | KRKQLAAGGKHLSKEEEEEL | 86 | 3 |
| L-HDAg-gt1-#13 | 1 | HLSKEEEEELKRLTEEDERR | 87 | 3 |
| L-HDAg-gt1-#14 | 1 | KRLTEEDERRERRTAGPSVG | 88 | 3 |
| L-HDAg-gt1-#15 | 1 | ERRTAGPSVGGVNPLEGGSR | 89 | 3 |
| L-HDAg-gt1-#16 | 1 | GVNPLEGGSRGAPGGGFVPN | 90 | 4 |
| L-HDAg-gt1-#17 | 1 | GAPGGGFVPNMLSVPESPFS | 91 | 4 |
| L-HDAg-gt1-#18 | 1 | MLSVPESPFSRTGEGLDVRG | 92 | 4 |
| L-HDAg-gt1-#19 | 1 | RTGEGLDVRGNQGFPWDILF | 93 | 4 |
| L-HDAg-gt1-#20 | 1 | NQGFPWDILFPADPPFSPQS | 94 | 4 |
| L-HDAg-gt1-#21 | 1 | PADPPFSPQSCRPQ | 95 | 4 |
| L-HDAg-gt2-#1 | 2 | MGQPDSRRPRRGREESLGKW | 96 | 1 |
| L-HDAg-gt2-#2 | 2 | RGREESLGKWIDARRRKEEL | 97 | 1 |
| L-HDAg-gt2-#3 | 2 | IDARRRKEELERDLRKVNKT | 98 | 1 |
| L-HDAg-gt2-#4 | 2 | ERDLRKVNKTIKRLEEDNPW | 99 | 1 |
| L-HDAg-gt2-#5 | 2 | IKRLEEDNPWLGNIRGIIGR | 100 | 1 |
| L-HDAg-gt2-#6 | 2 | LGNIRGIIGRKDKDGEGAPP | 101 | 2 |
| L-HDAg-gt2-#7 | 2 | KDKDGEGAPPAKRARTDQME | 102 | 2 |
| L-HDAg-gt2-#8 | 2 | AKRARTDQMEVDSGPRKRKH | 103 | 2 |
| L-HDAg-gt2-#9 | 2 | VDSGPRKRKHPGGFTEQERR | 104 | 2 |
| L-HDAg-gt2-#10 | 2 | PGGFTEQERRDHRRRKALEN | 105 | 2 |
| L-HDAg-gt2-#11 | 2 | DHRRRKALENKKKQLSSGGK | 106 | 3 |
| L-HDAg-gt2-#12 | 2 | KKKQLSSGGKDLSREEEEEL | 107 | 3 |
| L-HDAg-gt2-#13 | 2 | DLSREEEEELRRLTEEDERR | 108 | 3 |
| L-HDAg-gt2-#14 | 2 | RRLTEEDERRERRVAGPRVG | 109 | 3 |
| L-HDAg-gt2-#15 | 2 | ERRVAGPRVGDVNPLDGGPR | 110 | 3 |

TABLE 1-continued

Peptide pool design. A total of twenty-one 20-mer peptides (each having 10 amino acid (aa) overlap) covering the full-length HDV large antigen of genotype 1 and 2 were purchased from Sigma Aldrich (St. Louis, MO). The twenty-one peptides were divided into four peptide pools as outlined in the table.

| Peptide Name | Genotype | Sequence | SEQ ID NO: | Peptide pool |
|---|---|---|---|---|
| L-HDAg-gt2-#16 | 2 | DVNPLDGGPRGAPGGGFVPS | 111 | 4 |
| L-HDAg-gt2-#17 | 2 | GAPGGGFVPSMQGIPESPFT | 112 | 4 |
| L-HDAg-gt2-#18 | 2 | MQGIPESPFTRRGDGLDTRG | 113 | 4 |
| L-HDAg-gt2-#19 | 2 | RRGDGLDTRGTQEFPWVNPQ | 114 | 4 |
| L-HDAg-gt2-#20 | 2 | TQEFPWVNPQPPPPRLPLLE | 115 | 4 |
| L-HDAg-gt2-#21 | 2 | PPPPRLPLLECTPQ | 116 | 4 |

For FIG. 5, there were ten constructs tested at both two weeks and then 6 weeks.

Additional Alternatives

Delta 1 wild type constructs can be manufactured with a DNA sequence comprising a sequence set forth in SEQ ID NO: 11, which also comprises restriction sites (HindIII/EcoRI). In some alternatives, the delta 1 construct is optimized for expression in humans and comprises a sequence set forth in SEQ ID NO: 13 (Delta 1 optimized with restriction sites (HindIII and EcoRI).

Delta 2 wild type constructs can be manufactured with a DNA sequence comprising a sequence set forth in SEQ ID NO: 16, which also comprises restriction sites (HindIII/EcoRI). In some alternatives, the Delta 2 construct is optimized for expression in humans and comprises a sequence set forth in SEQ ID NO: 17 or 18 (Delta 2 optimized with restriction sites (HindIII and EcoRI). In some alternatives, the Delta 2 protein comprises a sequence set forth in SEQ ID NO: 19.

Delta 3 wild type constructs can be manufactured with a DNA sequence comprising a sequence set forth in SEQ ID NO: 20 or 21 (with restriction sites HindIII and EcoR1). In some alternatives, the Delta 3 construct is optimized for expression in humans and comprises a sequence set forth in SEQ ID NO: 22 or 23 (Delta 3 codon optimized with restriction sites (HindIII and EcoRI). In some alternatives, the Delta 3 protein comprises a sequence set forth in SEQ ID NO: 24.

Delta 4 wild type constructs can be manufactured with a DNA sequence comprising a sequence set forth in SEQ ID NO: 25 or 26 (with restriction sites HindIII and EcoR1). In some alternatives, the Delta 4 construct is codon optimized for expression in humans and comprises a sequence set forth in SEQ ID NO: 27 or 28 (Delta 4 optimized with restriction sites (HindIII and EcoRI). In some alternatives, the Delta 4 protein comprises a sequence set forth in SEQ ID NO: 29.

Delta 5 wild type constructs can be manufactured with a DNA sequence comprising a sequence set forth in SEQ ID NO: 30 or 31 (with restriction sites HindIII and EcoRI). In some alternatives, the Delta 5 construct is codon optimized for expression in humans and comprises a sequence set forth in SEQ ID NO: 32 or 33 (Delta 5 optimized with restriction sites (HindIII and EcoRI). In some alternatives, the Delta 5 protein comprises a sequence set forth in SEQ ID NO: 34.

Delta 6 wild type constructs can be manufactured with a DNA sequence comprising a sequence set forth in SEQ ID NO: 35 or 36 (with restriction sites HindIII and EcoR1). In some alternatives, the Delta 6 construct is codon optimized for expression in humans and comprises a sequence set forth in SEQ ID NO: 37 or 38 (Delta 6 optimized with restriction sites (HindIII and EcoRI). In some alternatives, the Delta 6 protein comprises a sequence set forth in SEQ ID NO: 39.

Delta 7 wild type constructs can be manufactured with a DNA sequence comprising a sequence set forth in SEQ ID NO: 40 or 41 (with restriction sites HindIII and EcoR1). In some alternatives, the Delta 7 construct is codon optimized for expression in humans and comprises a sequence set forth in SEQ ID NO: 42 or 43 (Delta 7 optimized with restriction sites (HindIII and EcoRI). In some alternatives, the Delta 7 protein comprises a sequence set forth in SEQ ID NO: 44.

Delta 8 wild type constructs can be manufactured with a DNA sequence comprising a sequence set forth in SEQ ID NO: 45 or 46 (with restriction sites HindIII and EcoR1). In some alternatives, the Delta 8 construct is codon optimized for expression in humans and comprises a sequence set forth in SEQ ID NO: 47 or 48 (Delta 8 optimized with restriction sites (HindIII and EcoRI). In some alternatives, the Delta 8 protein comprises a sequence set forth in SEQ ID NO: 49.

Delta 9 wild type constructs can be manufactured with a DNA sequence comprising a sequence set forth in SEQ ID NO: 50 or 51 (with restriction sites HindIII and EcoR1). In some alternatives, the Delta 9 construct is codon optimized for expression in humans and comprises a sequence set forth in SEQ ID NO: 52 or 53 (Delta 9 optimized with restriction sites (HindIII and EcoRI). In some alternatives, the Delta 9 protein comprises a sequence set forth in SEQ ID NO: 54.

Delta 10 wild type constructs can be manufactured with a DNA sequence comprising a sequence set forth in SEQ ID NO: 55 or 56 (with restriction sites HindIII and EcoR1). In some alternatives, the Delta 10 construct is codon optimized for expression in humans and comprises a sequence set forth in SEQ ID NO: 57 or 58 (Delta 10 optimized with restriction sites (HindIII and EcoRI). In some alternatives, the Delta 10 protein comprises a sequence set forth in SEQ ID NO: 59.

Core 1 wild type constructs can be manufactured with a DNA sequence comprising a sequence set forth in SEQ ID NO: 60 or 61 (with restriction sites HindIII and EcoR1). In some alternatives, the Core 1 construct is codon optimized for expression in humans and comprises a sequence set forth in SEQ ID NO: 62 or 63 (Core 1 optimized with restriction sites (HindIII and EcoRI). In some alternatives, the Core 1 protein comprises a sequence set forth in SEQ ID NO: 64.

Pre-C-gt-H wild type constructs can be manufactured with a DNA sequence comprising a sequence set forth in SEQ ID NO: 65 or 66 (with restriction sites HindIII and EcoR1). In some alternatives, the Pre-C-gt-H construct is codon optimized for expression in humans and comprises a sequence set forth in SEQ ID NO: 67 or 68 (Pre-C-gt-H optimized with restriction sites (HindIII and EcoRI) for cloning purposes). In some alternatives, the Pre-C-gt-H protein comprises a sequence set forth in SEQ ID NO: 69.

PreC-C-Mut-gt-H wild type constructs can be manufactured with a DNA sequence comprising a sequence set forth in SEQ ID NO: 70 or 71 (with restriction sites HindIII and EcoR1). In some alternatives, the PreC-C-Mut-gt-H construct is codon optimized for expression in humans and comprises a sequence set forth in SEQ ID NO: 72 or 73 (PreC-C-Mut-gt-H optimized with restriction sites (HindIII and EcoRI) for cloning purposes). In some alternatives, the PreC-C-Mut-gt-H protein comprises a sequence set forth in SEQ ID NO: 74.

In some alternatives, a chimeric gene comprising Core sequences is provided. In some alternatives, the chimeric gene further comprises HDAg sequences. In some alternatives, a protein encoded by the chimeric gene is provided. In some alternatives, a composition is provided, wherein the composition comprises the chimeric gene. In some alternatives, a composition is provided, wherein the composition comprises the protein.

In some alternatives, a chimeric gene comprising HDAg sequences is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62.

In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans.

In some alternatives, a chimeric protein comprising at least two HDAg protein domains, encoded by the chimeric gene of anyone of the alternatives described herein is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49.

In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59 In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans.

In some alternatives, a composition comprising anyone or more of the chimeric genes of any one of the alternatives is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In some alternatives, the chimeric gene or composition of any one of the alternatives is for use in generating an immune response in a subject or for DNA vaccination so as to inhibit, ameliorate, treat, or prevent HBV and/or HDV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In some alternatives, the chimeric gene or composition of any one of the alternatives herein, is for use in generating an antibody, T-lymphocyte or CTL-specific response in a subject so as to inhibit, ameliorate, treat, or prevent an HBV and/or HDV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In some alternatives, the chimeric gene or composition of any one of the alternatives described herein is for DNA vaccination or to induce an immunogenic response against HBV and/or HDV in a subject that has been identified as having and HDV and/or HBV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and Thosea asigna virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In some alternatives, a method of eliciting an immune response is provided, wherein the method comprises administering to a subject having HDV infection and/or HBV infection the nucleic acid or composition of any one of the alternatives herein. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by the nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21. In some alternatives, said administering comprises injecting said nucleic acid into a patient, such as using an IVIN needle, Medpulsar®, or ICHOR device with or without electroporation. In some alternatives, the method further comprising administering a second administration of a nucleic acid or composition of any one of the alternatives described herein. In some alternatives, the method further comprises providing an adjuvant. In some alternatives, said adjuvant is a nucleic acid encoding a polypeptide adjuvant, such as IL-12, IL-15, or IL-21. In some alternatives, said adjuvant is IL-12, IL-15, or IL-21. In some alternatives, said second administration is given after said first time. In some alternatives, said adjuvant is given before, during, or after administration of said nucleic acid or composition of any one of claims 1-45. In some alternatives, said second administration is given one week, two weeks, three weeks, four weeks, five weeks, or six weeks after the first administration of said nucleic acid or composition of any one of claims 1-45. In some alternatives, the subject has been identified as a person at risk of contracting HDV or that has HDV. In some alternatives, the method further comprises evaluating the subject for an immunoresponse after administering the compositions of anyone of the alternatives here. In some alternatives, the evaluating is performed by an ELISpot assay. In some alternatives, the ELISpot assay is performed using any one of the peptides comprising a sequence set forth in SEQ ID NO: 75-116.

In some alternatives, a method of increasing preS1 antibodies in a subject in need, the method comprising administering the compositions of anyone of the alternatives described herein to the subject in need. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein, wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein, wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprises a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprises a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21. In some alternatives, the method further comprises evaluating the subject for an immunoresponse after administering the compositions of anyone of the alternatives here. In some alternatives, the evaluating is performed by an ELISpot assay. In some alternatives, the ELISpot assay is performed using any one of the peptides comprising a sequence set forth in SEQ ID NO: 75-116.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific alternatives disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. Aspects of the invention may also include one or more of the following sequences, alone or in combination or a sequence encoding one or more of the peptide sequences provided:

```
Pre S1 A
                                                                SEQ ID NO: 1
GTNLSTSNPLGFFPDHQLDPAFRANSANPDWDFNPNKDTWPDANKVG

PreS1 B
                                                                SEQ ID NO: 2
GQNLSTSNPLGFFPDHQLDPAFRANTANPDWDFNPNKDTWPDANKVG

HDAg genotype 1 A
                                                                SEQ ID NO: 3
AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAG
```

HDAg genotype 1 B nucleic acid                                         SEQ ID NO: 4
AGCCGCAGCGAAAGCAAAAAAAACCGCGGCGGCCGCGAAGAAGTGCTGGAA

CAGTGGGTGAACGGCCGCAAAAAACTGGAAGAACTGGAACGCGAACTGCGC

CGCGCGCGCAAAAAAATTAAAAAACTGGAAGATGATAACCCGTGGCTGGGC

AACGTGAAAGGCATTCTGGGCAAAAAAGATAAAGATGGCGAAGGCGCGCCG

CCGGCGAAACGCGCGCGCACCGATCAGATGGAAATTGATAGCGGCCCGCGCA

AACGCCCGCTGCGCGGCGGCTTTACCGATCGCGAACGCCAGGATCATCGCCG

CCGCAAAGCGCTGAAAAACAAAAAAAAACAGCTGAGCGCGGGCGGCAAAAG

CCTGAGCAAAGAAGAAGAAGAAGAACTGAAACGCCTGACCCGCGAAGATGA

AGAACGCAAAAAAGAAGAACATGGCCCGAGCCGCCTGGGCGTGAACCCGAG

CGAAGGCGGCCCGCGCGGCGCGCCGGGCGGCGGCTTTGTGCCGAGCATGCAG

GGCATTCCGGAAAGCCGCTTTACCCGCACCGGCGAAGGCCTGGATGTGCGCG

GCAGCCGCGGCTTTCCGCAGGATATTCTGTTTCCGAGCGATCCGCCGTTTAGC

CCGCAGAGCTGCCGCCCGCAG preS1 derived sequence is preS1                                        SEQ ID NO: 5
GGCACCAACCTGAGCACCAGCAACCCGCTGGGCTTTTTTCCGGATCATCAGCT

GGATCCGGCGTTTCGCGCGAACAGCGCGAACCCGGATTGGGATTTTAACCCG

AACAAAGATACCTGGCCGGATGCGAACAAAGTGGGC preS1 B                                                                SEQ ID NO: 6
GGCCAGAACCTGAGCACCAGCAACCCGCTGGGCTTTTTTCCGGATCATCAGCT

GGATCCGGCGTTTCGCGCGAACACCGCGAACCCGGATTGGGATTTTAACCCG

AACAAAGATACCTGGCCGGATGCGAACAAAGTGGGC

T2A nucleic acid                                                       SEQ ID NO:
GGAAGCGGAGCTACTAACTTCAGCCTGCTGAAGCAGGCTGGAGACGTGGAGG

AGAACCCTGGACCT

HDAg gentotype 2 A (wt)                                                SEQ ID NO: 8
ATGAGCCAGAGCGAAACCCGCCGCGGCCGCCGCGGCACCCGCGAAGAAACC

CTGGAAAAATGGATTACCGCGCGCAAAAAAGCGGAAGAACTGGAAAAAGAT

CTGCGCAAAACCCGCAAAACCATTAAAAAACTGGAAGAAGAAAACCCGTGG

CTGGGCAACATTGTGGGCATTATTCGCAAAGGCAAAGATGGCGAAGGCGCGC

CGCCGGCGAAACGCCCGCGCACCGATCAGATGGAAGTGGATAGCGGCCCGG

GCAAACGCCCGCATAAAAGCGGCTTTACCGATAAAGAACGCGAAGATCATCG

CCGCCGCAAAGCGCTGGAAAACAAAAAAAAACAGCTGAGCGCGGGCGGCAA

AATTCTGAGCAAAGAAGAAGAAGAAGAACTGCGCCGCCTGACCGATGAAGA

TGAAGAACGCAAACGCCGCGTGGCGGGCCCGCGCGTGGGCGATGTGAACCC

GAGCCGCGGCGGCCCGCGCGGCGCGCCGGGCGGCGGCTTTGTGCCGCAGATG

GCGGGCGTGCCGGAAAGCCCGTTTAGCCGCACCGGCGAAGGCCTGGATATTC

GCGGCACCCAGGGCTTTCCGTGGGTGAGCCCGAGCCCGCCGCAGCAGCGCCT

GCCGCTGCTGGAATGCACCCCGCAG

-continued

HDAg gentotype 2 B (wt)

SEQ ID NO: 9

AGCCAGAGCGAAAGCAAAAAAAACCGCCGCGGCGGCCGCGAAGATATTCTG

GAAAAATGGATTACCACCCGCCGCAAAGCGGAAGAACTGGAAAAAGATCTG

CGCAAAGCGCGCAAAACCATTAAAAAACTGGAAGATGAAAACCCGTGGCTG

GGCAACATTATTGGCATTATTCGCAAAGGCAAAGATGGCGAAGGCGCGCCGC

CGGCGAAACGCCCGCGCACCGATCAGATGGAAATTGATAGCGGCACCGGCA

AACGCCCGCATAAAAGCGGCTTTACCGATAAAGAACGCGAAGATCATCGCCG

CCGCAAAGCGCTGGAAAACAAAAAAAAACAGCTGAGCAGCGGCGGCAAAAA

CCTGAGCCGCGAAGAAGAAGAAGAACTGGGCCGCCTGACCGTGGAAGATGA

AGAACGCCGCCGCCGCGTGGCGGGCCCGCGCACCGGCGATGTGAACCTGAGC

GGCGGCGGCCCGCGCGGCGCGCCGGGCGGCGGCTTTGTGCCGCGCATGGAAG

GCGTGCCGGAAAGCCCGTTTACCCGCACCGGCGAAGGCCTGGATATTCGCGG

CAACCAGGGCTTTCCGTGGGTGCGCCCGAGCCCGCCGCAGCAGCGCCTGCCG

CTGCTGGAATGCACCCCGCAG delta 1 wt

SEQ ID NO: 10

AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGAGCCGCAGCGAAAGCAAAAAAAACCGCGGC

GGCCGCGAAGAAGTGCTGGAACAGTGGGTGAACGGCCGCAAAAAACTGGAA

GAACTGGAACGCGAACTGCGCCGCGCGCGCAAAAAAATTAAAAAACTGGAA

GATGATAACCCGTGGCTGGGCAACGTGAAAGGCATTCTGGGCAAAAAAGATA

AAGATGGCGAAGGCGCGCCGCCGGCGAAACGCGCGCGCACCGATCAGATGG

AAATTGATAGCGGCCCGCGCAAACGCCCGCTGCGCGGCGGCTTTACCGATCG

CGAACGCCAGGATCATCGCCGCCGCAAAGCGCTGAAAAACAAAAAAAAACA

GCTGAGCGCGGGCGGCAAAAGCCTGAGCAAAGAAGAAGAAGAAGAACTGAA

ACGCCTGACCCGCGAAGATGAAGAACGCAAAAAAGAAGAACATGGCCCGAG

CCGCCTGGGCGTGAACCCGAGCGAAGGCGGCCCGCGCGGCGCGCCGGGCGG

CGGCTTTGTGCCGAGCATGCAGGGCATTCCGGAAAGCCGCTTTACCCGCACC

GGCGAAGGCCTGGATGTGCGCGGCAGCCGCGGCTTTCCGCAGGATATTCTGT

TTCCGAGCGATCCGCCGTTTAGCCCGCAGAGCTGCCGCCCGCAGGGCACCAA

CCTGAGCACCAGCAACCCGCTGGGCTTTTTTCCGGATCATCAGCTGGATCCGG

-continued

```
CGTTTCGCGCGAACAGCGCGAACCCGGATTGGGATTTTAACCCGAACAAAGA
TACCTGGCCGGATGCGAACAAAGTGGGCGGCCAGAACCTGAGCACCAGCAA
CCCGCTGGGCTTTTTTCCGGATCATCAGCTGGATCCGGCGTTTCGCGCGAACA
CCGCGAACCCGGATTGGGATTTTAACCCGAACAAAGATACCTGGCCGGATGC
GAACAAAGTGGGCGGAAGCGGAGCTACTAACTTCAGCCTGCTGAAGCAGGCT
GGAGACGTGGAGGAGAACCCTGGACCTATGAGCCAGAGCGAAACCCGCCGC
GGCCGCCGCGGCACCCGCGAAGAAACCCTGGAAAAATGGATTACCGCGCGC
AAAAAAGCGGAAGAACTGGAAAAAGATCTGCGCAAAACCCGCAAAACCATT
AAAAAACTGGAAGAAGAAAACCCGTGGCTGGGCAACATTGTGGGCATTATTC
GCAAAGGCAAAGATGGCGAAGGCGCGCCGCCGGCGAAACGCCCGCGCACCG
ATCAGATGGAAGTGGATAGCGGCCCGGGCAAACGCCCGCATAAAAGCGGCTT
TACCGATAAAGAACGCGAAGATCATCGCCGCCGCAAAGCGCTGGAAAACAA
AAAAAAACAGCTGAGCGCGGGCGGCAAAATTCTGAGCAAAGAAGAAGAAGA
AGAACTGCGCCGCCTGACCGATGAAGATGAAGAACGCAAACGCCGCGTGGC
GGGCCCGCGCGTGGGCGATGTGAACCCGAGCCGCGGCGGCCCGCGCGGCGC
GCCGGGCGGCGGCTTTGTGCCGCAGATGGCGGGCGTGCCGGAAAGCCCGTTT
AGCCGCACCGGCGAAGGCCTGGATATTCGCGGCACCCAGGGCTTTCCGTGGG
TGAGCCCGAGCCCGCCGCAGCAGCGCCTGCCGCTGCTGGAATGCACCCCGCA
GAGCCAGAGCGAAAGCAAAAAAAACCGCCGCGGCGGCCGCGAAGATATTCT
GGAAAAATGGATTACCACCCGCCGCAAAGCGGAAGAACTGGAAAAAGATCT
GCGCAAAGCGCGCAAAACCATTAAAAAACTGGAAGATGAAAACCCGTGGCT
GGGCAACATTATTGGCATTATTCGCAAAGGCAAAGATGGCGAAGGCGCGCCG
CCGGCGAAACGCCCGCGCACCGATCAGATGGAAATTGATAGCGGCACCGGCA
AACGCCCGCATAAAAGCGGCTTTACCGATAAAGAACGCGAAGATCATCGCCG
CCGCAAAGCGCTGGAAAACAAAAAAAAACAGCTGAGCAGCGGCGGCAAAAA
CCTGAGCCGCGAAGAAGAAGAAGAACTGGGCCGCCTGACCGTGGAAGATGA
AGAACGCCGCCGCCGCGTGGCGGGCCCGCGCACCGGCGATGTGAACCTGAGC
GGCGGCGGCCCGCGCGGCGCGCCGGGCGGCGGCTTTGTGCCGCGCATGGAAG
GCGTGCCGGAAAGCCCGTTTACCCGCACCGGCGAAGGCCTGGATATTCGCGG
CAACCAGGGCTTTCCGTGGGTGCGCCCGAGCCCGCCGCAGCAGCGCCTGCCG
CTGCTGGAATGCACCCCGCAGGGCACCAACCTGAGCACCAGCAACCCGCTGG
GCTTTTTTCCGGATCATCAGCTGGATCCGGCGTTTCGCGCGAACAGCGCGAAC
CCGGATTGGGATTTTAACCCGAACAAAGATACCTGGCCGGATGCGAACAAAG
TGGGCGGCCAGAACCTGAGCACCAGCAACCCGCTGGGCTTTTTTCCGGATCAT
CAGCTGGATCCGGCGTTTCGCGCGAACACCGCGAACCCGGATTGGGATTTTA
ACCCGAACAAAGATACCTGGCCGGATGCGAACAAAGTGGGC
``` delta1 wt with restriction sites (HindIII/EcoRI)

SEQ ID NO: 11

```
A↓AGCTTGCACCATGGCCAGCCGCAGCGAAAGCAAAAAAAACCGCGGCGGC
CGCGAAGAAATTCTGGAACAGTGGGTGGGCGCGCGCAAAAAACTGGAAGAA
CTGGAACGCGATCTGCGCAAAATTAAAAAAAAAATTAAAAAACTGGAAGAA
```

-continued

```
GAAAACCCGTGGCTGGGCAACATTAAAGGCATTCTGGGCAAAAAGATCGCG
AAGGCGAAGGCGCGCCGCCGGCGAAACGCGCGCGCGGATCAGATGGAAG
TGGATAGCGGCCCGCGCAAACGCCCGTTTCGCGGCGAATTTACCGATAAAGA
ACGCCGCGATCATCGCCGCCGCAAAGCGCTGGAAAACAAACGCAAACAGCT
GAGCAGCGGCGGCAAAAGCCTGAGCAAAGAAGAAGAAGAAGAACTGCGCAA
ACTGACCGAAGAAGATGAACGCCGCGAACGCCGCGTGGCGGGCCCGCGCGT
GGGCGGCGTGAACCCGCTGGAAGGCGGCACCCGCGGCGCGCCGGGCGGCGG
CTTTGTGCCGAGCATGCAGGGCGTGCCGGAAAGCCCGTTTGCGCGCACCGGC
GAAGGCCTGGATGTGCGCGGCAACCAGGGCTTTCCGTGGGATATTCTGTTTCC
GGCGGATCCGCCGTTTAGCCCGCAGAGCTGCCGCCCGCAGAGCCGCAGCGAA
AGCAAAAAAAACCGCGGCGGCCGCGAAGAAGTGCTGGAACAGTGGGTGAAC
GGCCGCAAAAACTGGAAGAACTGGAACGCGAACTGCGCCGCGCGCGCAAA
AAAATTAAAAAACTGGAAGATGATAACCCGTGGCTGGGCAACGTGAAAGGC
ATTCTGGGCAAAAAGATAAAGATGGCGAAGGCGCGCCGCCGGCGAAACGC
GCGCGCACCGATCAGATGGAAATTGATAGCGGCCCGCGCAAACGCCCGCTGC
GCGGCGGCTTTACCGATCGCGAACGCCAGGATCATCGCCGCCGCAAAGCGCT
GAAAACAAAAAAAAACAGCTGAGCGCGGGCGGCAAAAGCCTGAGCAAAGA
AGAAGAAGAAGAACTGAAACGCCTGACCCGCGAAGATGAAGAACGCAAAAA
AGAAGAACATGGCCCGAGCCGCCTGGGCGTGAACCCGAGCGAAGGCGGCCC
GCGCGGCGCGCCGGGCGGCGGCTTTGTGCCGAGCATGCAGGGCATTCCGGAA
AGCCGCTTTACCCGCACCGGCGAAGGCCTGGATGTGCGCGGCAGCCGCGGCT
TTCCGCAGGATATTCTGTTTCCGAGCGATCCGCCGTTTAGCCCGCAGAGCTGC
CGCCCGCAGGGCACCAACCTGAGCACCAGCAACCCGCTGGGCTTTTTTCCGG
ATCATCAGCTGGATCCGGCGTTTCGCGCGAACAGCGCGAACCCGGATTGGGA
TTTTAACCCGAACAAAGATACCTGGCCGGATGCGAACAAAGTGGGCGGCCAG
AACCTGAGCACCAGCAACCCGCTGGGCTTTTTTCCGGATCATCAGCTGGATCC
GGCGTTTCGCGCGAACACCGCGAACCCGGATTGGGATTTTAACCCGAACAAA
GATACCTGGCCGGATGCGAACAAAGTGGGCGGAAGCGGAGCTACTAACTTCA
GCCTGCTGAAGCAGGCTGGAGACGTGGAGGAGAACCCTGGACCTATGAGCC
AGAGCGAAACCCGCCGCGGCCGCCGCGGCACCCGCGAAGAAACCCTGGAAA
AATGGATTACCGCGCGCAAAAAAGCGGAAGAACTGGAAAAAGATCTGCGCA
AAACCCGCAAAACCATTAAAAAACTGGAAGAAGAAAACCCGTGGCTGGGCA
ACATTGTGGGCATTATTCGCAAAGGCAAAGATGGCGAAGGCGCGCCGCCGGC
GAAACGCCCGCGCACCGATCAGATGGAAGTGGATAGCGGCCCGGGCAAACG
CCCGCATAAAAGCGGCTTTACCGATAAAGAACGCGAAGATCATCGCCGCCGC
AAAGCGCTGGAAAACAAAAAAAAACAGCTGAGCGCGGGCGGCAAAATTCTG
AGCAAAGAAGAAGAAGAAGAACTGCGCCGCCTGACCGATGAAGATGAAGAA
CGCAAACGCCGCGTGGCGGGCCCGCGCGTGGGCGATGTGAACCCGAGCCGCG
GCGGCCCGCGCGGCGCGCCGGGCGGCGGCTTTGTGCCGCAGATGGCGGGCGT
GCCGGAAAGCCCGTTTAGCCGCACCGGCGAAGGCCTGGATATTCGCGGCACC
CAGGGCTTTCCGTGGGTGAGCCCGAGCCCGCCGCAGCAGCGCCTGCCGCTGC
```

-continued

```
TGGAATGCACCCCGCAGAGCCAGAGCGAAAGCAAAAAAAACCGCCGCGGCG

GCCGCGAAGATATTCTGGAAAAATGGATTACCACCCGCCGCAAAGCGGAAGA

ACTGGAAAAAGATCTGCGCAAAGCGCGCAAAACCATTAAAAAACTGGAAGA

TGAAAACCCGTGGCTGGGCAACATTATTGGCATTATTCGCAAAGGCAAAGAT

GGCGAAGGCGCGCCGCCGGCGAAACGCCCGCGCACCGATCAGATGGAAATT

GATAGCGGCACCGGCAAACGCCCGCATAAAAGCGGCTTTACCGATAAAGAAC

GCGAAGATCATCGCCGCCGCAAAGCGCTGGAAAACAAAAAAAAACAGCTGA

GCAGCGGCGGCAAAAACCTGAGCCGCGAAGAAGAAGAAGAACTGGGCCGCC

TGACCGTGGAAGATGAAGAACGCCGCCGCCGCGTGGCGGGCCCGCGCACCG

GCGATGTGAACCTGAGCGGCGGCGGCCCGCGCGGCGCGCCGGGCGGCGGCTT

TGTGCCGCGCATGGAAGGCGTGCCGGAAAGCCCGTTTACCCGCACCGGCGAA

GGCCTGGATATTCGCGGCAACCAGGGCTTTCCGTGGGTGCGCCCGAGCCCGC

CGCAGCAGCGCCTGCCGCTGCTGGAATGCACCCCGCAGGGCACCAACCTGAG

CACCAGCAACCCGCTGGGCTTTTTTCCGGATCATCAGCTGGATCCGGCGTTTC

GCGCGAACAGCGCGAACCCGGATTGGGATTTTAACCCGAACAAAGATACCTG

GCCGGATGCGAACAAAGTGGGCGGCCAGAACCTGAGCACCAGCAACCCCGCT

GGGCTTTTTTCCGGATCATCAGCTGGATCCGGCGTTTCGCGCGAACACCGCGA

ACCCGGATTGGGATTTTAACCCGAACAAAGATACCTGGCCGGATGCGAACAA

AGTGGGCTGATGAG↓AATTCCGT codon optimized delta 1
                                                    SEQ ID NO: 12
GCCAGCAGAAGTGAATCAAAAAGAATCGGGGAGGGCGGAAGAAATCCTGGAACAGTGG

GTCGGAGCACGGAAGAAACTGGAAGAACTGGAGAGGGACCTGCGCAAGATCAAGAAGAAG

ATCAAGAAGCTGGAGGAGGAGAACCCCTGGCTGGGCAATATCAAGGGCATCCTGGGCAAG

AAGGATCGGGAGGGAGAGGGAGCACCACCTGCAAAGAGGGCCAGAGCCGACCAGATGGAG

GTGGATAGCGGACCAAGGAAGCGCCCTTTCAGAGGAGAGTTTACCGACAAGGAGCGGAGA

GATCACAGGCGCCGGAAGGCCCTGGAGAACAAGAGGAAGCAGCTGAGCTCCGGCGGCAAG

TCCCTGTCTAAGGAGGAGGAGGAGGAGCTGCGCAAGCTGACAGAGGAGGACGAGAGAAGG

GAGAGGAGGGTGGCAGGACCTAGGGTGGGAGGCGTGAACCCACTGGAGGGAGGAACCAGA

GGAGCACCTGGAGGAGGATTCGTGCCATCCATGCAGGGAGTGCCCGAGTCTCCTTTTGCC

CGGACAGGCGAGGGCCTGGATGTGAGAGGCAATCAGGGCTTCCCCTGGGACATCCTGTTT

CCTGCCGATCCACCCTTCTCTCCTCAGAGCTGCCGGCCACAGAGCAGATCCGAGTCTAAG

AAGAACAGGGGAGGAAGAGAGGAGGTGCTGGAGCAGTGGGTGAATGGCCGGAAGAAGCTG

GAGGAGCTGGAGCGGGAGCTGAGAAGGGCCAGAAAGAAGATCAAGAAGCTGGAAGACGAT

AATCCTTGGCTGGGCAATGTGAAAGGCATCCTGGGCAAGAAGGACAAGGATGGAGAGGGA

GCACCTCCAGCAAAGAGGGCAAGAACCGACCAGATGGAGATCGATTCTGGACCAAGGAAG

CGCCCCCTGAGAGGAGGCTTCACAGACCGGGAGAGACAGGATCACCGCCGGAGAAAGGCC

CTGAAGAACAAGAAGAAGCAGCTGTCCGCCGGAGGCAAGAGCCTGTCCAAAGAAGAGGAA

GAGGAGCTGAAGAGGCTGACCCGCGAGGACGAGGAGAGGAAGAAGGAGGAGCACGGACCA

AGCAGGCTGGGAGTGAATCCTTCCGAGGGAGGACCTAGGGGAGCACCAGGAGGAGGCTTC

GTGCCATCTATGCAGGGCATCCCCGAGAGCCGGTTTACCAGAACAGGAGAGGGCCTGGAC
```

-continued

```
GTGAGGGGCTCCCGCGGCTTTCCTCAGGACATCCTGTTCCCATCTGATCCCCCTTTTTCC

CCCCAGTCTTGTAGGCCTCAGGGCACCAACCTGTCTACAAGCAATCCACTGGGCTTCTTT

CCCGACCACCAGCTGGATCCTGCCTTCCGCGCCAACAGCGCCAATCCCGACTGGGACTTC

AACCCAAATAAGGACACCTGGCCAGATGCCAACAAGGTCGGCGGCCAGAACCTGTCCACA

TCTAATCCTCTGGGCTTCTTTCCAGACCACCAGCTGGATCCAGCCTTCCGGGCCAACACA

GCTAACCCTGACTGGGACTTCAACCCCAATAAGGATACTTGGCCCGACGCCAACAAGGTC

GGCGGAAGCGGAGCTACTAACTTCAGCCTGCTGAAGCAGGCTGGAGACGTGGAGGAGAAC

CCTGGACCTATGAGCCAGTCCGAGACAAGGAGGGGCCGGAGAGGAACCAGGGAGGAGACA

CTGGAGAAGTGGATCACAGCCCGCAAGAAGGCCGAGGAGCTGGAGAAGGACCTGCGGAAG

ACCAGAAAGACAATCAAGAAGCTGGAAGAAGAGAACCCATGGCTGGGCAATATCGTGGGC

ATCATCAGAAAGGGCAAGGACGGCGAGGGAGCACCACCAGCAAAGAGGCCCAGGACTGAT

CAGATGGAAGTCGATAGCGGACCAGGCAAGCGGCCTCACAAGTCCGGCTTCACAGACAAG

GAGAGAGAGGACCATAGGCGCCGGAAGGCCCTGGAAAACAAGAAGAAGCAATTATCCGCC

GGCGGCAAGATCCTGTCCAAAGAGGAAGAAGAGGAGCTGAGAAGGCTGACCGACGAGGAT

GAGGAGAGGAAAAGAAGGGTGGCAGGACCAAGGGTGGGCGACGTGAATCCCAGCAGGGGA

GGACCAAGAGGCGCCCCTGGCGGCGGCTTCGTGCCACAGATGGCAGGAGTGCCAGAGAGC

CCCTTTTCCAGGACAGGAGAGGGCCTGGATATCAGAGGCACCCAGGGCTTTCCTTGGGTG

TCTCCAAGCCCTCCACAGCAGCGGCTGCCACTGCTGGAGTGCACCCCTCAGTCCCAGTCT

GAGAGCAAGAAGAACAGAAGGGGCGGCAGAGAGGACATCCTGGAGAAGTGGATCACCACA

CGCAGAAAAGCTGAAGAACTGGAAAAGGACCTGAGGAAGGCCCGCAAAACAATCAAGAAG

CTGGAGGATGAAAATCCATGGCTGGGAAACATCATCGGCATCATCAGGAAGGGCAAGGAC

GGGGAAGGCGCACCACCTGCAAAGCGGCCTAGAACAGATCAGATGGAAATCGATTCTGGC

ACCGGCAAGAGGCCACACAAGAGCGGCTTCACCGACAAGGAGCGCGAGGATCACAGAAGG

C

GCAAGGCCCTGGAGAACAAGAAGAAGCAATTAAGCAGCGGCGGCAAGAATCTGTCCAGAG

AAGAAGAGGAGGAGCTGGGCCGCCTGACCGTGGAGGACGAGGAGCGGAGAAGGCGCGTGG

CAGGACCACGCACAGGCGATGTGAACCTGTCCGGAGGAGGACCAAGGGGAGCACCTGGAG

GCGGCTTCGTGCCTAGAATGGAGGGAGTGCCTGAGTCCCCCTTCACCCGCACCGGAGAGG

GCCTGGACATCAGAGGCAATCAGGGATTCCCATGGGTGAGGCCCAGCCCACCACAGCAGC

GCCTGCCACTGCTGGAGTGTACCCCCCAGGGCACAAACCTGTCCACCTCTAATCCCCTGG

GCTTCTTTCCTGATCATCAGCTGGACCCAGCCTTCAGGGCCAACTCCGCCAATCCAGATT

GGGACTTCAACCCGAATAAGGATACTTGGCCAGATGCAAACAAGGTCGGAGGACAGAACC

TGAGCACATCCAACCCTCTGGGCTTCTTTCCTGACCATCAGCTGGATCCCGCCTTTCGCG

CCAATACCGCCAACCCTGATTGGGACTTCAACCCTAATAAGGATACTTGGCCTGATGCTA

ATAAGGTCGGG

SEQ ID NO: 13: Delta 1 optimized with restriction sites (HindIII
and EcoRI)
A↓AGCTT*GCACC***ATG**GCCAGCAGAAGTGAATCAAAAAAGAATCGGGGAGGG

CGGGAAGAAATCCTGGAACAGTGGGTCGGAGCACGGAAGAAACTGGAAGAA

CTGGAGAGGGACCTGCGCAAGATCAAGAAGAAGATCAAGAAGCTGGAGGAG

GAGAACCCCTGGCTGGGCAATATCAAGGGCATCCTGGGCAAGAAGGATCGGG
```

-continued

```
AGGGAGAGGGAGCACCACCTGCAAAGAGGGCCAGAGCCGACCAGATGGAGG
TGGATAGCGGACCAAGGAAGCGCCCTTTCAGAGGAGAGTTTACCGACAAGGA
GCGGAGAGATCACAGGCGCCGGAAGGCCCTGGAGAACAAGAGGAAGCAGCT
GAGCTCCGGCGGCAAGTCCCTGTCTAAGGAGGAGGAGGAGGAGCTGCGCAA
GCTGACAGAGGAGGACGAGAGAAGGGAGAGGAGGGTGGCAGGACCTAGGGT
GGGAGGCGTGAACCCACTGGAGGGAGGAACCAGAGGAGCACCTGGAGGAGG
ATTCGTGCCATCCATGCAGGGAGTGCCCGAGTCTCCTTTTGCCCGGACAGGCG
AGGGCCTGGATGTGAGAGGCAATCAGGGCTTCCCCTGGGACATCCTGTTTCCT
GCCGATCCACCCTTCTCTCCTCAGAGCTGCCGGCCACAGAGCAGATCCGAGTC
TAAGAAGAACAGGGGAGGAAGAGAGGAGGTGCTGGAGCAGTGGGTGAATGG
CCGGAAGAAGCTGGAGGAGCTGGAGCGGGAGCTGAGAAGGGCCAGAAAGAA
GATCAAGAAGCTGGAAGACGATAATCCTTGGCTGGGCAATGTGAAAGGCATC
CTGGGCAAGAAGGACAAGGATGGAGAGGGAGCACCTCCAGCAAAGAGGGCA
AGAACCGACCAGATGGAGATCGATTCTGGACCAAGGAAGCGCCCCCTGAGAG
GAGGCTTCACAGACCGGGAGAGACAGGATCACCGCCGGAGAAAGGCCCTGA
AGAACAAGAAGAAGCAGCTGTCCGCCGGAGGCAAGAGCCTGTCCAAAGAAG
AGGAAGAGGAGCTGAAGAGGCTGACCCGCGAGGACGAGGAGAGGAAGAAG
GAGGAGCACGGACCAAGCAGGCTGGGAGTGAATCCTTCCGAGGGAGGACCT
AGGGGAGCACCAGGAGGAGGCTTCGTGCCATCTATGCAGGGCATCCCCGAGA
GCCGGTTTACCAGAACAGGAGAGGGCCTGGACGTGAGGGGCTCCCGCGGCTT
TCCTCAGGACATCCTGTTCCCATCTGATCCCCCTTTTTCCCCCCAGTCTTGTAG
GCCTCAGGGCACCAACCTGTCTACAAGCAATCCACTGGGCTTCTTTCCCGACC
ACCAGCTGGATCCTGCCTTCCGCGCCAACAGCGCCAATCCCGACTGGGACTTC
AACCCAAATAAGGACACCTGGCCAGATGCCAACAAGGTCGGCGGCCAGAAC
CTGTCCACATCTAATCCTCTGGGCTTCTTTCCAGACCACCAGCTGGATCCAGC
CTTCCGGGCCAACACAGCTAACCCTGACTGGGACTTCAACCCCAATAAGGAT
ACTTGGCCCGACGCCAACAAGGTCGGCGGAAGCGGAGCTACTAACTTCAGCC
TGCTGAAGCAGGCTGGAGACGTGGAGGAGAACCCTGGACCTATGAGCCAGTC
CGAGACAAGGAGGGGCCGGAGAGGAACCAGGGAGGAGACACTGGAGAAGT
GGATCACAGCCCGCAAGAAGGCCGAGGAGCTGGAGAAGGACCTGCGGAAGA
CCAGAAAGACAATCAAGAAGCTGGAAGAAGAGAACCCATGGCTGGGCAATA
TCGTGGGCATCATCAGAAAGGGCAAGGACGGCGAGGGAGCACCACCAGCAA
AGAGGCCCAGGACTGATCAGATGGAAGTCGATAGCGGACCAGGCAAGCGGC
CTCACAAGTCCGGCTTCACAGACAAGGAGAGAGAGGACCATAGGCGCCGGA
AGGCCCTGGAAAACAAGAAGAAGCAATTATCCGCCGGCGGCAAGATCCTGTC
CAAAGAGGAAGAAGAGGAGCTGAGAAGGCTGACCGACGAGGATGAGGAGA
GGAAAAGAAGGGTGGCAGGACCAAGGGTGGGCGACGTGAATCCCAGCAGGG
GAGGACCAAGAGGCGCCCCTGGCGGCGGCTTCGTGCCACAGATGGCAGGAGT
GCCAGAGAGCCCCTTTTCCAGGACAGGAGAGGGCCTGGATATCAGAGGCACC
CAGGGCTTTCCTTGGGTGTCTCCAAGCCCTCCACAGCAGCGGCTGCCACTGCT
GGAGTGCACCCCTCAGTCCCAGTCTGAGAGCAAGAAGAACAGAAGGGGCGG
```

```
CAGAGAGGACATCCTGGAGAAGTGGATCACCACACGCAGAAAAGCTGAAGA

ACTGGAAAAGGACCTGAGGAAGGCCCGCAAAACAATCAAGAAGCTGGAGGA

TGAAAATCCATGGCTGGGAAACATCATCGGCATCATCAGGAAGGGCAAGGAC

GGGGAAGGCGCACCACCTGCAAAGCGGCCTAGAACAGATCAGATGGAAATC

GATTCTGGCACCGGCAAGAGGCCACACAAGAGCGGCTTCACCGACAAGGAG

CGCGAGGATCACAGAAGGC

GCAAGGCCCTGGAGAACAAGAAGAAGCAATTAAGCAGCGGCGGCAAGAATC

TGTCCAGAGAAGAAGAGGAGGAGCTGGGCCGCCTGACCGTGGAGGACGAGG

AGCGGAGAAGGCGCGTGGCAGGACCACGCACAGGCGATGTGAACCTGTCCG

GAGGAGGACCAAGGGGAGCACCTGGAGGCGGCTTCGTGCCTAGAATGGAGG

GAGTGCCTGAGTCCCCCTTCACCCGCACCGGAGAGGGCCTGGACATCAGAGG

CAATCAGGGATTCCCATGGGTGAGGCCCAGCCCACCACAGCAGCGCCTGCCA

CTGCTGGAGTGTACCCCCCAGGGCACAAACCTGTCCACCTCTAATCCCCTGGG

CTTCTTTCCTGATCATCAGCTGGACCCAGCCTTCAGGGCCAACTCCGCCAATC

CAGATTGGGACTTCAACCCCGAATAAGGATACTTGGCCAGATGCAAACAAGGT

CGGAGGACAGAACCTGAGCACATCCAACCCTCTGGGCTTCTTTCCTGACCATC

AGCTGGATCCCGCCTTTCGCGCCAATACCGCCAACCCTGATTGGGACTTCAAC

CCTAATAAGGATACTTGGCCTGATGCTAATAAGGTCGGGTGATGAG↓AATTC

CGT

DELTA 1 protein                                      SEQ ID NO: 14

MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKA

LENKRKQLSSGGKSLSKEEEEELRKLTEEDERRERRVAGPRVGGVNPLEGGTRG

APGGGFVPSMQGVPESPFARTGEGLDVRGNQGFPWDILFPADPPFSPQSCRPQSR

SESKKNRGGREEVLEQWVNGRKKLEELERELRRARKKIKKLEDDNPWLGNVKGI

LGKKDKDGEGAPPAKRARTDQMEIDSGPRKRPLRGGFTDRERQDHRRRKALKN

KKKQLSAGGKSLSKEEEEELKRLTREDEERKKEEHGPSRLGVNPSEGGPRGAPGG

GFVPSMQGIPESRFTRTGEGLDVRGSRGFPQDILFPSDPPFSPQSCRPQGTNLSTSN

PLGFFPDHQLDPAFRANSANPDWDFNPNKDTWPDANKVGGQNLSTSNPLGFFPD

HQLDPAFRANTANPDWDFNPNKDTWPDANKVGGSGATNFSLLKQAGDVEENPG

PMSQSETRRGRRGTREETLEKWITARKKAEELEKDLRKTRKTIKKLEEENPWLGN

IVGIIRKGKDGEGAPPAKRPRTDQMEVDSGPGKRPHKSGFTDKEREDHRRRKALE

NKKKQLSAGGKILSKEEEEELRRLTDEDEERKRRVAGPRVGDVNPSRGGPRGAP

GGGFVPQMAGVPESPFSRTGEGLDIRGTQGFPWVSPSPPQQRLPLLECTPQSQSES

KKNRRGGREDILEKWITTRRKAEELEKDLRKARKTIKKLEDENPWLGNIIGIIRKG

KDGEGAPPAKRPRTDQMEIDSGTGKRPHKSGFTDKEREDHRRRKALENKKKQLS

SGGKNLSREEEEELGRLTVEDEERRRVAGPRTGDVNLSGGGPRGAPGGGFVPR

MEGVPESPFTRTGEGLDIRGNQGFPWVRPSPPQQRLPLLECTPQGTNLSTSNPLGF

FPDHQLDPAFRANSANPDWDFNPNKDTWPDANKVGGQNLSTSNPLGFFPDHQL

DPAFRANTANPDWDFNPNKDTWPDANKVG Delta 1 protein
```

-continued

Delta 2 sequence wt

SEQ ID NO: 15

GGCACCAACCTGAGCACCAGCAACCCGCTGGGCTTTTTTCCGGATCATCAGCT

GGATCCGGCGTTTCGCGCGAACAGCGCGAACCCGGATTGGGATTTTAACCCG

AACAAAGATACCTGGCCGGATGCGAACAAAGTGGGCGGCCAGAACCTGAGC

ACCAGCAACCCGCTGGGCTTTTTTCCGGATCATCAGCTGGATCCGGCGTTTCG

CGCGAACACCGCGAACCCGGATTGGGATTTTAACCCGAACAAAGATACCTGG

CCGGATGCGAACAAAGTGGGCAGCCGCAGCGAAAGCAAAAAAAACCGCGGC

GGCCGCGAAGAAATTCTGGAACAGTGGGTGGGCGCGCAAAAAACTGGAA

GAACTGGAACGCGATCTGCGCAAAATTAAAAAAAAATTAAAAAACTGGAA

GAAGAAACCCGTGGCTGGGCAACATTAAAGGCATTCTGGGCAAAAAAGATC

GCGAAGGCGAAGGCGCGCCGCCGGCGAAACGCGCGCGCGGATCAGATGG

AAGTGGATAGCGGCCCGCGCAAACGCCCGTTTCGCGGCGAATTTACCGATAA

AGAACGCCGCGATCATCGCCGCCGCAAAGCGCTGGAAAACAAACGCAAACA

GCTGAGCAGCGGCGGCAAAAGCCTGAGCAAAGAAGAAGAAGAAGAACTGCG

CAAACTGACCGAAGAAGATGAACGCCGCGAACGCCGCGTGGCGGGCCCGCG

CGTGGGCGGCGTGAACCCGCTGGAAGGCGGCACCCGCGGCGCGCCGGGCGG

CGGCTTTGTGCCGAGCATGCAGGGCGTGCCGGAAAGCCCGTTTGCGCGCACC

GGCGAAGGCCTGGATGTGCGCGGCAACCAGGGCTTTCCGTGGGATATTCTGT

TTCCGGCGGATCCGCCGTTTAGCCCGCAGAGCTGCCGCCCGCAGAGCCGCAG

CGAAAGCAAAAAAAACCGCGGCGGCCGCGAAGAAGTGCTGGAACAGTGGGT

GAACGGCCGCAAAAAACTGGAAGAACTGGAACGCGAACTGCGCCGCGCGCG

CAAAAAAATTAAAAAACTGGAAGATGATAACCCGTGGCTGGGCAACGTGAA

AGGCATTCTGGGCAAAAAAGATAAAGATGGCGAAGGCGCGCCGCCGGCGAA

ACGCGCGCACCGATCAGATGGAAATTGATAGCGGCCCGCGCAAACGCCCG

CTGCGCGGCGGCTTTACCGATCGCGAACGCCAGGATCATCGCCGCCGCAAAG

CGCTGAAAACAAAAAAAAACAGCTGAGCGCGGGCGGCAAAAGCCTGAGCA

AAGAAGAAGAAGAAGAACTGAAACGCCTGACCCGCGAAGATGAAGAACGCA

AAAAAGAAGAACATGGCCCGAGCCGCCTGGGCGTGAACCCGAGCGAAGGCG

GCCCGCGCGGCGCGCCGGGCGGCGGCTTTGTGCCGAGCATGCAGGGCATTCC

GGAAAGCCGCTTTACCCGCACCGGCGAAGGCCTGGATGTGCGCGGCAGCCGC

GGCTTTCCGCAGGATATTCTGTTTCCGAGCGATCCGCCGTTTAGCCCGCAGAG

CTGCCGCCCGCAGGGAAGCGGAGCTACTAACTTCAGCCTGCTGAAGCAGGCT

GGAGACGTGGAGGAGAACCCTGGACCTATGGGCACCAACCTGAGCACCAGC

AACCCGCTGGGCTTTTTTCCGGATCATCAGCTGGATCCGGCGTTTCGCGCGAA

CAGCGCGAACCCGGATTGGGATTTTAACCCGAACAAAGATACCTGGCCGGAT

GCGAACAAAGTGGGCGGCCAGAACCTGAGCACCAGCAACCCGCTGGGCTTTT

TTCCGGATCATCAGCTGGATCCGGCGTTTCGCGCGAACACCGCGAACCCGGA

TTGGGATTTTAACCCGAACAAAGATACCTGGCCGGATGCGAACAAAGTGGGC

AGCCAGAGCGAAACCCGCCGCGGCCGCCGCGGCACCCGCGAAGAAACCCTG

GAAAAATGGATTACCGCGCGCAAAAAAGCGGAAGAACTGGAAAAAGATCTG

CGCAAAACCCGCAAAACCATTAAAAAACTGGAAGAAGAAAACCCGTGGCTG

-continued

```
GGCAACATTGTGGGCATTATTCGCAAAGGCAAAGATGGCGAAGGCGCGCCGC
CGGCGAAACGCCCGCGCACCGATCAGATGGAAGTGGATAGCGGCCCGGGCA
AACGCCCGCATAAAAGCGGCTTTACCGATAAAGAACGCGAAGATCATCGCCG
CCGCAAAGCGCTGGAAAACAAAAAAAAACAGCTGAGCGCGGGCGGCAAAAT
TCTGAGCAAAGAAGAAGAAGAAGAACTGCGCCGCCTGACCGATGAAGATGA
AGAACGCAAACGCCGCGTGGCGGGCCCGCGCGTGGGCGATGTGAACCCGAG
CCGCGGCGGCCCGCGCGGCGCGCCGGGCGGCGGCTTTGTGCCGCAGATGGCG
GGCGTGCCGGAAAGCCCGTTTAGCCGCACCGGCGAAGGCCTGGATATTCGCG
GCACCCAGGGCTTTCCGTGGGTGAGCCCGAGCCCGCCGCAGCAGCGCCTGCC
GCTGCTGGAATGCACCCCGCAGAGCCAGAGCGAAAGCAAAAAAAACCGCCG
CGGCGGCCGCGAAGATATTCTGGAAAAATGGATTACCACCCGCCGCAAAGCG
GAAGAACTGGAAAAAGATCTGCGCAAAGCGCGCAAAACCATTAAAAAACTG
GAAGATGAAAACCCGTGGCTGGGCAACATTATTGGCATTATTCGCAAAGGCA
AAGATGGCGAAGGCGCGCCGCCGGCGAAACGCCCGCGCACCGATCAGATGG
AAATTGATAGCGGCACCGGCAAACGCCCGCATAAAAGCGGCTTTACCGATAA
AGAACGCGAAGATCATCGCCGCCGCAAAGCGCTGGAAAACAAAAAAAAACA
GCTGAGCAGCGGCGGCAAAAACCTGAGCCGCGAAGAAGAAGAAGAACTGGG
CCGCCTGACCGTGGAAGATGAAGAACGCCGCCGCCGCGTGGCGGGCCCGCGC
ACCGGCGATGTGAACCTGAGCGGCGGCGGCCCGCGCGGCGCGCCGGGCGGC
GGCTTTGTGCCGCGCATGGAAGGCGTGCCGGAAAGCCCGTTTACCCGCACCG
GCGAAGGCCTGGATATTCGCGGCAACCAGGGCTTTCCGTGGGTGCGCCCGAG
CCCGCCGCAGCAGCGCCTGCCGCTGCTGGAATGCACCCCGCAG
```

Delta 2 wt with restriction sites (HindIII/EcoRI)    SEQ ID NO: 16

```
A|AGCTTGCACCATGGCCGGCACCAACCTGAGCACCAGCAACCCGCTGGGCT
TTTTTCCGGATCATCAGCTGGATCCGGCGTTTCGCGCGAACAGCGCGAACCCG
GATTGGGATTTTAACCCGAACAAAGATACCTGGCCGGATGCGAACAAAGTGG
GCGGCCAGAACCTGAGCACCAGCAACCCGCTGGGCTTTTTTCCGGATCATCA
GCTGGATCCGGCGTTTCGCGCGAACACCGCGAACCCGGATTGGGATTTTAAC
CCGAACAAAGATACCTGGCCGGATGCGAACAAAGTGGGCAGCCGCAGCGAA
AGCAAAAAAAACCGCGGCGGCCGCGAAGAAATTCTGGAACAGTGGGTGGGC
GCGCGCAAAAAACTGGAAGAACTGGAACGCGATCTGCGCAAAATTAAAAAA
AAAATTAAAAAACTGGAAGAAGAAAACCCGTGGCTGGGCAACATTAAAGGC
ATTCTGGGCAAAAAAGATCGCGAAGGCGAAGGCGCGCCGCCGGCGAAACGC
GCGCGCGCGGATCAGATGGAAGTGGATAGCGGCCCGCGCAAACGCCCGTTTC
GCGGCGAATTTACCGATAAAGAACGCCGCGATCATCGCCGCCGCAAAGCGCT
GGAAAACAAACGCAAACAGCTGAGCAGCGGCGGCAAAAGCCTGAGCAAAGA
AGAAGAAGAAGAACTGCGCAAACTGACCGAAGAAGATGAACGCCGCGAACG
CCGCGTGGCGGGCCCGCGCGTGGGCGGCGTGAACCCGCTGGAAGGCGGCACC
CGCGGCGCGCCGGGCGGCGGCTTTGTGCCGAGCATGCAGGGCGTGCCGGAAA
GCCCGTTTGCGCGCACCGGCGAAGGCCTGGATGTGCGCGGCAACCAGGGCTT
```

-continued

```
TCCGTGGGATATTCTGTTTCCGGCGGATCCGCCGTTTAGCCCGCAGAGCTGCC
GCCCGCAGAGCCGCAGCGAAAGCAAAAAAAACCGCGGCGGCCGCGAAGAAG
TGCTGGAACAGTGGGTGAACGGCCGCAAAAAACTGGAAGAACTGGAACGCG
AACTGCGCCGCGCGCGCAAAAAAATTAAAAAACTGGAAGATGATAACCCGTG
GCTGGGCAACGTGAAAGGCATTCTGGGCAAAAAGATAAAGATGGCGAAGG
CGCGCCGCCGGCGAAACGCGCGCGCACCGATCAGATGGAAATTGATAGCGGC
CCGCGCAAACGCCCGCTGCGCGGCGGCTTTACCGATCGCGAACGCCAGGATC
ATCGCCGCCGCAAAGCGCTGAAAAACAAAAAAAAACAGCTGAGCGCGGGCG
GCAAAAGCCTGAGCAAAGAAGAAGAAGAAGAACTGAAACGCCTGACCCGCG
AAGATGAAGAACGCAAAAAAGAAGAACATGGCCCGAGCCGCCTGGGCGTGA
ACCCGAGCGAAGGCGGCCCGCGCGGCGCGCCGGGCGGCGGCTTTGTGCCGAG
CATGCAGGGCATTCCGGAAAGCCGCTTTACCCGCACCGGCGAAGGCCTGGAT
GTGCGCGGCAGCCGCGGCTTTCCGCAGGATATTCTGTTTCCGAGCGATCCGCC
GTTTAGCCCGCAGAGCTGCCGCCCGCAGGGAAGCGGAGCTACTAACTTCAGC
CTGCTGAAGCAGGCTGGAGACGTGGAGGAGAACCCTGGACCTATGGGCACC
AACCTGAGCACCAGCAACCCGCTGGGCTTTTTTCCGGATCATCAGCTGGATCC
GGCGTTTCGCGCGAACAGCGCGAACCCGGATTGGGATTTTAACCCGAACAAA
GATACCTGGCCGGATGCGAACAAAGTGGGCGGCCAGAACCTGAGCACCAGC
AACCCGCTGGGCTTTTTTCCGGATCATCAGCTGGATCCGGCGTTTCGCGCGAA
CACCGCGAACCCGGATTGGGATTTTAACCCGAACAAAGATACCTGGCCGGAT
GCGAACAAAGTGGGCAGCCAGAGCGAAACCCGCCGCGGCCGCCGCGGCACC
CGCGAAGAAACCCTGGAAAAATGGATTACCGCGCGCAAAAAAGCGGAAGAA
CTGGAAAAAGATCTGCGCAAAACCCGCAAAACCATTAAAAAACTGGAAGAA
GAAAACCCGTGGCTGGGCAACATTGTGGGCATTATTCGCAAAGGCAAAGATG
GCGAAGGCGCGCCGCCGGCGAAACGCCCGCGCACCGATCAGATGGAAGTGG
ATAGCGGCCCGGGCAAACGCCCGCATAAAAGCGGCTTTACCGATAAAGAACG
CGAAGATCATCGCCGCCGCAAAGCGCTGAAAACAAAAAAAAACAGCTGAG
CGCGGGCGGCAAAATTCTGAGCAAAGAAGAAGAAGAAGAACTGCGCCGCCT
GACCGATGAAGATGAAGAACGCAAACGCCGCGTGGCGGGCCCGCGCGTGGG
CGATGTGAACCCGAGCCGCGGCGGCCCGCGCGGCGCGCCGGGCGGCGGCTTT
GTGCCGCAGATGGCGGGCGTGCCGGAAAGCCCGTTTAGCCGCACCGGCGAAG
GCCTGGATATTCGCGGCACCCAGGGCTTTCCGTGGGTGAGCCCGAGCCCGCC
GCAGCAGCGCCTGCCGCTGCTGGAATGCACCCCGCAGAGCCAGAGCGAAAGC
AAAAAAAACCGCCGCGGCGGCCGCGAAGATATTCTGGAAAAATGGATTACCA
CCCGCCGCAAAGCGGAAGAACTGGAAAAAGATCTGCGCAAAGCGCGCAAAA
CCATTAAAAAACTGGAAGATGAAAACCCGTGGCTGGGCAACATTATTGGCAT
TATTCGCAAAGGCAAAGATGGCGAAGGCGCGCCGCCGGCGAAACGCCCGCG
CACCGATCAGATGGAAATTGATAGCGGCACCGGCAAACGCCCGCATAAAAGC
GGCTTTACCGATAAAGAACGCGAAGATCATCGCCGCCGCAAAGCGCTGGAAA
ACAAAAAAAAACAGCTGAGCAGCGGCGGCAAAAACCTGAGCCGCGAAGAAG
AAGAAGAACTGGGCCGCCTGACCGTGGAAGATGAAGAACGCCGCCGCCGCG
```

```
TGGCGGGCCCGCGCACCGGCGATGTGAACCTGAGCGGCGGCGGCCCCGCGCGG

CGCGCCGGGCGGCGGCTTTGTGCCGCGCATGGAAGGCGTGCCGGAAAGCCCG

TTTACCCGCACCGGCGAAGGCCTGGATATTCGCGGCAACCAGGGCTTTCCGTG

GGTGCGCCCGAGCCCGCCGCAGCAGCGCCTGCCGCTGCTGGAATGCACCCCG

CAGTGATGAG↓AATTCCGT
``` delta 2 optimized

SEQ ID NO: 17

```
GCCGGCACTAACCTGTCTACATCAAACCCTCTGGGATTTTTCCCCGATCATCAGCTGGAC

CCCGCATTTCGCGCTAACTCTGCTAACCCTGACTGGGATTTCAACCCTAATAAGGACACA

TGGCCAGATGCCAACAAGGTCGGCGGCCAGAACCTGTCCACCTCTAATCCCCTGGGCTTC

TTTCCTGACCACCAGCTGGATCCTGCCTTCAGGGCCAACACCGCCAATCCCGACTGGGAC

TTCAACCCAAATAAGGATACCTGGCCTGACGCTAACAAGGTCGGCAGCCGGTCCGAGTCT

AAGAAGAATAGGGGAGGAAGGGAGGAGATCCTGGAGCAGTGGGTGGGCGCCAGAAAGAAG

CTGGAGGAGCTGGAGCGGGACCTGAGAAAGATCAAGAAGAAGATCAAGAAGCTGGAGGAG

GAGAACCCCTGGCTGGGCAATATCAAGGGCATCCTGGGCAAGAAGGATCGGGAGGGAGAG

GGAGCACCACCTGCAAAGAGGGCCAGAGCCGACCAGATGGAGGTGGATTCCGGCCCTAGG

AAGCGCCCATTCAGAGGCGAGTTTACAGACAAGGAGCGGAGAGATCACAGGCGCCGGAAG

GCCCTGGAGAACAAGAGGAAGCAGCTGAGCTCCGGCGGCAAGAGCCTGTCCAAGGAGGAG

GAGGAGGAGCTGCGCAAGCTGACCGAGGAGGACGAGAGAAGGGAGAGGAGGGTGGCAGGA

CCTAGGGTGGGAGGCGTGAACCCACTGGAGGGAGGAACAAGAGGAGCACCCGGAGGAGGC

TTCGTGCCTTCTATGCAGGGCGTGCCTGAGAGCCCATTTGCCAGGACCGGAGAGGGCCTG

GACGTGAGAGGCAATCAGGGCTTCCCATGGGACATCCTGTTTCCCGCCGATCCACCCTTC

AGCCCACAGTCCTGCAGGCCCCAGTCTCGCAGCGAGTCCAAGAAGAACAGAGGCGGAAGG

GAGGAGGTGCTGGAGCAGTGGGTGAATGGCAGGAAGAAGCTGGAAGAACTGGAGAGGGAG

CTGAGAAGGGCCCGCAAGAAGATCAAGAAGCTGGAAGACGATAATCCTTGGCTGGGCAAT

GTGAAAGGCATCCTGGGCAAGAAGGACAAGGATGGAGAGGGGAGCACCTCCAGCAAAGAGG

GCAAGAACAGACCAGATGGAGATCGATTCCGGACCAAGGAAGCGCCCTCTGAGGGGAGGC

TTCACCGACCGGGAGAGACAGGATCACCGCCGGAGAAAGGCCCTGAAGAACAAGAAGAAG

CAGCTGAGCGCCGGCGGCAAGTCTCTGAGTAAAGAAGAAGAGGAGGAGCTGAAGCGGCTG

ACAAGAGAGGACGAGGAGAGGAAGAAGGAGGAGCACGGACCATCCAGGCTGGGAGTGAAT

CCTTCTGAGGGAGGACCAAGGGGCGCCCCTGGCGGAGGCTTCGTGCCTAGCATGCAGGGC

ATCCCAGAGTCCAGGTTTACCAGGACAGGCGAAGGCCTGGACGTGCGGGGCTCTAGAGGC

TTTCCCCAGGACATCCTGTTCCCTAGCGATCCCCCTTTTTCTCCTCAGAGCTGTAGACCA

CAGGGAAGCGGAGCTACTAACTTCAGCCTGCTGAAGCAGGCTGGAGACGTGGAGGAGAAC

CCTGGACCTATGGGCACCAACCTGTCCACATCTAACCCTCTGGGCTTCTTTCCAGATCAT

CAGCTGGACCCAGCCTTCAGGGCCAACAGCGCCAATCCAGACTGGGACTTCAACCCCAAT

AAGGACACATGGCCTGACGCAAACAAGGTCGGAGGACAGAACCTGAGCACCTCCAATCCA

CTGGGCTTCTTTCCCGACCACCAGCTGGATCCAGCCTTCCGCGCCAACACTGCTAACCCT

GATTGGGACTTCAACCCTAATAAGGATACATGGCCTGATGCCAATAAGGTCGGCTCTCAG

AGCGAGACAAGGAGGGGCCGGAGAGGAACCAGGGAGGAGACACTGGAGAAGTGGATCACC

GCCCGCAAGAAGGCCGAGGAGCTGGAGAAGGACCTGAGGAAGACCCGCAAGACAATCAAG
```

-continued

```
AAGCTGGAAGAAGAGAACCCATGGCTGGGCAATATCGTGGGCATCATCAGAAAGGGCAAG
GACGGCGAGGGAGCACCACCAGCAAAGAGGCCCCGCACAGATCAGATGGAAGTGGATTCC
GGACCTGGCAAGCGGCCACACAAGTCTGGCTTCACCGACAAGGAGAGAGAGGACCATAGG
CGCCGGAAGGCCCTGGAAAACAAGAAGAAGCAATTATCTGCCGGCGGCAAGATCCTGAGT
AAAGAAGAGGAAGAGGAGCTGAGAAGGCTGACCGACGAGGATGAGGAGAGGAAGCGCCGG
GTGGCCGGCCCACGCGTGGGCGACGTGAATCCCTCCAGGGGAGGACCAAGAGGAGCACCT
GGAGGCGGCTTCGTGCCCCAGATGGCCGGCGTGCCCGAGTCCCCTTTTTCTCGGACCGGC
GAGGGCCTGGATATCAGAGGCACACAGGGCTTTCCATGGGTGTCCCCCTCTCCTCCACAG
CAGAGGCTGCCACTGCTGGAGTGCACACCCCAGAGCCAGAGCGAATCTAAGAAGAACAGA
A
GGGGAGGCCGCGAGGACATCCTGGAAAAATGGATCACCACACGCAGAAAAGCTGAAGAAC
TGGAAAAGGACCTGCGGAAGGCCAGAAAGACCATCAAGAAGCTGGAGGATGAAAATCCAT
GGCTGGGAAACATCATCGGCATCATCCGGAAGGGCAAGGACGGGGAAGGCGCACCACCTG
CAAAGCGGCCTAGAACCGATCAGATGGAAATCGATAGCGGCACAGGCAAGAGGCCACACA
AGTCCGGCTTCACCGATAAAGAGCGCGAGGATCACAGAAGGCGCAAGGCCCTGGAGAACA
AGAAGAAGCAATTAAGCAGCGGCGGCAAGAATCTGTCCAGAGAAGAGGAGGAAGAGCTGG
GCCGCCTGACAGTGGAGGACGAGGAGCGGAGAAGGCGCGTGGCAGGACCCAGAACCGGCG
ATGTGAACCTGTCCGGAGGAGGACCTAGGGGAGCACCAGGAGGCGGCTTCGTGCCTAGAA
TGGAGGGCGTGCCAGAGTCTCCCTTTACCCGGACAGGCGAGGGCCTGGACATCAGAGGCA
ATCAGGGCTTTCCCTGGGTCCGCCCCTCCCCCCCTCAGCAGAGACTGCCACTGCTGGAAT
GCACACCACAG
``` delta 2 codon optimized + Restriction sites

SEQ ID NO: 18

```
A↓AGCTTGCACCATGGCCGGCACTAACCTGTCTACATCAAACCCTCTGGGATTTTTCCCC
GATCATCAGCTGGACCCCGCATTTCGCGCTAACTCTGCTAACCCTGACTGGGATTTCAAC
CCTAATAAGGACACATGGCCAGATGCCAACAAGGTCGGCGGCCAGAACCTGTCCACCTCT
AATCCCCTGGGCTTCTTTCCTGACCACCAGCTGGATCCTGCCTTCAGGGCCAACACCGCC
AATCCCGACTGGGACTTCAACCCAAATAAGGATACCTGGCCTGACGCTAACAAGGTCGGC
AGCCGGTCCGAGTCTAAGAAGAATAGGGGAGGAAGGGAGGAGATCCTGGAGCAGTGGGTG
GGCGCCAGAAAGAAGCTGGAGGAGCTGGAGCGGGACCTGAGAAAGATCAAGAAGAAGATC
AAGAAGCTGGAGGAGGAGAACCCCTGGCTGGGCAATATCAAGGGCATCCTGGGCAAGAAG
GATCGGGAGGGAGAGGGAGCACCACCTGCAAAGAGGGCCAGAGCCGACCAGATGGAGGTG
GATTCCGGCCCTAGGAAGCGCCCATTCAGAGGCGAGTTTACAGACAAGGAGCGGAGAGAT
CACAGGCGCCGAAGGCCCTGGAGAACAAGAGGAAGCAGCTGAGCTCCGGCGGCAAGAGC
CTGTCCAAGGAGGAGGAGGAGGAGCTGCGCAAGCTGACCGAGGAGGACGAGAGAAGGGAG
AGGAGGGTGGCAGGACCTAGGGTGGGAGGCGTGAACCCACTGGAGGGAGGAACAAGAGGA
GCACCCGGAGGAGGCTTCGTGCCTTCTATGCAGGGCGTGCCTGAGAGCCCATTTGCCAGG
ACCGGAGAGGGCCTGGACGTGAGAGGCAATCAGGGCTTCCCATGGGACATCCTGTTTCCC
GCCGATCCACCCTTCAGCCCACAGTCCTGCAGGCCCCAGTCTCGCAGCGAGTCCAAGAAG
AACAGAGGCGGAAGGGAGGAGGTGCTGGAGCAGTGGGTGAATGGCAGGAAGAAGCTGGAA
GAACTGGAGAGGGAGCTGAGAAGGGCCCGCAAGAAGATCAAGAAGCTGGAAGACGATAAT
CCTTGGCTGGGCAATGTGAAAGGCATCCTGGGCAAGAAGGACAAGGATGGAGAGGGAGCA
```

-continued

```
CCTCCAGCAAAGAGGGCAAGAACAGACCAGATGGAGATCGATTCCGGACCAAGGAAGCGC

CCTCTGAGGGGAGGCTTCACCGACCGGGAGAGACAGGATCACCGCCGGAGAAAGGCCCTG

AAGAACAAGAAGAAGCAGCTGAGCGCCGGCGGCAAGTCTCTGAGTAAAGAAGAAGAGGAG

GAGCTGAAGCGGCTGACAAGAGAGGACGAGGAGAGGAAGAAGGAGGAGCACGGACCATCC

AGGCTGGGAGTGAATCCTTCTGAGGGAGGACCAAGGGGCGCCCCTGGCGGAGGCTTCGTG

CCTAGCATGCAGGGCATCCCAGAGTCCAGGTTTACCAGGACAGGCGAAGGCCTGGACGTG

CGGGGCTCTAGAGGCTTTCCCCAGGACATCCTGTTCCCTAGCGATCCCCCTTTTTCTCCT

CAGAGCTGTAGACCACAGGGAAGCGGAGCTACTAACTTCAGCCTGCTGAAGCAGGCTGGA

GACGTGGAGGAGAACCCTGGACCTATGGGCACCAACCTGTCCACATCTAACCCTCTGGGC

TTCTTTCCAGATCATCAGCTGGACCCAGCCTTCAGGGCCAACAGCGCCAATCCAGACTGG

GACTTCAACCCCAATAAGGACACATGGCCTGACGCAAACAAGGTCGGAGGACAGAACCTG

AGCACCTCCAATCCACTGGGCTTCTTTCCCGACCACCAGCTGGATCCAGCCTTCCGCGCC

AACACTGCTAACCCTGATTGGGACTTCAACCCTAATAAGGATACATGGCCTGATGCCAAT

AAGGTCGGCTCTCAGAGCGAGACAAGGAGGGGCCGGAGAGGAACCAGGGAGGAGACACTG

GAGAAGTGGATCACCGCCCGCAAGAAGGCCGAGGAGCTGGAGAAGGACCTGAGGAAGACC

CGCAAGACAATCAAGAAGCTGGAAGAAGAGAACCCATGGCTGGGCAATATCGTGGGCATC

ATCAGAAAGGGCAAGGACGGCGAGGGAGCACCACCAGCAAAGAGGCCCCGCACAGATCAG

ATGGAAGTGGATTCCGGACCTGGCAAGCGGCCACACAAGTCTGGCTTCACCGACAAGGAG

AGAGAGGACCATAGGCGCCGGAAGGCCCTGGAAAACAAGAAGAAGCAATTATCTGCCGGC

GGCAAGATCCTGAGTAAAGAAGAGGAAGAGGAGCTGAGAAGGCTGACCGACGAGGATGAG

GAGAGGAAGCGCCGGGTGGCCGGCCCACGCGTGGGCGACGTGAATCCCTCCAGGGGAGGA

CCAAGAGGAGCACCTGGAGGCGGCTTCGTGCCCCAGATGGCCGGCGTGCCCGAGTCCCCT

TTTTCTCGGACCGGCGAGGGCCTGGATATCAGAGGCACACAGGGCTTTCCATGGGTGTCC

CCCTCTCCTCCACAGCAGAGGCTGCCACTGCTGGAGTGCACACCCCAGAGCCAGAGCGAA

TCTAAGAAGAACAGAA

GGGGAGGCCGCGAGGACATCCTGGAAAAATGGATCACCACACGCAGAAAAGCTGAAGAAC

TGGAAAAGGACCTGCGGAAGGCCAGAAAGACCATCAAGAAGCTGGAGGATGAAAATCCAT

GGCTGGGAAACATCATCGGCATCATCCGGAAGGGCAAGGACGGGGAAGGCGCACCACCTG

CAAAGCGGCCTAGAACCGATCAGATGGAAATCGATAGCGGCACAGGCAAGAGGCCACACA

AGTCCGGCTTCACCGATAAAGAGCGCGAGGATCACAGAAGGCGCAAGGCCCTGGAGAACA

AGAAGAAGCAATTAAGCAGCGGCGGCAAGAATCTGTCCAGAGAAGAGGAGGAAGAGCTGG

GCCGCCTGACAGTGGAGGACGAGGAGCGGAGAAGGCGCGTGGCAGGACCCAGAACCGGCG

ATGTGAACCTGTCCGGAGGAGGACCTAGGGGAGCACCAGGAGGCGGCTTCGTGCCTAGAA

TGGAGGGCGTGCCAGAGTCTCCCTTTACCCGGACAGGCGAGGGCCTGGACATCAGAGGCA

ATCAGGGCTTTCCCTGGGTCCGCCCCTCCCCCCCTCAGCAGAGACTGCCACTGCTGGAAT

GCACACCACAGTGATGAG↓AATTCCGT
``` delta 2 protein
SEQ ID NO: 19

```
MAGTNLSTSNPLGFFPDHQLDPAPRANSANPDWDFNPNKDTWPDANKVGGQNL

STSNPLGFFPDHQLDPAFRANTANPDWDFNPNKDTWPDANKVGSRSESKKNRG

GREEILEQWVGARKKLEELERDLRKIKKKIKKLEEENPWLGNIKGILGKKDREGE
```

-continued

GAPPAKRARADQMEVDSGPRKRPFRGEFTDKERRDHRRRKALENKRKQLSSGG

KSLSKEEEEELRKLTEEDERRERRVAGPRVGGVNPLEGGTRGAPGGGFVPSMQG

VPESPFARTGEGLDVRGNQGFPWDILFPADPPFSPQSCRPQSRSESKKNRGGREEV

LEQWVNGRKKLEELERELRRARKKIKKLEDDNPWLGNVKGILGKKDKDGEGAP

PAKRARTDQMEIDSGPRKRPLRGGFTDRERQDHRRRKALKNKKKQLSAGGKSLS

KEEEEELKRLTREDEERKKEEHGPSRLGVNPSEGGPRGAPGGGFVPSMQGIPESR

FTRTGEGLDVRGSRGFPQDILFPSDPPFSPQSCRPQGSGATNFSLLKQAGDVEENP

GPMGTNLSTSNPLGFFPDHQLDPAFRANSANPDWDFNPNKDTWPDANKVGGQN

LSTSNPLGFFPDHQLDPAFRANTANPDWDFNPNKDTWPDANKVGSQSETRRGRR

GTREETLEKWITARKKAEELEKDLRKTRKTIKKLEEENPWLGNIVGIIRKGKDGE

GAPPAKRPRTDQMEVDSGPGKRPHKSGFTDKEREDHRRRKALENKKKQLSAGG

KILSKEEEEELRRLTDEDEERKRRVAGPRVGDVNPSRGGPRGAPGGGFVPQMAG

VPESPFSRTGEGLDIRGTQGFPWVSPSPPQQRLPLLECTPQSQSESKKNRRGGREDI

LEKWITTRRKAEELEKDLRKARKTIKKLEDENPWLGNIIGIIRKGKDGEGAPPAKR

PRTDQMEIDSGTGKRPHKSGFTDKEREDHRRRKALENKKKQLSSGGKNLSREEE

EELGRLTVEDEERRRRVAGPRTGDVNLSGGGPRGAPGGGFVPRMEGVPESPFTR

TGEGLDIRGNQGFPWVRPSPPQQRLPLLECTPQ

SEQ ID NO: 20: delta 3 wt
GGCACCAACCTGAGCACCAGCAACCCGCTGGGCTTTTTTCCGGATCATCAGCT

GGATCCGGCGTTTCGCGCGAACAGCGCGAACCCGGATTGGGATTTTAACCCG

AACAAAGATACCTGGCCGGATGCGAACAAAGTGGGCGGCCAGAACCTGAGC

ACCAGCAACCCGCTGGGCTTTTTTCCGGATCATCAGCTGGATCCGGCGTTTCG

CGCGAACACCGCGAACCCGGATTGGGATTTTAACCCGAACAAAGATACCTGG

CCGGATGCGAACAAAGTGGGCAGCCGCAGCGAAAGCAAAAAAAACCGCGGC

GGCCGCGAAGAAATTCTGGAACAGTGGGTGGGCGCGCGCAAAAAACTGGAA

GAACTGGAACGCGATCTGCGCAAAATTAAAAAAAAAATTAAAAAACTGGAA

GAAGAAAACCCGTGGCTGGGCAACATTAAAGGCATTCTGGGCAAAAAAGATC

GCGAAGGCGAAGGCGCGCCGCCGGCGAAACGCGCGCGCGGATCAGATGG

AAGTGGATAGCGGCCCCGCGCAAACGCCCGTTTCGCGGCGAATTTACCGATAA

AGAACGCCGCGATCATCGCCGCCGCAAAGCGCTGGAAAACAAACGCAAACA

GCTGAGCAGCGGCGGCAAAAGCCTGAGCAAAGAAGAAGAAGAAGAACTGCG

CAAACTGACCGAAGAAGATAACGCCGCGAACGCCGCGTGGCGGGCCCGCG

CGTGGGCGGCGTGAACCCGCTGGAAGGCGGCACCCGCGGCGCGCCGGGCGG

CGGCTTTGTGCCGAGCATGCAGGGCGTGCCGGAAAGCCCGTTTGCGCGCACC

GGCGAAGGCCTGGATGTGCGCGGCAACCAGGGCTTTCCGTGGGATATTCTGT

TTCCGGCGGATCCGCCGTTTAGCCCGCAGAGCTGCCGCCCGCAGAGCCGCAG

CGAAAGCAAAAAAAACCGCGGCGGCCGCGAAGAAGTGCTGGAACAGTGGGT

GAACGGCCGCAAAAAACTGGAAGAACTGGAACGCGAACTGCGCCGCGCGCG

CAAAAAAATTAAAAAACTGGAAGATGATAACCCGTGGCTGGGCAACGTGAA

AGGCATTCTGGGCAAAAAAGATAAAGATGGCGAAGGCGCGCCGCCGGCGAA

ACGCGCGCGCACCGATCAGATGGAAATTGATAGCGGCCCGCGCAAACGCCCG

-continued

```
CTGCGCGGCGGCTTTACCGATCGCGAACGCCAGGATCATCGCCGCCGCAAAG
CGCTGAAAAACAAAAAAAAACAGCTGAGCGCGGGCGGCAAAAGCCTGAGCA
AAGAAGAAGAAGAAGAACTGAAACGCCTGACCCGCGAAGATGAAGAACGCA
AAAAAGAAGAACATGGCCCGAGCCGCCTGGGCGTGAACCCGAGCGAAGGCG
GCCCGCGCGGCGCGCCGGGCGGCGGCTTTGTGCCGAGCATGCAGGGCATTCC
GGAAAGCCGCTTTACCCGCACCGGCGAAGGCCTGGATGTGCGCGGCAGCCGC
GGCTTTCCGCAGGATATTCTGTTTCCGAGCGATCCGCCGTTTAGCCCGCAGAG
CTGCCGCCCGCAGGGCACCAACCTGAGCACCAGCAACCCGCTGGGCTTTTTTC
CGGATCATCAGCTGGATCCGGCGTTTCGCGCGAACAGCGCGAACCCGGATTG
GGATTTTAACCCGAACAAAGATACCTGGCCGGATGCGAACAAAGTGGGCGGC
CAGAACCTGAGCACCAGCAACCCGCTGGGCTTTTTTCCGGATCATCAGCTGGA
TCCGGCGTTTCGCGCGAACACCGCGAACCCGGATTGGGATTTTAACCCGAAC
AAAGATACCTGGCCGGATGCGAACAAAGTGGGCGGAAGcGGAGCTACTAACTTC
AGCCTGCTGAAGCAGGCTGGAGACGTGGAGGAGAACCCTGGACCTATGGGCACCAAC
CTGAGCACCAGCAACCCGCTGGGCTTTTTTCCGGATCATCAGCTGGATCCGGC
GTTTCGCGCGAACAGCGCGAACCCGGATTGGGATTTTAACCCGAACAAAGAT
ACCTGGCCGGATGCGAACAAAGTGGGCGGCCAGAACCTGAGCACCAGCAAC
CCGCTGGGCTTTTTTCCGGATCATCAGCTGGATCCGGCGTTTCGCGCGAACAC
CGCGAACCCGGATTGGGATTTTAACCCGAACAAAGATACCTGGCCGGATGCG
AACAAAGTGGGCAGCCAGAGCGAAACCCGCCGCGGCCGCCGCGGCACCCGC
GAAGAAACCCTGGAAAAATGGATTACCGCGCGCAAAAAAGCGGAAGAACTG
GAAAAAGATCTGCGCAAAACCCGCAAAACCATTAAAAAACTGGAAGAAGAA
AACCCGTGGCTGGGCAACATTGTGGGCATTATTCGCAAAGGCAAAGATGGCG
AAGGCGCGCCGCCGGCGAAACGCCCGCGCACCGATCAGATGGAAGTGGATA
GCGGCCCGGGCAAACGCCCGCATAAAAGCGGCTTTACCGATAAAGAACGCG
AAGATCATCGCCGCCGCAAAGCGCTGGAAAACAAAAAAAAACAGCTGAGCG
CGGGCGGCAAAATTCTGAGCAAAGAAGAAGAAGAACTGCGCCGCCTGA
CCGATGAAGATGAAGAACGCAAACGCCGCGTGGCGGGCCCGCGCGTGGGCG
ATGTGAACCCGAGCCGCGGCGGCCCGCGCGGCGCGCCGGGCGGCGGCTTTGT
GCCGCAGATGGCGGGCGTGCCGGAAAGCCCGTTTAGCCGCACCGGCGAAGGC
CTGGATATTCGCGGCACCCAGGGCTTTCCGTGGGTGAGCCCGAGCCCGCCGC
AGCAGCGCCTGCCGCTGCTGGAATGCACCCCGCAGAGCCAGAGCGAAAGCA
AAAAAAACCGCCGCGGCGGCCGCGAAGATATTCTGGAAAAATGGATTACCAC
CCGCCGCAAAGCGGAAGAACTGGAAAAAGATCTGCGCAAAGCGCGCAAAAC
CATTAAAAAACTGGAAGATGAAAAACCCGTGGCTGGGCAACATTATTGGCATT
ATTCGCAAAGGCAAAGATGGCGAAGGCGCGCCGCCGGCGAAACGCCCGCGC
ACCGATCAGATGGAAATTGATAGCGGCACCGGCAAACGCCCGCATAAAAGCG
GCTTTACCGATAAAGAACGCGAAGATCATCGCCGCCGCAAAGCGCTGGAAAA
CAAAAAAAAACAGCTGAGCAGCGGCGGCAAAAACCTGAGCCGCGAAGAAGA
AGAAGAACTGGGCCGCCTGACCGTGGAAGATGAAGAACGCCGCCGCCGCGT
GGCGGGCCCGCGCACCGGCGATGTGAACCTGAGCGGCGGCGGCCCGCGCGG
```

-continued

```
CGCGCCGGGCGGCGGCTTTGTGCCGCGCATGGAAGGCGTGCCGGAAAGCCCG

TTTACCCGCACCGGCGAAGGCCTGGATATTCGCGGCAACCAGGGCTTTCCGTG

GGTGCGCCCGAGCCCGCCGCAGCAGCGCCTGCCGCTGCTGGAATGCACCCCG

CAGGGCACCAACCTGAGCACCAGCAACCCGCTGGGCTTTTTTCCGGATCATC

AGCTGGATCCGGCGTTTCGCGCGAACAGCGCGAACCCGGATTGGGATTTTAA

CCCGAACAAAGATACCTGGCCGGATGCGAACAAAGTGGGCGGCCAGAACCT

GAGCACCAGCAACCCGCTGGGCTTTTTTCCGGATCATCAGCTGGATCCGGCGT

TTCGCGCGAACACCGCGAACCCGGATTGGGATTTTAACCCGAACAAAGATAC

CTGGCCGGATGCGAACAAAGTGGGC
``` delta 3 wt + with restriction sites (HindIII/EcoRI)

SEQ ID NO: 21

```
A|AGCTTGCACCATGGCCGGCACCAACCTGAGCACCAGCAACCCGCTGGGCTTTT

TTCCGGATCATCAGCTGGATCCGGCGTTTCGCGCGAACAGCGCGAACCCGGA

TTGGGATTTTAACCCGAACAAAGATACCTGGCCGGATGCGAACAAAGTGGGC

GGCCAGAACCTGAGCACCAGCAACCCGCTGGGCTTTTTTCCGGATCATCAGCT

GGATCCGGCGTTTCGCGCGAACACCGCGAACCCGGATTGGGATTTTAACCCG

AACAAAGATACCTGGCCGGATGCGAACAAAGTGGGCAGCCGCAGCGAAAGC

AAAAAAAACCGCGGCGGCCGCGAAGAAATTCTGGAACAGTGGGTGGGCGCG

CGCAAAAAACTGGAAGAACTGGAACGCGATCTGCGCAAAATTAAAAAAAAA

ATTAAAAAACTGGAAGAAGAAAAACCCGTGGCTGGGCAACATTAAAGGCATTC

TGGGCAAAAAAGATCGCGAAGGCGAAGGCGCGCCGCCGGCGAAACGCGCGC

GCGCGGATCAGATGGAAGTGGATAGCGGCCCGCGCAAACGCCCGTTTCGCGG

CGAATTTACCGATAAAGAACGCCGCGATCATCGCCGCCGCAAAGCGCTGGAA

AACAAACGCAAACAGCTGAGCAGCGGCGGCAAAAGCCTGAGCAAAGAAGAA

GAAGAAGAACTGCGCAAACTGACCGAAGAAGATGAACGCCGCGAACGCCGC

GTGGCGGGCCCGCGCGTGGGCGGCGTGAACCCGCTGGAAGGCGGCACCCGC

GGCGCGCCGGGCGGCGGCTTTGTGCCGAGCATGCAGGGCGTGCCGGAAAGCC

CGTTTGCGCGCACCGGCGAAGGCCTGGATGTGCGCGGCAACCAGGGCTTTCC

GTGGGATATTCTGTTTCCGGCGGATCCGCCGTTTAGCCCGCAGAGCTGCCGCC

CGCAGAGCCGCAGCGAAAGCAAAAAAAACCGCGGCGGCCGCGAAGAAGTGC

TGGAACAGTGGGTGAACGGCCGCAAAAAACTGGAAGAACTGGAACGCGAAC

TGCGCCGCGCGCGCAAAAAAATTAAAAAACTGGAAGATGATAACCCGTGGCT

GGGCAACGTGAAAGGCATTCTGGGCAAAAAAGATAAAGATGGCGAAGGCGC

GCCGCCGGCGAAACGCGCGCGCACCGATCAGATGGAAATTGATAGCGGCCCG

CGCAAACGCCCGCTGCGCGGCGGCTTTACCGATCGCGAACGCCAGGATCATC

GCCGCCGCAAAGCGCTGAAAAACAAAAAAAAACAGCTGAGCGCGGGCGGCA

AAAGCCTGAGCAAAGAAGAAGAAGAAGAACTGAAACGCCTGACCCGCGAAG

ATGAAGAACGCAAAAAAGAAGAACATGGCCCGAGCCGCCTGGGCGTGAACC

CGAGCGAAGGCGGCCCGCGCGGCGCGCCGGGCGGCGGCTTTGTGCCGAGCAT

GCAGGGCATTCCGGAAAGCCGCTTTACCCGCACCGGCGAAGGCCTGGATGTG

CGCGGCAGCCGCGGCTTTCCGCAGGATATTCTGTTTCCGAGCGATCCGCCGTT
```

-continued

```
TAGCCCGCAGAGCTGCCGCCCGCAGGGCACCAACCTGAGCACCAGCAACCCG

CTGGGCTTTTTTCCGGATCATCAGCTGGATCCGGCGTTTCGCGCGAACAGCGC

GAACCCGGATTGGGATTTTAACCCGAACAAAGATACCTGGCCGGATGCGAAC

AAAGTGGGCGGCCAGAACCTGAGCACCAGCAACCCGCTGGGCTTTTTTCCGG

ATCATCAGCTGGATCCGGCGTTTCGCGCGAACACCGCGAACCCGGATTGGGA

TTTTAACCCGAACAAAGATACCTGGCCGGATGCGAACAAAGTGGGCGGAAGCG

GAGCTACTAACTTCAGCCTGCTGAAGCAGGCTGGAGACGTGGAGGAGAACCCTGGACCT

ATGGGCACCAACCTGAGCACCAGCAACCCGCTGGGCTTTTTTCCGGATCATC

AGCTGGATCCGGCGTTTCGCGCGAACAGCGCGAACCCGGATTGGGATTTTAA

CCCGAACAAAGATACCTGGCCGGATGCGAACAAAGTGGGCGGCCAGAACCT

GAGCACCAGCAACCCGCTGGGCTTTTTTCCGGATCATCAGCTGGATCCGGCGT

TTCGCGCGAACACCGCGAACCCGGATTGGGATTTTAACCCGAACAAAGATAC

CTGGCCGGATGCGAACAAAGTGGGCAGCCAGAGCGAAACCCGCCGCGGCCG

CCGCGGCACCCGCGAAGAAACCCTGGAAAATGGATTACCGCGCGCAAAAA

AGCGGAAGAACTGGAAAAAGATCTGCGCAAAACCCGCAAAACCATTAAAAA

ACTGGAAGAAGAAAACCCGTGGCTGGGCAACATTGTGGGCATTATTCGCAAA

GGCAAAGATGGCGAAGGCGCGCCGCCGGCGAAACGCCCGCGCACCGATCAG

ATGGAAGTGGATAGCGGCCCGGGCAAACGCCCGCATAAAAGCGGCTTTACCG

ATAAAGAACGCGAAGATCATCGCCGCCGCAAAGCGCTGGAAAACAAAAAAA

AACAGCTGAGCGCGGGCGGCAAAATTCTGAGCAAAGAAGAAGAAGAAGAAC

TGCGCCGCCTGACCGATGAAGATGAAGAACGCAAACGCCGCGTGGCGGGCCC

GCGCGTGGGCGATGTGAACCCGAGCCGCGGCGGCCCGCGCGGCGCGCCGGG

CGGCGGCTTTGTGCCGCAGATGGCGGGCGTGCCGGAAAGCCCGTTTAGCCGC

ACCGGCGAAGGCCTGGATATTCGCGGCACCCAGGGCTTTCCGTGGGTGAGCC

CGAGCCCGCCGCAGCAGCGCCTGCCGCTGCTGGAATGCACCCCGCAGAGCCA

GAGCGAAAGCAAAAAAAACCGCCGCGGCGGCCGCGAAGATATTCTGGAAAA

ATGGATTACCACCCGCCGCAAAGCGGAAGAACTGGAAAAAGATCTGCGCAA

AGCGCGCAAAACCATTAAAAAACTGGAAGATGAAAACCCGTGGCTGGGCAA

CATTATTGGCATTATTCGCAAAGGCAAAGATGGCGAAGGCGCGCCGCCGGCG

AAACGCCCGCGCACCGATCAGATGGAAATTGATAGCGGCACCGGCAAACGCC

CGCATAAAAGCGGCTTTACCGATAAAGAACGCGAAGATCATCGCCGCCGCAA

AGCGCTGGAAAACAAAAAAAACAGCTGAGCAGCGGCGGCAAAAAACCTGAG

CCGCGAAGAAGAAGAAGAACTGGGCCGCCTGACCGTGGAAGATGAAGAACG

CCGCCGCCGCGTGGCGGGCCCGCGCACCGGCGATGTGAACCTGAGCGGCGGC

GGCCCGCGCGGCGCGCCGGGCGGCGGCTTTGTGCCGCGCATGGAAGGCGTGC

CGGAAAGCCCGTTTACCCGCACCGGCGAAGGCCTGGATATTCGCGGCAACCA

GGGCTTTCCGTGGGTGCGCCCGAGCCCGCCGCAGCAGCGCCTGCCGCTGCTG

GAATGCACCCCGCAGGGCACCAACCTGAGCACCAGCAACCCGCTGGGCTTTT

TTCCGGATCATCAGCTGGATCCGGCGTTTCGCGCGAACAGCGCGAACCCGGA

TTGGGATTTTAACCCGAACAAAGATACCTGGCCGGATGCGAACAAAGTGGGC

GGCCAGAACCTGAGCACCAGCAACCCGCTGGGCTTTTTTCCGGATCATCAGCT
```

```
GGATCCGGCGTTTCGCGCGAACACCGCGAACCCGGATTGGGATTTTAACCCG

AACAAAGATACCTGGCCGGATGCGAACAAAGTGGGCTGATGAG↓AATTCCGT

SEQ ID NO: 22: delta 3 optimized
GCCGGCACCAATCTGTCTACCTCAAATCCCCTGGGCTTCTTCCCCGATCATCA

GCTGGACCCTGCCTTCCGAGCAAATTCCGCTAATCCTGATTGGGATTTCAACC

CAAATAAGGACACATGGCCAGATGCCAACAAGGTCGGCGGCCAGAACCTGTC

CACCTCTAATCCTCTGGGCTTCTTTCCAGACCACCAGCTGGATCCCGCCTTCA

GGGCCAACACAGCCAATCCCGACTGGGACTTCAACCCTAATAAGGACACCTG

GCCTGACGCCAACAAGGTCGGCAGCAGGTCCGAGTCTAAGAAGAATAGGGG

AGGAAGGGAGGAGATCCTGGAGCAGTGGGTGGGAGCACGCAAGAAGCTGGA

GGAGCTGGAGCGGGACCTGAGAAAGATCAAGAAGAAGATCAAGAAGCTGGA

GGAGGAGAACCCCTGGCTGGGCAATATCAAGGGCATCCTGGGCAAGAAGGA

TCGGGAGGGAGAGGGAGCACCACCTGCAAAGAGGGCCAGAGCCGACCAGAT

GGAGGTGGATTCCGGACCAAGGAAGCGCCCTTTCAGAGGAGAGTTTACAGAC

AAGGAGCGGAGAGATCACAGGCGCCGGAAGGCCCTGGAGAACAAGCGGAAG

CAGCTGAGCTCCGGCGGCAAGAGCCTGTCCAAGGAGGAGGAGGAGGAGCTG

AGAAAGCTGACCGAGGAGGACGAGAGAAGGGAGAGGAGGGTGGCCGGCCCC

AGGGTGGGCGGCGTGAACCCTCTGGAGGGAGGAACAAGGGGAGCACCAGGA

GGAGGCTTCGTGCCTTCCATGCAGGGCGTGCCCGAGTCTCCTTTTGCCAGGAC

CGGAGAGGGCCTGGACGTGCGCGGCAATCAGGGCTTCCCATGGGACATCCTG

TTTCCCGCCGATCCACCCTTCTCTCCCCAGAGCTGCAGGCCTCAGTCTCGCAG

CGAGTCCAAGAAGAACAGAGGCGGAAGGGAGGAGGTGCTGGAGCAGTGGGT

GAATGGCAGGAAGAAGCTGGAAGAACTGGAGAGGGAGCTGAGAAGGGCCCG

CAAGAAGATCAAGAAGCTGGAAGACGATAATCCTTGGCTGGGCAATGTGAAA

GGCATCCTGGGCAAGAAGGACAAGGATGGAGAGGGAGCACCTCCAGCAAAG

AGGGCAAGAACAGACCAGATGGAGATCGATTCTGGACCAAGGAAGCGCCCC

CTGAGGGGAGGCTTCACCGACCGGGAGAGACAGGATCACCGCCGGAGAAAG

GCCCTGAAGAACAAGAAGAAGCAGCTGAGCGCCGGCGGCAAGTCTCTGAGT

AAAGAAGAAGAGGAGGAGCTGAAGCGGCTGACCAGAGAGGACGAGGAGCG

GAAGAAGGAGGAGCACGGCCCAAGCAGACTGGGAGTGAATCCATCCGAGGG

AGGACCTAGAGGCGCCCCTGGCGGCGGCTTCGTGCCTTCTATGCAGGGCATC

CCAGAGAGCAGGTTTACCAGGACAGGCGAAGGCCTGGACGTGCGGGGCTCCA

GAGGCTTTCCCCAGGACATCCTGTTCCCTTCTGATCCCCCTTTTTCCCCACAGT

CTTGTAGGCCCCAGGGCACCAACCTGTCCACATCTAACCCACTGGGCTTCTTT

CCTGATCACCAGCTGGATCCAGCCTTCCGCGCCAACTCCGCCAATCCAGACTG

GGACTTCAACCCCAATAAGGACACATGGCCTGATGCTAACAAGGTCGGAGGC

CAGAACCTGAGCACCTCCAATCCCCTGGGCTTCTTTCCTGACCACCAGCTGGA

TCCTGCCTTCCGCGCCAACACAGCTAACCCTGATTGGGACTTCAACCCAAATA

AGGATACCTGGCCTGATGCAAACAAGGTCGGAGGAAGCGGAGCTACTAACTT

CAGCCTGCTGAAGCAGGCTGGAGACGTGGAGGAGAACCCTGGACCTATGGGC

ACCAACCTGTCTACAAGCAATCCACTGGGCTTCTTTCCCGACCATCAGCTGGA
```

-continued

```
CCCAGCCTTCAGGGCCAACAGCGCCAACCCTGACTGGGACTTCAACCCAAAT

AAGGACACGTGGCCTGATGCCAACAAGGTCGGAGGACAAAACCTGTCCACCT

CTAACCCCTGGGCTTCTTTCCCGATCATCAATTAGACCCAGCCTTCCGCGCT

AACACTGCTAACCCTGACTGGGACTTCAACCCGAATAAGGATACTTGGCCTG

ATGCCAATAAGGTCGGCAGCCAGTCCGAGACAAGGAGGGGCCGGAGAGGAA

CCAGGGAGGAGACACTGGAGAAGTGGATCACCGCCAGAAAGAAGGCCGAGG

AGCTGGAGAAGGACCTGAGGAAGACCCGCAAGACAATCAAGAAGCTGGAAG

AAGAGAACCCTTGGCTGGGCAATATCGTGGGCATCATCAGAAAGGGCAAGGA

CGGCGAGGGAGCACCACCAGCCAAGAGGCCACGCACAGATCAGATGGAAGT

GGATAGCGGACCAGGCAAGAGGCCTCACAAGTCCGGCTTCACCGACAAGGA

GAGGGAGGACCATAGGCGCCGGAAGGCCCTGGAAAACAAGAAGAAGCAATT

ATCCGCCGGCGGCAAGATCCTGTCTAAAGAAGAGGAAGAAGAGC

TGAGAAGGCTGACCGACGAGGATGAGGAGAGGAAGAGGAGGGTGGCAGGAC

CTAGAGTGGGCGACGTGAATCCATCCAGGGGAGGACCAAGAGGAGCACCAG

GAGGCGGCTTCGTGCCACAGATGGCAGGAGTGCCAGAGAGCCCCTTTTCCAG

GACAGGAGAGGGCCTGGATATCAGGGGAACCCAGGGCTTTCCTTGGGTGTCT

CCAAGCCCTCCACAGCAGCGGCTGCCACTGCTGGAGTGCACACCCCAGTCCC

AGTCTGAGAGCAAGAAGAACAGAAGGGGCGGCAGAGAGGACATCCTGGAAA

AATGGATCACCACACGCAGAAAAGCTGAAGAACTGGAAAAGGACCTGCGGA

AGGCCAGAAAGACCATCAAGAAGCTGGAGGATGAAAATCCATGGCTGGGAA

ATATCATCGGCATCATCCGGAAGGGCAAGGACGGGGAAGGCGCACCACCTGC

AAAGCGGCCCAGGACCGATCAGATGGAAATCGATTCTGGAACCGGCAAGCG

GCCTCACAAGAGTGGCTTCACCGATAAGGAGAGAGAGGATCACAGAAGGCG

CAAGGCCCTGGAGAACAAGAAGAAGCAATTAAGCAGCGGCGGCAAGAATCT

GTCCAGAGAAGAGGAAGAGGAGCTGGGCAGACTGACAGTGGAGGACGAGGA

GCGGAGAAGGCGCGTGGCAGGACCAAGAACCGGCGATGTGAACCTGTCCGG

AGGAGGACCAAGGGGAGCACCTGGGGAGGCTTCGTGCCAAGGATGGAGGG

AGTGCCTGAGTCCCCCTTCACCAGAACCGGCGAAGGCCTGGACATCAGGGGC

AATCAGGGATTCCCATGGGTGCGGCCCTCCCCACCCCAGCAGAGACTGCCTC

TGCTGGAGTGTACCCCACAGGGCACTAACCTGTCCACCTCTAACCCGTTAGGC

TTCTTTCCTGACCATCAATTAGATCCCGCCTTCCGGGCCAACAGCGCCAATCC

TGATTGGGACTTCAACCCGAATAAGGACACCTGGCCCGACGCAAACAAGGTC

GGAGGGCAAAACCTGAGCACCTCCAACCCTTTAGGCTTCTTTCCAGATCATCA

GCTGGATCCAGCCTTTAGAGCCAATACCGCCAACCCTGACTGGGATTTCAACC

CTAACAAAGATACCTGGCCCGACGCTAACAAAGTGGGA
``` delta 3 codon optimized with restriction sites (HindIII/EcoRI)

SEQ ID NO: 23

A↓AGCTT*GCACC*ATGGCCGGCACCAATCTGTCTACCTCAAATCCCCTGGGCTT

```
CTTCCCCGATCATCAGCTGGACCCTGCCTTCCGAGCAAATTCCGCTAATCCTG

ATTGGGATTTCAACCCAAATAAGGACACATGGCCAGATGCCAACAAGGTCGG

CGGCCAGAACCTGTCCACCTCTAATCCTCTGGGCTTCTTTCCAGACCACCAGC
```

```
-continued
TGGATCCCGCCTTCAGGGCCAACACAGCCAATCCCGACTGGGACTTCAACCC

TAATAAGGACACCTGGCCTGACGCCAACAAGGTCGGCAGCAGGTCCGAGTCT

AAGAAGAATAGGGGAGGAAGGGAGGAGATCCTGGAGCAGTGGGTGGGAGCA

CGCAAGAAGCTGGAGGAGCTGGAGCGGGACCTGAGAAAGATCAAGAAGAAG

ATCAAGAAGCTGGAGGAGGAGAACCCCTGGCTGGGCAATATCAAGGGCATCC

TGGGCAAGAAGGATCGGGAGGGAGAGGGAGCACCACCTGCAAAGAGGGCCA

GAGCCGACCAGATGGAGGTGGATTCCGGACCAAGGAAGCGCCCTTTCAGAGG

AGAGTTTACAGACAAGGAGCGGAGAGATCACAGGCGCCGGAAGGCCCTGGA

GAACAAGCGGAAGCAGCTGAGCTCCGGCGGCAAGAGCCTGTCCAAGGAGGA

GGAGGAGGAGCTGAGAAAGCTGACCGAGGAGGACGAGAGAAGGGAGAGGA

GGGTGGCCGGCCCCAGGGTGGGCGGCGTGAACCCTCTGGAGGGAGGAACAA

GGGGAGCACCAGGAGGAGGCTTCGTGCCTTCCATGCAGGGCGTGCCCGAGTC

TCCTTTTGCCAGGACCGGAGAGGGCCTGGACGTGCGCGGCAATCAGGGCTTC

CCATGGGACATCCTGTTTCCCGCCGATCCACCCTTCTCTCCCCAGAGCTGCAG

GCCTCAGTCTCGCAGCGAGTCCAAGAAGAACAGAGGCGGAAGGGAGGAGGT

GCTGGAGCAGTGGGTGAATGGCAGGAAGAAGCTGGAAGAACTGGAGAGGGA

GCTGAGAAGGGCCCGCAAGAAGATCAAGAAGCTGGAAGACGATAATCCTTG

GCTGGGCAATGTGAAAGGCATCCTGGGCAAGAAGGACAAGGATGGAGAGGG

AGCACCTCCAGCAAAGAGGGCAAGAACAGACCAGATGGAGATCGATTCTGG

ACCAAGGAAGCGCCCCCTGAGGGGAGGCTTCACCGACCGGGAGAGACAGGA

TCACCGCCGGAGAAAGGCCCTGAAGAACAAGAAGAAGCAGCTGAGCGCCGG

CGGCAAGTCTCTGAGTAAAGAAGAAGAGGAGGAGCTGAAGCGGCTGACCAG

AGAGGACGAGGAGCGGAAGAAGGAGGAGCACGGCCCAAGCAGACTGGGAGT

GAATCCATCCGAGGGAGGACCTAGAGGCGCCCCTGGCGGCGGCTTCGTGCCT

TCTATGCAGGGCATCCCAGAGAGCAGGTTTACCAGGACAGGCGAAGGCCTGG

ACGTGCGGGCTCCAGAGGCTTTCCCCAGGACATCCTGTTCCCTTCTGATCCC

CCTTTTTCCCCACAGTCTTGTAGGCCCCAGGGCACCAACCTGTCCACATCTAA

CCCACTGGGCTTCTTTCCTGATCACCAGCTGGATCCAGCCTTCCGCGCCAACT

CCGCCAATCCAGACTGGGACTTCAACCCCAATAAGGACACATGGCCTGATGC

TAACAAGGTCGGAGGCCAGAACCTGAGCACCTCCAATCCCCTGGGCTTCTTTC

CTGACCACCAGCTGGATCCTGCCTTCCGCGCCAACACAGCTAACCCTGATTGG

GACTTCAACCCAAATAAGGATACCTGGCCTGATGCAAACAAGGTCGGAGGAA

GCGGAGCTACTAACTTCAGCCTGCTGAAGCAGGCTGGAGACGTGGAGGAGAA

CCCTGGACCTATGGGCACCAACCTGTCTACAAGCAATCCACTGGGCTTCTTTC

CCGACCATCAGCTGGACCCAGCCTTCAGGGCCAACAGCGCCAACCCTGACTG

GGACTTCAACCCAAATAAGGACACGTGGCCTGATGCCAACAAGGTCGGAGGA

CAAAACCTGTCCACCTCTAACCCCCTGGGCTTCTTTCCCGATCATCAATTAGA

CCCAGCCTTCCGCGCTAACACTGCTAACCCTGACTGGGACTTCAACCCGAATA

AGGATACTTGGCCTGATGCCAATAAGGTCGGCAGCCAGTCCGAGACAAGGAG

GGGCCGGAGAGGAACCAGGGAGGAGACACTGGAGAAGTGGATCACCGCCAG

AAAGAAGGCCGAGGAGCTGGAGAAGGACCTGAGGAAGACCCGCAAGACAAT
```

```
CAAGAAGCTGGAAGAAGAGAACCCTTGGCTGGGCAATATCGTGGGCATCATC
AGAAAGGGCAAGGACGGCGAGGGAGCACCACCAGCCAAGAGGCCACGCACA
GATCAGATGGAAGTGGATAGCGGACCAGGCAAGAGGCCTCACAAGTCCGGCT
TCACCGACAAGGAGAGGGAGGACCATAGGCGCCGGAAGGCCCTGGAAAACA
AGAAGAAGCAATTATCCGCCGGCGGCAAGATCCTGTCTAAAGAAGAGGAAG
AAGAGC
TGAGAAGGCTGACCGACGAGGATGAGGAGAGGAAGAGGAGGGTGGCAGGAC
CTAGAGTGGGCGACGTGAATCCATCCAGGGGAGGACCAAGAGGAGCACCAG
GAGGCGGCTTCGTGCCACAGATGGCAGGAGTGCCAGAGAGCCCCTTTTCCAG
GACAGGAGAGGGCCTGGATATCAGGGGAACCCAGGGCTTTCCTTGGGTGTCT
CCAAGCCCTCCACAGCAGCGGCTGCCACTGCTGGAGTGCACACCCCAGTCCC
AGTCTGAGAGCAAGAAGAACAGAAGGGGCGGCAGAGAGGACATCCTGGAAA
AATGGATCACCACACGCAGAAAAGCTGAAGAACTGGAAAAGGACCTGCGGA
AGGCCAGAAAGACCATCAAGAAGCTGGAGGATGAAAATCCATGGCTGGGAA
ATATCATCGGCATCATCCGGAAGGGCAAGGACGGGGAAGGCGCACCACCTGC
AAAGCGGCCCAGGACCGATCAGATGGAAATCGATTCTGGAACCGGCAAGCG
GCCTCACAAGAGTGGCTTCACCGATAAGGAGAGAGAGGATCACAGAAGGCG
CAAGGCCCTGGAGAACAAGAAGAAGCAATTAAGCAGCGGCGGCAAGAATCT
GTCCAGAGAAGAGGAAGAGGAGCTGGGCAGACTGACAGTGGAGGACGAGGA
GCGGAGAAGGCGCGTGGCAGGACCAAGAACCGGCGATGTGAACCTGTCCGG
AGGAGGACCAAGGGGAGCACCTGGGGGAGGCTTCGTGCCAAGGATGGAGGG
AGTGCCTGAGTCCCCCTTCACCAGAACCGGCGAAGGCCTGGACATCAGGGGC
AATCAGGGATTCCCATGGGTGCGGCCCTCCCCACCCCAGCAGAGACTGCCTC
TGCTGGAGTGTACCCCACAGGGCACTAACCTGTCCACCTCTAACCCGTTAGGC
TTCTTTCCTGACCATCAATTAGATCCCGCCTTCCGGGCCAACAGCGCCAATCC
TGATTGGGACTTCAACCCGAATAAGGACACCTGGCCCGACGCAAACAAGGTC
GGAGGGCAAAACCTGAGCACCTCCAACCCTTTAGGCTTCTTTCCAGATCATCA
GCTGGATCCAGCCTTTAGAGCCAATACCGCCAACCCTGACTGGGATTTCAACC
CTAACAAAGATACCTGGCCCGACGCTAACAAAGTGGGATGATGAG↓AATTCC
GT
```

Delta 3 protein                                         SEQ ID NO: 24

```
MAGTNLSTSNPLGFFPDHQLDPAPRANSANPDWDFNPNKDTWPDANKVGGQNL
STSNPLGFFPDHQLDPAFRANTANPDWDFNPNKDTWPDANKVGSRSESKKNRG
GREEILEQWVGARKKLEELERDLRKIKKKIKKLEEENPWLGNIKGILGKKDREGE
GAPPAKRARADQMEVDSGPRKRPFRGEFTDKERRDHRRRKALENKRKQLSSGG
KSLSKEEEEELRKLTEEDERRERRVAGPRVGGVNPLEGGTRGAPGGGFVPSMQG
VPESPFARTGEGLDVRGNQGFPWDILFPADPPFSPQSCRPQSRSESKKNRGGREEV
LEQWVNGRKKLEELERELRRARKKIKKLEDDNPWLGNVKGILGKKDKDGEGAP
PAKRARTDQMEIDSGPRKRPLRGGFTDRERQDHRRRKALKNKKKQLSAGGKSLS
KEEEEELKRLTREDEERKKEEHGPSRLGVNPSEGGPRGAPGGGFVPSMQGIPESR
```

-continued

```
FTRTGEGLDVRGSRGFPQDILFPSDPPFSPQSCRPQGTNLSTSNPLGFFPDHQLDPA

IRANSANPDWDFNPNKDTWPDANKVGGQNLSTSNPLGFFPDHQLDPAFRANTA

NPDWDFNPNKDTWPDANKVGGSGATNFSLLKQAGDVEENPGPMGTNLSTSNPL

GFFPDHQLDPAFRANSANPDWDFNPNKDTWPDANKVGGQNLSTSNPLGFFPDH

QLDPAFRANTANPDWDFNPNKDTWPDANKVGSQSETRRGRRGTREETLEKWIT

ARKKAEELEKDLRKTRKTIKKLEEENPWLGNIVGIIRKGKDGEGAPPAKRPRTDQ

MEVDSGPGKRPHKSGFTDKEREDHRRRKALENKKKQLSAGGKILSKEEEEELRR

LTDEDEERKRRVAGPRVGDVNPSRGGPRGAPGGGFVPQMAGVPESPFSRTGEGL

DIRGTQGFPWVSPSPPQQRLPLLECTPQSQSESKKNRRGGREDILEKWITTRRKAE

ELEKDLRKARKTIKKLEDENPWLGNIIGIIRKGKDGEGAPPAKRPRTDQMEIDSGT

GKRPHKSGFTDKEREDHRRRKALENKKKQLSSGGKNLSREEEEELGRLTVEDEE

RRRRVAGPRTGDVNLSGGGPRGAPGGGFVPRMEGVPESPFTRTGEGLDIRGNQG

FPWVRPSPPQQRLPLLECTPQGTNLSTSNPLGFFPDHQLDPAFRANSANPDWDFN

PNKDTWPDANKVGGQNLSTSNPLGFFPDHQLDPAFRANTANPDWDFNPNKDTW

PDANKVG
``` delta 4 wt                                                SEQ ID NO: 25

```
AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGGGCACCAACCTGAGCACCAGCAACCCGCTGG

GCTTTTTTCCGGATCATCAGCTGGATCCGGCGTTTCGCGCGAACAGCGCGAAC

CCGGATTGGGATTTTAACCCGAACAAAGATACCTGGCCGGATGCGAACAAAG

TGGGCGGCCAGAACCTGAGCACCAGCAACCCGCTGGGCTTTTTTCCGGATCAT

CAGCTGGATCCGGCGTTTCGCGCGAACACCGCGAACCCGGATTGGGATTTTA

ACCCGAACAAAGATACCTGGCCGGATGCGAACAAAGTGGGCGGAAGCGGAGCT

ACTAACTTCAGCCTGCTGAAGCAGGCTGGAGACGTGGAGGAGAACCCTGGACCTATGAG

CCGCAGCGAAAGCAAAAAAAACCGCGGCGGCCGCGAAGAAGTGCTGGAACA

GTGGGTGAACGGCCGCAAAAAACTGGAAGAACTGGAACGCGAACTGCGCCG

CGCGCGCAAAAAAATTAAAAAACTGGAAGATGATAACCCGTGGCTGGGCAA

CGTGAAAGGCATTCTGGGCAAAAAAGATAAAGATGGCGAAGGCGCGCCGCC

GGCGAAACGCGCGCGCACCGATCAGATGGAAATTGATAGCGGCCCGCGCAA

ACGCCCGCTGCGCGGCGGCTTTACCGATCGCGAACGCCAGGATCATCGCCGC
```

```
CGCAAAGCGCTGAAAAACAAAAAAAAACAGCTGAGCGCGGGCGGCAAAAGC

CTGAGCAAAGAAGAAGAAGAAGAACTGAAACGCCTGACCCGCGAAGATGAA

GAACGCAAAAAGAAGAACATGGCCCGAGCCGCCTGGGCGTGAACCCGAGC

GAAGGCGGCCCGCGCGGCGCGCCGGGCGGCGGCTTTGTGCCGAGCATGCAGG

GCATTCCGGAAAGCCGCTTTACCCGCACCGGCGAAGGCCTGGATGTGCGCGG

CAGCCGCGGCTTTCCGCAGGATATTCTGTTTCCGAGCGATCCGCCGTTTAGCC

CGCAGAGCTGCCGCCCGCAGGGCACCAACCTGAGCACCAGCAACCCGCTGGG

CTTTTTTCCGGATCATCAGCTGGATCCGGCGTTTCGCGCGAACAGCGCGAACC

CGGATTGGGATTTTAACCCGAACAAAGATACCTGGCCGGATGCGAACAAAGT

GGGCGGCCAGAACCTGAGCACCAGCAACCCGCTGGGCTTTTTTCCGGATCAT

CAGCTGGATCCGGCGTTTCGCGCGAACACCGCGAACCCGGATTGGGATTTTA

ACCCGAACAAAGATACCTGGCCGGATGCGAACAAAGTGGGCGGAAGCGGAGCT

ACTAACTTCAGCCTGCTGAAGCAGGCTGGAGACGTGGAGGAGAACCCTGGACCTATGAG

CCAGAGCGAAACCCGCCGCGGCCGCCGCGGCACCCGCGAAGAAACCCTGGA

AAAATGGATTACCGCGCGCAAAAAAGCGGAAGAACTGGAAAAAGATCTGCG

CAAAACCCGCAAAACCATTAAAAAACTGGAAGAAGAAACCCGTGGCTGGG

CAACATTGTGGGCATTATTCGCAAAGGCAAAGATGGCGAAGGCGCGCCGCCG

GCGAAACGCCCGCGCACCGATCAGATGGAAGTGGATAGCGGCCCGGGCAAA

CGCCCGCATAAAAGCGGCTTTACCGATAAAGAACGCGAAGATCATCGCCGCC

GCAAAGCGCTGGAAAACAAAAAAAAACAGCTGAGCGCGGGCGGCAAAATTC

TGAGCAAAGAAGAAGAAGAACTGCGCCGCCTGACCGATGAAGATGAAG

AACGCAAACGCCGCGTGGCGGGCCCGCGCGTGGGCGATGTGAACCCGAGCC

GCGGCGGCCCGCGCGGCGCGCCGGGCGGCGGCTTTGTGCCGCAGATGGCGGG

CGTGCCGGAAAGCCCGTTTAGCCGCACCGGCGAAGGCCTGGATATTCGCGGC

ACCCAGGGCTTTCCGTGGGTGAGCCCGAGCCCGCCGCAGCAGCGCCTGCCGC

TGCTGGAATGCACCCCGCAGGGCACCAACCTGAGCACCAGCAACCCGCTGGG

CTTTTTTCCGGATCATCAGCTGGATCCGGCGTTTCGCGCGAACAGCGCGAACC

CGGATTGGGATTTTAACCCGAACAAAGATACCTGGCCGGATGCGAACAAAGT

GGGCGGCCAGAACCTGAGCACCAGCAACCCGCTGGGCTTTTTTCCGGATCAT

CAGCTGGATCCGGCGTTTCGCGCGAACACCGCGAACCCGGATTGGGATTTTA

ACCCGAACAAAGATACCTGGCCGGATGCGAACAAAGTGGGCGGAAGCGGAGCT

ACTAACTTCAGCCTGCTGAAGCAGGCTGGAGACGTGGAGGAGAACCCTGGACCTATGAG

CCAGAGCGAAAGCAAAAAAAACCGCCGCGGCCGCCGCGAAGATATTCTGGA

AAAATGGATTACCACCCGCCGCAAAGCGGAAGAACTGGAAAAAGATCTGCG

CAAAGCGCGCAAAACCATTAAAAAACTGGAAGATGAAACCCGTGGCTGGG

CAACATTATTGGCATTATTCGCAAAGGCAAAGATGGCGAAGGCGCGCCGCCG

GCGAAACGCCCGCGCACCGATCAGATGGAAATTGATAGCGGCACCGGCAAA

CGCCCGCATAAAAGCGGCTTTACCGATAAAGAACGCGAAGATCATCGCCGCC

GCAAAGCGCTGGAAAACAAAAAAAAACAGCTGAGCAGCGGCGGCAAAAACC

TGAGCCGCGAAGAAGAAGAAGAACTGGGCCGCCTGACCGTGGAAGATGAAG
```

-continued

```
AACGCCGCCGCCGCGTGGCGGGCCCGCGCACCGGCGATGTGAACCTGAGCGG

CGGCGGCCCGCGCGGCGCGCCGGGCGGCGGCTTTGTGCCGCGCATGGAAGGC

GTGCCGGAAAGCCCGTTTACCCGCACCGGCGAAGGCCTGGATATTCGCGGCA

ACCAGGGCTTTCCGTGGGTGCGCCCGAGCCCGCCGCAGCAGCGCCTGCCGCT

GCTGGAATGCACCCCGCAGGGCACCAACCTGAGCACCAGCAACCCGCTGGGC

TTTTTTCCGGATCATCAGCTGGATCCGGCGTTTCGCGCGAACAGCGCGAACCC

GGATTGGGATTTTAACCCGAACAAAGATACCTGGCCGGATGCGAACAAAGTG

GGCGGCCAGAACCTGAGCACCAGCAACCCGCTGGGCTTTTTTCCGGATCATC

AGCTGGATCCGGCGTTTCGCGCGAACACCGCGAACCCGGATTGGGATTTTAA

CCCGAACAAAGATACCTGGCCGGATGCGAACAAAGTGGGC
``` delta 4 wt with restriction sites (HindIII/EcoRI)        SEQ ID NO: 26

```
A|AGCTTGCACCATGGCCAGCCGCAGCGAAAGCAAAAAAAACCGCGGCGGCCG

CGAAGAAATTCTGGAACAGTGGGTGGGCGCGCGCAAAAAACTGGAAGAACT

GGAACGCGATCTGCGCAAAATTAAAAAAAAAATTAAAAAACTGGAAGAAGA

AAACCCGTGGCTGGGCAACATTAAAGGCATTCTGGGCAAAAAAGATCGCGAA

GGCGAAGGCGCGCCGCCGGCGAAACGCGCGCGCGCGGATCAGATGGAAGTG

GATAGCGGCCCGCGCAAACGCCCGTTTCGCGGCGAATTTACCGATAAAGAAC

GCCGCGATCATCGCCGCCGCAAAGCGCTGGAAAACAAACGCAAACAGCTGA

GCAGCGGCGGCAAAAGCCTGAGCAAAGAAGAAGAAGAAGAACTGCGCAAAC

TGACCGAAGAAGATGAACGCCGCGAACGCCGCGTGGCGGGCCCGCGCGTGG

GCGGCGTGAACCCGCTGGAAGGCGGCACCCGCGGCGCGCCGGGCGGCGGCTT

TGTGCCGAGCATGCAGGGCGTGCCGGAAAGCCCGTTTGCGCGCACCGGCGAA

GGCCTGGATGTGCGCGGCAACCAGGGCTTTCCGTGGGATATTCTGTTTCCGGC

GGATCCGCCGTTTAGCCCGCAGAGCTGCCGCCCGCAGGGCACCAACCTGAGC

ACCAGCAACCCGCTGGGCTTTTTTCCGGATCATCAGCTGGATCCGGCGTTTCG

CGCGAACAGCGCGAACCCGGATTGGGATTTTAACCCGAACAAAGATACCTGG

CCGGATGCGAACAAAGTGGGCGGCCAGAACCTGAGCACCAGCAACCCGCTG

GGCTTTTTTCCGGATCATCAGCTGGATCCGGCGTTTCGCGCGAACACCGCGAA

CCCGGATTGGGATTTTAACCCGAACAAAGATACCTGGCCGGATGCGAACAAA

GTGGGCGGAAGCGGAGCTACTAACTTCAGCCTGCTGAAGCAGGCTGGAGACGTGGAGGA

GAACCCTGGACCTATGAGCCGCAGCGAAAGCAAAAAAAACCGCGGCGGCCGCG

AAGAAGTGCTGGAACAGTGGGTGAACGGCCGCAAAAAACTGGAAGAACTGG

AACGCGAACTGCGCCGCGCGCAAAAAAATTAAAAAACTGGAAGATGATA

ACCCGTGGCTGGGCAACGTGAAAGGCATTCTGGGCAAAAAAGATAAAGATG

GCGAAGGCGCGCCGCCGGCGAAACGCGCGCGCACCGATCAGATGGAAATTG

ATAGCGGCCCGCGCAAACGCCCGCTGCGCGGCGGCTTTACCGATCGCGAACG

CCAGGATCATCGCCGCCGCAAAGCGCTGAAAAACAAAAAAAAACAGCTGAG

CGCGGGCGGCAAAAGCCTGAGCAAAGAAGAAGAAGAAGAACTGAAACGCCT

GACCCGCGAAGATGAAGAACGCAAAAAAGAAGAACATGGCCCGAGCCGCCT

GGGCGTGAACCCGAGCGAAGGCGGCCCGCGCGGCGCGCCGGGCGGCGGCTT

TGTGCCGAGCATGCAGGGCATTCCGGAAAGCCGCTTTACCCGCACCGGCGAA
```

```
GGCCTGGATGTGCGCGGCAGCCGCGGCTTTCCGCAGGATATTCTGTTTCCGAG

CGATCCGCCGTTTAGCCCGCAGAGCTGCCGCCCGCAGGGCACCAACCTGAGC

ACCAGCAACCCGCTGGGCTTTTTTCCGGATCATCAGCTGGATCCGGCGTTTCG

CGCGAACAGCGCGAACCCGGATTGGGATTTTAACCCGAACAAAGATACCTGG

CCGGATGCGAACAAAGTGGGCGGCCAGAACCTGAGCACCAGCAACCCGCTG

GGCTTTTTTCCGGATCATCAGCTGGATCCGGCGTTTCGCGCGAACACCGCGAA

CCCGGATTGGGATTTTAACCCGAACAAAGATACCTGGCCGGATGCGAACAAA

GTGGGCGGAAGCGGAGCTACTAACTTCAGCCTGCTGAAGCAGGCTGGAGACGTGGAGGA

GAACCCTGGACCTATGAGCCAGAGCGAAACCCGCCGCGGCCGCCGCGGCACCC

GCGAAGAAACCCTGGAAAAATGGATTACCGCGCGCAAAAAAGCGGAAGAAC

TGGAAAAAGATCTGCGCAAAACCCGCAAAACCATTAAAAAACTGGAAGAAG

AAAACCCGTGGCTGGGCAACATTGTGGGCATTATTCGCAAAGGCAAAGATGG

CGAAGGCGCGCCGCCGGCGAAACGCCCGCGCACCGATCAGATGGAAGTGGA

TAGCGGCCCGGGCAAACGCCCGCATAAAAGCGGCTTTACCGATAAAGAACGC

GAAGATCATCGCCGCCGCAAAGCGCTGGAAAACAAAAAAAAACAGCTGAGC

GCGGGCGGCAAAATTCTGAGCAAAGAAGAAGAAGAAGAACTGCGCCGCCTG

ACCGATGAAGATGAAGAACGCAAACGCCGCGTGGCGGGCCCGCGCGTGGGC

GATGTGAACCCGAGCCGCGGCGGCCCGCGCGGCGCGCCGGGCGGCGGCTTTG

TGCCGCAGATGGCGGGCGTGCCGGAAAGCCCGTTTAGCCGCACCGGCGAAGG

CCTGGATATTCGCGGCACCCAGGGCTTTCCGTGGGTGAGCCCGAGCCCGCCG

CAGCAGCGCCTGCCGCTGCTGGAATGCACCCCGCAGGGCACCAACCTGAGCA

CCAGCAACCCGCTGGGCTTTTTTCCGGATCATCAGCTGGATCCGGCGTTTCGC

GCGAACAGCGCGAACCCGGATTGGGATTTTAACCCGAACAAAGATACCTGGC

CGGATGCGAACAAAGTGGGCGGCCAGAACCTGAGCACCAGCAACCCGCTGG

GCTTTTTTCCGGATCATCAGCTGGATCCGGCGTTTCGCGCGAACACCGCGAAC

CCGGATTGGGATTTTAACCCGAACAAAGATACCTGGCCGGATGCGAACAAAG

TGGGCGGAAGCGGAGCTACTAACTTCAGCCTGCTGAAGCAGGCTGGAGACGTGGAGGAG

AACCCTGGACCTATGAGCCAGAGCGAAAGCAAAAAAAACCGCCGCGGCGGCC

GCGAAGATATTCTGGAAAAATGGATTACCACCCGCCGCAAAGCGGAAGAACT

GGAAAAAGATCTGCGCAAAGCGCGCAAAACCATTAAAAAACTGGAAGATGA

AAACCCGTGGCTGGGCAACATTATTGGCATTATTCGCAAAGGCAAAGATGGC

GAAGGCGCGCCGCCGGCGAAACGCCCGCGCACCGATCAGATGGAAATTGAT

AGCGGCACCGGCAAACGCCCGCATAAAAGCGGCTTTACCGATAAAGAACGC

GAAGATCATCGCCGCCGCAAAGCGCTGGAAAACAAAAAAAAACAGCTGAGC

AGCGGCGGCAAAAACCTGAGCCGCGAAGAAGAAGAAGAACTGGGCCGCCTG

ACCGTGGAAGATGAAGAACGCCGCCGCCGCGTGGCGGGCCCGCGCACCGGC

GATGTGAACCTGAGCGGCGGCGGCCCGCGCGGCGCGCCGGGCGGCGGCTTTG

TGCCGCGCATGGAAGGCGTGCCGGAAAGCCCGTTTACCCGCACCGGCGAAGG

CCTGGATATTCGCGGCAACCAGGGCTTTCCGTGGGTGCGCCCGAGCCCGCCG

CAGCAGCGCCTGCCGCTGCTGGAATGCACCCCGCAGGGCACCAACCTGAGCA
```

```
CCAGCAACCCGCTGGGCTTTTTTCCGGATCATCAGCTGGATCCGGCGTTTCGC

GCGAACAGCGCGAACCCGGATTGGGATTTTAACCCGAACAAAGATACCTGGC

CGGATGCGAACAAAGTGGGCGGCCAGAACCTGAGCACCAGCAACCCGCTGG

GCTTTTTTCCGGATCATCAGCTGGATCCGGCGTTTCGCGCGAACACCGCGAAC

CCGGATTGGGATTTTAACCCGAACAAAGATACCTGGCCGGATGCGAACAAAG

TGGGCTGATGAG↓AATTCCGT
``` delta 4 codon optimized

SEQ ID NO: 27
```
GCCAGTCGGAGCGAATCAAAGAAAAATAGGGGAGGGCGGGAAGAAATCCTGGAGCAGTGG

GTCGGAGCACGAAAGAAACTGGAAGAACTGGAGAGGGACCTGCGCAAGATCAAGAAGAAG

ATCAAGAAGCTGGAGGAGGAGAACCCCTGGCTGGGCAATATCAAGGGCATCCTGGGCAAG

AAGGATCGGGAGGGAGAGGGAGCACCACCTGCAAAGAGGGCCAGAGCCGACCAGATGGAG

GTGGATAGCGGCCCTAGGAAGCGCCCATTCAGAGGCGAGTTTACAGACAAGGAGCGGAGA

GATCACAGGCGCCGGAAGGCCCTGGAGAACAAGCGGAAGCAGCTGAGCTCCGGCGGCAAG

TCCCTGTCTAAGGAGGAGGAGGAGGAGCTGAGAAAGCTGACCGAGGAGGACGAGAGAAGG

GAGAGGAGGGTGGCAGGACCTAGGGTGGGAGGCGTGAACCCACTGGAGGGAGGAACAAGG

GGAGCACCTGGAGGAGGATTCGTGCCATCCATGCAGGGAGTGCCTGAGTCTCCATTTGCC

AGGACCGGAGAGGGCCTGGATGTGCGCGGAAATCAGGGCTTCCCCTGGGACATCCTGTTT

CCTGCCGATCCACCCTTCTCCCCACAGTCTTGCAGGCCACAGGGAACCAACCTGAGCACA

TCCAATCCTCTGGGCTTCTTTCCAGACCACCAGCTGGATCCTGCCTTCAGAGCCAACTCC

GCCAATCCAGACTGGGACTTCAACCCCAATAAGGACACATGGCCTGATGCCAACAAGGTC

GGCGGCCAGAACCTGTCTACCAGCAATCCCCTGGGCTTCTTTCCTGACCACCAGCTGGAT

CCAGCCTTCCGGGCCAACACTGCTAACCCTGATTGGGACTTCAACCCTAATAAGGATACC

TGGCCAGACGCCAACAAGGTCGGCGGAAGCGGAGCTACTAACTTCAGCCTGCTGAAGCAG

GCTGGAGACGTGGAGGAGAACCCTGGACCTATGTCCAGGTCTGAGAGCAAGAAGAATAGG

GGAGGAAGAGAGGAGGTGCTGGAGCAGTGGGTGAACGGCCGCAAGAAGCTGGAGGAGCTG

GAGAGGGAGCTGAGAAGGGCCCGCAAGAAGATCAAGAAGCTGGAAGACGATAATCCTTGG

CTGGGCAATGTGAAAGGCATCCTGGGCAAGAAGGACAAGGATGGAGAGGGAGCACCTCCA

GCAAAGAGGGCAAGAACAGACCAGATGGAGATCGATTCTGGACCAAGGAAGCGCCCTCTG

AGGGGAGGCTTCACCGACCGGGAGAGACAGGATCACCGCCGGAGAAAGGCCCTGAAGAAC

AAGAAGAAGCAGCTGTCCGCCGGCGGCAAGTCCCTGAGCAAAGAAGAGGAAGAGGAGCTG

AAGAGGCTGACCCGCGAGGACGAGGAGCGGAAGAAGGAGGAGCACGACCAAGCAGACTG

GGAGTGAATCCTTCCGAGGGAGGACCAAGAGGAGCACCCGGAGGAGGCTTCGTGCCATCT

ATGCAGGGCATCCCCGAGAGCCGGTTTACCAGAACAGGAGAGGGCCTGGACGTGAGGGGC

TCCCGCGGCTTTCCTCAGGACATCCTGTTCCCATCTGATCCCCCTTTTAGCCCACAGTCC

TGTAGGCCCCAGGGCACTAACCTGAGCACATCCAACCCACTGGGCTTCTTTCCTGATCAT

CAGCTGGACCCAGCCTTCCGCGCCAACAGCGCCAACCCTGACTGGGACTTCAACCCAAAT

AAGGACACATGGCCAGATGCTAACAAGGTCGGAGGACAAAACCTGTCTACCAGCAACCCT

CTGGGCTTCTTTCCCGATCATCAGCTGGACCCCGCCTTCAGGGCCAACACAGCCAATCCC

GACTGGGACTTCAACCCGAATAAGGACACCTGGCCAGATGCAAACAAGGTCGGAGGAAGC

GGAGCTACTAACTTCAGCCTGCTGAAGCAGGCTGGAGACGTGGAGGAGAACCCTGGACCT

ATGAGCCAGTCTGAGACAAGGAGGGGCCGGAGAGGAACCAGGGAGGAGACACTGGAGAAG
```

-continued

```
TGGATCACCGCCAGAAAGAAGGCCGAGGAGCTGGAGAAGGACCTGCGGAAGACCAGAAAG

ACAATCAAGAAGCTGGAAGAAGAGAACCCATGGCTGGGCAATATCGTGGGCATCATCCGC

AAGGGCAAGGACGGCGAGGGAGCACCACCAGCAAAGAGGCCCCGCACAGATCAGATGGAA

GTGGATAGCGGCCCTGGCAAGAGGCCACACAAGTCCGGCTTCACCGACAAGGAGAGGGAG

GACCATAGGCGCCGGAAGGCCCTGGAAAACAAGAAGAAGCAATTATCCGCCGGCGGCAAG

ATCCTGTCCAAAGAGGAAGAAGAGGAGCTGAGAAGGCTGACCGACGAGGATGAGGAGAGG

AAAAGAAGGGTGGCAGGACCAAGAGTGGGCGACGTGAATCCCAGCAGAGGCGGACCAAGA

GGAGCACCTGGAGGCGGCTTCGTGCCCCAGATGGCCGGCGTGCCCGAGTCTCCTTTTAGC

AGAACTGGAGAGGGCCTGGATATCAGGGGAACACAGGGCTTTCCATGGGTGAGCCCATCC

C

CTCCACAGCAGAGGCTGCCACTGCTGGAGTGCACCCCTCAGGGAACCAACCTGTCTACCA

GCAACCCGCTGGGCTTCTTTCCCGACCATCAGCTGGACCCTGCCTTCCGCGCCAACTCCG

CCAACCCTGATTGGGACTTCAACCCGAATAAGGATACCTGGCCCGACGCTAACAAGGTCG

GAGGCCAGAACCTGTCCACCTCTAACCCCTTAGGCTTCTTTCCCGATCACCAGCTGGATC

CCGCCTTCAGAGCCAACACTGCTAACCCCGATTGGGACTTCAACCCGAATAAGGACACGT

GGCCAGACGCTAACAAGGTCGGGGGAAGCGGAGCTACTAACTTCAGCCTGCTGAAGCAGG

CTGGAGACGTGGAGGAGAACCCTGGACCTATGTCGCAGTCCGAGTCTAAGAAGAATAGAA

GGGGCGGCCGGGAGGATATCCTGGAAAAATGGATCACCACACGCAGAAAAGCTGAAGAAC

TGGAAAAGGACCTGAGGAAGGCCCGCAAGACCATCAAGAAGCTGGAGGATGAAAATCCAT

GGCTGGGAAACATCATCGGCATCATCAGAAAGGGCAAGGACGGGGAAGGCGCCCCACCTG

CAAAGCGGCCTAGAACCGATCAGATGGAAATCGATTCTGGCACAGGCAAGCGGCCACACA

AGAGTGGCTTCACCGATAAGGAGAGAGAGGATCACAGAAGGCGCAAGGCCCTGGAGAACA

AGAAGAAGCAATTAAGCAGCGGCGGCAAGAATCTGTCCAGAGAAGAAGAGGAGGAGCTGG

GCAGACTGACAGTGGAGGACGAGGAGCGGAGAAGGCGCGTGGCAGGACCAAGGACCGGCG

ATGTGAACCTGAGCGGAGGAGGACCTAGGGGAGCACCAGGAGGCGGCTTCGTGCCTAGGA

TGGAGGGAGTGCCAGAGTCCCCCTTTACCAGGACTGGCGAGGGCCTGGACATCAGGGGAA

ATCAGGGATTCCCATGGGTGCGGCCTAGCCCACCACAGCAGAGACTGCCACTGCTGGAGT

GTACACCCCAGGGCACAAACCTGAGCACATCCAATCCGCTGGGCTTCTTTCCAGATCATC

AATTAGATCCAGCCTTCAGGGCCAACTCCGCCAATCCGGATTGGGACTTCAACCCGAATA

AGGACACTTGGCCCGACGCAAACAAGGTCGGAGGGCAAAACCTGTCTACCAGCAATCCAC

TTGGCTTCTTTCCTGACCATCAGCTGGATCCCGCCTTTCGCGCCAATACCGCCAATCCTG

ACTGGGACTTCAATCCTAACAAAGACACCTGGCCCGACGCAAACAAAGTGGGA
``` delta 4 optimized with restriction sites (HindIII/EcoRI)

SEQ ID NO: 28

```
A↓AGCTTGCACCATGGCCAGTCGGAGCGAATCAAAGAAAAATAGGGGAGGGCGGGAAGAA

ATCCTGGAGCAGTGGGTCGGAGCACGAAAGAAACTGGAAGAACTGGAGAGGGACCTGCGC

AAGATCAAGAAGAAGATCAAGAAGCTGGAGGAGGAGAACCCCTGGCTGGGCAATATCAAG

GGCATCCTGGGCAAGAAGGATCGGAGGGAGAGGGAGCACCACCTGCAAAGAGGGCCAGA

GCCGACCAGATGGAGGTGGATAGCGGCCCTAGGAAGCGCCCATTCAGAGGCGAGTTTACA

GACAAGGAGCGGAGAGATCACAGGCGCCGGAAGGCCCTGGAGAACAAGCGGAAGCAGCTG

AGCTCCGGCGGCAAGTCCCTGTCTAAGGAGGAGGAGGAGGAGCTGAGAAAGCTGACCGAG
```

-continued
```
GAGGACGAGAGAAGGGAGAGGAGGGTGGCAGGACCTAGGGTGGGAGGCGTGAACCCACTG

GAGGGAGGAACAAGGGGAGCACCTGGAGGAGGATTCGTGCCATCCATGCAGGGAGTGCCT

GAGTCTCCATTTGCCAGGACCGGAGAGGGCCTGGATGTGCGCGGAAATCAGGGCTTCCCC

TGGGACATCCTGTTTCCTGCCGATCCACCCTTCTCCCCACAGTCTTGCAGGCCACAGGGA

ACCAACCTGAGCACATCCAATCCTCTGGGCTTCTTTCCAGACCACCAGCTGGATCCTGCC

TTCAGAGCCAACTCCGCCAATCCAGACTGGGACTTCAACCCCAATAAGGACACATGGCCT

GATGCCAACAAGGTCGGCGGCCAGAACCTGTCTACCAGCAATCCCCTGGGCTTCTTTCCT

GACCACCAGCTGGATCCAGCCTTCCGGGCCAACACTGCTAACCCTGATTGGGACTTCAAC

CCTAATAAGGATACCTGGCCAGACGCCAACAAGGTCGGCGGAAGCGGAGCTACTAACTTC

AGCCTGCTGAAGCAGGCTGGAGACGTGGAGGAGAACCCTGGACCTATGTCCAGGTCTGAG

AGCAAGAAGAATAGGGGAGGAAGAGAGGAGGTGCTGGAGCAGTGGGTGAACGGCCGCAAG

AAGCTGGAGGAGCTGGAGAGGGAGCTGAGAAGGGCCCGCAAGAAGATCAAGAAGCTGGAA

GACGATAATCCTTGGCTGGGCAATGTGAAAGGCATCCTGGGCAAGAAGGACAAGGATGGA

GAGGGAGCACCTCCAGCAAAGAGGGCAAGAACAGACCAGATGGAGATCGATTCTGGACCA

AGGAAGCGCCCTCTGAGGGGAGGCTTCACCGACCGGGAGAGACAGGATCACCGCCGGAGA

AAGGCCCTGAAGAACAAGAAGAAGCAGCTGTCCGCCGGCGGCAAGTCCCTGAGCAAAGAA

GAGGAAGAGGAGCTGAAGAGGCTGACCCGCGAGGACGAGGAGCGGAAGAAGGAGGAGCAC

GGACCAAGCAGACTGGGAGTGAATCCTTCCGAGGGAGGACCAAGAGGAGCACCCGGAGGA

GGCTTCGTGCCATCTATGCAGGGCATCCCCGAGAGCCGGTTTACCAGAACAGGAGAGGGC

CTGGACGTGAGGGGCTCCCGCGGCTTTCCTCAGGACATCCTGTTCCCATCTGATCCCCCT

TTTAGCCCACAGTCCTGTAGGCCCCAGGGCACTAACCTGAGCACATCCAACCCACTGGGC

TTCTTTCCTGATCATCAGCTGGACCCAGCCTTCCGCGCCAACAGCGCCAACCCTGACTGG

GACTTCAACCCAAATAAGGACACATGGCCAGATGCTAACAAGGTCGGAGGACAAAACCTG

TCTACCAGCAACCCTCTGGGCTTCTTTCCCGATCATCAGCTGGACCCCGCCTTCAGGGCC

AACACAGCCAATCCCGACTGGGACTTCAACCCGAATAAGGACACCTGGCCAGATGCAAAC

AAGGTCGGAGGAAGCGGAGCTACTAACTTCAGCCTGCTGAAGCAGGCTGGAGACGTGGAG

GAGAACCCTGGACCTATGAGCCAGTCTGAGACAAGGAGGGGCCGGAGAGGAACCAGGGAG

GAGACACTGGAGAAGTGGATCACCGCCAGAAAGAAGGCCGAGGAGCTGGAGAAGGACCTG

CGGAAGACCAGAAAGACAATCAAGAAGCTGGAAGAAGAGAACCCATGGCTGGGCAATATC

GTGGGCATCATCCGCAAGGGCAAGGACGGCGAGGGAGCACCACCAGCAAAGAGGCCCCGC

ACAGATCAGATGGAAGTGGATAGCGGCCCTGGCAAGAGGCCACACAAGTCCGGCTTCACC

GACAAGGAGAGGGAGGACCATAGGCGCCGGAAGGCCCTGGAAAACAAGAAGAAGCAATTA

TCCGCCGGCGGCAAGATCCTGTCCAAAGAGGAAGAAGAGGAGCTGAGAAGGCTGACCGAC

GAGGATGAGGAGAGGAAAGAAGGGTGGCAGGACCAAGAGTGGGCGACGTGAATCCCAGC

AGAGGCGGACCAAGAGGAGCACCTGGAGGCGGCTTCGTGCCCCAGATGGCCGGCGTGCCC

GAGTCTCCTTTTAGCAGAACTGGAGAGGGCCTGGATATCAGGGGAACACAGGGCTTTCCA

TGGGTGAGCCCATCCC

CTCCACAGCAGAGGCTGCCACTGCTGGAGTGCACCCCTCAGGGAACCAACCTGTCTACCA

GCAACCCGCTGGGCTTCTTTCCCGACCATCAGCTGGACCCTGCCTTCCGCGCCAACTCCG

CCAACCCTGATTGGGACTTCAACCCGAATAAGGATACCTGGCCCGACGCTAACAAGGTCG

GAGGCCAGAACCTGTCCACCTCTAACCCCTTAGGCTTCTTTCCCGATCACCAGCTGGATC
```

-continued

```
CCGCCTTCAGAGCCAACACTGCTAACCCCGATTGGGACTTCAACCCGAATAAGGACACGT

GGCCAGACGCTAACAAGGTCGGGGGAAGCGGAGCTACTAACTTCAGCCTGCTGAAGCAGG

CTGGAGACGTGGAGGAGAACCCTGGACCTATGTCGCAGTCCGAGTCTAAGAAGAATAGAA

GGGGCGGCCGGGAGGATATCCTGGAAAAATGGATCACCACACGCAGAAAAGCTGAAGAAC

TGGAAAAGGACCTGAGGAAGGCCCGCAAGACCATCAAGAAGCTGGAGGATGAAAATCCAT

GGCTGGGAAACATCATCGGCATCATCAGAAAGGGCAAGGACGGGGAAGGCGCCCCACCTG

CAAAGCGGCCTAGAACCGATCAGATGGAAATCGATTCTGGCACAGGCAAGCGGCCACACA

AGAGTGGCTTCACCGATAAGGAGAGAGAGGATCACAGAAGGCGCAAGGCCCTGGAGAACA

AGAAGAAGCAATTAAGCAGCGGCGGCAAGAATCTGTCCAGAGAAGAAGAGGAGGAGCTGG

GCAGACTGACAGTGGAGGACGAGGAGCGGAGAAGGCGCGTGGCAGGACCAAGGACCGGCG

ATGTGAACCTGAGCGGAGGAGGACCTAGGGGAGCACCAGGAGGCGGCTTCGTGCCTAGGA

TGGAGGGAGTGCCAGAGTCCCCCTTTACCAGGACTGGCGAGGGCCTGGACATCAGGGGAA

ATCAGGGATTCCCATGGGTGCGGCCTAGCCCACCACAGCAGAGACTGCCACTGCTGGAGT

GTACACCCCAGGGCACAAACCTGAGCACATCCAATCCGCTGGGCTTCTTTCCAGATCATC

AATTAGATCCAGCCTTCAGGGCCAACTCCGCCAATCCGGATTGGGACTTCAACCCGAATA

AGGACACTTGGCCCGACGCAAACAAGGTCGGAGGGCAAAACCTGTCTACCAGCAATCCAC

TTGGCTTCTTTCCTGACCATCAGCTGGATCCCGCCTTTCGCGCCAATACCGCCAATCCTG

ACTGGGACTTCAATCCTAACAAAGACACCTGGCCCGACGCAAACAAAGTGGGATGATGAG

↓AATTCCGT
``` delta 4 protein                                                    SEQ ID NO: 29

```
MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKA

LENKRKQLSSGGKSLSKEEEEELRKLTEEDERRERRVAGPRVGGVNPLEGGTRG

APGGGFVPSMQGVPESPFARTGEGLDVRGNQGFPWDILFPADPPFSPQSCRPQGT

NLSTSNPLGFFPDHQLDPAFRANSANPDWDFNPNKDTWPDANKVGGQNLSTSNP

LGFFPDHQLDPAFRANTANPDWDFNPNKDTWPDANKVGGSGATNFSLLKQAGD

VEENPGPMSRSESKKNRGGREEVLEQWVNGRKKLEELERELRRARKKIKKLEDD

NPWLGNVKGILGKKDKDGEGAPPAKRARTDQMEIDSGPRKRPLRGGFTDRERQ

DHRRRKALKNKKKQLSAGGKSLSKEEEEELKRLTREDEERKKEEHGPSRLGVNP

SEGGPRGAPGGGFVPSMQGIPESRFTRTGEGLDVRGSRGFPQDILFPSDPPFSPQSC

RPQGTNLSTSNPLGFFPDHQLDPAFRANSANPDWDFNPNKDTWPDANKVGGQN

LSTSNPLGFFPDHQLDPAFRANTANPDWDFNPNKDTWPDANKVGGSGATNFSLL

KQAGDVEENPGPMSQSETRRGRRGTREETLEKWITARKKAEELEKDLRKTRKTI

KKLEEENPWLGNIVGIIRKGKDGEGAPPAKRPRTDQMEVDSGPGKRPHKSGFTD

KEREDHRRRKALENKKKQLSAGGKILSKEEEEELRRLTDEDEERKRRVAGPRVG

DVNPSRGGPRGAPGGGFVPQMAGVPESPFSRTGEGLDIRGTQGFPWVSPSPPQQR

LPLLECTPQGTNLSTSNPLGFFPDHQLDPAFRANSANPDWDFNPNKDTWPDANK

VGGQNLSTSNPLGFFPDHQLDPAFRANTANPDWDFNPNKDTWPDANKVGGSGA

TNFSLLKQAGDVEENPGPMSQSESKKNRGGREDILEKWITTRRKAEELEKDLRK

ARKTIKKLEDENPWLGNIIGIIRKGKDGEGAPPAKRPRTDQMEIDSGTGKRPHKSG
```

FTDKEREDHRRRKALENKKKQLSSGGKNLSREEEEELGRLTVEDEERRRRVAGP

RTGDVNLSGGGPRGAPGGGFVPRMEGVPESPFTRTGEGLDIRGNQGFPWVRPSPP

QQRLPLLECTPQGTNLSTSNPLGFFPDHQLDPAFRANSANPDWDFNPNKDTWPD

ANKVGGQNLSTSNPLGFFPDHQLDPAFRANTANPDWDFNPNKDTWPDANKVG delta 5 wt

SEQ ID NO: 30

AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGAGCCGCAGCGAAAGCAAAAAAAACCGCGGC

GGCCGCGAAGAAGTGCTGGAACAGTGGGTGAACGGCCGCAAAAAACTGGAA

GAACTGGAACGCGAACTGCGCCGCGCGCGCAAAAAAATTAAAAAACTGGAA

GATGATAACCCGTGGCTGGGCAACGTGAAAGGCATTCTGGGCAAAAAAGATA

AAGATGGCGAAGGCGCGCCGCCGGCGAAACGCGCGCGCACCGATCAGATGG

AAATTGATAGCGGCCCGCGCAAACGCCCGCTGCGCGGCGGCTTTACCGATCG

CGAACGCCAGGATCATCGCCGCCGCAAAGCGCTGAAAAACAAAAAAAAACA

GCTGAGCGCGGGCGGCAAAAGCCTGAGCAAAGAAGAAGAAGAAGAACTGAA

ACGCCTGACCCGCGAAGATGAAGAACGCAAAAAAGAAGAACATGGCCCGAG

CCGCCTGGGCGTGAACCCGAGCGAAGGCGGCCCGCGCGGCGCGCCGGGCGG

CGGCTTTGTGCCGAGCATGCAGGGCATTCCGGAAAGCCGCTTTACCCGCACC

GGCGAAGGCCTGGATGTGCGCGGCAGCCGCGGCTTTCCGCAGGATATTCTGT

TTCCGAGCGATCCGCCGTTTAGCCCGCAGAGCTGCCGCCCGCAGGGAAGCGGAG

CTACTAACTTCAGCCTGCTGAAGCAGGCTGGAGACGTGGAGGAGAACCCTGGACCATG

AGCCAGAGCGAAACCCGCCGCGGCCGCCGCGGCACCCGCGAAGAAACCCTG

GAAAAATGGATTACCGCGCGCAAAAAAGCGGAAGAACTGGAAAAAGATCTG

CGCAAAACCCGCAAAACCATTAAAAAACTGGAAGAAGAAAACCCGTGGCTG

GGCAACATTGTGGGCATTATTCGCAAAGGCAAAGATGGCGAAGGCGCGCCGC

CGGCGAAACGCCCGCGCACCGATCAGATGGAAGTGGATAGCGGCCCGGGCA

AACGCCCGCATAAAAGCGGCTTTACCGATAAAGAACGCGAAGATCATCGCCG

CCGCAAAGCGCTGGAAAACAAAAAAAAACAGCTGAGCGCGGGCGGCAAAAT

TCTGAGCAAAGAAGAAGAAGAAGAACTGCGCCGCCTGACCGATGAAGATGA

AGAACGCAAACGCCGCGTGGCGGGCCCGCGCGTGGGCGATGTGAACCCGAG

CCGCGGCGGCCCGCGCGGCGCGCCGGGCGGCGGCTTTGTGCCGCAGATGGCG

```
GGCGTGCCGGAAAGCCCGTTTAGCCGCACCGGCGAAGGCCTGGATATTCGCG
GCACCCAGGGCTTTCCGTGGGTGAGCCCGAGCCCGCCGCAGCAGCGCCTGCC
GCTGCTGGAATGCACCCCGCAGAGCCAGAGCGAAAGCAAAAAAAACCGCCG
CGGCGGCCGCGAAGATATTCTGGAAAAATGGATTACCACCCGCCGCAAAGCG
GAAGAACTGGAAAAAGATCTGCGCAAAGCGCGCAAAACCATTAAAAAACTG
GAAGATGAAAACCCGTGGCTGGGCAACATTATTGGCATTATTCGCAAAGGCA
AAGATGGCGAAGGCGCGCCGCCGGCGAAACGCCCGCGCACCGATCAGATGG
AAATTGATAGCGGCACCGGCAAACGCCCGCATAAAAGCGGCTTTACCGATAA
AGAACGCGAAGATCATCGCCGCCGCAAAGCGCTGGAAAACAAAAAAAAACA
GCTGAGCAGCGGCGGCAAAAACCTGAGCCGCGAAGAAGAAGAAGAACTGGG
CCGCCTGACCGTGGAAGATGAAGAACGCCGCCGCCGCGTGGCGGGCCCGCGC
ACCGGCGATGTGAACCTGAGCGGCGGCGGCCCGCGCGGCGCGCCGGGCGGC
GGCTTTGTGCCGCGCATGGAAGGCGTGCCGGAAAGCCCGTTTACCCGCACCG
GCGAAGGCCTGGATATTCGCGGCAACCAGGGCTTTCCGTGGGTGCGCCCGAG
CCCGCCGCAGCAGCGCCTGCCGCTGCTGGAATGCACCCCGCAG
``` delta 5 wt with restriction sites (HindIII/EcoRI)                        SEQ ID NO: 31

```
A↓AGCTTGCACCATGGCCAGCCGCAGCGAAAGCAAAAAAAACCGCGGCGGCCG
CGAAGAAATTCTGGAACAGTGGGTGGGCGCGCGCAAAAAACTGGAAGAACT
GGAACGCGATCTGCGCAAAATTAAAAAAAAAATTAAAAAACTGGAAGAAGA
AAACCCGTGGCTGGGCAACATTAAAGGCATTCTGGGCAAAAAAGATCGCGAA
GGCGAAGGCGCGCCGCCGGCGAAACGCGCGCGCGGATCAGATGGAAGTG
GATAGCGGCCCGCGCAAACGCCCGTTTCGCGGCGAATTTACCGATAAAGAAC
GCCGCGATCATCGCCGCCGCAAAGCGCTGGAAAACAAACGCAAACAGCTGA
GCAGCGGCGGCAAAAGCCTGAGCAAAGAAGAAGAAGAAGAACTGCGCAAAC
TGACCGAAGAAGATGAACGCCGCGAACGCCGCGTGGCGGGCCCGCGCGTGG
GCGGCGTGAACCCGCTGGAAGGCGGCACCCGCGGCGCGCCGGGCGGCGGCTT
TGTGCCGAGCATGCAGGGCGTGCCGGAAAGCCCGTTTGCGCGCACCGGCGAA
GGCCTGGATGTGCGCGGCAACCAGGGCTTTCCGTGGGATATTCTGTTTCCGGC
GGATCCGCCGTTTAGCCCGCAGAGCTGCCGCCCGCAGAGCCGCAGCGAAAGC
AAAAAAAACCGCGGCGGCCGCGAAGAAGTGCTGGAACAGTGGGTGAACGGC
CGCAAAAAACTGGAAGAACTGGAACGCGAACTGCGCCGCGCGCGCAAAAAA
ATTAAAAAACTGGAAGATGATAACCCGTGGCTGGGCAACGTGAAAGGCATTC
TGGGCAAAAAAGATAAAGATGGCGAAGGCGCGCCGCCGGCGAAACGCGCGC
GCACCGATCAGATGGAAATTGATAGCGGCCCGCGCAAACGCCCGCTGCGCGG
CGGCTTTACCGATCGCGAACGCCAGGATCATCGCCGCCGCAAAGCGCTGAAA
AACAAAAAAAAACAGCTGAGCGCGGGCGGCAAAAGCCTGAGCAAAGAAGAA
GAAGAAGAACTGAAACGCCTGACCCGCGAAGATGAAGAACGCAAAAAAGAA
GAACATGGCCCGAGCCGCCTGGGCGTGAACCCGAGCGAAGGCGGCCCGCGC
GGCGCGCCGGGCGGCGGCTTTGTGCCGAGCATGCAGGGCATTCCGGAAAGCC
GCTTTACCCGCACCGGCGAAGGCCTGGATGTGCGCGGCAGCCGCGGCTTTCC
```

-continued

```
GCAGGATATTCTGTTTCCGAGCGATCCGCCGTTTAGCCCGCAGAGCTGCCGCC

CGCAGGGAAGCGGAGCTACTAACTTCAGCCTGCTGAAGCAGGCTGGAGACGTGGAGGAG

AACCCTGGACCTATGAGCCAGAGCGAAACCCGCCGCGGCCGCCGCGGCACCCG

CGAAGAAACCCTGGAAAAATGGATTACCGCGCGCAAAAAAGCGGAAGAACT

GGAAAAAGATCTGCGCAAAACCCGCAAAACCATTAAAAAACTGGAAGAAGA

AAACCCGTGGCTGGGCAACATTGTGGGCATTATTCGCAAAGGCAAAGATGGC

GAAGGCGCGCCGCCGGCGAAACGCCCGCGCACCGATCAGATGGAAGTGGAT

AGCGGCCCGGGCAAACGCCCGCATAAAAGCGGCTTTACCGATAAAGAACGC

GAAGATCATCGCCGCCGCAAAGCGCTGGAAAACAAAAAAAAACAGCTGAGC

GCGGGCGGCAAAATTCTGAGCAAAGAAGAAGAAGAAGAACTGCGCCGCCTG

ACCGATGAAGATGAAGAACGCAAACGCCGCGTGGCGGGCCCGCGCGTGGGC

GATGTGAACCCGAGCCGCGGCGGCCCGCGCGGCGCGCCGGGCGGCGGCTTTG

TGCCGCAGATGGCGGGCGTGCCGGAAAGCCCGTTTAGCCGCACCGGCGAAGG

CCTGGATATTCGCGGCACCCAGGGCTTTCCGTGGGTGAGCCCGAGCCCGCCG

CAGCAGCGCCTGCCGCTGCTGGAATGCACCCCGCAGAGCCAGAGCGAAAGCA

AAAAAACCGCCGCGGCGGCCGCGAAGATATTCTGGAAAAATGGATTACCAC

CCGCCGCAAAGCGGAAGAACTGGAAAAAGATCTGCGCAAAGCGCGCAAAAC

CATTAAAAAACTGGAAGATGAAAACCCGTGGCTGGGCAACATTATTGGCATT

ATTCGCAAAGGCAAAGATGGCGAAGGCGCGCCGCCGGCGAAACGCCCGCGC

ACCGATCAGATGGAAATTGATAGCGGCACCGGCAAACGCCCGCATAAAGCG

GCTTTACCGATAAAGAACGCGAAGATCATCGCCGCCGCAAAGCGCTGGAAAA

CAAAAAAAAACAGCTGAGCAGCGGCGGCAAAAACCTGAGCCGCGAAGAAGA

AGAAGAACTGGGCCGCCTGACCGTGGAAGATGAAGAACGCCGCCGCCGCGT

GGCGGGCCCGCGCACCGGCGATGTGAACCTGAGCGGCGGCGGCCCGCGCGG

CGCGCCGGGCGGCGGCTTTGTGCCGCGCATGGAAGGCGTGCCGGAAAGCCCG

TTTACCCGCACCGGCGAAGGCCTGGATATTCGCGGCAACCAGGGCTTTCCGTG

GGTGCGCCCGAGCCCGCCGCAGCAGCGCCTGCCGCTGCTGGAATGCACCCCG

CAGTGATGAGAATTCCGT
``` delta 5 codon optimized

SEQ ID NO: 32

```
GCCTCACGGTCAGAGTCAAAGAAAAATAGGGGGGGCGGGAAGAAATCCTGGAACAGTGG

GTCGGAGCACGGAAAAAACTGGAAGAGCTGGAGAGGGACCTGCGCAAGATCAAGAAGAAG

ATCAAGAAGCTGGAGGAGGAGAACCCCTGGCTGGGCAATATCAAGGGCATCCTGGGCAAG

AAGGATCGGAGGGAGAGGGAGCACCACCTGCAAAGAGGGCCAGAGCCGACCAGATGGAG

GTGGATAGCGGCCCTAGGAAGCGCCCATTCAGAGGCGAGTTTACCGACAAGGAGCGGAGA

GATCACAGGCGCCGGAAGGCCCTGGAGAACAAGCGGAAGCAGCTGAGCTCCGGCGGCAAG

TCCCTGTCTAAGGAGGAGGAGGAGGAGCTGAGAAAGCTGACAGAGGAGGACGAGAGAAGG

GAGCGCCGGGTGGCCGGCCCAAGGGTGGGCGGCGTGAACCCCCTGGAGGGAGGAACCAGG

GGAGCACCTGGAGGAGGCTTCGTGCCATCTATGCAGGGCGTGCCTGAGAGCCCATTTGCC

AGGACAGGAGAGGGCCTGGATGTGCGCGGCAATCAGGGCTTCCCCTGGGACATCCTGTTT

CCTGCCGATCCACCCTTCAGCCCACAGTCCTGCAGGCCTCAGAGCAGATCCGAGTCTAAG

AAGAACAGGGGAGGAAGAGAGGAGGTGCTGGAGCAGTGGGTGAATGGCCGGAAGAAGCTG
```

-continued

```
GAGGAGCTGGAGCGGGAGCTGAGAAGGGCCAGAAAGAAGATCAAGAAGCTGGAAGACGAT

AATCCTTGGCTGGGCAATGTGAAAGGCATCCTGGGCAAGAAGGACAAGGATGGAGAGGGA

GCACCTCCAGCAAAGAGGGCAAGAACCGACCAGATGGAGATCGATAGCGGACCAAGGAAG

CGCCCTCTGAGAGGAGGCTTCACAGACCGGGAGAGACAGGATCACCGCCGGAGAAAGGCC

CTGAAGAACAAGAAGAAGCAGCTGTCCGCCGGAGGCAAGAGCCTGTCCAAAGAAGAGGAA

GAGGAGCTGAAGAGGCTGACCCGCGAGGACGAGGAGCGGAAGAAGGAGGAGCACGGCCCT

TCCAGACTGGGCGTGAATCCATCTGAGGGAGGACCAAGGGGAGCACCAGGCGGCGGCTTC

GTGCCAAGCATGCAGGGCATCCCCGAGTCCCGGTTTACCAGAACAGGAGAGGGCCTGGAC

GTGAGGGGCTCTCGCGGCTTTCCTCAGGACATCCTGTTCCCAAGCGATCCCCCTTTTTCT

CCACAGAGCTGTCGCCCCCAGGGAAGCGGAGCTACTAACTTCAGCCTGCTGAAGCAGGCT

GGAGACGTGGAGGAGAACCCTGGACCTATGTCTCAGAGCGAGACAAGGAGGGCCGGAGA

GGAACCAGGAGGAGACACTGGAGAAGTGGATCACAGCCAGAAAGAAGGCCGAGGAGCTG

GAGAAGGACCTGCGGAAGACCAGAAAGACAATCAAGAAGCTGGAAGAAGAAATCCATGG

CTGGGAAATATCGTGGGCATCATCAGGAAGGGCAAGGACGGCGAGGGAGCACCACCAGCC

AAGAGGCCTCGCACTGATCAGATGGAGGTGGATTCCGGCCCTGGCAAGAGGCCACACAAG

TCTGGCTTCACAGACAAGGAGAGGGAGGACCATAGGCGCCGGAAGGCCCTGGAAAACAAG

AAGAAGCAATTATCTGCCGGCGGCAAGATCCTGAGCAAAGAGGAAGAGGAGGAGCTGAGA

AGGCTGACCGACGAGGATGAGGAGAGGAAGAGGAGGGTGGCAGGACCAAGAGTGGGCGAC

GTGAATCCTAGCAGAGGCGGACCAAGAGGCGCCCCAGGCGGGGGCTTCGTGCCACAGATG

GCAGGAGTGCCAGAGTCCCCTTTTTCTAGGACCGGAGAGGGCCTGGATATCAGGGGAACA

CAGGGCTTTCCATGGGTGTCCCCATCTCCTCCACAGCAGAGGCTGCCACTGCTGGAGTGC

ACCCCTCAGAGCCAGTCCGAGTCTAAGAAGAATAGAAGGGGCGGCCGCGAGGACATCCTG

GAGAAGTGGATCACCACACGCAGAAAAGCTGAAGAACTGGAAAAGGACCTGAGGAAGGCC

CGCAAAACAATCAAGAAGCTGGAGGATGAGAACCCTTGGCTGGGCAATATCATCGGAATT

ATCAGGAAGGGCAAGGATGGCGAAGGCGCCCCACCTGCAAAGCGGCCAAGGACTGATCAG

ATGGAAATCGATAGCGGAACAGGCAAGCGGCCCCACAAGTCCGGCTTCACCGACAAGGAG

AGAGAGGATCACAGAAGGCGCAAGGCCCTGGAGAACAAGAAGAAGCAATTAAGCAGCGGC

GGCAAGAATCTGTCCAGAGAAGAAGAGGAGGAGCTGGGCAGACTGACCGTGGAGGACGAG

GAGCGGAGAAGGCGCGTGGCAGGACCTCGCACAGGCGATGTGAACCTGTCCGGAGGAGGA

CCTAGGGGAGCACCAGGAGGCGGCTTCGTGCCACGCATGGAGGGCGTGCCAGAGTCTCCC

TTTACCCGCACCGGAGAGGGCCTGGACATCAGGGGCAATCAGGGCTTTCCCTGGGTCCGC

CCCTCCCCCCCTCAGCAGAGACTGCCCCTGCTGGAATGCACACCACAG delta 5 codon optimized with restriction sites (HindIII/EcoRI)
                                                        SEQ ID NO: 33
A↓AGCTTGCACCATGGCCTCACGGTCAGAGTCAAAGAAAAATAGGGGGGGCGGAAGAA

ATCCTGGAACAGTGGGTCGGAGCACGGAAAAAACTGGAAGAGCTGGAGAGGGACCTGCGC

AAGATCAAGAAGAAGATCAAGAAGCTGGAGGAGGAGAACCCCTGGCTGGGCAATATCAAG

GGCATCCTGGGCAAGAAGGATCGGAGGGAGAGGGAGCACCACCTGCAAAGAGGGCCAGA

GCCGACCAGATGGAGGTGGATAGCGGCCCTAGGAAGCGCCCATTCAGAGGCGAGTTTACC

GACAAGGAGCGGAGAGATCACAGGCGCCGGAAGGCCCTGGAGAACAAGCGGAAGCAGCTG

AGCTCCGGCGGCAAGTCCCTGTCTAAGGAGGAGGAGGAGGAGCTGAGAAAGCTGACAGAG
```

```
-continued
GAGGACGAGAGAAGGGAGCGCCGGGTGGCCGGCCCAAGGGTGGGCGGCGTGAACCCCCTG

GAGGGAGGAACCAGGGGAGCACCTGGAGGAGGCTTCGTGCCATCTATGCAGGGCGTGCCT

GAGAGCCCATTTGCCAGGACAGGAGAGGGCCTGGATGTGCGCGGCAATCAGGGCTTCCCC

TGGGACATCCTGTTTCCTGCCGATCCACCCTTCAGCCCACAGTCCTGCAGGCCTCAGAGC

AGATCCGAGTCTAAGAAGAACAGGGGAGGAAGAGAGGAGGTGCTGGAGCAGTGGGTGAAT

GGCCGGAAGAAGCTGGAGGAGCTGGAGCGGGAGCTGAGAAGGGCCAGAAAGAAGATCAAG

AAGCTGGAAGACGATAATCCTTGGCTGGGCAATGTGAAAGGCATCCTGGGCAAGAAGGAC

AAGGATGGAGAGGGAGCACCTCCAGCAAAGAGGGCAAGAACCGACCAGATGGAGATCGAT

AGCGGACCAAGGAAGCGCCCTCTGAGAGGAGGCTTCACAGACCGGGAGAGACAGGATCAC

CGCCGGAGAAAGGCCCTGAAGAACAAGAAGAAGCAGCTGTCCGCCGGAGGCAAGAGCCTG

TCCAAGAAGAGGAAGAGGAGCTGAAGAGGCTGACCCGCGAGGACGAGGAGCGGAAGAAG

GAGGAGCACGGCCCTTCCAGACTGGGCGTGAATCCATCTGAGGGGAGGACCAAGGGGAGCA

CCAGGCGGCGGCTTCGTGCCAAGCATGCAGGGCATCCCCGAGTCCCGGTTTACCAGAACA

GGAGAGGGCCTGGACGTGAGGGGCTCTCGCGGCTTTCCTCAGGACATCCTGTTCCCAAGC

GATCCCCCTTTTTCTCCACAGAGCTGTCGCCCCCAGGGAAGCGGAGCTACTAACTTCAGC

CTGCTGAAGCAGGCTGGAGACGTGGAGGAGAACCCTGGACCTATGTCTCAGAGCGAGACA

AGGAGGGGCCGGAGAGGAACCAGGGAGGAGACACTGGAGAAGTGGATCACAGCCAGAAAG

AAGGCCGAGGAGCTGGAGAAGGACCTGCGGAAGACCAGAAAGACAATCAAGAAGCTGGAA

GAAGAAAATCCATGGCTGGGAAATATCGTGGGCATCATCAGGAAGGGCAAGGACGGCGAG

GGAGCACCACCAGCCAAGAGGCCTCGCACTGATCAGATGGAGGTGGATTCCGGCCCTGGC

AAGAGGCCACACAAGTCTGGCTTCACAGACAAGGAGAGGGAGGACCATAGGCGCCGGAAG

GCCCTGGAAAACAAGAAGAAGCAATTATCTGCCGGCGGCAAGATCCTGAGCAAAGAGGAA

GAGGAGGAGCTGAGAAGGCTGACCGACGAGGATGAGGAGAGGAAGAGGAGGGTGGCAGGA

CCAAGAGTGGGCGACGTGAATCCTAGCAGAGGCGGACCAAGAGGCGCCCCAGGCGGGGGC

TTCGTGCCACAGATGGCAGGAGTGCCAGAGTCCCCTTTTTCTAGGACCGGAGAGGGCCTG

GATATCAGGGGAACACAGGGCTTTCCATGGGTGTCCCCATCTCCTCCACAGCAGAGGCTG

CCACTGCTGGAGTGCACCCCTCAGAGCCAGTCCGAGTCTAAGAAGAATAGAAGGGGCGGC

CGCGAGGACATCCTGGAGAAGTGGATCACCACACGCAGAAAAGCTGAAGAACTGGAAAAG

GACCTGAGGAAGGCCCGCAAAACAATCAAGAAGCTGGAGGATGAGAACCCTTGGCTGGGC

AATATCATCGGAATTATCAGGAAGGGCAAGGATGGCGAAGGCGCCCCACCTGCAAAGCGG

CCAAGGACTGATCAGATGGAAATCGATAGCGGAACAGGCAAGCGGCCCCACAAGTCCGGC

TTCACCGACAAGGAGAGAGAGGATCACAGAAGGCGCAAGGCCCTGGAGAACAAGAAGAAG

CAATTAAGCAGCGGCGGCAAGAATCTGTCCAGAGAAGAAGAGGAGGAGCTGGGCAGACTG

ACCGTGGAGGACGAGGAGCGGAGAAGGCGCGTGGCAGGACCTCGCACAGGCGATGTGAAC

CTGTCCGGAGGAGGACCTAGGGGAGCACCAGGAGGCGGCTTCGTGCCACGCATGGAGGGC

GTGCCAGAGTCTCCCTTTACCCGCACCGGAGAGGGCCTGGACATCAGGGGCAATCAGGGC

TTTCCCTGGGTCCGCCCCTCCCCCCCTCAGCAGAGACTGCCCCTGCTGGAATGCACACCA

CAGTGATGAG↓AATTCCGT delta 5 protein
                                                        SEQ ID NO: 34
MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKA
```

LENKRKQLSSGGKSLSKEEEEELRKLTEEDERRERRVAGPRVGGVNPLEGGTRG

APGGGFVPSMQGVPESPFARTGEGLDVRGNQGFPWDILFPADPPFSPQSCRPQSR

SESKKNRGGREEVLEQWVNGRKKLEELERELRRARKKIKKLEDDNPWLGNVKGI

LGKKDKDGEGAPPAKRARTDQMEIDSGPRKRPLRGGFTDRERQDHRRRKALKN

KKKQLSAGGKSLSKEEEEELKRLTREDEERKKEEHGPSRLGVNPSEGGPRGAPGG

GFVPSMQGIPESRFTRTGEGLDVRGSRGFPQDILFPSDPPFSPQSCRPQGSGATNFS

LLKQAGDVEENPGPMSQSETRRGRRGTREETLEKWITARKKAEELEKDLRKTRK

TIKKLEEENPWLGNIVGIIRKGKDGEGAPPAKRPRTDQMEVDSGPGKRPHKSGFT

DKEREDHRRRKALENKKKQLSAGGKILSKEEEEELRRLTDEDEERKRRVAGPRV

GDVNPSRGGPRGAPGGGFVPQMAGVPESPFSRTGEGLDIRGTQGFPWVSPSPPQQ

RLPLLECTPQSQSESKKNRRGGREDILEKWITTRRKAEELEKDLRKARKTIKKLED

ENPWLGNIIGIIRKGKDGEGAPPAKRPRTDQMEIDSGTGKRPHKSGFTDKEREDH

RRRKALENKKKQLSSGGKNLSREEEEELGRLTVEDEERRRRVAGPRTGDVNLSG

GGPRGAPGGGFVPRMEGVPESPFTRTGEGLDIRGNQGFPWVRPSPPQQRLPLLEC

TPQ delta 6 wt                                              SEQ ID NO: 35

AGCCGCAGCGAAAGCAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAAACCCGTGGCTGGGC

AACATTAAAGGCATTCTGGGCAAAAAGATCGCGAAGGCGAAGGCGCGCCG

CCGGCGAAACGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGGGAAGCGGAGCTACTAACTTCAGCCTGCTGAAGCAG

GCTGGAGACGTGGAGGAGAACCCTGGACCTATGAGCCGCAGCGAAAGCAAAAAAA

ACCGCGGCGGCCGCGAAGAAGTGCTGGAACAGTGGGTGAACGGCCGCAAAA

AACTGGAAGAACTGGAACGCGAACTGCGCCGCGCGCGCAAAAAAATTAAAA

AACTGGAAGATGATAACCCGTGGCTGGGCAACGTGAAAGGCATTCTGGGCAA

AAAAGATAAAGATGGCGAAGGCGCGCCGCCGGCGAAACGCGCGCGCACCGA

TCAGATGGAAATTGATAGCGGCCCGCGCAAACGCCCGCTGCGCGGCGGCTTT

ACCGATCGCGAACGCCAGGATCATCGCCGCCGCAAAGCGCTGAAAAACAAA

AAAAAACAGCTGAGCGCGGGCGGCAAAAGCCTGAGCAAAGAAGAAGAAGAA

GAACTGAAACGCCTGACCCGCGAAGATGAAGAACGCAAAAAAGAAGAACAT

GGCCCGAGCCGCCTGGGCGTGAACCCGAGCGAAGGCGGCCCGCGCGGCGCG

CCGGGCGGCGGCTTTGTGCCGAGCATGCAGGGCATTCCGGAAAGCCGCTTTA

-continued

CCCGCACCGGCGAAGGCCTGGATGTGCGCGGCAGCCGCGGCTTTCCGCAGGA

TATTCTGTTTCCGAGCGATCCGCCGTTTAGCCCGCAGAGCTGCCGCCCGCAGG

GAAGCGGAGCTACTAACTTCAGCCTGCTGAAGCAGGCTGGAGACGTGGAGGAGAACCCTG

GACCTATGAGCCAGAGCGAAACCCGCCGCGGCCGCCGCGGCACCCGCGAAGA

AACCCTGGAAAAATGGATTACCGCGCGCAAAAAAGCGGAAGAACTGGAAAA

AGATCTGCGCAAAACCCGCAAAACCATTAAAAAACTGGAAGAAGAAAACCC

GTGGCTGGGCAACATTGTGGGCATTATTCGCAAAGGCAAAGATGGCGAAGGC

GCGCCGCCGGCGAAACGCCCGCGCACCGATCAGATGGAAGTGGATAGCGGC

CCGGGCAAACGCCCGCATAAAAGCGGCTTTACCGATAAAGAACGCGAAGATC

ATCGCCGCCGCAAAGCGCTGGAAAACAAAAAAAAACAGCTGAGCGCGGGCG

GCAAAATTCTGAGCAAAGAAGAAGAAGAAGAACTGCGCCGCCTGACCGATG

AAGATGAAGAACGCAAACGCCGCGTGGCGGGCCCGCGCGTGGGCGATGTGA

ACCCGAGCCGCGGCGGCCCGCGCGGCGCGCCGGGCGGCGGCTTTGTGCCGCA

GATGGCGGGCGTGCCGGAAAGCCCGTTTAGCCGCACCGGCGAAGGCCTGGAT

ATTCGCGGCACCCAGGGCTTTCCGTGGGTGAGCCCGAGCCCGCCGCAGCAGC

GCCTGCCGCTGCTGGAATGCACCCCGCAGGGAAGCGGAGCTACTAACTTCAGCCTG

CTGAAGCAGGCTGGAGACGTGGAGGAGAACCCTGGACCATGAGCCAGAGCGAAAG

CAAAAAAAACCGCCGCGGCGGCCGCGAAGATATTCTGGAAAAATGGATTACC

ACCCGCCGCAAAGCGGAAGAACTGGAAAAAGATCTGCGCAAAGCGCGCAAA

ACCATTAAAAAACTGGAAGATGAAAACCCGTGGCTGGGCAACATTATTGGCA

TTATTCGCAAAGGCAAAGATGGCGAAGGCGCGCCGCCGGCGAAACGCCCGC

GCACCGATCAGATGGAAATTGATAGCGGCACCGGCAAACGCCCGCATAAAAG

CGGCTTTACCGATAAAGAACGCGAAGATCATCGCCGCCGCAAAGCGCTGGAA

AACAAAAAAAAACAGCTGAGCAGCGGCGGCAAAAACCTGAGCCGCGAAGAA

GAAGAAGAACTGGGCCGCCTGACCGTGGAAGATGAAGAACGCCGCCGCCGC

GTGGCGGGCCCGCGCACCGGCGATGTGAACCTGAGCGGCGGCGGCCCGCGCG

GCGCGCCGGGCGGCGGCTTTGTGCCGCGCATGGAAGGCGTGCCGGAAAGCCC

GTTTACCCGCACCGGCGAAGGCCTGGATATTCGCGGCAACCAGGGCTTTCCGT

GGGTGCGCCCGAGCCCGCCGCAGCAGCGCCTGCCGCTGCTGGAATGCACCCC

GCAG delta 6 wt with restriction sites (HindIII/EcoRI)

SEQ ID NO: 36

A↓AGCTT*GCACC*ATGGCCAGCCGCAGCGAAAGCAAAAAAAACCGCGGCGGCCG

CGAAGAAATTCTGGAACAGTGGGTGGGCGCGCGCAAAAAACTGGAAGAACT

GGAACGCGATCTGCGCAAAATTAAAAAAAAATTAAAAAACTGGAAGAAGA

AAACCCGTGGCTGGGCAACATTAAAGGCATTCTGGGCAAAAAAGATCGCGAA

GGCGAAGGCGCGCCGCCGGCGAAACGCGCGCGCGGATCAGATGGAAGTG

GATAGCGGCCCGCGCAAACGCCCGTTTCGCGGCGAATTTACCGATAAAGAAC

GCCGCGATCATCGCCGCCGCAAAGCGCTGGAAAACAAACGCAAACAGCTGA

GCAGCGGCGGCAAAAGCCTGAGCAAAGAAGAAGAAGAAGAACTGCGCAAAC

TGACCGAAGAAGATGAACGCCGCGAACGCCGCGTGGCGGGCCCGCGCGTGG

GCGGCGTGAACCCGCTGGAAGGCGGCACCCGCGGCGCGCCGGGCGGCGGCTT

-continued

```
TGTGCCGAGCATGCAGGGCGTGCCGGAAAGCCCGTTTGCGCGCACCGGCGAA

GGCCTGGATGTGCGCGGCAACCAGGGCTTTCCGTGGGATATTCTGTTTCCGGC

GGATCCGCCGTTTAGCCCGCAGAGCTGCCGCCCGCAGGGAAGCGGAGCTACTAA

CTTCAGCCTGCTGAAGCAGGCTGGAGACGTGGAGGAGAACCCTGGACCTATGAGCCGC

AGCGAAAGCAAAAAAAACCGCGGCGGCCGCGAAGAAGTGCTGGAACAGTGG

GTGAACGGCCGCAAAAAACTGGAAGAACTGGAACGCGAACTGCGCCGCGCG

CGCAAAAAAATTAAAAAACTGGAAGATGATAACCCGTGGCTGGGCAACGTG

AAAGGCATTCTGGGCAAAAAAGATAAAGATGGCGAAGGCGCGCCGCCGGCG

AAACGCGCGCACCGATCAGATGGAAATTGATAGCGGCCCGCGCAAACGCC

CGCTGCGCGGCGGCTTTACCGATCGCAACGCCAGGATCATCGCCGCCGCAA

AGCGCTGAAAAACAAAAAAAAACAGCTGAGCGCGGGCGGCAAAAGCCTGAG

CAAAGAAGAAGAAGAAGAACTGAAACGCCTGACCCGCGAAGATGAAGAACG

CAAAAAAGAAGAACATGGCCCGAGCCGCCTGGGCGTGAACCCGAGCGAAGG

CGGCCCGCGCGGCGCGCCGGGCGGCGGCTTTGTGCCGAGCATGCAGGGCATT

CCGGAAAGCCGCTTTACCCGCACCGGCGAAGGCCTGGATGTGCGCGGCAGCC

GCGGCTTTCCGCAGGATATTCTGTTTCCGAGCGATCCGCCGTTTAGCCCGCAG

AGCTGCCGCCCGCAGGGAAGCGGAGCTACTAACTTCAGCCTGCTGAAGCAGGCTGGA

GACGTGGAGGAGAACCCTGGACCTATGAGCCAGAGCGAAACCCGCCGCGGCCGCC

GCGGCACCCGCGAAGAAACCCTGGAAAAATGGATTACCGCGCGCAAAAAAG

CGGAAGAACTGGAAAAAGATCTGCGCAAAACCCGCAAAACCATTAAAAAAC

TGGAAGAAGAAAACCCGTGGCTGGGCAACATTGTGGGCATTATTCGCAAAGG

CAAAGATGGCGAAGGCGCGCCGCCGGCGAAACGCCCGCGCACCGATCAGAT

GGAAGTGGATAGCGGCCCGGGCAAACGCCCGCATAAAAGCGGCTTTACCGAT

AAAGAACGCGAAGATCATCGCCGCCGCAAAGCGCTGGAAAACAAAAAAAAA

CAGCTGAGCGCGGGCGGCAAAATTCTGAGCAAAGAAGAAGAAGAAGAACTG

CGCCGCCTGACCGATGAAGATGAAGAACGCAAACGCCGCGTGGCGGGCCCG

CGCGTGGGCGATGTGAACCCGAGCCGCGGCGGCCCGCGCGGCGCGCCGGGC

GGCGGCTTTGTGCCGCAGATGGCGGGCGTGCCGGAAAGCCCGTTTAGCCGCA

CCGGCGAAGGCCTGGATATTCGCGGCACCCAGGGCTTTCCGTGGGTGAGCCC

GAGCCCGCCGCAGCAGCGCCTGCCGCTGCTGGAATGCACCCCGCAGGGAAGCG

GAGCTACTAACTTCAGCCTGCTGAAGCAGGCTGGAGACGTGGAGGAGAACCCTGGACCT

ATGAGCCAGAGCGAAAGCAAAAAAAACCGCCGCGGCGGCCGCGAAGATATT

CTGGAAAAATGGATTACCACCCGCCGCAAAGCGGAAGAACTGGAAAAAGAT

CTGCGCAAAGCGCGCAAAACCATTAAAAAACTGGAAGATGAAAACCCGTGG

CTGGGCAACATTATTGGCATTATTCGCAAAGGCAAAGATGGCGAAGGCGCGC

CGCCGGCGAAACGCCCGCGCACCGATCAGATGGAAATTGATAGCGGCACCGG

CAAACGCCCGCATAAAAGCGGCTTTACCGATAAAGAACGCGAAGATCATCGC

CGCCGCAAAGCGCTGGAAAACAAAAAAAAACAGCTGAGCAGCGGCGGCAAA

AACCTGAGCCGCGAAGAAGAAGAAGAACTGGGCCGCCTGACCGTGGAAGAT

GAAGAACGCCGCCGCCGCGTGGCGGGCCCGCGCACCGGCGATGTGAACCTGA
```

-continued

GCGGCGGCGGCCCGCGCGGCGCGCCGGGCGGCGGCTTTGTGCCGCGCATGGA

AGGCGTGCCGGAAAGCCCGTTTACCCGCACCGGCGAAGGCCTGGATATTCGC

GGCAACCAGGGCTTTCCGTGGGTGCGCCCGAGCCCGCCGCAGCAGCGCCTGC

CGCTGCTGGAATGCACCCCGCAGTGATGAG↓AATTCCGT delta 6 codon optimized

SEQ ID NO: 37

GCCTCACGGTCAGAGTCAAAGAAGAACAGAGGCGGAAGAGAAGAAATCCTGGAGCAGTGG

GTCGGAGCACGGAAAAAGCTGGAAGAACTGGAGAGGGACCTGCGCAAGATCAAGAAGAAG

ATCAAGAAGCTGGAGGAGGAGAACCCCTGGCTGGGCAATATCAAGGGCATCCTGGGCAAG

AAGGATAGGGAGGGAGAGGGAGCACCACCTGCAAAGAGGGCCAGAGCCGACCAGATGGAG

GTGGATAGCGGACCAAGGAAGCGCCCCTTCCGCGGAGAGTTTACCGACAAGGAGCGGAGA

GATCACAGGCGCCGGAAGGCCCTGGAGAACAAGAGGAAGCAGCTGAGCTCCGGCGGCAAG

TCCCTGTCTAAGGAGGAGGAGGAGGAGCTGCGCAAGCTGACAGAGGAGGACGAGAGAAGG

GAGAGGAGGGTGGCAGGACCAAGGGTGGGAGGAGTGAATCCTCTGGAGGGAGGAACCAGA

GGAGCACCAGGAGGAGGCTTCGTGCCAAGCATGCAGGGAGTGCCAGAGTCCCCCTTTGCC

AGGACAGGAGAGGGCCTGGACGTGAGAGGCAACCAGGGCTTCCCTTGGGACATCCTGTTT

CCAGCCGATCCACCCTTCAGCCCTCAGTCCTGCAGGCCACAGGGAAGCGGAGCTACTAAC

TTCAGCCTGCTGAAGCAGGCTGGAGACGTGGAGGAGAACCCTGGACCTATGAGCCGGTCC

GAGTCTAAGAAGAATAGGGGAGGAAGAGAGGAGGTGCTGGAGCAGTGGGTGAACGGCAGA

AAGAAGCTGGAGGAGCTGGAGAGGGAGCTGAGAAGGGCCCGCAAGAAGATCAAGAAGCTG

GAAGACGATAATCCTTGGCTGGGCAATGTGAAAGGCATCCTGGGCAAGAAGGACAAGGAT

GGAGAGGGAGCACCTCCAGCAAAGAGGGCAAGAACCGACCAGATGGAGATCGATAGCGGA

CCTAGGAAGCGCCCACTGAGGGGAGGCTTTACAGACCGGGAGAGACAGGATCACCGCCGG

AGAAAGGCCCTGAAGAACAAGAAGAAGCAGCTGTCCGCCGGAGGCAAGAGCCTGTCCAAA

GAAGAGGAAGAGGAGCTGAAGAGGCTGACCCGCGAGGACGAGGAGAGGAAGAAGGAGGAG

CACGGACCATCTAGGCTGGGAGTGAATCCCAGCGAGGGAGGACCAAGGGGAGCACCTGGA

GGAGGCTTCGTGCCCTCCATGCAGGGCATCCCTGAGTCTCGGTTTACCAGAACCGGCGAG

GGCCTGGACGTGAGGGGCAGCCGCGGCTTTCCACAGGACATCCTGTTCCCCTCCGATCCC

CCTTTTTCTCCCCAGAGCTGTCGCCCTCAAGGAAGCGGAGCTACTAACTTCAGCCTGCTG

AAGCAGGCTGGAGACGTGGAGGAGAACCCTGGACCTATGTCTCAGAGCGAGACAAGGAGG

GGCCGGAGAGGAACCAGGGAGGAGACACTGGAGAAGTGGATCACAGCCCGCAAGAAGGCC

GAGGAGCTGGAGAAGGACCTGCGGAAGACCAGAAAGACAATCAAGAAGCTGGAAGAAGAG

AACCCTTGGCTGGGCAATATCGTGGGCATCATCAGGAAGGGCAAGGACGGCGAGGGAGCA

CCACCAGCCAAGAGGCCACGCACTGATCAGATGGAGGTGGATTCTGGACCAGGCAAGCGG

CCCCACAAGAGCGGCTTCACAGACAAGGAGAGAGAGGACCATAGGCGCCGGAAGGCCCTG

GAAAACAAGAAGAAGCAATTAAGCGCCGGCGGCAAGATCCTGTCCAAAGAGGAAGAGGAG

GAGCTGAGAAGGCTGACCGACGAGGATGAGGAGAGGAAAGAAGGGTGGCAGGACCTAGG

GTGGGCGACGTGAATCCAAGCAGGGGAGGACCTAGAGGAGCACCAGGAGGCGGCTTCGTG

CCACAGATGGCAGGAGTGCCTGAGTCCCCATTTTCTCGGACCGGCGAGGGCCTGGATATC

AGAGGCACACAGGGCTTCCCCTGGGTGTCCCCTTCTCCTCCACAGCAGCGGCTGCCTCTG

CTGGAGTGCACCCCTCAGGGAAGCGGAGCTACTAACTTCAGCCTGCTGAAGCAGGCTGGA

GACGTGGAGGAGAACCCTGGACCTATGTCGCAGAGCGAATCTAAGAAGAATAGAAGGGGC

-continued

```
GGCAGAGAGGATATCCTGGAGAAGTGGATCACCACACGCAGAAAAGCTGAAGAACTGGAA

AAGGACCTGAGGAAGGCCCGCAAGACCATCAAGAAGCTGGAGGATGAAAATCCATGGCTG

GGAAATATCATCGGCATCATCCGGAAGGGCAAGGACGGGGAAGGCGCCCCACCTGCAAAG

CGGCCCAGGACTGATCAGATGGAAATCGATTCCGGCACAGGCAAGAGGCCTCACAAGTCT

GGCTTCACAGATAAAGAGCGCGAGGATCACAGAAGGCGCAAGGCCCTGGAGAACAAGAAG

AAGCAATTATCTAGCGGCGGCAAGAATCTGTCCAGAGAAGAAGAGGAGGAGCTGGGCCGC

CTGACCGTGGAGGACGAGGAGCGGAGAAGGCGCGTGGCAGGACCAAGAACAGGCGATGTG

AACCTGTCTGGAGGCGGCCCAAGGGGCGCCCCCGGCGGAGGCTTCGTGCCAAGAATGGAA

GGCGTGCCAGAGTCCCCTTTTACCCGGACAGGGGAAGGCCTGGACATTAGAGGCAATCAG

GGCTTTCCCTGGGTGCGACCAAGCCCCCCTCAGCAGCGACTGCCTCTGCTGGAGTGTACC

CCTCAG
``` delta 6 codon optimized with restriction sites (HindIII/EcoRI)
SEQ ID NO: 38

```
A↓AGCTTGCACCATGGCCTCACGGTCAGAGTCAAAGAAGAACAGAGGCGGAAGAGAAGAA

ATCCTGGAGCAGTGGGTCGGAGCACGGAAAAAGCTGGAAGAACTGGAGAGGGACCTGCGC

AAGATCAAGAAGAAGATCAAGAAGCTGGAGGAGGAGAACCCCTGGCTGGGCAATATCAAG

GGCATCCTGGGCAAGAAGGATAGGGAGGGAGAGGGAGCACCACCTGCAAAGAGGGCCAGA

GCCGACCAGATGGAGGTGGATAGCGGACCAAGGAAGCGCCCCTTCCGCGGAGAGTTTACC

GACAAGGAGCGGAGAGATCACAGGCGCCGGAAGGCCCTGGAGAACAAGAGGAAGCAGCTG

AGCTCCGGCGGCAAGTCCCTGTCTAAGGAGGAGGAGGAGGAGCTGCGCAAGCTGACAGAG

GAGGACGAGAGAAGGGAGAGGAGGGTGGCAGGACCAAGGGTGGGAGGAGTGAATCCTCTG

GAGGGAGGAACCAGAGGAGCACCAGGAGGAGGCTTCGTGCCAAGCATGCAGGGAGTGCCA

GAGTCCCCCTTTGCCAGGACAGGAGAGGGCCTGGACGTGAGAGGCAACCAGGGCTTCCCT

TGGGACATCCTGTTTCCAGCCGATCCACCCTTCAGCCCTCAGTCCTGCAGGCCACAGGGA

AGCGGAGCTACTAACTTCAGCCTGCTGAAGCAGGCTGGAGACGTGGAGGAGAACCCTGGA

CCTATGAGCCGGTCCGAGTCTAAGAAGAATAGGGGAGGAAGAGAGGAGGTGCTGGAGCAG

TGGGTGAACGGCAGAAAGAAGCTGGAGGAGCTGGAGAGGGAGCTGAGAAGGGCCCGCAAG

AAGATCAAGAAGCTGGAAGACGATAATCCTTGGCTGGGCAATGTGAAAGGCATCCTGGGC

AAGAAGGACAAGGATGGAGAGGGAGCACCTCCAGCAAAGAGGGCAAGAACCGACCAGATG

GAGATCGATAGCGGACCTAGGAAGCGCCCACTGAGGGGAGGCTTTACAGACCGGAGAGA

CAGGATCACCGCCGGAGAAAGGCCCTGAAGAACAAGAAGAAGCAGCTGTCCGCCGGAGGC

AAGAGCCTGTCCAAAGAAGAGGAAGAGGAGCTGAAGAGGCTGACCCGCGAGGACGAGGAG

AGGAAGAAGGAGGAGCACGGACCATCTAGGCTGGGAGTGAATCCCAGCGAGGGAGGACCA

AGGGGAGCACCTGGAGGAGGCTTCGTGCCCTCCATGCAGGGCATCCCTGAGTCTCGGTTT

ACCAGAACCGGCGAGGGCCTGGACGTGAGGGGCAGCCGCGGCTTTCCACAGGACATCCTG

TTCCCCTCCGATCCCCCTTTTTCTCCCCAGAGCTGTCGCCCTCAAGGAAGCGGAGCTACT

AACTTCAGCCTGCTGAAGCAGGCTGGAGACGTGGAGGAGAACCCTGGACCTATGTCTCAG

AGCGAGACAAGGAGGGGCCGGAGAGGAACCAGGGAGGAGACACTGGAGAAGTGGATCACA

GCCCGCAAGAAGGCCGAGGAGCTGGAGAAGGACCTGCGGAAGACCAGAAAGACAATCAAG

AAGCTGGAAGAAGAACCCTTGGCTGGGCAATATCGTGGGCATCATCAGGAAGGGCAAG

GACGGCGAGGGAGCACCACCAGCCAAGAGGCCACGCACTGATCAGATGGAGGTGGATTCT
```

```
GGACCAGGCAAGCGGCCCCACAAGAGCGGCTTCACAGACAAGGAGAGAGAGGACCATAGG

CGCCGGAAGGCCCTGGAAAACAAGAAGAAGCAATTAAGCGCCGGCGGCAAGATCCTGTCC

AAAGAGGAAGAGGAGGAGCTGAGAAGGCTGACCGACGAGGATGAGGAGAGGAAAAGAAGG

GTGGCAGGACCTAGGGTGGGCGACGTGAATCCAAGCAGGGGAGGACCTAGAGGAGCACCA

GGAGGCGGCTTCGTGCCACAGATGGCAGGAGTGCCTGAGTCCCCATTTTCTCGGACCGGC

GAGGGCCTGGATATCAGAGGCACACAGGGCTTCCCCTGGGTGTCCCCTTCTCCTCCACAG

CAGCGGCTGCCTCTGCTGGAGTGCACCCCTCAGGGAAGCGGAGCTACTAACTTCAGCCTG

CTGAAGCAGGCTGGAGACGTGGAGGAGAACCCTGGACCTATGTCGCAGAGCGAATCTAAG

AAGAATAGAAGGGGCGGCAGAGAGGATATCCTGGAGAAGTGGATCACCACACGCAGAAAA

GCTGAAGAACTGGAAAAGGACCTGAGGAAGGCCCGCAAGACCATCAAGAAGCTGGAGGAT

GAAAATCCATGGCTGGGAAATATCATCGGCATCATCCGGAAGGGCAAGGACGGGGAAGGC

GCCCCACCTGCAAAGCGGCCCAGGACTGATCAGATGGAAATCGATTCCGGCACAGGCAAG

AGGCCTCACAAGTCTGGCTTCACAGATAAAGAGCGCGAGGATCACAGAAGGCGCAAGGCC

CTGGAGAACAAGAAGAAGCAATTATCTAGCGGCGGCAAGAATCTGTCCAGAGAAGAAGAG

GAGGAGCTGGGCCGCCTGACCGTGGAGGACGAGGAGCGGAGAAGGCGCGTGGCAGGACCA

AGAACAGGCGATGTGAACCTGTCTGGAGGCGGCCCAAGGGGCGCCCCCGGCGGAGGCTTC

GTGCCAAGAATGGAAGGCGTGCCAGAGTCCCCTTTTACCCGACAGGGGAAGGCCTGGAC

ATTAGAGGCAATCAGGGCTTTCCCTGGGTGCGACCAAGCCCCCCTCAGCAGCGACTGCCT

CTGCTGGAGTGTACCCCTCAGTGATGAG↓AATTCCGT delta 6 protein                                           SEQ ID NO: 39

MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKA

LENKRKQLSSGGKSLSKEEEELRKLTEEDERRERRVAGPRVGGVNPLEGGTRG

APGGGFVPSMQGVPESPFARTGEGLDVRGNQGFPWDILFPADPPFSPQSCRPQGS

GATNFSLLKQAGDVEENPGPMSRSESKKNRGGREEVLEQWVNGRKKLEELEREL

RRARKKIKKLEDDNPWLGNVKGILGKKDKDGEGAPPAKRARTDQMEIDSGPRK

RPLRGGFTDRERQDHRRRKALKNKKKQLSAGGKSLSKEEEELKRLTREDEERK

KEEHGPSRLGVNPSEGGPRGAPGGGFVPSMQGIPESRFTRTGEGLDVRGSRGFPQ

DILFPSDPPFSPQSCRPQGSGATNFSLLKQAGDVEENPGPMSQSETRRGRRGTREE

TLEKWITARKKAEELEKDLRKTRKTIKKLEEENPWLGNIVGIIRKGKDGEGAPPA

KRPRTDQMEVDSGPGKRPHKSGFTDKEREDHRRRKALENKKKQLSAGGKILSKE

EEEELRRLTDEDEERKRRVAGPRVGDVNPSRGGPRGAPGGGFVPQMAGYPESPF

SRTGEGLDIRGTQGFPWVSPSPPQQRLPLLECTPQGSGATNFSLLKQAGDVEENP

GPMSQSESKKNRGGREDILEKWITTRRKAEELEKDLRKARKTIKKLEDENPWL

GNIIGIIRKGKDGEGAPPAKRPRTDQMEIDSGTGKRPHKSGFTDKEREDHRRRKA

LENKKKQLSSGGKNLSREEEEELGRLTVEDEERRRVAGPRTGDVNLSGGGPRG

APGGGFVPRMEGVPESPFTRTGEGLDIRGNQGFPWVRPSPPQQRLPLLECTPQ delta 7 wt                                                SEQ ID NO: 40

AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAAACTGGAAGAAGAAAACCCGTGGCTGGGC
```

```
AACATTAAAGGCATTCTGGGCAAAAAAGATCGCGAAGGCGAAGGCGCGCCG
CCGGCGAAACGCGCGCGCGGATCAGATGGAAGTGGATAGCGGCCCGCGC
AAACGCCCGTTTCGCGGCGAATTTACCGATAAAGAACGCCGCGATCATCGCC
GCCGCAAAGCGCTGGAAAACAAACGCAAACAGCTGAGCAGCGGCGGCAAAA
GCCTGAGCAAAGAAGAAGAAGAAGAACTGCGCAAACTGACCGAAGAAGATG
AACGCCGCGAACGCCGCGTGGCGGGCCCGCGCGTGGGCGGCGTGAACCCGCT
GGAAGGCGGCACCCGCGGCGCGCCGGGCGGCGGCTTTGTGCCGAGCATGCAG
GGCGTGCCGGAAAGCCCGTTTGCGCGCACCGGCGAAGGCCTGGATGTGCGCG
GCAACCAGGGCTTTCCGTGGGATATTCTGTTTCCGGCGGATCCGCCGTTTAGC
CCGCAGAGCTGCCGCCCGCAGAGCCGCAGCGAAAGCAAAAAAAACCGCGGC
GGCCGCGAAGAAGTGCTGGAACAGTGGGTGAACGGCCGCAAAAAACTGGAA
GAACTGGAACGCGAACTGCGCCGCGCGCGCAAAAAAATTAAAAAACTGGAA
GATGATAACCCGTGGCTGGGCAACGTGAAAGGCATTCTGGGCAAAAAAGATA
AAGATGGCGAAGGCGCGCCGCCGGCGAAACGCGCGCGCACCGATCAGATGG
AAATTGATAGCGGCCCGCGCAAACGCCCGCTGCGCGGCGGCTTTACCGATCG
CGAACGCCAGGATCATCGCCGCCGCAAAGCGCTGAAAAACAAAAAAAAACA
GCTGAGCGCGGGCGGCAAAAGCCTGAGCAAAGAAGAAGAAGAAGAACTGAA
ACGCCTGACCCGCGAAGATGAAGAACGCAAAAAAGAAGAACATGGCCCGAG
CCGCCTGGGCGTGAACCCGAGCGAAGGCGGCCCGCGCGGCGCGCCGGGCGG
CGGCTTTGTGCCGAGCATGCAGGGCATTCCGGAAAGCCGCTTTACCCGCACC
GGCGAAGGCCTGGATGTGCGCGGCAGCCGCGGCTTTCCGCAGGATATTCTGT
TTCCGAGCGATCCGCCGTTTAGCCCGCAGAGCTGCCGCCCGCAGGGCACCAA
CCTGAGCACCAGCAACCCGCTGGGCTTTTTTCCGGATCATCAGCTGGATCCGG
CGTTTCGCGCGAACAGCGCGAACCCGGATTGGGATTTTAACCCGAACAAAGA
TACCTGGCCGGATGCGAACAAAGTGGGCGGCCAGAACCTGAGCACCAGCAA
CCCGCTGGGCTTTTTTCCGGATCATCAGCTGGATCCGGCGTTTCGCGCGAACA
CCGCGAACCCGGATTGGGATTTTAACCCGAACAAAGATACCTGGCCGGATGC
GAACAAAGTGGGC
``` delta 7 wt with restriction sites (HindIII/EcoRI)                          SEQ ID NO: 41

```
A↓AGCTTGCACCATGGCCAGCCGCAGCGAAAGCAAAAAAAACCGCGGCGGCCG
CGAAGAAATTCTGGAACAGTGGGTGGCGCGCGCAAAAAACTGGAAGAACT
GGAACGCGATCTGCGCAAAATTAAAAAAAAATTAAAAAACTGGAAGAAGA
AAACCCGTGGCTGGGCAACATTAAAGGCATTCTGGGCAAAAAAGATCGCGAA
GGCGAAGGCGCGCCGCCGGCGAAACGCGCGCGCGCGGATCAGATGGAAGTG
GATAGCGGCCCGCGCAAACGCCCGTTTCGCGGCGAATTTACCGATAAAGAAC
GCCGCGATCATCGCCGCCGCAAAGCGCTGGAAAACAAACGCAAACAGCTGA
GCAGCGGCGGCAAAAGCCTGAGCAAAGAAGAAGAAGAAGAACTGCGCAAAC
TGACCGAAGAAGATGAACGCCGCGAACGCCGCGTGGCGGGCCCGCGCGTGG
GCGGCGTGAACCCGCTGGAAGGCGGCACCCGCGGCGCGCCGGGCGGCGGCTT
TGTGCCGAGCATGCAGGGCGTGCCGGAAAGCCCGTTTGCGCGCACCGGCGAA
```

-continued

```
GGCCTGGATGTGCGCGGCAACCAGGGCTTTCCGTGGGATATTCTGTTTCCGGC

GGATCCGCCGTTTAGCCCGCAGAGCTGCCGCCCGCAGAGCCGCAGCGAAAGC

AAAAAAAACCGCGGCGGCCGCGAAGAAGTGCTGGAACAGTGGGTGAACGGC

CGCAAAAAACTGGAAGAACTGGAACGCGAACTGCGCCGCGCGCGCAAAAAA

ATTAAAAAACTGGAAGATGATAACCCGTGGCTGGGCAACGTGAAAGGCATTC

TGGGCAAAAAGATAAAGATGGCGAAGGCGCGCCGCCGGCGAAACGCGCGC

GCACCGATCAGATGGAAATTGATAGCGGCCCGCGCAAACGCCCGCTGCGCGG

CGGCTTTACCGATCGCAACGCCAGGATCATCGCCGCCGCAAAGCGCTGAAA

AACAAAAAAAAACAGCTGAGCGCGGGCGGCAAAAGCCTGAGCAAAGAAGAA

GAAGAAGAACTGAAACGCCTGACCCGCGAAGATGAAGAACGCAAAAAAGAA

GAACATGGCCCGAGCCGCCTGGGCGTGAACCCGAGCGAAGGCGGCCCCGCGC

GGCGCGCCGGGCGGCGGCTTTGTGCCGAGCATGCAGGGCATTCCGGAAAGCC

GCTTTACCCGCACCGGCGAAGGCCTGGATGTGCGCGGCAGCCGCGGCTTTCC

GCAGGATATTCTGTTTCCGAGCGATCCGCCGTTTAGCCCGCAGAGCTGCCGCC

CGCAGGGCACCAACCTGAGCACCAGCAACCCGCTGGGCTTTTTTCCGGATCA

TCAGCTGGATCCGGCGTTTCGCGCGAACAGCGCGAACCCGGATTGGGATTTT

AACCCGAACAAAGATACCTGGCCGGATGCGAACAAAGTGGGCGGCCAGAAC

CTGAGCACCAGCAACCCGCTGGGCTTTTTTCCGGATCATCAGCTGGATCCGGC

GTTTCGCGCGAACACCGCGAACCCGGATTGGGATTTTAACCCGAACAAAGAT

ACCTGGCCGGATGCGAACAAAGTGGGCTGATGAG↓AATTCCGT
``` delta 7 codon optimized

SEQ ID NO: 42

```
GCCTCACGGTCTGAGTCAAAGAAGAATCGGGGGGAAGAGAAGAAATCCTGGAACAGTGG

GTCGGCGCACGGAAAAAACTGGAAGAACTGGAGCGGGACCTGAGAAAGATCAAGAAGAAG

ATCAAGAAGCTGGAGGAAGAGAACCCCTGGCTGGGCAATATCAAGGGCATCCTGGGCAAG

AAGGATCGGAGGGCGAGGGAGCACCACCTGCAAAGAGGGCAAGGGCAGACCAGATGGAG

GTGGATTCCGGACCTAGGAAGCGGCCCTTCCGGGGAGAGTTTACCGACAAGGAGCGGAGA

GATCACAGGCGCCGGAAGGCCCTGGAGAACAAGCGGAAGCAGCTGAGCTCCGGCGGCAAG

TCTCTGAGCAAGGAGGAGGAGGAGGAGCTGAGAAAGCTGACAGAGGAGGACGAGAGAAGG

GAGCGCCGGGTGGCCGGCCCAAGGGTGGGCGGCGTGAACCCCCTGGAGGGAGGAACCAGG

GGAGCACCAGGAGGAGGCTTCGTGCCTTCTATGCAGGGCGTGCCAGAGAGCCCCTTTGCC

AGGACAGGAGAGGGCCTGGATGTGCGCGGCAATCAGGGCTTCCCATGGGACATCCTGTTT

CCCGCCGATCCACCCTTCTCCCCTCAGTCTTGCAGGCCACAGTCCCGCTCTGAGAGCAAG

AAGAACAGGGGAGGAAGGGAGGAGGTGCTGGAGCAGTGGGTGAATGGCAGGAAGAAGCTG

GAGGAGCTGGAGCGGGAGCTGAGAAGGGCCAGAAAGAAGATCAAGAAGCTGGAAGACGAT

AATCCTTGGCTGGGCAATGTGAAAGGCATCCTGGGCAAGAAGGACAAGGATGGAGAGGGA

GCACCTCCAGCAAAGAGGGCACGCACCGACCAGATGGAGATCGATTCCGGACCAAGGAAG

CGGCCCCTGAGGGGAGGCTTCACAGACAGGGAGCGCCAGGATCACCGCCGGAGAAAGGCC

CTGAAGAACAAGAAGAAGCAGCTGTCTGCCGGCGGCAAGTCCCTGTCTAAAGAAGAGGAG

GAGGAGCTGAAGCGGCTGACCAGAGAGGACGAGGAGCGGAAGAAGGAGGAGCACGGCCCT

TCCAGACTGGGCGTGAATCCATCTGAGGGAGGACCAAGAGGCGCCCCTGGCCGGAGGCTTC

GTGCCTAGCATGCAGGGCATCCCAGAGTCCAGGTTTACCAGAACCGGAGAGGGCCTGGAC
```

-continued

GTGCGGGGCTCTAGAGGCTTTCCCCAGGACATCCTGTTCCCTAGCGATCCCCCTTTTAGC

CCCCAGTCCTGTAGGCCTCAGGGCACCAACCTGAGCACATCCAATCCACTGGGCTTCTTT

CCAGACCACCAGCTGGATCCAGCCTTCCGCGCCAACAGCGCCAATCCAGACTGGGACTTC

AACCCCAATAAGGACACCTGGCCTGATGCCAACAAGGTCGGCGGCCAGAACCTGTCTACA

AGCAATCCTCTGGGCTTCTTTCCTGATCACCAGCTGGATCCTGCCTTTCGGGCCAATACA

GCCAACCCTGACTGGGACTTCAATCCTAACAAAGACACTTGGCCCGATGCTAATAAGGTC

GGC delta 7 codon optimized with restriction sites (HindIII/EcoRI)
SEQ ID NO: 43
A↓AGCTT*GCACC*ATGGCCTCACGGTCTGAGTCAAAGAAGAATCGGGGGGAAGAGAAGAA

ATCCTGGAACAGTGGGTCGGCGCACGGAAAAAACTGGAAGAACTGGAGCGGGACCTGAGA

AAGATCAAGAAGAAGATCAAGAAGCTGGAGGAAGAGAACCCCTGGCTGGGCAATATCAAG

GGCATCCTGGGCAAGAAGGATCGGGAGGGCGAGGGAGCACCACCTGCAAAGAGGGCAAGG

GCAGACCAGATGGAGGTGGATTCCGGACCTAGGAAGCGGCCCTTCCGGGGAGAGTTTACC

GACAAGGAGCGGAGAGATCACAGGCGCCGGAAGGCCCTGGAGAACAAGCGGAAGCAGCTG

AGCTCCGGCGGCAAGTCTCTGAGCAAGGAGGAGGAGGAGGAGCTGAGAAAGCTGACAGAG

GAGGACGAGAGAAGGGAGCGCGGGTGGCCGGCCCAAGGGTGGGCGGCGTGAACCCCCTG

GAGGGAGGAACCAGGGGAGCACCAGGAGGAGGCTTCGTGCCTTCTATGCAGGGCGTGCCA

GAGAGCCCCTTTGCCAGGACAGGAGAGGGCCTGGATGTGCGCGGCAATCAGGGCTTCCCA

TGGGACATCCTGTTTCCCGCCGATCCACCCTTCTCCCCTCAGTCTTGCAGGCCACAGTCC

CGCTCTGAGAGCAAGAAGAACAGGGGAGGAAGGGAGGAGGTGCTGGAGCAGTGGGTGAAT

GGCAGGAAGAAGCTGGAGGAGCTGGAGCGGGAGCTGAGAAGGGCCAGAAAGAAGATCAAG

AAGCTGGAAGACGATAATCCTTGGCTGGGCAATGTGAAAGGCATCCTGGGCAAGAAGGAC

AAGGATGGAGAGGGAGCACCTCCAGCAAAGAGGGCACGCACCGACCAGATGGAGATCGAT

TCCGGACCAAGGAAGCGGCCCCTGAGGGGAGGCTTCACAGACAGGGAGCGCCAGGATCAC

CGCCGGAGAAAGGCCCTGAAGAACAAGAAGAAGCAGCTGTCTGCCGGCGGCAAGTCCCTG

TCTAAAGAAGAGGAGGAGGAGCTGAAGCGGCTGACCAGAGAGGACGAGGAGCGGAAGAAG

GAGGAGCACGGCCCTTCCAGACTGGGCGTGAATCCATCTGAGGGAGGACCAAGAGGCGCC

CCTGGCGGAGGCTTCGTGCCTAGCATGCAGGGCATCCCAGAGTCCAGGTTTACCAGAACC

GGAGAGGGCCTGGACGTGCGGGGCTCTAGAGGCTTTCCCCAGGACATCCTGTTCCCTAGC

GATCCCCCTTTTAGCCCCCAGTCCTGTAGGCCTCAGGGCACCAACCTGAGCACATCCAAT

CCACTGGGCTTCTTTCCAGACCACCAGCTGGATCCAGCCTTCCGCGCCAACAGCGCCAAT

CCAGACTGGGACTTCAACCCCAATAAGGACACCTGGCCTGATGCCAACAAGGTCGGCGGC

CAGAACCTGTCTACAAGCAATCCTCTGGGCTTCTTTCCTGATCACCAGCTGGATCCTGCC

TTTCGGGCCAATACAGCCAACCCTGACTGGGACTTCAATCCTAACAAAGACACTTGGCCC

GATGCTAATAAGGTCGGCTGATGAG↓AATTCCGT delta 7 protein
SEQ ID NO: 44
MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKA

LENKRKQLSSGGKSLSKEEEELRKLTEEDERRERRVAGPRVGGVNPLEGGTRG

APGGGFVPSMQGVPESPFARTGEGLDVRGNQGFPWDILFPADPPFSPQSCRPQSR

-continued

```
SESKKNRGGREEVLEQWVNGRKKLEELERELRRARKKIKKLEDDNPWLGNVKGI

LGKKDKDGEGAPPAKRARTDQMEIDSGPRKRPLRGGFTDRERQDHRRRKALKN

KKKQLSAGGKSLSKEEEEELKRLTREDEERKKEEHGPSRLGVNPSEGGPRGAPGG

GFVPSMQGIPESRFTRTGEGLDVRGSRGFPQDILFPSDPPFSPQSCRPQGTNLSTSN

PLGFFPDHQLDPAFRANSANPDWDFNPNKDTWPDANKVGGQNLSTSNPLGFFPD

HQLDPAFRANTANPDWDFNPNKDTWPDANKVG delta 8 wt
                                                              SEQ ID NO: 45
AGCCAGAGCGAAACCCGCCGCGGCCGCCGCGGCACCCGCGAAGAAACCCTG

GAAAAATGGATTACCGCGCGCAAAAAAGCGGAAGAACTGGAAAAAGATCTG

CGCAAAACCCGCAAAACCATTAAAAAACTGGAAGAAGAAAACCCGTGGCTG

GGCAACATTGTGGGCATTATTCGCAAAGGCAAAGATGGCGAAGGCGCGCCGC

CGGCGAAACGCCCGCGCACCGATCAGATGGAAGTGGATAGCGGCCCGGGCA

AACGCCCGCATAAAAGCGGCTTTACCGATAAAGAACGCGAAGATCATCGCCG

CCGCAAAGCGCTGGAAAACAAAAAAAAACAGCTGAGCGCGGGCGGCAAAAT

TCTGAGCAAAGAAGAAGAAGAAGAACTGCGCCGCCTGACCGATGAAGATGA

AGAACGCAAACGCCGCGTGGCGGGCCCGCGCGTGGGCGATGTGAACCCGAG

CCGCGGCGGCCCGCGCGGCGCGCCGGGCGGCGGCTTTGTGCCGCAGATGGCG

GGCGTGCCGGAAAGCCCGTTTAGCCGCACCGGCGAAGGCCTGGATATTCGCG

GCACCCAGGGCTTTCCGTGGGTGAGCCCGAGCCCGCCGCAGCAGCGCCTGCC

GCTGCTGGAATGCACCCCGCAGAGCCAGAGCGAAAGCAAAAAAAACCGCCG

CGGCGGCCGCGAAGATATTCTGGAAAAATGGATTACCACCCGCCGCAAAGCG

GAAGAACTGGAAAAAGATCTGCGCAAAGCGCGCAAAACCATTAAAAAACTG

GAAGATGAAAACCCGTGGCTGGGCAACATTATTGGCATTATTCGCAAAGGCA

AAGATGGCGAAGGCGCGCCGCCGGCGAAACGCCCGCGCACCGATCAGATGG

AAATTGATAGCGGCACCGGCAAACGCCCGCATAAAAGCGGCTTTACCGATAA

AGAACGCGAAGATCATCGCCGCCGCAAAGCGCTGGAAAACAAAAAAAAACA

GCTGAGCAGCGGCGGCAAAAAACCTGAGCCGCGAAGAAGAAGAAGAACTGGG

CCGCCTGACCGTGGAAGATGAAGAACGCCGCCGCCGCGTGGCGGGCCCGCGC

ACCGGCGATGTGAACCTGAGCGGCGGCGGCCCGCGCGGCGCGCCGGGCGGC

GGCTTTGTGCCGCGCATGGAAGGCGTGCCGGAAAGCCCGTTTACCCGCACCG

GCGAAGGCCTGGATATTCGCGGCAACCAGGGCTTTCCGTGGGTGCGCCCGAG

CCCGCCGCAGCAGCGCCTGCCGCTGCTGGAATGCACCCCGCAGGGCACCAAC

CTGAGCACCAGCAACCCGCTGGGCTTTTTTCCGGATCATCAGCTGGATCCGGC

GTTTCGCGCGAACAGCGCGAACCCGGATTGGGATTTTAACCCGAACAAAGAT

ACCTGGCCGGATGCGAACAAAGTGGGCGGCCAGAACCTGAGCACCAGCAAC

CCGCTGGGCTTTTTTCCGGATCATCAGCTGGATCCGGCGTTTCGCGCGAACAC

CGCGAACCCGGATTGGGATTTTAACCCGAACAAAGATACCTGGCCGGATGCG

AACAAAGTGGGC delta 8 wt with restriction sites (HindIII/EcoRI)
                                                              SEQ ID NO: 46
A↓AGCTT*GCACC***ATG**GCCAGCAGAGCGAAACCCGCCGCGGCCGCCGCGGCACC

CGCGAAGAAACCCTGGAAAAATGGATTACCGCGCGCAAAAAAGCGGAAGAA
```

-continued

```
CTGGAAAAAGATCTGCGCAAAACCCGCAAAACCATTAAAAAACTGGAAGAA

GAAAACCCGTGGCTGGGCAACATTGTGGGCATTATTCGCAAAGGCAAAGATG

GCGAAGGCGCGCCGCCGGCGAAACGCCCGCGCACCGATCAGATGGAAGTGG

ATAGCGGCCCGGGCAAACGCCCGCATAAAAGCGGCTTTACCGATAAAGAACG

CGAAGATCATCGCCGCCGCAAAGCGCTGGAAAACAAAAAAAAACAGCTGAG

CGCGGGCGGCAAAATTCTGAGCAAAGAAGAAGAAGAAGAACTGCGCCGCCT

GACCGATGAAGATGAAGAACGCAAACGCCGCGTGGCGGGCCCGCGCGTGGG

CGATGTGAACCCGAGCCGCGGCGGCCCGCGCGGCGCGCCGGGCGGCGGCTTT

GTGCCGCAGATGGCGGGCGTGCCGGAAAGCCCGTTTAGCCGCACCGGCGAAG

GCCTGGATATTCGCGGCACCCAGGGCTTTCCGTGGGTGAGCCCGAGCCCGCC

GCAGCAGCGCCTGCCGCTGCTGGAATGCACCCCGCAGAGCCAGAGCGAAAGC

AAAAAAACCGCCGCGGCGGCCGCGAAGATATTCTGGAAAAATGGATTACCA

CCCGCCGCAAAGCGGAAGAACTGGAAAAAGATCTGCGCAAAGCGCGCAAAA

CCATTAAAAAACTGGAAGATGAAAACCCGTGGCTGGGCAACATTATTGGCAT

TATTCGCAAAGGCAAAGATGGCGAAGGCGCGCCGCCGGCGAAACGCCCGCG

CACCGATCAGATGGAAATTGATAGCGGCACCGGCAAACGCCCGCATAAAAGC

GGCTTTACCGATAAAGAACGCGAAGATCATCGCCGCCGCAAAGCGCTGGAAA

ACAAAAAAAAACAGCTGAGCAGCGGCGGCAAAAAACCTGAGCCGCGAAGAAG

AAGAAGAACTGGGCCGCCTGACCGTGGAAGATGAAGAACGCCGCCGCCGCG

TGGCGGGCCCGCGCACCGGCGATGTGAACCTGAGCGGCGGCGGCCCGCGCGG

CGCGCCGGGCGGCGGCTTTGTGCCGCGCATGGAAGGCGTGCCGGAAAGCCCG

TTTACCCGCACCGGCGAAGGCCTGGATATTCGCGGCAACCAGGGCTTTCCGTG

GGTGCGCCCGAGCCCGCCGCAGCAGCGCCTGCCGCTGCTGGAATGCACCCCG

CAGGGCACCAACCTGAGCACCAGCAACCCGCTGGGCTTTTTTCCGGATCATC

AGCTGGATCCGGCGTTTCGCGCGAACAGCGCGAACCCGGATTGGGATTTTAA

CCCGAACAAAGATACCTGGCCGGATGCGAACAAAGTGGGCGGCCAGAACCT

GAGCACCAGCAACCCGCTGGGCTTTTTTCCGGATCATCAGCTGGATCCGGCGT

TTCGCGCGAACACCGCGAACCCGGATTGGGATTTTAACCCGAACAAAGATAC

CTGGCCGGATGCGAACAAAGTGGGCTGATGAG|AATTCCGT
``` delta 8 optimized

SEQ ID NO: 47

```
GCCAGTCAGAGCGAGACCCGCAGAGGACGGAGAGGAACACGAGAAGAGACACTGGAGAAA

TGGATTACAGCACGGAAGAAGGCAGAAGAGCTGGAGAAGGACCTGAGGAAGACCCGCAAG

ACAATCAAGAAGCTGGAGGAGGAGAACCCCTGGCTGGGCAATATCGTGGGCATCATCAGG

AAGGGCAAGGATGGAGAGGGAGCACCACCTGCCAAGAGGCCTCGCACAGACCAGATGGAG

GTGGATAGCGGACCAGGCAAGCGGCCTCACAAGTCCGGCTTCACCGACAAGGAGAGAGAG

GATCACCGGAGAAGGAAGGCCCTGGAGAACAAGAAGAAGCAGCTGTCCGCCGGCGGCAAG

ATCCTGTCTAAGGAGGAGGAGGAGGAGCTGCGCCGGCTGACAGACGAGGATGAGGAGAGG

AAGAGAAGGGTGGCAGGACCAAGGGTGGGCGACGTGAATCCTTCTAGGGGAGGACCAAGG

GGAGCACCAGGAGGAGGCTTCGTGCCTCAGATGGCCGGCGTGCCAGAGTCTCCCTTTAGC

CGGACAGGCGAGGGCCTGGATATCAGAGGCACCCAGGGCTTTCCTTGGGTGTCTCCAAGC
```

```
CCACCACAGCAGCGGCTGCCACTGCTGGAGTGCACACCCCAGTCCCAGTCTGAGAGCAAG

AAGAACAGGAGGGGAGGAAGAGAGGACATCCTGGAGAAGTGGATCACCACAAGAAGGAAG

GCCGAGGAGCTGGAGAAGGACCTGCGGAAGGCCAGAAAGACCATCAAGAAGCTGGAGGAT

GAAAATCCTTGGCTGGGAAATATCATCGGAATTATTAGAAAAGGCAAGGACGGAGAGGGA

GCACCTCCAGCAAAGCGGCCAAGAACAGACCAGATGGAGATCGATTCTGGAACCGGCAAG

AGGCCCCACAAGAGTGGCTTCACCGATAAGGAGCGCGAGGATCACCGCCGGAGAAAGGCC

CTGGAAAACAAGAAGAAGCAATTAAGCTCCGGCGGCAAGAATCTGAGCAGAGAAGAAGAG

GAGGAGCTGGGCCGCCTGACAGTGGAGGACGAGGAGAGGCGCCGGAGAGTGGCAGGACCT

AGAACCGGCGATGTGAACCTGTCCGGAGGCGGCCCAAGGGGAGCACCTGGAGGCGGCTTC

GTGCCACGCATGGAGGGCGTGCCTGAGTCTCCCTTCACCAGGACAGGAGAGGGCCTGGAC

ATCAGAGGCAATCAGGGATTCCCATGGGTGCGGCCCAGCCCACCTCAGCAGAGACTGCCT

CTGCTGGAGTGTACCCCACAGGGCACAAACCTGTCCACCTCTAATCCTCTGGGCTTCTTT

CCAGACCACCAGCTGGATCCAGCCTTCAGGGCCAACTCCGCCAACCCTGACTGGGACTTC

AACCCTAATAAGGACACATGGCCAGATGCCAACAAGGTCGGCGGCCAGAACCTGAGCACC

TCCAATCCCCTGGGCTTCTTTCCTGACCACCAGCTGGATCCCGCCTTTCGCGCCAATACC

GCCAATCCCGACTGGGACTTCAATCCAAATAAGGACACCTGGCCCGATGCTAACAAAGTG

GGA delta 8 codon optimized with restriction sites (HindIII/EcoRI)
                                                        SEQ ID NO: 48
A↓AGCTT*GCACC***ATG**GCCAGTCAGAGCGAGACCCGCAGAGGACGGAGAGGAACACGAGAA

GAGACACTGGAGAAATGGATTACAGCACGGAAGAAGGCAGAAGAGCTGGAGAAGGACCTG

AGGAAGACCCGCAAGACAATCAAGAAGCTGGAGGAGGAGAACCCCTGGCTGGGCAATATC

GTGGGCATCATCAGGAAGGGCAAGGATGGAGAGGGAGCACCACCTGCCAAGAGGCCTCGC

ACAGACCAGATGGAGGTGGATAGCGGACCAGGCAAGCGGCCTCACAAGTCCGGCTTCACC

GACAAGGAGAGAGAGGATCACCGGAGAAGGAAGGCCCTGGAGAACAAGAAGAAGCAGCTG

TCCGCCGGCGGCAAGATCCTGTCTAAGGAGGAGGAGGAGGAGCTGCGCCGGCTGACAGAC

GAGGATGAGGAGAGGAAGAGAAGGGTGGCAGGACCAAGGGTGGGCGACGTGAATCCTTCT

AGGGGAGGACCAAGGGGAGCACCAGGAGGAGGCTTCGTGCCTCAGATGGCCGGCGTGCCA

GAGTCTCCCTTTAGCCGGACAGGCGAGGGCCTGGATATCAGAGGCACCCAGGGCTTTCCT

TGGGTGTCTCCAAGCCCACCACAGCAGCGGCTGCCACTGCTGGAGTGCACACCCCAGTCC

CAGTCTGAGAGCAAGAAGAACAGGAGGGGAGGAAGAGAGGACATCCTGGAGAAGTGGATC

ACCACAAGAAGGAAGGCCGAGGAGCTGGAGAAGGACCTGCGGAAGGCCAGAAAGACCATC

AAGAAGCTGGAGGATGAAAATCCTTGGCTGGGAAATATCATCGGAATTATTAGAAAAGGC

AAGGACGGAGAGGGAGCACCTCCAGCAAAGCGGCCAAGAACAGACCAGATGGAGATCGAT

TCTGGAACCGGCAAGAGGCCCCACAAGAGTGGCTTCACCGATAAGGAGCGCGAGGATCAC

CGCCGGAGAAAGGCCCTGGAAAACAAGAAGAAGCAATTAAGCTCCGGCGGCAAGAATCTG

AGCAGAGAAGAAGAGGAGGAGCTGGGCCGCCTGACAGTGGAGGACGAGGAGAGGCGCCGG

AGAGTGGCAGGACCTAGAACCGGCGATGTGAACCTGTCCGGAGGCGGCCCAAGGGGAGCA

CCTGGAGGCGGCTTCGTGCCACGCATGGAGGGCGTGCCTGAGTCTCCCTTCACCAGGACA

GGAGAGGGCCTGGACATCAGAGGCAATCAGGGATTCCCATGGGTGCGGCCCAGCCCACCT

CAGCAGAGACTGCCTCTGCTGGAGTGTACCCCACAGGGCACAAACCTGTCCACCTCTAAT

CCTCTGGGCTTCTTTCCAGACCACCAGCTGGATCCAGCCTTCAGGGCCAACTCCGCCAAC
```

```
CCTGACTGGGACTTCAACCCTAATAAGGACACATGGCCAGATGCCAACAAGGTCGGCGGC

CAGAACCTGAGCACCTCCAATCCCCTGGGCTTCTTTCCTGACCACCAGCTGGATCCCGCC

TTTCGCGCCAATACCGCCAATCCCGACTGGGACTTCAATCCAAATAAGGACACCTGGCCC

GATGCTAACAAAGTGGGATGATGAG↓AATTCCGT
``` delta 8 protein                                          SEQ ID NO: 49

```
MASQSETRRGRRGTREETLEKWITARKKAEELEKDLRKTRKTIKKLEEENPWLG

NIVGIIRKGKDGEGAPPAKRPRTDQMEVDSGPGKRPHKSGFTDKEREDHRRRKA

LENKKKQLSAGGKILSKEEEEELRRLTDEDEERKRRVAGPRVGDVNPSRGGPRG

APGGGFVPQMAGVPESPFSRTGEGLDIRGTQGFPWVSPSPPQQRLPLLECTPQSQS

ESKKNRRGGREDILEKWITTRRKAEELEKDLRKARKTIKKLEDENPWLGNIIGIIR

KGKDGEGAPPAKRPRTDQMEIDSGTGKRPHKSGFTDKEREDHRRRKALENKKK

QLSSGGKNLSREEEEELGRLTVEDEERRRRVAGPRTGDVNLSGGGPRGAPGGGF

VPRMEGVPESPFTRTGEGLDIRGNQGFPWVRPSPPQQRLPLLECTPQGTNLSTSNP

LGFFPDHQLDPAFRANSANPDWDFNPNKDTWPDANKVGGQNLSTSNPLGFFPDH

QLDPAFRANTANPDWDFNPNKDTWPDANKVG
``` delta 9 wt                                               SEQ ID NO: 50

```
AGCCGCAGCGAAAGCAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGAGCCGCAGCGAAAGCAAAAAAACCGCGGC

GGCCGCGAAGAAGTGCTGGAACAGTGGGTGAACGGCCGCAAAAAACTGGAA

GAACTGGAACGCGAACTGCGCCGCGCGCGCAAAAAAATTAAAAAACTGGAA

GATGATAACCCGTGGCTGGGCAACGTGAAAGGCATTCTGGGCAAAAAAGATA

AAGATGGCGAAGGCGCGCCGCCGGCGAAACGCGCGCGCACCGATCAGATGG

AAATTGATAGCGGCCCGCGCAAACGCCCGCTGCGCGGCGGCTTTACCGATCG

CGAACGCCAGGATCATCGCCGCCGCAAAGCGCTGAAAAACAAAAAAAAACA

GCTGAGCGCGGGCGGCAAAAGCCTGAGCAAAGAAGAAGAAGAAGAACTGAA

ACGCCTGACCCGCGAAGATGAAGAACGCAAAAAAGAAGAACATGGCCCGAG

CCGCCTGGGCGTGAACCCGAGCGAAGGCGGCCCGCGCGGCGCGCCGGGCGG

CGGCTTTGTGCCGAGCATGCAGGGCATTCCGGAAAGCCGCTTTACCCGCACC

GGCGAAGGCCTGGATGTGCGCGGCAGCCGCGGCTTTCCGCAGGATATTCTGT
```

-continued

TTCCGAGCGATCCGCCGTTTAGCCCGCAGAGCTGCCGCCCGCAG delta 9 wt with restriction sites (HindIII/EcoRI)
SEQ ID NO: 51

A↓AGCTT*GCACC*ATGGCCAGCCGCAGCGAAAGCAAAAAAAACCGCGGCGGCCG

CGAAGAAATTCTGGAACAGTGGGTGGGCGCGCGCAAAAAACTGGAAGAACT

GGAACGCGATCTGCGCAAAATTAAAAAAAAAATTAAAAAACTGGAAGAAGA

AAACCCGTGGCTGGGCAACATTAAAGGCATTCTGGGCAAAAAAGATCGCGAA

GGCGAAGGCGCGCCGCCGGCGAAACGCGCGCGCGGATCAGATGGAAGTG

GATAGCGGCCCGCGCAAACGCCCGTTTCGCGGCGAATTTACCGATAAAGAAC

GCCGCGATCATCGCCGCCGCAAAGCGCTGGAAAACAAACGCAAACAGCTGA

GCAGCGGCGGCAAAAGCCTGAGCAAAGAAGAAGAAGAAGAACTGCGCAAAC

TGACCGAAGAAGATGAACGCCGCGAACGCCGCGTGGCGGGCCCGCGCGTGG

GCGGCGTGAACCCGCTGGAAGGCGGCACCCGCGGCGCGCCGGGCGGCGGCTT

TGTGCCGAGCATGCAGGGCGTGCCGGAAAGCCCGTTTGCGCGCACCGGCGAA

GGCCTGGATGTGCGCGGCAACCAGGGCTTTCCGTGGGATATTCTGTTTCCGGC

GGATCCGCCGTTTAGCCCGCAGAGCTGCCGCCCGCAGAGCCGCAGCGAAAGC

AAAAAAAACCGCGGCGGCCGCGAAGAAGTGCTGGAACAGTGGGTGAACGGC

CGCAAAAAACTGGAAGAACTGGAACGCGAACTGCGCCGCGCGCGCAAAAAA

ATTAAAAAACTGGAAGATGATAACCCGTGGCTGGGCAACGTGAAAGGCATTC

TGGGCAAAAAAGATAAAGATGGCGAAGGCGCGCCGCCGGCGAAACGCGCGC

GCACCGATCAGATGGAAATTGATAGCGGCCCGCGCAAACGCCCGCTGCGCGG

CGGCTTTACCGATCGCGAACGCCAGGATCATCGCCGCCGCAAAGCGCTGAAA

AACAAAAAAAAACAGCTGAGCGCGGGCGGCAAAAGCCTGAGCAAAGAAGAA

GAAGAAGAACTGAAACGCCTGACCCGCGAAGATGAAGAACGCAAAAAAGAA

GAACATGGCCCGAGCCGCCTGGGCGTGAACCCGAGCGAAGGCGGCCCCGCGC

GGCGCGCCGGGCGGCGGCTTTGTGCCGAGCATGCAGGGCATTCCGGAAAGCC

GCTTTACCCGCACCGGCGAAGGCCTGGATGTGCGCGGCAGCCGCGGCTTTCC

GCAGGATATTCTGTTTCCGAGCGATCCGCCGTTTAGCCCGCAGAGCTGCCGCC

CGCAGTGATGAG↓AATTCCGT delta 9 codon optimized
SEQ ID NO: 52

GCCAGTCGGAGCGAATCAAAGAAAAATAGAGGGGAAGAGAAGAAATCCTGGAGCAGTGG

GTCGGGGCACGGAAAAAACTGGAAGAACTGGAGCGGGACCTGAGAAAGATCAAGAAGAAG

ATCAAGAAGCTGGAGGAAGAGAACCCCTGGCTGGGCAATATCAAGGGCATCCTGGGCAAG

AAGGATAGGGAGGGCGAGGGAGCACCACCTGCAAAGAGGGCAAGGGCAGACCAGATGGAG

GTGGATTCCGGACCAAGGAAGCGGCCCTTCCGGGGAGAGTTTACCGACAAGGAGCGGAGA

GATCACAGGCGCCGGAAGGCCCTGGAGAACAAGCGGAAGCAGCTGAGCTCCGGCGGCAAG

TCTCTGAGCAAGGAGGAGGAGGAGGAGCTGAGAAAGCTGACAGAGGAGGACGAGAGAAGG

GAGAGGAGGGTGGCAGGACCTAGGGTGGGAGGCGTGAACCCACTGGAGGGAGGAACCAGG

GGAGCACCTGGAGGAGGCTTTGTGCCATCTATGCAGGGAGTGCCAGAGAGCCCTTTCGCC

AGGACAGGAGAGGGCCTGGATGTGCGCGGCAATCAGGGCTTCCCCTGGGACATCCTGTTT

CCTGCCGATCCACCCTTCAGCCCACAGTCCTGCAGGCCACAGTCCCGCTCTGAGAGCAAG

AAGAACAGGGGAGGAAGGGAGGAGGTGCTGGAGCAGTGGGTGAATGGCCGGAAGAAGCTG

```
GAGGAGCTGGAGCGGGAGCTGAGAAGGGCCAGAAAGAAGATCAAGAAGCTGGAAGACGAT

AATCCTTGGCTGGGCAATGTGAAAGGCATCCTGGGCAAGAAGGACAAGGATGGAGAGGGA

GCACCTCCAGCAAAGAGGGCACGCACCGACCAGATGGAGATCGATTCTGGACCTAGGAAG

CGGCCCCTGAGAGGAGGCTTTACAGACAGGGAGCGCCAGGATCACCGCCGGAGAAAGGCC

CTGAAGAACAAGAAGAAGCAGCTGAGCGCCGGCGGCAAGTCCCTGTCTAAAGAAGAGGAG

GAGGAGCTGAAGCGGCTGACCAGAGAGGACGAGGAGCGGAAGAAGGAGGAGCACGGACCA

TCCAGACTGGGAGTGAATCCTTCTGAGGGAGGACCAAGAGGCGCCCCAGGCGGCGGCTTT

GTGCCAAGCATGCAGGGCATCCCCGAGTCCAGGTTCACCAGAACCGGCGAAGGCCTGGAT

GTGCGGGGCAGCAGAGGCTTCCCCCAGGATATTCTGTTTCCCTCCGACCCCCCCCTTCAGT

CCCCAGTCTTGCCGACCTCAG
``` delta 9 codon optimized with restriction sites (HindIII/EcoRI)
SEQ ID NO: 53

```
A↓AGCTTGCACCATGGCCAGTCGGAGCGAATCAAAGAAAAATAGAGGGGGAAGAGAAGAA

ATCCTGGAGCAGTGGGTCGGGGCACGGAAAAAACTGGAAGAACTGGAGCGGGACCTGAGA

AAGATCAAGAAGAAGATCAAGAAGCTGGAGGAAGAGAACCCCTGGCTGGGCAATATCAAG

GGCATCCTGGGCAAGAAGGATAGGGAGGGCGAGGGAGCACCACCTGCAAAGAGGGCAAGG

GCAGACCAGATGGAGGTGGATTCCGGACCAAGGAAGCGGCCCTTCCGGGGAGAGTTTACC

GACAAGGAGCGGAGAGATCACAGGCGCCGGAAGGCCCTGGAGAACAAGCGGAAGCAGCTG

AGCTCCGGCGGCAAGTCTCTGAGCAAGGAGGAGGAGGAGGAGCTGAGAAAGCTGACAGAG

GAGGACGAGAGAAGGGAGAGGAGGGTGGCAGGACCTAGGGTGGGAGGCGTGAACCCACTG

GAGGGAGGAACCAGGGGAGCACCTGGAGGAGGCTTTGTGCCATCTATGCAGGGAGTGCCA

GAGAGCCCTTTCGCCAGGACAGGAGAGGGCCTGGATGTGCGCGGCAATCAGGGCTTCCCC

TGGGACATCCTGTTTCCTGCCGATCCACCCTTCAGCCCACAGTCCTGCAGGCCACAGTCC

CGCTCTGAGAGCAAGAAGAACAGGGGAGGAAGGGAGGAGGTGCTGGAGCAGTGGGTGAAT

GGCCGGAAGAAGCTGGAGGAGCTGGAGCGGGAGCTGAGAAGGGCCAGAAAGAAGATCAAG

AAGCTGGAAGACGATAATCCTTGGCTGGGCAATGTGAAAGGCATCCTGGGCAAGAAGGAC

AAGGATGGAGAGGGAGCACCTCCAGCAAAGAGGGCACGCACCGACCAGATGGAGATCGAT

TCTGGACCTAGGAAGCGGCCCCTGAGAGGAGGCTTTACAGACAGGGAGCGCCAGGATCAC

CGCCGGAGAAAGGCCCTGAAGAACAAGAAGAAGCAGCTGAGCGCCGGCGGCAAGTCCCTG

TCTAAAGAAGAGGAGGAGGAGCTGAAGCGGCTGACCAGAGAGGACGAGGAGCGGAAGAAG

GAGGAGCACGGACCATCCAGACTGGGAGTGAATCCTTCTGAGGGAGGACCAAGAGGCGCC

CCAGGCGGCGGCTTTGTGCCAAGCATGCAGGGCATCCCCGAGTCCAGGTTCACCAGAACC

GGCGAAGGCCTGGATGTGCGGGGCAGCAGAGGCTTCCCCCAGGATATTCTGTTTCCCTCC

GACCCCCCCTTCAGTCCCCAGTCTTGCCGACCTCAGTGATGAG↓AATTCCGT
``` delta 9 protein
SEQ ID NO: 54

```
MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKA

LENKRKQLSSGGKSLSKEEEELRKLTEEDERRERRVAGPRVGGVNPLEGGTRG

APGGGFVPSMQGVPESPFARTGEGLDVRGNQGFPWDILFPADPPFSPQSCRPQSR

SESKKNRGGREEVLEQWVNGRKKLEELERELRRARKKIKKLEDDNPWLGNVKGI

LGKKDKDGEGAPPAKRARTDQMEIDSGPRKRPLRGGFTDRERQDHRRRKALKN
```

```
KKKQLSAGGKSLSKEEEEELKRLTREDEERKKEEHGPSRLGVNPSEGGPRGAPGG

GFVPSMQGIPESRFTRTGEGLDVRGSRGFPQDILFPSDPPFSPQSCRPQ
``` delta 10 wt

SEQ ID NO: 55

```
AGCCAGAGCGAAACCCGCCGCGGCCGCCGCGGCACCCGCGAAGAAACCCTG

GAAAATGGATTACCGCGCGCAAAAAAGCGGAAGAACTGGAAAAAGATCTG

CGCAAAACCCGCAAAACCATTAAAAAACTGGAAGAAGAAAACCCGTGGCTG

GGCAACATTGTGGGCATTATTCGCAAAGGCAAAGATGGCGAAGGCGCGCCGC

CGGCGAAACGCCCGCGCACCGATCAGATGGAAGTGGATAGCGGCCCGGGCA

AACGCCCGCATAAAAGCGGCTTTACCGATAAAGAACGCGAAGATCATCGCCG

CCGCAAAGCGCTGGAAAACAAAAAAAAACAGCTGAGCGCGGGCGGCAAAAT

TCTGAGCAAAGAAGAAGAAGAAGAACTGCGCCGCCTGACCGATGAAGATGA

AGAACGCAAACGCCGCGTGGCGGGCCCGCGCGTGGGCGATGTGAACCCGAG

CCGCGGCGGCCCGCGCGGCGCGCCGGGCGGCGGCTTTGTGCCGCAGATGGCG

GGCGTGCCGGAAAGCCCGTTTAGCCGCACCGGCGAAGGCCTGGATATTCGCG

GCACCCAGGGCTTTCCGTGGGTGAGCCCGAGCCCGCCGCAGCAGCGCCTGCC

GCTGCTGGAATGCACCCCGCAGAGCCAGAGCGAAAGCAAAAAAAACCGCCG

CGGCGGCCGCGAAGATATTCTGGAAAAATGGATTACCACCCGCCGCAAAGCG

GAAGAACTGGAAAAAGATCTGCGCAAAGCGCGCAAAACCATTAAAAAACTG

GAAGATGAAAACCCGTGGCTGGGCAACATTATTGGCATTATTCGCAAAGGCA

AAGATGGCGAAGGCGCGCCGCCGGCGAAACGCCCGCGCACCGATCAGATGG

AAATTGATAGCGGCACCGGCAAACGCCCGCATAAAAGCGGCTTTACCGATAA

AGAACGCGAAGATCATCGCCGCCGCAAAGCGCTGGAAAACAAAAAAAACA

GCTGAGCAGCGGCGGCAAAAACCTGAGCCGCGAAGAAGAAGAAGAACTGGG

CCGCCTGACCGTGGAAGATGAAGAACGCCGCCGCCGCGTGGCGGGCCCGCGC

ACCGGCGATGTGAACCTGAGCGGCGGCGGCCCGCGCGGCGCGCCGGGCGGC

GGCTTTGTGCCGCGCATGGAAGGCGTGCCGGAAAGCCCGTTTACCCGCACCG

GCGAAGGCCTGGATATTCGCGGCAACCAGGGCTTTCCGTGGGTGCGCCCGAG

CCCGCCGCAGCAGCGCCTGCCGCTGCTGGAATGCACCCCGCAG
``` delta 10 wt with restriction sites (HindIII/EcoRI)

SEQ ID NO: 56

```
A↓AGCTTGCACCATGGCCAGCCAGAGCGAAACCCGCCGCGGCCGCCGCGGCACC

CGCGAAGAAACCCTGGAAAATGGATTACCGCGCGCAAAAAAGCGGAAGAA

CTGGAAAAAGATCTGCGCAAAACCCGCAAAACCATTAAAAAACTGGAAGAA

GAAAACCCGTGGCTGGGCAACATTGTGGGCATTATTCGCAAAGGCAAAGATG

GCGAAGGCGCGCCGCCGGCGAAACGCCCGCGCACCGATCAGATGGAAGTGG

ATAGCGGCCCGGGCAAACGCCCGCATAAAAGCGGCTTTACCGATAAAGAACG

CGAAGATCATCGCCGCCGCAAAGCGCTGGAAAACAAAAAAAAACAGCTGAG

CGCGGGCGGCAAAATTCTGAGCAAAGAAGAAGAAGAAGAACTGCGCCGCCT

GACCGATGAAGATGAAGAACGCAAACGCCGCGTGGCGGGCCCGCGCGTGGG

CGATGTGAACCCGAGCCGCGGCGGCCCGCGCGGCGCGCCGGGCGGCGGCTTT

GTGCCGCAGATGGCGGGCGTGCCGGAAAGCCCGTTTAGCCGCACCGGCGAAG

GCCTGGATATTCGCGGCACCCAGGGCTTTCCGTGGGTGAGCCCGAGCCCGCC
```

-continued

```
GCAGCAGCGCCTGCCGCTGCTGGAATGCACCCCGCAGAGCCAGAGCGAAAGC

AAAAAAAACCGCCGCGGCGGCCGCGAAGATATTCTGGAAAAATGGATTACCA

CCCGCCGCAAAGCGGAAGAACTGGAAAAAGATCTGCGCAAAGCGCGCAAAA

CCATTAAAAAACTGGAAGATGAAAACCCGTGGCTGGGCAACATTATTGGCAT

TATTCGCAAAGGCAAAGATGGCGAAGGCGCGCCGCCGGCGAAACGCCCGCG

CACCGATCAGATGGAAATTGATAGCGGCACCGGCAAACGCCCGCATAAAAGC

GGCTTTACCGATAAAGAACGCGAAGATCATCGCCGCCGCAAAGCGCTGGAAA

ACAAAAAAAAACAGCTGAGCAGCGGCGGCAAAAACCTGAGCCGCGAAGAAG

AAGAAGAACTGGGCCGCCTGACCGTGGAAGATGAAGAACGCCGCCGCCGCG

TGGCGGGCCCGCGCACCGGCGATGTGAACCTGAGCGGCGGCGGCCCGCGCGG

CGCGCCGGGCGGCGGCTTTGTGCCGCGCATGGAAGGCGTGCCGGAAAGCCCG

TTTACCCGCACCGGCGAAGGCCTGGATATTCGCGGCAACCAGGGCTTTCCGTG

GGTGCGCCCGAGCCCGCCGCAGCAGCGCCTGCCGCTGCTGGAATGCACCCCG

CAGTGATGAG↓AATTCCGT
``` delta 10 codon optimized

SEQ ID NO: 57

```
GCCTCACAGAGCGAAACACGGCGGGGGCGGAGGGGAACTAGAGAGGAAACACTGGAAAAA

TGGATTACAGCACGGAAAAAGGCAGAGGAACTGGAGAAGGACCTGAGGAAGACCCGCAAG

ACAATCAAGAAGCTGGAGGAGGAGAACCCATGGCTGGGCAATATCGTGGGCATCATCCGG

AAGGGCAAGGATGGAGAGGGAGCACCACCTGCAAAGAGGCCCCGCACCGACCAGATGGAG

GTGGATTCTGGCCCTGGCAAGAGGCCACACAAGAGCGGCTTCACAGACAAGGAGCGCGAG

GATCACCGGAGAAGGAAGGCCCTGGAGAACAAGAAGAAGCAGCTGAGCGCCGGCGGCAAG

ATCCTGTCCAAGGAGGAGGAGGAGGAGCTGCGCCGGCTGACCGACGAGGATGAGGAGCGG

AAGAGAAGGGTGGCAGGACCAAGAGTGGGCGACGTGAATCCCTCTAGGGGAGGACCAAGG

GGAGCACCTGGAGGAGGCTTCGTGCCTCAGATGGCAGGAGTGCCAGAGTCCCCTTTTTCT

AGGACCGGAGAGGGCCTGGATATCAGGGGAACACAGGGCTTTCCATGGGTGTCTCCAAGC

CCACCACAGCAGAGGCTGCCACTGCTGGAGTGCACCCCTCAGTCCCAGTCTGAGAGCAAG

AAGAACAGGAGGGGAGGAAGGGAGGACATCCTGGAGAAGTGGATCACCACAAGAAGGAAG

GCCGAGGAGCTGGAGAAGGACCTGCGGAAGGCCAGAAAAACAATCAAGAAGCTGGAAGAT

GAGAACCCCTGGCTGGGCAATATCATCGGCATCATCAGAAAAGGCAAGGACGGCGAGGGA

GCACCTCCAGCAAAGCGGCCTAGAACCGACCAGATGGAGATCGATTCCGGCACAGGCAAG

CGGCCACACAAGTCTGGCTTCACCGACAAGGAGAGAGAGGATCACCGCCGGAGAAAGGCC

CTGGAAAACAAGAAGAAGCAATTAAGCTCCGGCGGCAAGAATCTGAGCAGAGAAGAAGAG

GAGGAGCTGGGCAGACTGACCGTGGAGGACGAGGAGAGGCGCCGGAGAGTGGCAGGACCC

AGAACAGGCGATGTGAACCTGAGCGGAGGAGGACCTAGGGGAGCACCAGGAGGCGGCTTC

GTGCCTAGAATGGAGGGCGTGCCAGAGTCCCCCTTTACCAGGACAGGAGAGGGCCTGGAC

ATCAGGGGCAATCAGGGCTTTCCCTGGGTCCGCCCTTCACCACCACAGCAGAGACTGCCC

CTGCTGGAATGCACACCACAG
``` delta 10 codon optimized with restriction sites (HindIII/EcoRI)

SEQ ID NO: 58

```
A↓AGCTT*GCACC***ATG**GCCTCACAGAGCGAAACACGGCGGGGGCGGAGGGGAACTAGAGAG

GAAACACTGGAAAAATGGATTACAGCACGGAAAAAGGCAGAGGAACTGGAGAAGGACCTG
```

```
-continued
AGGAAGACCCGCAAGACAATCAAGAAGCTGGAGGAGGAGAACCCATGGCTGGGCAATATC

GTGGGCATCATCCGGAAGGGCAAGGATGGAGAGGGAGCACCACCTGCAAAGAGGCCCCGC

ACCGACCAGATGGAGGTGGATTCTGGCCCTGGCAAGAGGCCACACAAGAGCGGCTTCACA

GACAAGGAGCGCGAGGATCACCGGAGAAGGAAGGCCCTGGAGAACAAGAAGAAGCAGCTG

AGCGCCGGCGGCAAGATCCTGTCCAAGGAGGAGGAGGAGGAGCTGCGCCGGCTGACCGAC

GAGGATGAGGAGCGGAAGAGAAGGGTGGCAGGACCAAGAGTGGGCGACGTGAATCCCTCT

AGGGGAGGACCAAGGGGAGCACCTGGAGGAGGCTTCGTGCCTCAGATGGCAGGAGTGCCA

GAGTCCCCTTTTTCTAGGACCGGAGAGGGCCTGGATATCAGGGGAACACAGGGCTTTCCA

TGGGTGTCTCCAAGCCCACCACAGCAGAGGCTGCCACTGCTGGAGTGCACCCCTCAGTCC

CAGTCTGAGAGCAAGAAGAACAGGAGGGGAGGAAGGGAGGACATCCTGGAGAAGTGGATC

ACCACAAGAAGGAAGGCCGAGGAGCTGGAGAAGGACCTGCGGAAGGCCAGAAAAACAATC

AAGAAGCTGGAAGATGAGAACCCCTGGCTGGGCAATATCATCGGCATCATCAGAAAAGGC

AAGGACGGCGAGGGAGCACCTCCAGCAAAGCGGCCTAGAACCGACCAGATGGAGATCGAT

TCCGGCACAGGCAAGCGGCCACACAAGTCTGGCTTCACCGACAAGGAGAGAGAGGATCAC

CGCCGGAGAAAGGCCCTGGAAAACAAGAAGAAGCAATTAAGCTCCGGCGGCAAGAATCTG

AGCAGAGAAGAAGAGGAGGAGCTGGGCAGACTGACCGTGGAGGACGAGGAGAGGCGCCGG

AGAGTGGCAGGACCCAGAACAGGCGATGTGAACCTGAGCGGAGGAGGACCTAGGGGAGCA

CCAGGAGGCGGCTTCGTGCCTAGAATGGAGGGCGTGCCAGAGTCCCCCTTTACCAGGACA

GGAGAGGGCCTGGACATCAGGGGCAATCAGGGCTTTCCCTGGGTCCGCCCTTCACCACCA

CAGCAGAGACTGCCCCTGCTGGAATGCACACCACAGTGATGAG↓AATTCCGT delta 10 protein
                                                        SEQ ID NO: 59
MASQSETRRGRRGTREETLEKWITARKKAEELEKDLRKTRKTIKKLEEENPWLG

NIVGIIRKGKDGEGAPPAKRPRTDQMEVDSGPGKRPHKSGFTDKEREDHRRRKA

LENKKKQLSAGGKILSKEEEEELRRLTDEDEERKRRVAGPRVGDVNPSRGGPRG

APGGGFVPQMAGVPESPFSRTGEGLDIRGTQGFPWVSPSPPQQRLPLLECTPQSQS

ESKKNRRGGREDILEKWITTRRKAEELEKDLRKARKTIKKLEDENPWLGNIIGIIR

KGKDGEGAPPAKRPRTDQMEIDSGTGKRPHKSGFTDKEREDHRRRKALENKKK

QLSSGGKNLSREEEEELGRLTVEDEERRRVAGPRTGDVNLSGGGPRGAPGGGF

VPRMEGVPESPFTRTGEGLDIRGNQGFPWVRPSPPQQRLPLLECTPQ

Core 1 wt (C-gt-H)
                                                        SEQ ID NO: 60
GATATTGATCCGTATAAAGAATTTGGCGCGAGCGTGGAACTGCTGAGCTTTCTGCCGAGC

GATTTTTTTCCGAGCGTGCGCGATCTGCTGGATACCGCGAGCGCGCTGTATCGCGATGCG

CTGGAAAGCCCGGAACATTGCACCCCGAACCATACCGCGCTGCGCCAGGCGATTCTGTGC

TGGGGCGAACTGATGACCCTGGCGAGCTGGGTGGGCAACAACCTGGAAGATCCGGCGGCG

CGCGATCTGGTGGTGAACTATGTGAACACCAACATGGGCCTGAAAATTCGCCAGCTGCTG

TGGTTTCATATTAGCTGCCTGACCTTTGGCCGCGAAACCGTGCTGGAATATCTGGTGAGC

TTTGGCGTGTGGATTCGCACCCCGCCGGCGTATCGCCCGCCGAACGCGCCGATTCTGAGC

ACCCTGCCGGAAACCACCGTGGTGCGCCAGCGCGGCCGCGCGCCGCGCCGCCGCACCCCG

AGCCCGCGCCGCCGCCGCAGCCAGAGCCCGCGCCGCCGCCGCAGCCAGAGCCCGGCGAGC

CAGTGC
```

-continued core 1 wt with restriction sites (HindIII/EcoRI)
SEQ ID NO: 61

A↓AGCTT*GCACC*ATGGATATTGATCCGTATAAAGAATTTGGCGCGAGCGTGGAACTGCTG

AGCTTTCTGCCGAGCGATTTTTTTCCGAGCGTGCGCGATCTGCTGGATACCGCGAGCGCG

CTGTATCGCGATGCGCTGGAAAGCCCGGAACATTGCACCCCGAACCATACCGCGCTGCGC

CAGGCGATTCTGTGCTGGGGCGAACTGATGACCCTGGCGAGCTGGGTGGGCAACAACCTG

GAAGATCCGGCGGCGCGCGATCTGGTGGTGAACTATGTGAACACCAACATGGGCCTGAAA

ATTCGCCAGCTGCTGTGGTTTCATATTAGCTGCCTGACCTTTGGCCGCGAAACCGTGCTG

GAATATCTGGTGAGCTTTGGCGTGTGGATTCGCACCCCGCCGGCGTATCGCCCGCCGAAC

GCGCCGATTCTGAGCACCCTGCCGGAAACCACCGTGGTGCGCCAGCGCGGCCGCGCGCCG

CGCCGCCGCACCCCGAGCCCGCGCCGCCGCCGCAGCCAGAGCCCGCGCCGCCGCCGCAGC

CAGAGCCCGGCGAGCCAGTGCTGATGAG↓AATTCCGT core 1 codon optimized
SEQ ID NO: 62

GATATTGATCCCTATAAGGAGTTTGGAGCCTCTGTGGAGCTGCTGAGTTTTCTGCCATCC

GATTTCTTTCCCAGTGTCCGAGACCTGCTGGACACCGCAAGCGCCCTGTACAGGGATGCA

CTGGAGTCCCCAGAGCACTGCACCCCTAACCACACAGCCCTGAGGCAGGCAATCCTGTGC

TGGGGAGAGCTGATGACCCTGGCAAGCTGGGTGGGCAACAATCTGGAGGACCCTGCAGCA

CGGGATCTGGTGGTGAATTATGTGAACACAAATATGGGCCTGAAGATCCGGCAGCTGCTG

TGGTTCCACATCTCTTGCCTGACCTTTGGCAGAGAGACAGTGCTGGAGTACCTGGTGAGC

TTCGGCGTGTGGATCAGGACCCCCACCTGCATATAGGCCACCAAACGCACCAATCCTGTCC

ACACTGCCAGAGACAACAGTGGTGCGCCAGAGGGGAAGAGCACCACGGAGAAGGACACCT

TCTCCAAGACGAAGGCGAAGCCAGAGCCCCAGGCGAAGACGAAGCCAGTCCCCAGCAAGC

CAGTGC core 1 codon optimized with restriction sites (HindIII/EcoRI)
SEQ ID NO: 63

A↓AGCTT*GCACC*ATGGATATTGATCCCTATAAGGAGTTTGGAGCCTCTGTGGAGCTGCTG

AGTTTTCTGCCATCCGATTTCTTTCCCAGTGTCCGAGACCTGCTGGACACCGCAAGCGCC

CTGTACAGGGATGCACTGGAGTCCCCAGAGCACTGCACCCCTAACCACACAGCCCTGAGG

CAGGCAATCCTGTGCTGGGGAGAGCTGATGACCCTGGCAAGCTGGGTGGGCAACAATCTG

GAGGACCCTGCAGCACGGGATCTGGTGGTGAATTATGTGAACACAAATATGGGCCTGAAG

ATCCGGCAGCTGCTGTGGTTCCACATCTCTTGCCTGACCTTTGGCAGAGAGACAGTGCTG

GAGTACCTGGTGAGCTTCGGCGTGTGGATCAGGACCCCCACCTGCATATAGGCCACCAAAC

GCACCAATCCTGTCCACACTGCCAGAGACAACAGTGGTGCGCCAGAGGGGAAGAGCACCA

CGGAGAAGGACACCTTCTCCAAGACGAAGGCGAAGCCAGAGCCCCAGGCGAAGACGAAGC

CAGTCCCCAGCAAGCCAGTGCTGATGAG↓AATTCCGT core 1 protein
SEQ ID NO: 64

MDIDPYKEFGASVELLSFLPSDFFPSVRDLLDTASALYRDALESPEHCTPNHTALR

QAILCWGELMTLASWVGNNLEDPAARDLVVNYVNTNMGLKIRQLLWFHISCLT

FGRETVLEYLVSFGVWIRTPPAYRPPNAPILSTLPETTVVRQRGRAPRRRTPSPRR

RRSQSPRRRRSQSPASQC

Pre-C-gt-H wt
SEQ ID NO: 65

CAGCTGTTTCATCTGTGCCTGATTATTTTTTGCAGCTGCCCGACCGTGCAGGCGAGCAAA

CTGTGCCTGGGCTGGCTGTGGGGCATGGATATTGATCCGTATAAAGAATTTGGCGCGAGC

```
GTGGAACTGCTGAGCTTTCTGCCGAGCGATTTTTTTCCGAGCGTGCGCGATCTGCTGGAT

ACCGCGAGCGCGCTGTATCGCGATGCGCTGGAAAGCCCGGAACATTGCACCCCGAACCAT

ACCGCGCTGCGCCAGGCGATTCTGTGCTGGGGCGAACTGATGACCCTGGCGAGCTGGGTG

GGCAACAACCTGGAAGATCCGGCGGCGCGCGATCTGGTGGTGAACTATGTGAACACCAAC

ATGGGCCTGAAAATTCGCCAGCTGCTGTGGTTTCATATTAGCTGCCTGACCTTTGGCCGC

GAAACCGTGCTGGAATATCTGGTGAGCTTTGGCGTGTGGATTCGCACCCCGCCGGCGTAT

CGCCCGCCGAACGCGCCGATTCTGAGCACCCTGCCGGAAACCACCGTGGTGCGCCAGCGC

GGCCGCGCGCCGCGCCGCCGCACCCCGAGCCCGCGCCGCCGCCAGCCAGAGCCCGCGC

CGCCGCCGCAGCCAGAGCCCGGCGAGCCAGTGC
```

Pre-C-gt-H wt with restriction sites (HindIII/EcoRI)
SEQ ID NO: 66

```
A↓AGCTTGCACCATGGCCCAGCTGTTTCATCTGTGCCTGATTATTTTTTGCAGCTGCCCG

ACCGTGCAGGCGAGCAAACTGTGCCTGGGCTGGCTGTGGGGCATGGATATTGATCCGTAT

AAAGAATTTGGCGCGAGCGTGGAACTGCTGAGCTTTCTGCCGAGCGATTTTTTTCCGAGC

GTGCGCGATCTGCTGGATACCGCGAGCGCGCTGTATCGCGATGCGCTGGAAAGCCCGGAA

CATTGCACCCCGAACCATACCGCGCTGCGCCAGGCGATTCTGTGCTGGGGCGAACTGATG

ACCCTGGCGAGCTGGGTGGGCAACAACCTGGAAGATCCGGCGGCGCGCGATCTGGTGGTG

AACTATGTGAACACCAACATGGGCCTGAAAATTCGCCAGCTGCTGTGGTTTCATATTAGC

TGCCTGACCTTTGGCCGCGAAACCGTGCTGGAATATCTGGTGAGCTTTGGCGTGTGGATT

CGCACCCCGCCGGCGTATCGCCCGCCGAACGCGCCGATTCTGAGCACCCTGCCGGAAACC

ACCGTGGTGCGCCAGCGCGGCCGCGCGCCGCGCCGCCGCCGCCGCACCCCGAGCCCGCGCCGCCGC

CGCAGCCAGAGCCCGCGCCGCCGCCGCAGCCAGAGCCCGGCGAGCCAGTGCTGATGAG↓A

ATTCCGT
```

Pre-C-gt-H codon optimized
SEQ ID NO: 67

```
GCCCAGCTGTTTCATCTGTGCCTGATTATTTTTCTGTTCATGCCCTACCGTCCAGGCTTCT

AAAACTGTGCCTGGGGTGGCTGTGGGGAATGGACATCGATCCCTACAAGGAGTTCGGCGCC

AGCGTGGAGCTGCTGAGCTTTCTGCCCTCCGACTTCTTTCCTTCTGTGCGGGACCTGCTG

GATACCGCAAGCGCCCTGTATAGAGATGCACTGGAGTCCCCAGAGCACTGCACCCCCAAAC

CACACAGCCCTGAGGCAGGCAATCCTGTGCTGGGGAGAGCTGATGACCCTGGCATCCTGG

GTGGGCAACAATCTGGAGGACCCTGCCGCCAGAGATCTGGTGGTGAATTACGTGAACACA

AATATGGGCCTGAAGATCAGGCAGCTGCTGTGGTTCCACATCTCTTGCCTGACCTTTGGC

CGCGAGACAGTGCTGGAGTACCTGGTGAGCTTCGGCGTGTGGATCAGGACCCCACCTGCA

TATAGGCCACCAAACGCACCTATCCTGTCCACACTGCCAGAGACAACAGTGGTGCGCCAG

AGGGGAAGAGCACCACGGAGAAGGACACCTTCTCCAAGGAGGAGAAGAAGCCAGTCCCCA

CGAAGAAGACGAAGCCAGAGCCCAGCCAGCCAGTGT
```

Pre-C-gt-H codon optimized with restriction sites (HindIII/EcoRI)
SEQ ID NO: 68

```
A↓AGCTTGCACCATGGCCCAGCTGTTTCATCTGTGCCTGATTATTTTTCTGTTCATGCCCT

ACCGTCCAGGCTTCTAAAACTGTGCCTGGGGTGGCTGTGGGGAATGGACATCGATCCCTAC

AAGGAGTTCGGCGCCAGCGTGGAGCTGCTGAGCTTTCTGCCCTCCGACTTCTTTCCTTCT

GTGCGGGACCTGCTGGATACCGCAAGCGCCCTGTATAGAGATGCACTGGAGTCCCCAGAG

CACTGCACCCCAAACCACACAGCCCTGAGGCAGGCAATCCTGTGCTGGGGAGAGCTGATG
```

-continued

```
ACCCTGGCATCCTGGGTGGGCAACAATCTGGAGGACCCTGCCGCCAGAGATCTGGTGGTG

AATTACGTGAACACAAATATGGGCCTGAAGATCAGGCAGCTGCTGTGGTTCCACATCTCT

TGCCTGACCTTTGGCCGCGAGACAGTGCTGGAGTACCTGGTGAGCTTCGGCGTGTGGATC

AGGACCCCACCTGCATATAGGCCACCAAACGCACCTATCCTGTCCACACTGCCAGAGACA

ACAGTGGTGCGCCAGAGGGGAAGAGCACCACGGAGAAGGACACCTTCTCCAAGGAGGAGA

AGAAGCCAGTCCCCACGAAGAAGACGAAGCCAGAGCCCAGCCAGCCAGTGTGATGAG↓A

ATTCCGT
```

Pre-C-gt-H protein

SEQ ID NO: 69

```
MAQLFHLCLIIFCSCPTVQASKLCLGWLWGMDIDPYKEFGASVELLSFLPSDFFPS

VRDLLDTASALYRDALESPEHCTPNHTALRQAILCWGELMTLASWVGNNLEDPA

ARDLVVNYVNTNMGLKIRQLLWFHISCLTFGRETVLEYLVSFGVWIRTPPAYRPP

NAPILSTLPETTVVRQRGRAPRRRTPSPRRRRSQSPRRRRSQSPASQC
```

PreC-C-Mut-gt-H wt

SEQ ID NO: 70

```
CAGCTGTTTCATCTGTGCCTGATTATTTTTTGCAGCTGCCCGACCTTTCAGTTTCCGAAA

CTGTGCCTGGGCTGGCTGTGGGGCATGGATATTGATCCGTATAAAGAATTTGGCGCGAGC

GTGGAACTGCTGAGCTTTCTGCCGAGCGATTTTTTTCCGAGCGTGCGCGATCTGCTGGAT

ACCGCGAGCGCGCTGTATCGCGATGCGCTGGAAAGCCCGGAACATTGCACCCCGAACCAT

ACCGCGCTGCGCCAGGCGATTCTGTGCTGGGGCGAACTGATGACCCTGGCGAGCTGGGTG

GGCAACAACCTGGAAGATCCGGCGGCGCGCGATCTGGTGGTGAACTATGTGAACACCAAC

ATGGGCCTGAAAATTCGCCAGCTGCTGTGGTTTCATATTAGCTGCCTGACCTTTGGCCGC

GAAACCGTGCTGGAATATCTGGTGAGCTTTGGCGTGTGGATTCGCACCCCGCCGGCGTAT

CGCCCGCCGAACGCGCCGATTCTGAGCACCCTGCCGGAAACCACCGTGGTGCGCCAGCGC

GGCCGCGCGCCGCGCCGCACCCCGAGCCCGCGCCGCCGCCGCAGCCAGAGCCCGCGC

CGCCGCCGCAGCCAGAGCCCGGCGAGCCAGTGC
```

PreC-C-Mut-gt-H wt with restriction sites (HindIII/EcoRI)

SEQ ID NO: 71

```
A↓AGCTT*GCACC***ATG**GCCCAGCTGTTTCATCTGTGCCTGATTATTTTTTGCAGCTGCCCG

ACCTTTCAGTTTCCGAAACTGTGCCTGGGCTGGCTGTGGGGCATGGATATTGATCCGTAT

AAAGAATTTGGCGCGAGCGTGGAACTGCTGAGCTTTCTGCCGAGCGATTTTTTTCCGAGC

GTGCGCGATCTGCTGGATACCGCGAGCGCGCTGTATCGCGATGCGCTGGAAAGCCCGGAA

CATTGCACCCCGAACCATACCGCGCTGCGCCAGGCGATTCTGTGCTGGGGCGAACTGATG

ACCCTGGCGAGCTGGGTGGGCAACAACCTGGAAGATCCGGCGGCGCGCGATCTGGTGGTG

AACTATGTGAACACCAACATGGGCCTGAAAATTCGCCAGCTGCTGTGGTTTCATATTAGC

TGCCTGACCTTTGGCCGCGAAACCGTGCTGGAATATCTGGTGAGCTTTGGCGTGTGGATT

CGCACCCCGCCGGCGTATCGCCCGCCGAACGCGCCGATTCTGAGCACCCTGCCGGAAACC

ACCGTGGTGCGCCAGCGCGGCCGCGCGCCGCGCCGCACCCCGAGCCCGCGCCGCCGC

CGCAGCCAGAGCCCGCGCCGCCGCCGCAGCCAGAGCCCGGCGAGCCAGTGCTGATGAG↓A

ATTCCGT
```

PreC-C-Mut-gt-H codon optimized

SEQ ID NO: 72

```
GCCCAGCTGTTTCATCTGTGCCTGATTATTTTCTGTTCATGCCCTACCTTCCAGTTCCCC

AAACTGTGCCTGGGGTGGCTGTGGGGAATGGACATCGATCCCTACAAGGAGTTCGGCGCC

AGCGTGGAGCTGCTGAGCTTTCTGCCCTCCGACTTCTTTCCTTCTGTGCGGGACCTGCTG
```

-continued

GATACCGCAAGCGCCCTGTATAGAGATGCACTGGAGTCCCCAGAGCACTGCACCCCAAAC

CACACAGCCCTGAGGCAGGCAATCCTGTGCTGGGGAGAGCTGATGACCCTGGCATCCTGG

GTGGGCAACAATCTGGAGGACCCTGCCGCCAGAGATCTGGTGGTGAATTACGTGAACACA

AATATGGGCCTGAAGATCAGGCAGCTGCTGTGGTTCCACATCTCTTGCCTGACCTTTGGC

CGCGAGACAGTGCTGGAGTACCTGGTGAGCTTCGGCGTGTGGATCAGGACCCCACCTGCA

TATAGGCCACCAAACGCACCTATCCTGTCCACACTGCCAGAGACAACAGTGGTGCGCCAG

AGGGGAAGAGCACCACGGAGAAGGACACCTTCTCCAAGGAGGAGAAGAAGCCAGTCCCCA

CGAAGAAGACGAAGCCAGAGCCCAGCCAGCCAGTGT

PreC-C-Mut-gt-H codon optimized with restriction sites (HindIII/EcoRI)
SEQ ID NO: 73

A↓AGCTT*GCACC*ATGGCCCAGCTGTTTCATCTGTGCCTGATTATTTTCTGTTCATGCCCT

ACCTTCCAGTTCCCCAAACTGTGCCTGGGGTGGCTGTGGGGAATGGACATCGATCCCTAC

AAGGAGTTCGGCGCCAGCGTGGAGCTGCTGAGCTTTCTGCCCTCCGACTTCTTTCCTTCT

GTGCGGGACCTGCTGGATACCGCAAGCGCCCTGTATAGAGATGCACTGGAGTCCCCAGAG

CACTGCACCCCAAACCACACAGCCCTGAGGCAGGCAATCCTGTGCTGGGGAGAGCTGATG

ACCCTGGCATCCTGGGTGGGCAACAATCTGGAGGACCCTGCCGCCAGAGATCTGGTGGTG

AATTACGTGAACACAAATATGGGCCTGAAGATCAGGCAGCTGCTGTGGTTCCACATCTCT

TGCCTGACCTTTGGCCGCGAGACAGTGCTGGAGTACCTGGTGAGCTTCGGCGTGTGGATC

AGGACCCCACCTGCATATAGGCCACCAAACGCACCTATCCTGTCCACACTGCCAGAGACA

ACAGTGGTGCGCCAGAGGGGAAGAGCACCACGGAGAAGGACACCTTCTCCAAGGAGGAGA

AGAAGCCAGTCCCCACGAAGAAGACGAAGCCAGAGCCCAGCCAGCCAGTGTGATGAG↓A

ATTCCGT

PreC-C-Mut-gt-H protein
SEQ ID NO: 74

MAQLFHLCLIIFCSCPTFQFPKLCLGWLWGMDIDPYKEFGASVELLSFLPSDFFPS

VRDLLDTASALYRDALESPEHCTPNHTALRQAILCWGELMTLASWVGNNLEDPA

ARDLVVNYVNTNMGLKIRQLLWFHISCLTFGRETVLEYLVSFGVWIRTPPAYRPP

NAPILSTLPETTVVRQRGRAPRRRTPSPRRRRSQSPRRRRSQSPASQC

---

What is claimed is:

1. A chimeric gene comprising at least two Hepatitis D Antigen (HDAg) sequences, the chimeric gene comprising:

a nucleic acid construct encoding at least two HDAg antigen sequences selected from the group consisting of HDAg genotype 1A, HDAg genotype 1 B, HDAg genotype 2A and HDAg genotype 2B;

at least one cleavage sequence; and at least one sequence encoding a pre-S 1 domain of a surface antigen of a hepatitis B virus.

2. The chimeric gene according to claim 1, wherein the at least two HDAg sequences comprise a full HDAg gene.

3. The chimeric gene according to claim 1, wherein the at least two HDAg sequences comprise a partial HDAg gene.

4. The chimeric gene according to claim 1, wherein the at least two HDAg antigen sequences are joined by the cleavage sequence.

5. The chimeric gene according to claim 1, wherein the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A).

6. The chimeric gene according to claim 5, wherein each cleavage sequence is modified to include a glycine-serine-glycine (GSG) motif at an N-terminus thereof.

7. The chimeric gene according to claim 1, wherein the at least one pre S1 sequence is preS1 A.

8. The chimeric gene according to claim 1, wherein the at least one pre S1 sequence is preS1B.

9. The chimeric gene according to claim 1, wherein the nucleic acid encoding HDAg genotype 1A comprises the amino acid sequence of SEQ ID NO: 3.

10. The chimeric gene according to claim 1, wherein the nucleic acid encoding HDAg genotype 1B comprises the nucleic acid sequence of SEQ ID NO: 4.

11. The chimeric gene according to claim 1, wherein the nucleic acid encoding HDAg genotype 2A comprises the nucleic acid sequence of SEQ ID NO: 8.

12. The chimeric gene according to claim 1, wherein the nucleic acid encoding HDAg genotype 2B comprises the nucleic acid sequence of SEQ ID NO: 9.

13. The chimeric gene according to claim 7, wherein the pre S1 A sequence is encoded by the nucleic acid sequence of SEQ ID NO: 5.

14. The chimeric gene according to claim 8, wherein the pre S1 A sequence is encoded by the nucleic acid sequence of SEQ ID NO: 6.

* * * * *

SEQUENCE LISTING

<160> NUMBER OF SEQ IDS NOS: 116

<210> SEQ ID NO 1
<211> LENGTH: 47
<212> TYPE: PRT
<213> ORGANISM: Artificial Sequence
<220> FEATURE:
<223> OTHER INFORMATION: Pre S1 A

<400> SEQUENCE: 1

Gly Thr Asn Leu Ser Thr Ser Asn Pro Leu Gly Phe Phe Pro Asp His
1               5                   10                  15

Gln Leu Asp Pro Ala Phe Arg Ala Asn Ser Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 2

```
<211> LENGTH: 47
<212> TYPE: PRT
<213> ORGANISM: Artificial Sequence
<220> FEATURE:
<223> OTHER INFORMATION: PreS1 B

<400> SEQUENCE: 2

Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45

<210> SEQ ID NO 3
<211> LENGTH: 639
<212> TYPE: PRT
<213> ORGANISM: Artificial Sequence
<220> FEATURE:
<223> OTHER INFORMATION: HDAg genotype 1 A

<400> SEQUENCE: 3

Ala Gly Cys Cys Gly Cys Ala Gly Cys Gly Ala Ala Gly Cys Ala
1               5                   10                  15

Ala Ala Ala Ala Ala Ala Cys Cys Gly Cys Gly Gly Cys Gly Gly
            20                  25                  30

Cys Cys Gly Cys Gly Ala Ala Gly Ala Ala Ala Thr Thr Cys Thr Gly
            35                  40                  45

Gly Ala Ala Cys Ala Gly Thr Gly Gly Gly Thr Gly Gly Gly Cys Gly
50                  55                  60

Cys Gly Cys Gly Cys Ala Ala Ala Ala Ala Cys Thr Gly Gly Ala
65                  70                  75                  80

Ala Gly Ala Ala Cys Thr Gly Gly Ala Ala Cys Gly Cys Gly Ala Thr
            85                  90                  95

Cys Thr Gly Cys Gly Cys Ala Ala Ala Thr Thr Ala Ala Ala Ala
            100                 105                 110

Ala Ala Ala Ala Ala Ala Thr Thr Ala Ala Ala Ala Ala Cys Thr
            115                 120                 125

Gly Gly Ala Ala Gly Ala Ala Gly Ala Ala Ala Cys Cys Cys Gly
            130                 135                 140

Thr Gly Gly Cys Thr Gly Gly Gly Cys Ala Ala Cys Ala Thr Thr Ala
145                 150                 155                 160

Ala Ala Gly Gly Cys Ala Thr Thr Cys Thr Gly Gly Gly Cys Ala Ala
                165                 170                 175

Ala Ala Ala Ala Gly Ala Thr Cys Gly Cys Gly Ala Ala Gly Gly Cys
                180                 185                 190

Gly Ala Ala Gly Gly Cys Gly Cys Gly Cys Gly Cys Gly Cys Gly Gly
            195                 200                 205

Cys Gly Ala Ala Ala Cys Gly Cys Gly Cys Gly Cys Gly Cys
            210                 215                 220

Gly Gly Ala Thr Cys Ala Gly Ala Thr Gly Gly Ala Ala Gly Thr Gly
225                 230                 235                 240

Gly Ala Thr Ala Gly Cys Gly Gly Cys Cys Gly Cys Gly Cys Ala
            245                 250                 255

Ala Ala Cys Gly Cys Cys Cys Gly Thr Thr Thr Cys Gly Gly Gly
            260                 265                 270

Cys Gly Ala Ala Thr Thr Thr Ala Cys Cys Gly Ala Thr Ala Ala Ala
```

```
                275                 280                 285
Gly Ala Ala Cys Gly Cys Cys Gly Cys Gly Ala Thr Cys Ala Thr Cys
        290                 295                 300
Gly Cys Cys Gly Cys Cys Gly Cys Ala Ala Gly Cys Gly Cys Thr
305                 310                 315                 320
Gly Gly Ala Ala Ala Cys Ala Ala Cys Gly Cys Ala Ala Ala
                325                 330                 335
Cys Ala Gly Cys Thr Gly Ala Gly Cys Ala Gly Cys Gly Gly Cys Gly
                340                 345                 350
Gly Cys Ala Ala Ala Gly Cys Cys Thr Gly Ala Gly Cys Ala Ala
                355                 360                 365
Ala Gly Ala Ala Gly Ala Ala Gly Ala Ala Gly Ala Ala Gly Ala Ala
                370                 375                 380
Cys Thr Gly Cys Gly Cys Ala Ala Ala Cys Thr Gly Ala Cys Cys Gly
385                 390                 395                 400
Ala Ala Gly Ala Ala Gly Ala Thr Gly Ala Ala Cys Gly Cys Cys Gly
                405                 410                 415
Cys Gly Ala Ala Cys Gly Cys Cys Gly Cys Gly Thr Gly Gly Cys Gly
                420                 425                 430
Gly Gly Cys Cys Cys Gly Cys Gly Cys Gly Thr Gly Gly Cys Gly
                435                 440                 445
Gly Cys Gly Thr Gly Ala Ala Cys Cys Cys Gly Cys Thr Gly Gly Ala
                450                 455                 460
Ala Gly Gly Cys Gly Gly Cys Ala Cys Cys Gly Cys Gly Gly Cys
465                 470                 475                 480
Gly Cys Gly Cys Cys Gly Gly Gly Cys Gly Gly Cys Gly Gly Cys Thr
                485                 490                 495
Thr Thr Gly Thr Gly Cys Cys Gly Ala Gly Cys Ala Thr Gly Cys Ala
                500                 505                 510
Gly Gly Gly Cys Gly Thr Gly Cys Cys Gly Gly Ala Ala Ala Gly Cys
                515                 520                 525
Cys Cys Gly Thr Thr Thr Gly Cys Gly Cys Gly Cys Ala Cys Cys Gly
                530                 535                 540
Gly Cys Gly Ala Ala Gly Gly Cys Cys Thr Gly Gly Ala Thr Gly Thr
545                 550                 555                 560
Gly Cys Gly Cys Gly Gly Cys Ala Ala Cys Cys Ala Gly Gly Gly Cys
                565                 570                 575
Thr Thr Thr Cys Cys Gly Thr Gly Gly Gly Ala Thr Ala Thr Thr Cys
                580                 585                 590
Thr Gly Thr Thr Thr Cys Cys Gly Thr Gly Gly Ala Thr Cys Cys
                595                 600                 605
Gly Cys Cys Gly Thr Thr Thr Ala Gly Cys Cys Cys Gly Cys Ala Gly
        610                 615                 620
Ala Gly Cys Thr Gly Cys Cys Gly Cys Cys Cys Gly Cys Ala Gly
625                 630                 635
```

<210> SEQ ID NO 4
<211> LENGTH: 639
<212> TYPE: DNA
<213> ORGANISM: Artificial Sequence
<220> FEATURE:
<223> OTHER INFORMATION: HDAg genotype 1 B nucleic acid

<400> SEQUENCE: 4
agccgcagcg aaagcaaaaa aaaccgcggc ggccgcgaag aagtgctgga acagtgggtg    60

```
aacggccgca aaaaactgga agaactggaa cgcgaactgc gccgcgcgcg caaaaaatt    120 aaaaaactgg aagatgataa cccgtggctg ggcaacgtga aaggcattct gggcaaaaaa    180
gataaagatg gcgaaggcgc gccgccggcg aaacgcgcgc gcaccgatca gatggaaatt    240
gatagcggcc gcgcaaacg cccgctgcgc ggcggcttta ccgatcgcga acgccaggat    300
catcgccgcc gcaaagcgct gaaaaacaaa aaaaacagc tgagcgcggg cggcaaaagc    360
ctgagcaaag aagaagaaga gaactgaaa cgcctgaccc gcaagatga agaacgcaaa    420 aaagaagaac atggcccgag ccgcctgggc gtgaacccga gcgaaggcgg cccgcgcggc    480
gcgccgggcg gcggctttgt gccgagcatg cagggcattc cggaaagccg ctttacccgc    540
accggcgaag gcctggatgt gcgcggcagc gcgggctttc gcaggatat tctgtttccg    600 agcgatccgc cgtttagccc gcagagctgc gccccgcag                         639

<210> SEQ ID NO 5
<211> LENGTH: 141
<212> TYPE: DNA
<213> ORGANISM: Artificial Sequence
<220> FEATURE:
<223> OTHER INFORMATION: PreS1 derived sequence is preS1

<400> SEQUENCE: 5
ggcaccaacc tgagcaccag caacccgctg ggcttttttc cggatcatca gctggatccg     60
gcgtttcgcg cgaacagcgc gaacccggat tgggatttta acccgaacaa agatacctgg    120
ccggatgcga acaaagtggg c                                              141

<210> SEQ ID NO 6
<211> LENGTH: 141
<212> TYPE: DNA
<213> ORGANISM: Artificial Sequence
<220> FEATURE:
<223> OTHER INFORMATION: PreS1 B

<400> SEQUENCE: 6
ggccagaacc tgagcaccag caacccgctg ggcttttttc cggatcatca gctggatccg     60
gcgtttcgcg cgaacaccgc gaacccggat tgggatttta acccgaacaa agatacctgg    120
ccggatgcga acaaagtggg c                                              141

<210> SEQ ID NO 7
<211> LENGTH: 66
<212> TYPE: DNA
<213> ORGANISM: Artificial Sequence
<220> FEATURE:
<223> OTHER INFORMATION: T2A nucleic acid

<400> SEQUENCE: 7
ggaagcggag ctactaactt cagcctgctg aagcaggctg agacgtggga ggagaaccct     60
ggacct                                                                66

<210> SEQ ID NO 8
<211> LENGTH: 642
<212> TYPE: DNA
<213> ORGANISM: Artificial Sequence
<220> FEATURE:
<223> OTHER INFORMATION: HDAg gentotype 2 A (wt)

<400> SEQUENCE: 8
atgagccaga gcgaaacccg ccgcggccgc cgcggcaccc gcgaagaaac cctggaaaaa     60
```

```
tggattaccg cgcgcaaaaa agcggaagaa ctggaaaaag atctgcgcaa aacccgcaaa    120
accattaaaa aactggaaga agaaaacccg tggctgggca acattgtggg cattattcgc    180
aaaggcaaag atggcgaagg cgcgccgccg gcgaaacgcc cgcgcaccga tcagatggaa    240
gtggatagcg gcccgggcaa acgcccgcat aaaagcggct ttaccgataa agaacgcgaa    300
gatcatcgcc gccgcaaagc gctggaaaac aaaaaaaaac agctgagcgc gggcggcaaa    360
attctgagca agaagaagaa agaagaactg cgccgcctga ccgatgaaga tgaagaacgc    420
aaacgccgcg tggcgggccc gcgcgtgggc gatgtgaacc cgagccgcgg cggcccgcgc    480
ggcgcgccgg gcggcggctt tgtgccgcag atggcgggcg tgccggaaag cccgtttagc    540
cgcaccggcg aaggcctgga tattcgcggc acccagggct ttccgtgggt gagcccgagc    600
ccgccgcagc agcgcctgcc gctgctggaa tgcacccccgc ag    642

<210> SEQ ID NO 9
<211> LENGTH: 639
<212> TYPE: DNA
<213> ORGANISM: Artificial Sequence
<220> FEATURE:
<223> OTHER INFORMATION: HDAg gentotype 2 B (wt)

<400> SEQUENCE: 9
agccagagcg aaagcaaaaa aaaccgccgc ggcggccgcg aagatattct ggaaaaatgg    60
attaccaccc gccgcaaagc ggaagaactg gaaaaagatc tgcgcaaagc gcgcaaaacc    120
attaaaaaac tggaagatga aaacccgtgg ctgggcaaca ttattggcat tattcgcaaa    180
ggcaaagatg gcgaaggcgc gccgccggcg aaacgcccgc gcaccgatca gatggaaatt    240
gatagcggca ccggcaaacg cccgcataaa agcggctttaccgataaaga acgcgaagat    300 catcgccgcc gcaaagcgct ggaaaacaaa aaaaacagc tgagcagcgg cggcaaaaac    360
ctgagccgcg aagaagaaga gaactgggc cgcctgaccg tggaagatga agaacgccgc    420
cgccgcgtgg cgggcccgcg caccggcgat gtgaacctga gcgcggcgg cccgcgcggc    480 gcgccgggcg gcggctttgt gccgcgcatg aaggcgtgc cggaaagccc gtttacccgc    540
accggcgaag gcctggatat tcgcggcaac cagggctttc cgtgggtgcg cccgagcccg    600
ccgcagcagc gcctgccgct gctggaatgc accccgcag    639

<210> SEQ ID NO 10
<211> LENGTH: 3189
<212> TYPE: DNA
<213> ORGANISM: Artificial Sequence
<220> FEATURE:
<223> OTHER INFORMATION: Delta 1 wt

<400> SEQUENCE: 10
agccgcagcg aaagcaaaaa aaaccgcggc ggccgcgaag aaattctgga acagtgggtg    60
ggcgcgcgca aaaactgga agaactgaa cgcgatctgc gcaaaattaa aaaaaaaatt    120
aaaaaactgg aagaagaaaa cccgtggctg gcaacatta aaggcattct gggcaaaaaa    180
gatcgcgaag gcgaaggcgc gccgccggcg aaacgcgcgc gcggatca gatggaagtg    240 gatagcggcc ccgcgcaaacg cccgtttcgc ggcgaattta ccgataaaga acgcgcgat    300 catcgccgcc gcaaagcgct ggaaaacaaa cgcaaacagc tgagcagcgg cggcaaaagc    360
ctgagcaaag aagaagaaga gaactgcgc aaactgaccg aagaagatga acgccgcgaa    420
cgccgcgtgg cgggcccgcg cgtgggcggc gtgaacccgc tgaaaggcgg cacccgcggc    480
gcgccgggcg gcggctttgt gccgagcatg caggcgtgc cggaaagccc gtttgcgcgc    540
```

```
accggcgaag gcctggatgt gcgcggcaac cagggctttc cgtgggatat tctgtttccg    600
gcggatccgc cgtttagccc gcagagctgc cgcccgcaga gccgcagcga aagcaaaaaa    660
aaccgcggcg gccgcgaaga agtgctggaa cagtgggtga acggccgcaa aaaactggaa    720
gaactggaac gcgaactgcg ccgcgcgcgc aaaaaaatta aaaaactgga agatgataac    780
ccgtggctgg gcaacgtgaa aggcattctg gcaaaaaaag ataaagatgg cgaaggcgcg    840
ccgccggcga aacgcgcgcg caccgatcag atggaaattg atagcggccc cgcaaacgc     900 ccgctgcgcg gcggctttac cgatcgcgaa cgccaggatc atcgccgccg caaagcgctg    960
aaaaacaaaa aaaaacagct gagcgcgggc ggcaaaagcc tgagcaaaga agaagaagaa   1020
gaactgaaac gcctgacccg cgaagatgaa gaacgcaaaa aagaagaaca tggcccgagc   1080 cgcctggggcg tgaacccgag cgaaggcggc ccgcgcggcg cgccgggcgg cggctttgtg   1140
ccgagcatgc agggcattcc ggaaagccgc tttacccgca ccggcgaagg cctggatgtg   1200
cgcggcagcc gcggctttcc gcaggatatt ctgtttccga gcgatccgcc gtttagcccg   1260
cagagctgcc gcccgcaggg caccaacctg agcaccagca acccgctggg ctttttttccg   1320 gatcatcagc tggatccggc gtttcgcgcg aacagcgcga accggattg ggatttaac     1380 ccgaacaaag atacctggcc ggatgcgaac aaagtgggcg ccagaacct gagcaccagc    1440 aacccgctgg gcttttttcc ggatcatcag ctggatccgg cgtttcgcgc gaacaccgcg   1500
aacccggatt gggattttaa cccgaacaaa gatacctggc cggatgcgaa caaagtgggc   1560
ggaagcggag ctactaactt cagcctgctg aagcaggctg gagacgtgga ggagaaccct   1620
ggacctatga gccagagcga aacccgccgc ggccgccgcg gcacccgcga gaaaccctg    1680 gaaaaatgga ttaccgcgcg caaaaaagcg gaagaactgg aaaagatct gcgcaaaacc    1740 cgcaaaacca ttaaaaaact ggaagaagaa aacccgtggc tgggcaacat tgtgggcatt   1800
attcgcaaag gcaaagatgg cgaaggcgcg ccgccggcga acgcccgcg caccgatcag    1860 atggaagtgg atagcggccc gggcaaacgc ccgcataaaa gcggctttac cgataaagaa   1920
cgcgaagatc atcgccgccg caaagcgctg gaaaacaaaa aaaaacagct gagcgcgggc   1980
ggcaaaattc tgagcaaaga agaagaagaa gaactgcgcc gcctgaccga tgaagatgaa   2040
gaacgcaaac gccgcgtggc gggccgcgc gtgggcgatg tgaacccgag ccgcggcggc   2100
ccgcgcggcg cgccgggcgg cggctttgtg ccgcagatgg cgggcgtgcc ggaaagcccg   2160
tttagccgca ccggcgaagg cctggatatt cgcggcaccc agggctttcc gtgggtgagc   2220
ccgagcccgc cgcagcagcg cctgccgctg ctggaatgca ccccgcagag ccagagcgaa   2280
agcaaaaaaa accgccgcgg cggccgcgaa gatattctgg aaaaatggat taccacccgc   2340
cgcaaagcgg aagaactgga aaagatctg cgcaaagcgc gcaaaccat taaaaaactg     2400 gaagatgaaa acccgtggct gggcaacatt attggcatta ttcgcaaagg caaagatggc   2460
gaaggcgcgc cgccggcgaa acgcccgcgc accgatcaga tggaaattga tagcggcacc   2520
ggcaaacgcc cgcataaaag cggctttacc gataaagaac gcgaagatca tcgccgccgc   2580
aaagcgctgg aaaacaaaaa aaaacagctg agcagcggcg gcaaaaacct gagccgcgaa   2640
gaagaagaag aactgggccg cctgacccgt gaagatgaag aacgccgccg ccgcgtggcg   2700
ggcccgcgca ccggcgatgt gaacctgagc ggcggcggcc cgcgcggcgc gccgggcggc   2760
ggctttgtgc cgcgcatgga aggcgtgccg gaaagcccgt ttacccgcac cggcgaaggc   2820
ctggatattc gcggcaacca gggctttccg tgggtgcgcc cgagcccgcc gcagcagcgc   2880
```

| | |
|---|---|
| ctgccgctgc tggaatgcac cccgcagggc accaacctga gcaccagcaa cccgctgggc | 2940 |
| ttttttccgg atcatcagct ggatccggcg tttcgcgcga acagcgcgaa cccggattgg | 3000 |
| gattttaacc cgaacaaaga tacctggccg gatgcgaaca aagtgggcgg ccagaacctg | 3060 |
| agcaccagca cccgctgggc ttttttccg gatcatcagc tggatccggc gtttcgcgcg | 3120 |
| aacaccgcga acccggattg ggattttaac ccgaacaaag atacctggcc ggatgcgaac | 3180 |
| aaagtgggc | 3189 |

<210> SEQ ID NO 11
<211> LENGTH: 3221
<212> TYPE: DNA
<213> ORGANISM: Artificial Sequence
<220> FEATURE:
<223> OTHER INFORMATION: Delta1 wt with restriction sites (HindIII/
      EcoRI)

<400> SEQUENCE: 11

| | |
|---|---|
| aagcttgcac catggccagc cgcagcgaaa gcaaaaaaaa ccgcggcggc cgcgaagaaa | 60 |
| ttctggaaca gtgggtgggc gcgcgcaaaa aactggaaga actggaacgc gatctgcgca | 120 |
| aaattaaaaa aaaaattaaa aaactggaag aagaaacccc gtggctgggc aacattaaag | 180 |
| gcattctggg caaaaaagat cgcgaaggcg aaggcgcgcc gccggcgaaa cgcgcgcgcg | 240 |
| cggatcagat ggaagtggat agcggcccgc gcaaacgccc gtttcgcggc gaatttaccg | 300 |
| ataaagaacg ccgcgatcat cgccgccgca aagcgctgga aaacaaacgc aaacagctga | 360 |
| gcagcggcgg caaaagcctg agcaaagaag aagaagaaga actgcgcaaa ctgaccgaag | 420 |
| aagatgaacg ccgcgaacgc gcgtggcgg gcccgcgcgt gggcggcgtg aacccgctgg | 480 |
| aaggcggcac ccgcggcgcg ccgggcggcg gctttgtgcc gagcatgcag ggcgtgccgg | 540 |
| aaagcccgtt tgcgcgcacc ggcgaaggcc tggatgtgcg cggcaaccag ggcttttccgt | 600 |
| gggatattct gtttccggcg gatccgccgt ttagcccgca gagctgccgc ccgcagagcc | 660 |
| gcagcgaaag caaaaaaaac cgcggcggcc gcgaagaagt gctggaacag tgggtgaacg | 720 |
| gccgcaaaaa actggaagaa ctggaacgcg aactgcgccg cgcgcgcaaa aaaattaaaa | 780 |
| aactggaaga tgataacccg tggctgggca acgtgaaagg cattctgggc aaaaaagata | 840 |
| aagatggcga aggcgcgccc ccggcgaaac gcgcgcgcac cgatcagatg gaaattgata | 900 |
| gcggcccgcg caaacgcccg ctgcgcggcg ctttaccga tcgcgaacgc caggatcatc | 960 |
| gccgccgcaa agcgctgaaa acaaaaaaaa aacagctgag cgcgggcggc aaaagcctga | 1020 |
| gcaaagaaga agaagaagaa ctgaaacgcc tgacccgcga agatgaagaa cgcaaaaaag | 1080 |
| aagaacatgg cccgagccgc ctgggcgtga cccgagcga aggcggcccg cgcggcgcgc | 1140 |
| cggggcggcgg ctttgtgccg agcatgcagg gcattccgga aagccgcttt acccgcaccg | 1200 |
| gcgaaggcct ggatgtgcgc ggcagccgcg gctttccgca ggatattctg tttccgagcg | 1260 |
| atccgccgtt tagcccgcag agctgccgcc cgcaggcac caacctgagc accagcaacc | 1320 |
| cgctgggctt ttttccggat catcagctgg atccggcgtt tcgcgcgaac agcgcgaacc | 1380 |
| cggattggga ttttaacccg aacaaagata cctggccgga tgcgaacaaa gtgggcggcc | 1440 |
| agaacctgag caccagcaac ccgctgggct ttttccgga tcatcagctg gatccggcgt | 1500 |
| ttcgcgcgaa caccgcgaac ccggattggg attttaaccc gaacaaagat acctggccgg | 1560 |
| atgcgaacaa agtgggcgga agcggagcta ctaacttcag cctgctgaag caggctggag | 1620 |
| acgtggagga gaaccctgga cctatgagcc agagcgaaac ccgccgcggc cgccgcggca | 1680 |

```
cccgcgaaga aaccctggaa aaatggatta ccgcgcgcaa aaaagcggaa gaactggaaa     1740
aagatctgcg caaaacccgc aaaaccatta aaaaactgga agaagaaaac ccgtggctgg     1800
gcaacattgt gggcattatt cgcaaaggca agatggcgaa aggcgcgccg ccggcgaaac     1860
gcccgcgcac cgatcagatg gaagtggata cggcccgggg caaacgcccg cataaaagcg     1920
gctttaccga taaagaacgc gaagatcatc gccgccgcaa agcgctggaa acaaaaaaaa     1980
aacagctgag cgcgggcggc aaaattctga gcaaagaaga agaagaagaa ctgccgccgcc   2040
tgaccgatga agatgaagaa cgcaaacgcc gcgtggcggg cccgcgcgtg ggcgatgtga     2100
acccgagccg cggcggcccg cgcggcgcgc cgggcggcgg ctttgtgccg cagatggcgg     2160
gcgtgccgga agcccgtttt agccgcaccg gcgaaggcct ggatattcgc ggcacccagg     2220
gctttccgtg ggtgagcccg agccgccgc agcagcgcct gccgctgctg gaatgcaccc      2280
cgcagagcca gagcgaaagc aaaaaaaacc gccgcggcgg ccgcgaagat attctggaaa     2340
aatggattac caccgccgc aaagcggaag aactggaaaa agatctgcgc aaagcgcgca       2400
aaaccattaa aaaactggaa gatgaaaacc cgtggctggg caacattatt ggcattattc     2460
gcaaaggcaa agatggcgaa ggcgcgccgc cggcgaaacg cccgcgcacc gatcagatgg     2520
aaattgatag cggcaccggc aaacgcccgc ataaaagcgg ctttaccgat aaagaacgcg     2580
aagatcatcg ccgccgcaaa gcgctggaaa caaaaaaaaa acagctgagc agcggcggca     2640
aaaacctgag ccgcgaagaa gaagaagaac tgggccgcct gaccgtggaa gatgaagaac     2700
gccgccgccg cgtggcgggc ccgcgcaccg gcgatgtgaa cctgagcggc ggcggcccgc     2760
gcggcgcgcc gggcggcggc tttgtgccgc catggaagg cgtgccggaa agcccgttta     2820
cccgcaccgg cgaaggcctg gatattcgcg gcaaccaggg cttccgtgg gtgcgcccga      2880
gcccgccgca gcagcgcctg ccgctgctgg aatgcacccc gcagggcacc aacctgagca     2940
ccagcaaccc gctgggcttt tttccggatc atcagctgga tccggcgttt cgcgcgaaca     3000
gcgcgaaccc ggattgggat tttaacccga acaaagatac ctggccggat gcgaacaaag     3060
tgggcggcca gaacctgagc accagcaacc cgctgggctt ttttccggat catcagctgg     3120
atccggcgtt tcgcgcgaac accgcgaacc cggattggga ttttaacccg aacaaagata     3180
cctggccgga tgcgaacaaa gtgggctgat gagaattccg t                         3221

<210> SEQ ID NO 12
<211> LENGTH: 3192
<212> TYPE: DNA
<213> ORGANISM: Artificial Sequence
<220> FEATURE:
<223> OTHER INFORMATION: Codon optimized delta 1

<400> SEQUENCE: 12
gccagcagaa gtgaatcaaa aaagaatcgg ggagggcggg aagaaatcct ggaacagtgg       60
gtcggagcac ggaagaaact ggaagaactg gagagggacc tgcgcaagat caagaagaag      120
atcaagaagc tggaggagga gaaccctggg ctgggcaata tcaagggcat cctgggcaag      180
aaggatcggg agggagaggg agcaccacct gcaaagaggg ccagagccga ccagatggag      240
gtggatagcg gaccaaggaa gcgccctttc agaggagagt ttaccgacaa ggagcggaga      300
gatcacaggc gccggaaggc cctggagaac aagaggaagc agctgagctc cggcggcaag      360
tccctgtcta ggaggaggag ggaggagctg cgcaagctga cagaggagga cgagagaagg      420
gagaggaggg tggcaggacc tagggtggga ggcgtgaacc cactggaggg aggaaccaga      480
ggagcacctg gaggaggatt cgtgccatcc atgcagggag tgcccgagtc tccttttgcc      540
```

-continued

```
cggacaggcg agggcctgga tgtgagaggc aatcagggct tccsctggga catcctgttt      600
cctgccgatc cacccttctc tcctcagagc tgccggccac agagcagatc cgagtctaag      660
aagaacaggg gaggaagaga ggaggtgctg gagcagtggg tgaatggccg gaagaagctg      720
gaggagctgg agcgggagct gagaagggcc agaaagaaga tcaagaagct ggaagacgat      780
aatccttggc tgggcaatgt gaaaggcatc ctgggcaaga aggacaagga tggagaggga      840
gcacctccag caaagagggc aagaaccgac cagatggaga tcgattctgg accaaggaag      900
cgccccctga gaggaggctt cacagaccgg gagagacagg atcaccgccg agaaaggcc      960 ctgaagaaca agaagaagca gctgtccgcc ggaggcaaga gcctgtccaa agaagaggaa    1020
gaggagctga agaggctgac ccgcgaggac gaggagagga agaaggagga gcacggacca    1080
agcaggctgg gagtgaatcc ttccgaggga ggacctaggg gagcaccagg aggaggcttc    1140
gtgccatcta tgcagggcat ccccgagagc cggtttacca gaacaggaga gggcctggac    1200
gtgaggggct cccgcggctt tcctcaggac atcctgttcc catctgatcc ccctttttcc    1260
ccccagtctt gtaggcctca gggcaccaac ctgtctacaa gcaatccact gggcttcttt    1320
cccgaccacc agctggatcc tgccttccgc gccaacagcg ccaatcccga ctgggacttc    1380
aacccaaata aggacacctg gccagatgcc aacaaggtcg gcggccagaa cctgtccaca    1440
tctaatcctc tgggcttctt tccagaccac cagctggatc cagccttccg ggccaacaca    1500
gctaaccctg actgggactt caaccccaat aaggatactt ggcccgacgc caacaaggtc    1560
ggcggaagcg gagctactaa cttcagcctg ctgaagcagg ctggagacgt ggaggagaac    1620
cctggaccta tgagccagtc cgagacaagg aggggccgga gaggaaccag ggaggagaca    1680
ctggagaagt ggatcacagc ccgcaagaag gccgaggagc tggagaagga cctgcggaag    1740
accagaaaga caatcaagaa gctggaagaa gagaacccat ggctgggcaa tatcgtgggc    1800
atcatcagaa agggcaagga cggcgaggga gcaccaccag caaagaggcc caggactgat    1860
cagatggaag tcgatagcgg accaggcaag cggcctcaca gtccggcttc acagacaag     1920 gagagagagg accataggcg ccggaaggcc ctggaaaaca agaagaagca attatccgcc    1980
ggcggcaaga tcctgtccaa agaggaagaa gaggagctga aaggctgac cgacgaggat    2040 gaggagagga aaagaagggt ggcaggacca agggtgggcg acgtgaatcc cagcagggga    2100
ggaccaagag gcgcccctgg cggcggcttc gtgccacaga tggcaggagt gccagagagc    2160
cccttttcca ggacaggaga gggcctggat atcagaggca cccagggctt tccttgggtg    2220
tctccaagcc ctccacagca gcggctgcca ctgctggagt gcacccctca gtcccagtct    2280
gagagcaaga agaacagaag gggcggcaga gaggacatcc tggagaagtg gatcaccaca    2340
cgcagaaaag ctgaagaact ggaaaaggac ctgaggaagg cccgcaaaac aatcaagaag    2400
ctggaggatg aaaatccatg gctgggaaac atcatcggca tcatcaggaa gggcaaggac    2460
ggggaaggcg caccacctgc aaagcggcct agaacagatc agatgaaat cgattctggc    2520 accggcaaga ggccacacaa gagcggcttc accgacaagg agcgcgagga tcacagaagg    2580
cgcaaggccc tggagaacaa gaagaagcaa ttaagcagcg gcggcaagaa tctgtccaga    2640
gaagaagagg aggagctggg ccgcctgacc gtggaggacg aggagcggag aaggcgcgtg    2700
gcaggaccac gcacaggcga tgtgaacctg tccggaggag accaaggggg agcacctgga    2760
ggcggcttcg tgcctagaat ggagggagtg cctgagtccc ccttcacccg caccggagag    2820
ggcctggaca tcagaggcaa tcagggattc ccatgggtga ggcccagccc accacagcag    2880
```

| | |
|---|---|
| cgcctgccac tgctggagtg tacccccag ggcacaaacc tgtccacctc taatcccctg | 2940 |
| ggcttctttc ctgatcatca gctggaccca gccttcaggg ccaactccgc caatccagat | 3000 |
| tgggacttca acccgaataa ggatacttgg ccagatgcaa acaaggtcgg aggacagaac | 3060 |
| ctgagcacat ccaaccctct gggcttcttt cctgaccatc agctggatcc cgcctttcgc | 3120 |
| gccaataccg ccaaccctga ttgggacttc aaccctaata aggatacttg gcctgatgct | 3180 |
| aataaggtcg gg | 3192 |

```
<210> SEQ ID NO 13
<211> LENGTH: 3221
<212> TYPE: DNA
<213> ORGANISM: Artificial Sequence
<220> FEATURE:
<223> OTHER INFORMATION: Delta 1 optimized with restriction sites
      (HindIII and EcoRI)
```

<400> SEQUENCE: 13

| | |
|---|---|
| aagcttgcac catggccagc agaagtgaat caaaaaagaa tcggggaggg cgggaagaaa | 60 |
| tcctggaaca gtgggtcgga gcacggaaga aactggaaga actggagagg gacctgcgca | 120 |
| agatcaagaa gaagatcaag aagctggagg aggagaaccc ctggctgggc aatatcaagg | 180 |
| gcatcctggg caagaaggat cgggagggag agggagcacc acctgcaaag agggccagag | 240 |
| ccgaccagat ggaggtggat agcggaccaa ggaagcgccc tttcagagga gagtttaccg | 300 |
| acaaggagcg gagagatcac aggcgccgga aggccctgga gaacaagagg aagcagctga | 360 |
| gctccggcgg caagtccctg tctaaggagg aggaggagga gctgcgcaag ctgacagagg | 420 |
| aggacgagag aagggagagg agggtggcag gacctagggt gggaggcgtg aacccactgg | 480 |
| agggaggaac cagaggagca cctggaggag gattcgtgcc atccatgcag ggagtgcccg | 540 |
| agtctccttt tgcccggaca ggcgagggcc tggatgtgag aggcaatcag ggcttcccct | 600 |
| gggacatcct gtttcctgcc gatccaccct tctctcctca gagctgccgg ccacagagca | 660 |
| gatccgagtc taagaagaac aggggaggaa gagaggaggt gctggagcag tgggtgaatg | 720 |
| gccggaagaa gctggaggag ctggagcggg agctgagaag ggccagaaag aagatcaaga | 780 |
| agctggaaga cgataatcct tggctgggca atgtgaaagg catcctgggc aagaaggaca | 840 |
| aggatggaga gggagcacct ccagcaaaga gggcaagaac cgaccagatg gagatcgatt | 900 |
| ctggaccaag gaagcgcccc ctgagaggag gcttcacaga ccgggagaga caggatcacc | 960 |
| gccggagaaa ggccctgaag aacaagaaga agcagctgtc cgccggaggc aagagcctgt | 1020 |
| ccaaagaaga ggaagaggag ctgaagaggc tgacccgcga ggacgaggag aggaagaagg | 1080 |
| aggagcacgg accaagcagg ctgggagtga atccttccga gggaggacct aggggagcac | 1140 |
| caggaggagg cttcgtgcca tctatgcagg gcatccccga gagccggttt accagaacag | 1200 |
| gagagggcct ggacgtgagg ggctcccgcg gctttcctca ggacatcctg ttcccatctg | 1260 |
| atccccttt ttccccccag tcttgtaggc ctcaggcac caacctgtct acaagcaatc | 1320 |
| cactgggctt ctttcccgac caccagctgg atcctgcctt ccgcgccaac agcgccaatc | 1380 |
| ccgactggga cttcaaccca aataaggaca cctggccaga tgccaacaag gtcggcggcc | 1440 |
| agaacctgtc cacatctaat cctctgggct tctttccaga ccaccagctg gatccagcct | 1500 |
| tccgggccaa cacagctaac cctgactggg acttcaaccc caataaggat acttggcccg | 1560 |
| acgccaacaa ggtcggcgga agcggagcta ctaacttcag cctgctgaag caggctggag | 1620 |
| acgtggagga gaaccctgga cctatgagcc agtccgagac aaggagggc cggagaggaa | 1680 |

```
ccagggagga gacactggag aagtggatca cagcccgcaa gaaggccgag gagctggaga   1740
aggacctgcg gaagaccaga aagacaatca agaagctgga agaagagaac ccatggctgg   1800
gcaatatcgt gggcatcatc agaaagggca aggacggcga gggagcacca ccagcaaaga   1860
ggcccaggac tgatcagatg gaagtcgata gcggaccagg caagcggcct cacaagtccg   1920
gcttcacaga caaggagaga gaggaccata ggcgccggaa ggccctggaa aacaagaaga   1980
agcaattatc cgccggcggc aagatcctgt ccaaagagag aagaggag ctgagaaggc     2040
tgaccgacga ggatgaggag aggaaaagaa gggtggcagg accaagggtg ggcgacgtga   2100
atcccagcag ggaggaccca agaggcgccc ctggcggcgg cttcgtgcca cagatggcag   2160
gagtgccaga gagccccttt tccaggacag agagggcct ggatatcaga ggcacccagg    2220
gctttccttg ggtgtctcca agccctccac agcagcggct gccactgctg gagtgcaccc   2280
ctcagtccca gtctgagagc aagaagaaca gaaggggcgg cagagaggac atcctggaga   2340
agtggatcac cacacgcaga aaagctgaag aactggaaaa ggacctgagg aaggcccgca   2400
aaacaatcaa gaagctggag gatgaaaatc catggctggg aaacatcatc ggcatcatca   2460
ggaagggcaa ggacggggaa ggcgcaccac ctgcaaagcg gcctagaaca gatcagatgg   2520
aaatcgattc tggcaccggc aagaggccac acaagagcgg cttcaccgac aaggagcgcg   2580
aggatcacag aaggcgcaag gccctggaga caagaagaa gcaattaagc agcggcggca   2640
agaatctgtc cagagaagaa gaggaggagc tgggccgcct gaccgtggag gacgaggagc   2700
ggagaaggcg cgtggcagga ccacgcacag gcgatgtgaa cctgtccgga ggaggaccaa   2760
ggggagcacc tggaggcggc ttcgtgccta gaatggaggg agtgcctgag tccccccttca  2820
cccgcaccgg agagggcctg gacatcagag gcaatcaggg attcccatgg gtgaggccca   2880
gcccaccaca gcagcgcctg ccactgctgg agtgtacccc ccagggcaca aacctgtcca   2940
cctctaatcc cctgggcttc tttcctgatc atcagctgga cccagccttc agggccaact   3000
ccgccaatcc agattgggac ttcaacccga ataaggatac ttggccagat gcaaacaagg   3060
tcggaggaca gaacctgagc acatccaacc ctctgggctt cttttcctgac catcagctgg   3120
atcccgccttt tcgcgccaat accgccaacc tgattgggac cttcaaccct aataaggata   3180
cttggcctga tgctaataag gtcgggtgat gagaattccg t                       3221
```

<210> SEQ ID NO 14
<211> LENGTH: 1065
<212> TYPE: PRT
<213> ORGANISM: Artificial Sequence
<220> FEATURE:
<223> OTHER INFORMATION: Delta 1 protein

<400> SEQUENCE: 14

```
Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95
```

```
Asp Lys Glu Arg Arg Asp His Arg Arg Arg Lys Ala Leu Glu Asn Lys
            100                 105                 110

Arg Lys Gln Leu Ser Ser Gly Gly Lys Ser Leu Ser Lys Glu Glu Glu
            115                 120                 125

Glu Glu Leu Arg Lys Leu Thr Glu Glu Asp Glu Arg Arg Glu Arg Arg
        130                 135                 140

Val Ala Gly Pro Arg Val Gly Gly Val Asn Pro Leu Glu Gly Gly Thr
145                 150                 155                 160

Arg Gly Ala Pro Gly Gly Gly Phe Val Pro Ser Met Gln Gly Val Pro
                165                 170                 175

Glu Ser Pro Phe Ala Arg Thr Gly Glu Gly Leu Asp Val Arg Gly Asn
            180                 185                 190

Gln Gly Phe Pro Trp Asp Ile Leu Phe Pro Ala Asp Pro Pro Phe Ser
            195                 200                 205

Pro Gln Ser Cys Arg Pro Gln Ser Arg Ser Glu Ser Lys Lys Asn Arg
        210                 215                 220

Gly Gly Arg Glu Glu Val Leu Glu Gln Trp Val Asn Gly Arg Lys Lys
225                 230                 235                 240

Leu Glu Glu Leu Glu Arg Glu Leu Arg Arg Ala Arg Lys Lys Ile Lys
                245                 250                 255

Lys Leu Glu Asp Asp Asn Pro Trp Leu Gly Asn Val Lys Gly Ile Leu
            260                 265                 270

Gly Lys Lys Asp Lys Asp Gly Glu Gly Ala Pro Pro Ala Lys Arg Ala
        275                 280                 285

Arg Thr Asp Gln Met Glu Ile Asp Ser Gly Pro Arg Lys Arg Pro Leu
            290                 295                 300

Arg Gly Gly Phe Thr Asp Arg Glu Arg Gln Asp His Arg Arg Arg Lys
305                 310                 315                 320

Ala Leu Lys Asn Lys Lys Gln Leu Ser Ala Gly Lys Ser Leu
                325                 330                 335

Ser Lys Glu Glu Glu Glu Leu Lys Arg Leu Thr Arg Glu Asp Glu
            340                 345                 350

Glu Arg Lys Lys Glu Glu His Gly Pro Ser Arg Leu Gly Val Asn Pro
        355                 360                 365

Ser Glu Gly Gly Pro Arg Gly Ala Pro Gly Gly Gly Phe Val Pro Ser
370                 375                 380

Met Gln Gly Ile Pro Glu Ser Arg Phe Thr Arg Thr Gly Glu Gly Leu
385                 390                 395                 400

Asp Val Arg Gly Ser Arg Gly Phe Pro Gln Asp Ile Leu Phe Pro Ser
                405                 410                 415

Asp Pro Pro Phe Ser Pro Gln Ser Cys Arg Pro Gln Gly Thr Asn Leu
            420                 425                 430

Ser Thr Ser Asn Pro Leu Gly Phe Phe Pro Asp His Gln Leu Asp Pro
        435                 440                 445

Ala Phe Arg Ala Asn Ser Ala Asn Pro Asp Trp Asp Phe Asn Pro Asn
            450                 455                 460

Lys Asp Thr Trp Pro Asp Ala Asn Lys Val Gly Gly Gln Asn Leu Ser
465                 470                 475                 480

Thr Ser Asn Pro Leu Gly Phe Phe Pro Asp His Gln Leu Asp Pro Ala
                485                 490                 495

Phe Arg Ala Asn Thr Ala Asn Pro Asp Trp Asp Phe Asn Pro Asn Lys
            500                 505                 510
```

-continued

Asp Thr Trp Pro Asp Ala Asn Lys Val Gly Ser Gly Ala Thr Asn
            515                 520                 525

Phe Ser Leu Leu Lys Gln Ala Gly Asp Val Glu Glu Asn Pro Gly Pro
    530                 535                 540

Met Ser Gln Ser Glu Thr Arg Arg Gly Arg Arg Gly Thr Arg Glu Glu
545                 550                 555                 560

Thr Leu Glu Lys Trp Ile Thr Ala Arg Lys Lys Ala Glu Glu Leu Glu
                565                 570                 575

Lys Asp Leu Arg Lys Thr Arg Lys Thr Ile Lys Lys Leu Glu Glu Glu
            580                 585                 590

Asn Pro Trp Leu Gly Asn Ile Val Gly Ile Ile Arg Lys Gly Lys Asp
            595                 600                 605

Gly Glu Gly Ala Pro Pro Ala Lys Arg Pro Arg Thr Asp Gln Met Glu
    610                 615                 620

Val Asp Ser Gly Pro Gly Lys Arg Pro His Lys Ser Gly Phe Thr Asp
625                 630                 635                 640

Lys Glu Arg Glu Asp His Arg Arg Arg Lys Ala Leu Glu Asn Lys Lys
                645                 650                 655

Lys Gln Leu Ser Ala Gly Gly Lys Ile Leu Ser Lys Glu Glu Glu Glu
            660                 665                 670

Glu Leu Arg Arg Leu Thr Asp Glu Asp Glu Glu Arg Lys Arg Arg Val
    675                 680                 685

Ala Gly Pro Arg Val Gly Asp Val Asn Pro Ser Arg Gly Gly Pro Arg
    690                 695                 700

Gly Ala Pro Gly Gly Phe Val Pro Gln Met Ala Gly Val Pro Glu
705                 710                 715                 720

Ser Pro Phe Ser Arg Thr Gly Glu Gly Leu Asp Ile Arg Gly Thr Gln
                725                 730                 735

Gly Phe Pro Trp Val Ser Pro Ser Pro Gln Gln Arg Leu Pro Leu
            740                 745                 750

Leu Glu Cys Thr Pro Gln Ser Gln Ser Glu Ser Lys Lys Asn Arg Arg
    755                 760                 765

Gly Gly Arg Glu Asp Ile Leu Glu Lys Trp Ile Thr Thr Arg Arg Lys
    770                 775                 780

Ala Glu Glu Leu Glu Lys Asp Leu Arg Lys Ala Arg Lys Thr Ile Lys
785                 790                 795                 800

Lys Leu Glu Asp Glu Asn Pro Trp Leu Gly Asn Ile Ile Gly Ile Ile
                805                 810                 815

Arg Lys Gly Lys Asp Gly Glu Gly Ala Pro Pro Ala Lys Arg Pro Arg
            820                 825                 830

Thr Asp Gln Met Glu Ile Asp Ser Gly Thr Gly Lys Arg Pro His Lys
            835                 840                 845

Ser Gly Phe Thr Asp Lys Glu Arg Glu Asp His Arg Arg Arg Lys Ala
850                 855                 860

Leu Glu Asn Lys Lys Lys Gln Leu Ser Ser Gly Gly Lys Asn Leu Ser
865                 870                 875                 880

Arg Glu Glu Glu Glu Leu Gly Arg Leu Thr Val Glu Asp Glu Glu
                885                 890                 895

Arg Arg Arg Arg Val Ala Gly Pro Arg Thr Gly Asp Val Asn Leu Ser
            900                 905                 910

Gly Gly Gly Pro Arg Gly Ala Pro Gly Gly Phe Val Pro Arg Met
            915                 920                 925

Glu Gly Val Pro Glu Ser Pro Phe Thr Arg Thr Gly Glu Gly Leu Asp

```
                930           935           940
Ile Arg Gly Asn Gln Gly Phe Pro Trp Val Arg Pro Ser Pro Pro Gln
945                 950                 955                 960

Gln Arg Leu Pro Leu Leu Glu Cys Thr Pro Gln Gly Thr Asn Leu Ser
                965                 970                 975

Thr Ser Asn Pro Leu Gly Phe Phe Pro Asp His Gln Leu Asp Pro Ala
            980                 985                 990

Phe Arg Ala Asn Ser Ala Asn Pro Asp Trp Asp Phe Asn Pro Asn Lys
        995                1000                1005

Asp Thr Trp Pro Asp Ala Asn Lys Val Gly Gln Asn Leu Ser Thr
    1010                1015                1020

Ser Asn Pro Leu Gly Phe Phe Pro Asp His Gln Leu Asp Pro Ala Phe
1025                1030                1035                1040

Arg Ala Asn Thr Ala Asn Pro Asp Trp Asp Phe Asn Pro Asn Lys Asp
                1045                1050                1055

Thr Trp Pro Asp Ala Asn Lys Val Gly
            1060                1065

<210> SEQ ID NO 15
<211> LENGTH: 3189
<212> TYPE: DNA
<213> ORGANISM: Artificial Sequence
<220> FEATURE:
<223> OTHER INFORMATION: Delta 2 sequence wt

<400> SEQUENCE: 15
ggcaccaacc tgagcaccag caacccgctg gcttttttc cggatcatca gctggatccg      60
gcgtttcgcg cgaacagcgc gaacccggat tgggatttta acccgaacaa agatacctgg    120
ccggatgcga acaaagtggg cggccagaac ctgagcacca gcaacccgct gggcttttt     180
ccggatcatc agctggatcc ggcgtttcgc gcgaacaccg aacccgga ttgggatttt      240
aacccgaaca aagatacctg gccggatgcg aacaaagtgg gcagccgcag cgaaagcaaa    300
aaaaaccgcg gcggccgcga agaaattctg aacagtgggt gggcgcgcg caaaaaactg    360
gaagaactgg aacgcgatct gcgcaaaatt aaaaaaaaaa ttaaaaaact ggaagaagaa    420
aacccgtggc tgggcaacat taaaggcatt ctgggcaaaa agatcgcga aggcgaaggc    480
gcgccgccgg cgaaacgcgc gcgcgcggat cagatggaag tggatagcgg cccgcgcaaa    540
cgcccgtttc gcggcgaatt taccgataaa gaacgccgcg atcatcgccg ccgcaaagcg    600
ctggaaaaca acgcaaaca gctgagcagc ggcggcaaaa gcctgagcaa agaagaagaa    660
gaagaactgc gcaaactgac cgaagaagat gaacgccgcg aacgccgcgt ggcgggcccg    720
cgcgtgggcg cgtgaaccc gctggaaggc ggcaccccgcg gcgcgccggg cggcggcttt    780
gtgccgagca tgcagggcgt gccggaaagc ccgtttgcgc gcaccggcga aggcctggat    840
gtgcgcggca accagggctt ccgtgggat attctgtttc ggcggatcc gccgtttagc    900
ccgcagagct gccgcccgca gagccgcagc gaaagcaaaa aaaccgcgg cggccgcgaa    960
gaagtgctgg aacagtgggt gaacggccgc aaaaaactgg aagaactgga acgcgaactg   1020
cgccgcgcgc gcaaaaaat taaaaaactg gaagatgata cccgtggct gggcaacgtg    1080
aaaggcattc tgggcaaaaa agataaagat ggcgaaggcg cgccgccggc gaaacgcgcg   1140
cgcaccgatc agatggaaat tgatagcggc ccgcgcaaac gcccgctgcg cggcggcttt   1200
accgatcgcg aacgccagga tcatcgccgc cgcaaagcgc tgaaaacaa aaaaaaacag   1260
ctgagcgcgg gcggcaaaag cctgagcaaa gaagaagaag aagaactgaa acgcctgacc   1320
```

```
cgcgaagatg aagaacgcaa aaaagaagaa catggcccga gccgcctggg cgtgaacccg    1380
agcgaaggcg gcccgcgcgg cgcgccgggc ggcggctttg tgccgagcat gcagggcatt    1440
ccggaaagcc gctttacccg caccggcgaa ggcctggatg tgcgcggcag ccgcggcttt    1500
ccgcaggata ttctgtttcc gagcgatccg ccgtttagcc gcagagctg ccgcccgcag     1560 ggaagcggag ctactaactt cagcctgctg aagcaggctg agacgtgga ggagaaccct     1620 ggacctatgg gcaccaacct gagcaccagc aacccgctgg gcttttttcc ggatcatcag    1680
ctggatccgg cgtttcgcgc gaacagcgcg aacccggatt gggattttaa cccgaacaaa    1740
gatacctggc cggatgcgaa caaagtgggc ggccagaacc tgagcaccag caacccgctg    1800
ggcttttttc cggatcatca gctggatccg gcgtttcgcg cgaacaccgc gaacccggat    1860 tgggattttta acccgaacaa agatacctgg ccggatgcga acaaagtggg cagccagagc    1920
gaaacccgcc gcggccgccg cggcacccgc gaagaaaccc tggaaaaatg gattaccgcg    1980
cgcaaaaaag cggaagaact ggaaaaagat ctgcgcaaaa cccgcaaaac cattaaaaaa    2040
ctggaagaag aaaacccgtg gctgggcaac attgtgggca ttattcgcaa aggcaaagat    2100
ggcgaaggcg cgccgccggc gaaacgcccg cgcaccgatc agatggaagt ggatagcggc    2160
ccgggcaaac gcccgcataa aagcggcttt accgataaag aacgcgaaga tcatcgccgc    2220
cgcaaagcgc tggaaaacaa aaaaaaacag ctgagcgcgg cggcaaaaat tctgagcaaa    2280
gaagaagaag aagaactgcg ccgcctgacc gatgaagatg aagaacgcaa acgccgcgtg    2340
gcgggcccgc gcgtgggcga tgtgaacccg agccgcggcg gcccgcgcgg cgcgccgggc    2400
ggcggctttg tgccgcagat ggcgggcgtg ccggaaagcc cgtttagccg caccggcgaa    2460
ggcctggata ttcgcggcac ccagggctttt ccgtgggtga gcccgagccc gccgcagcag    2520
cgcctgccgc tgctggaatg caccccgcag agccagagcg aaagcaaaaa aaaccgccgc    2580
ggcggccgcg aagatattct ggaaaaatgg attaccaccc gccgcaaagc ggaagaactg    2640 gaaaagatc tgcgcaaagc gcgcaaaacc attaaaaaac tggaagatga aaacccgtgg    2700
ctgggcaaca ttattggcat tattcgcaaa ggcaaagatg gcgaaggcgc gccgccggcg    2760
aaacgcccgc gcaccgatca gatggaaatt gatagcggca ccggcaaacg cccgcataaa    2820
agcggcttta ccgataaaga acgcgaagat catcgccgcc gcaaagcgct ggaaaacaaa    2880
aaaaaacagc tgagcagcgg cggcaaaaac ctgagccgcg aagaagaaga gaactgggc     2940 cgcctgaccg tggaagatga agaacgccgc cgccgcgtgg cgggcccgcg caccggcgat    3000
gtgaacctga gcgcggcgg cccgcgcggc gcgccgggcg gcggctttgt gccgcgcatg    3060
gaaggcgtgc cggaaagccc gtttacccgc accggcgaag gcctggatat tcgcggcaac    3120
cagggctttc cgtgggtgcg cccgagcccg ccgcagcagc gcctgccgct gctggaatgc    3180
acccccgcag                                                          3189
```

<210> SEQ ID NO 16
<211> LENGTH: 3221
<212> TYPE: DNA
<213> ORGANISM: Artificial Sequence
<220> FEATURE:
<223> OTHER INFORMATION: Delta 2 wt with restriction sites (HindIII / EcoRI)

<400> SEQUENCE: 16

```
aagcttgcac catggccggc accaacctga gcaccagcaa cccgctgggc ttttttccgg     60
atcatcagct ggatccggcg tttcgcgcga acagcgcgaa cccggattgg gattttaacc    120
```

-continued

```
cgaacaaaga tacctggccg gatgcgaaca aagtgggcgg ccagaacctg agcaccagca      180
acccgctggg cttttttccg gatcatcagc tggatccggc gtttcgcgcg aacaccgcga      240
acccggattg ggattttaac ccgaacaaag atacctggcc ggatgcgaac aaagtgggca      300
gccgcagcga aagcaaaaaa aaccgcgcg gccgcgaaga aattctggaa cagtgggtgg       360
gcgcgcgcaa aaaactggaa gaactggaac gcgatctgcg caaaattaaa aaaaaaatta     420
aaaaactgga agaagaaaac ccgtggctgg caacattaa aggcattctg gcaaaaaag       480 atcgcgaagg cgaaggcgcg ccgccggcga aacgcgcgcg cgcggatcag atggaagtgg     540
atagcggccc gcgcaaacgc ccgtttcgcg gcgaatttac cgataaagaa cgccgcgatc    600
atcgccgccg caaagcgctg gaaaacaaac gcaaacagct gagcagcggc ggcaaaagcc    660
tgagcaaaga gaagaagaa gaactgcgca aactgaccga gaagatgaa cgccgcgaac       720 gccgcgtggc gggcccgcgc gtgggcggcg tgaacccgct ggaaggcggc acccgcggcg     780
cgccggggcg cggctttgtg ccgagcatgc agggcgtgcc ggaaagcccg tttgcgcgca     840
ccggcgaagg cctggatgtg cgcggcaacc agggctttcc gtgggatatt ctgtttccgg      900
cggatccgcc gtttagcccg cagagctgcc gcccgcagag ccgcagcgaa agcaaaaaaa    960
accgcggcgg ccgcgaagaa gtgctggaac agtgggtgaa cggccgcaaa aaactggaag   1020
aactggaacg cgaactgcgc cgcgcgcgca aaaaaattaa aaaactggaa gatgataacc    1080
cgtggctggg caacgtgaaa ggcattctgg gcaaaaaaga taaagatggc gaaggcgcgc    1140
cgccggcgaa acgcgcgcgc accgatcaga tggaaattga tagcggcccg cgcaaacgcc    1200
cgctgcgcgg cggctttacc gatcgcgaac gccaggatca tcgccgccgc aaagcgctga     1260
aaaacaaaaa aaaacagctg agcgcgggcg gcaaaagcct gagcaaagaa gaagaagaag    1320
aactgaaacg cctgacccgc gaagatgaag aacgcaaaaa agaagaacat ggcccgagcc    1380
gcctgggcgt gaacccgagc gaaggcgcc cgcgcggcgc gccgggcggc ggctttgtgc     1440
cgagcatgca gggcattccg gaaagccgct ttacccgcac cggcgaaggc ctggatgtgc    1500
gcggcagccg cggctttccg caggatattc tgtttccgag cgatccgccg tttagcccgc    1560
agagctgccg cccgcaggga agcggagcta ctaacttcag cctgctgaag caggctggag    1620
acgtggagga gaaccctgga cctatgggca ccaacctgag caccagcaac ccgctgggct    1680 ttttttccgga tcatcagctg gatccggcgt ttcgcgcgaa cagcgcgaac ccggattggg    1740
attttaaccc gaacaaagat acctggccgg atgcgaacaa agtgggcggc cagaacctga    1800
gcaccagcaa cccgctgggc ttttttccgg atcatcagct ggatccggcg tttcgcgcga    1860
acaccgcgaa cccggattgg gattttaacc cgaacaaaga tacctggccg gatgcgaaca    1920
aagtgggcag ccagagcgaa acccgccgcg ccgccgcgg cacccgcgaa gaaaccctgg     1980
aaaaatggat taccgcgcgc aaaaaagcgg aagaactgga aaaagatctg cgcaaaaccc    2040
gcaaaaccat taaaaaactg gaagaagaaa cccgtggct gggcaacatt gtgggcatta    2100
ttcgcaaagg caaagatggc gaaggcgcgc cgccggcgaa acgcccgcgc accgatcaga    2160
tggaagtgga tagcggcccg ggcaaacgcc cgcataaaag cggctttacc gataaagaac    2220
gcgaagatca tcgccgccgc aaagcgctgg aaaacaaaaa aaaacagctg agcgcgggcg    2280
gcaaaattct gagcaaagaa gaagaagaag aactgcgccg cctgaccgat gaagatgaag    2340
aacgcaaacg ccgcgtggcg ggcccgcgcg tgggcgatgt gaacccgagc gcggcggcc    2400 cgcgcggcgc gccgggcggc ggctttgtgc cgcagatggc gggcgtgccg gaaagcccgt    2460
```

```
ttagccgcac cggcgaaggc ctggatattc gcggcaccca gggctttccg tgggtgagcc    2520
cgagcccgcc gcagcagcgc ctgccgctgc tggaatgcac cccgcagagc cagagcgaaa    2580
gcaaaaaaaa ccgccgcggc ggccgcgaag atattctgga aaaatggatt accacccgcc    2640
gcaaagcgga agaactggaa aaagatctgc gcaaagcgcg caaaaccatt aaaaaactgg    2700
aagatgaaaa cccgtggctg ggcaacatta ttggcattat tcgcaaaggc aaagatggcg    2760
aaggcgcgcc gccggcgaaa cgcccgcgca ccgatcagat ggaaattgat agcggcaccg    2820
gcaaacgccc gcataaaagc ggcttttaccg ataaagaacg cgaagatcat cgccgccgca    2880
aagcgctgga aaacaaaaaa aaacagctga gcagcggcgg caaaaacctg agccgcgaag    2940
aagaagaaga actgggccgc ctgaccgtgg aagatgaaga acgccgccgc cgcgtggcgg    3000
gcccgcgcac cggcgatgtg aacctgagcg gcggcggccc gcgcggcgcg ccggcggcg     3060
gctttgtgcc gcgcatggaa ggcgtgccgg aaagcccgtt tacccgcacc ggcgaaggcc    3120
tggatattcg cggcaaccag ggctttccgt gggtgcgccc gagcccgccg cagcagcgcc    3180
tgccgctgct ggaatgcacc ccgcagtgat gagaattccg t                        3221

<210> SEQ ID NO 17
<211> LENGTH: 3192
<212> TYPE: DNA
<213> ORGANISM: Artificial Sequence
<220> FEATURE:
<223> OTHER INFORMATION: Delta 2 optimized

<400> SEQUENCE: 17
gccggcacta acctgtctac atcaaaccct ctgggatttt tccccgatca tcagctggac      60
cccgcatttc gcgctaactc tgctaaccct gactgggatt tcaaccctaa taaggacaca     120
tggccagatg ccaacaaggt cggcggccag aacctgtcca cctctaatcc cctgggcttc     180
tttcctgacc accagctgga tcctgccttc agggccaaca ccgccaatcc cgactgggac     240
ttcaacccaa ataaggatac ctggcctgac gctaacaagg tcggcagccg gtccgagtct     300
aagaagaata ggggaggaag ggaggagatc ctggagcagt gggtgggcgc cagaaagaag     360
ctggaggagc tggagcggga cctgagaaag atcaagaaga gatcaagaa gctggaggag      420
gagaaccct ggctgggcaa tatcaagggc atcctgggca agaaggatcg ggagggagag      480
ggagcaccac ctgcaaagag ggccagagcc gaccagatgg aggtggattc cggccctagg     540
aagcgcccat tcagaggcga gtttacagac aaggagcgga gagatcacag cgccggaag      600
gcccctggaga acaagaggaa gcagctgagc tccggcggca agagcctgtc caaggaggag     660
gaggaggagc tgcgcaagct gaccgaggag gacgagagaa gggagaggag ggtggcagga     720
cctagggtgg gaggcgtgaa cccactggag ggaggaacaa gaggagcacc cggaggaggc     780
ttcgtgcctt ctatgcaggg cgtgcctgag agcccatttg ccaggaccgg agagggcctg     840
gacgtgagag gcaatcaggg cttcccatgg gacatcctgt ttcccgccga tccaccttc      900
agcccacagt cctgcaggcc ccagtctcgc agcgagtcca agaagaacag aggcggaagg     960
gaggaggtgc tggagcagtg ggtgaatggc aggaagaagc tggaagaact ggagagggag    1020
ctgagaaggg cccgcaagaa gatcaagaag ctggaagacg ataatccttg ctgggcaat    1080
gtgaaaggca tcctgggcaa aaggacaag gatggagagg gagcacctcc agcaaagagg    1140
gcaagaacag accagatgga gatcgattcc ggaccaagga agcgccctct gaggggaggc    1200
ttcaccgacc gggagagaca ggatcaccgc cggagaaagg ccctgaagaa caagaagaag    1260
cagctgagcg ccggcggcaa gtctctgagt aaagaagaag aggaggagct gaagcggctg    1320
```

```
acaagagagg acgaggagag gaagaaggag gagcacggac catccaggct gggagtgaat    1380
ccttctgagg gaggaccaag gggcgcccct ggcggaggct tcgtgcctag catgcagggc    1440
atcccagagt ccaggtttac caggacaggc gaaggcctgg acgtgcgggg ctctagaggc    1500
tttccccagg acatcctgtt ccctagcgat ccccctttt ctcctcagag ctgtagacca    1560
cagggaagcg gagctactaa cttcagcctg ctgaagcagg ctggagacgt ggaggagaac    1620
cctggaccta tgggcaccaa cctgtccaca tctaaccctc tgggcttctt tccagatcat    1680
cagctggacc cagccttcag ggccaacagc gccaatccag actgggactt caaccccaat    1740
aaggacacat ggcctgacgc aaacaaggtc ggaggacaga acctgagcac ctccaatcca    1800
ctgggcttct ttcccgacca ccagctggat ccagccttcc gcgccaacac tgctaaccct    1860
gattgggact tcaaccctaa taaggataca tggcctgatg ccaataaggt cggctctcag    1920
agcgagacaa ggaggggccg gagaggaacc agggaggaga cactggagaa gtggatcacc    1980
gcccgcaaga aggccgagga gctggagaag gacctgagga agacccgcaa gacaatcaag    2040
aagctggaag aagagaaccc atggctgggc aatatcgtgg gcatcatcag aaagggcaag    2100
gacggcgagg gagcaccacc agcaaagagg ccccgcacag atcagatgga agtggattcc    2160
ggacctggca gcggccaca caagtctggc ttcaccgaca aggagagaga ggaccatagg    2220
cgccggaagg ccctggaaaa caagaagaag caattatctg ccggcggcaa gatcctgagt    2280
aaagaagagg aagaggagct gagaaggctg accgacgagg atgaggagag gaagcgccgg    2340
gtggccggcc cacgcgtggg cgacgtgaat ccctccaggg gaggaccaag aggagcacct    2400
ggaggcggct tcgtgcccca gatggccggc gtgcccgagt ccccttttc tcggaccggc    2460
gagggcctgg atatcagagg cacacagggc tttccatggg tgtcccccctc tcctccacag    2520
cagaggctgc cactgctgga gtgcacaccc cagagccaga gcgaatctaa gaagaacaga    2580
aggggaggcc gcgaggacat cctggaaaaa tggatcacca cacgcagaaa agctgaagaa    2640
ctggaaaagg acctgcggaa ggccagaaag accatcaaga agctggagga tgaaaatcca    2700
tggctgggaa acatcatcgg catcatccgg aagggcaagg acgggaagg cgcaccacct    2760
gcaaagcggc ctagaaccga tcagatgaaa atcgatagcg gcacaggcaa gaggccacac    2820
aagtccggct tcaccgataa agagcgcgag gatcacagaa ggcgcaaggc cctggagaac    2880
aagaagaagc aattaagcag cggcggcaag aatctgtcca gagaagagga ggaagagctg    2940
ggccgcctga cagtggagga cgaggagcgg agaaggcgcg tggcaggacc cagaaccggc    3000
gatgtgaacc tgtccggagg aggacctagg ggagcaccag gaggcggctt cgtgcctaga    3060
atggagggcg tgccagagtc tccctttacc cggacaggcg agggcctgga catcagaggc    3120
aatcagggct ttccctgggt ccgccccctcc ccccctcagc agagactgcc actgctggaa    3180
tgcacaccac ag                                                       3192
```

<210> SEQ ID NO 18
<211> LENGTH: 3221
<212> TYPE: DNA
<213> ORGANISM: Artificial Sequence
<220> FEATURE:
<223> OTHER INFORMATION: Delta 2 codon optimized + Restriction sites

<400> SEQUENCE: 18

```
aagcttgcac catggccggc actaacctgt ctacatcaaa ccctctggga tttttccccg     60
atcatcagct ggacccccgca tttcgcgcta actctgctaa ccctgactgg gatttcaacc    120
```

```
ctaataagga cacatggcca gatgccaaca aggtcggcgg ccagaacctg tccacctcta    180
atccctggg cttctttcct gaccaccagc tggatcctgc cttcaggcc aacaccgcca      240
atcccgactg ggacttcaac ccaaataagg atacctggcc tgacgctaac aaggtcggca   300
gccggtccga gtctaagaag aatagggag gaagggagga gatcctggag cagtgggtgg    360
gcgccagaaa gaagctggag gagctggagc gggacctgag aaagatcaag aagaagatca   420
agaagctgga ggaggagaac ccctggctgg gcaatatcaa gggcatcctg gcaagaagg    480
atcgggaggg agagggagca ccacctgcaa agagggccag agccgaccag atggaggtgg   540
attccggccc taggaagcgc ccattcagag gcgagtttac agacaaggag cggagagatc   600
acaggcgccg gaaggccctg gagaacaaga ggaagcagct gagctccggc ggcaagagcc   660
tgtccaagga ggaggaggag gagctgcgca agctgaccga ggaggacgag agaagggaga   720
ggagggtggc aggacctagg gtgggaggcg tgaacccact ggagggagga acaagaggag   780
cacccggagg aggcttcgtg ccttctatgc agggcgtgcc tgagagccca tttgccagga   840
ccggagaggg cctggacgtg agaggcaatc agggcttccc atgggacatc ctgtttcccg   900
ccgatccacc cttcagccca cagtcctgca ggccccagtc tcgcagcgag tccaagaaga   960
acagaggcgg aagggaggag gtgctggagc agtgggtgaa tggcaggaag aagctggaag  1020
aactggagag ggagctgaga agggcccgca gaagatcaa gaagctggaa gacgataatc    1080
cttggctggg caatgtgaaa ggcatcctgg gcaagaagga caaggatgga gagggagcac   1140
ctccagcaaa gagggcaaga acagaccaga tggagatcga ttccggacca aggaagcgcc   1200
ctctgagggg aggcttcacc gaccgggaga gacaggatca ccgccggaga aaggccctga   1260
agaacaagaa gaagcagctg agcgccggcg gcaagtctct gagtaaagaa gaagaggagg   1320
agctgaagcg gctgacaaga gaggacgagg agaggaagaa ggaggagcac ggaccatcca   1380
ggctgggagt gaatccttct gagggaggac caagggcgc ccctggcgga ggcttcgtgc    1440
ctagcatgca gggcatccca gagtccaggt ttaccaggac aggcgaaggc ctggacgtgc   1500
ggggctctag aggctttccc caggacatcc tgttccctag cgatccccct ttttctcctc   1560
agagctgtag accacaggga agcggagcta ctaacttcag cctgctgaag caggctggag   1620
acgtggagga gaaccctgga cctatgggca ccaacctgtc cacatctaac cctctgggct   1680
tcttccaga tcatcagctg gacccagcct cagggccaa cagcgccaat ccagactggg     1740
acttcaaccc caataaggac acatggcctg acgcaaacaa ggtcggagga cagaacctga   1800
gcacctccaa tccactgggc ttctttcccg accaccagct ggatccagcc ttccgcgcca   1860
acactgctaa ccctgattgg gacttcaacc ctaataagga tacatggcct gatgccaata   1920
aggtcggctc tcagagcgag acaaggaggg gccggagagg aaccaggag gagacactgg    1980
agaagtggat caccgcccgc aagaaggccg aggagctgga gaaggacctg aggaagaccc   2040
gcaagacaat caagaagctg gaagaagaga accatggct gggcaatatc gtgggcatca   2100
tcagaaaggg caaggacggc gagggagcac caccagcaaa gaggccccgc acagatcaga   2160
tggaagtgga ttccggacct ggcaagcggc cacacaagtc tggcttcacc gacaaggaga   2220
gagaggacca taggcgccgg aaggccctgg aaaacaagaa gaagcaatta tctgccggcg   2280
gcaagatcct gagtaaagaa gaggaagagg agctgagaag gctgaccgac gaggatgagg   2340
agaggaagcg ccgggtggcc ggcccacgcg tgggcgacgt gaatccctcc aggggaggac   2400
caagaggagc acctggaggc ggcttcgtgc cccagatgcc cggcgtgccc gagtcccctt   2460
tttctcggac cggcgaggc ctggatatca gaggcacaca gggctttcca tgggtgtccc   2520
```

-continued

```
cctctcctcc acagcagagg ctgccactgc tggagtgcac accccagagc cagagcgaat    2580
ctaagaagaa cagaagggga ggccgcgagg acatcctgga aaaatggatc accacacgca    2640
gaaaagctga agaactggaa aaggacctgc ggaaggccag aaagaccatc aagaagctgg    2700
aggatgaaaa tccatggctg gaaacatca tcggcatcat ccggaagggc aaggacgggg     2760
aaggcgcacc acctgcaaag cggcctagaa ccgatcagat ggaaatcgat agcggcacag    2820
gcaagaggcc acacaagtcc ggcttcaccg ataaagagcg cgaggatcac agaaggcgca    2880
aggccctgga gaacaagaag aagcaattaa gcagcggcgg caagaatctg tccagagaag    2940
aggaggaaga gctgggccgc ctgacagtgg aggacgagga gcggagaagg cgcgtggcag    3000
gacccagaac cggcgatgtg aacctgtccg gaggaggacc tagggagca ccaggaggcg     3060 gcttcgtgcc tagaatggag ggcgtgccag agtctccctt tacccggaca ggcgagggcc    3120
tggacatcag aggcaatcag ggctttccct gggtccgccc ctccccccct cagcagagac    3180
tgccactgct ggaatgcaca ccacagtgat gagaattccg t                        3221
```

<210> SEQ ID NO 19
<211> LENGTH: 1065
<212> TYPE: PRT
<213> ORGANISM: Artificial Sequence
<220> FEATURE:
<223> OTHER INFORMATION: Delta 2 protein

<400> SEQUENCE: 19

```
Met Ala Gly Thr Asn Leu Ser Thr Ser Asn Pro Leu Gly Phe Phe Pro
1               5                   10                  15

Asp His Gln Leu Asp Pro Ala Phe Arg Ala Asn Ser Ala Asn Pro Asp
            20                  25                  30

Trp Asp Phe Asn Pro Asn Lys Asp Thr Trp Pro Asp Ala Asn Lys Val
        35                  40                  45

Gly Gly Gln Asn Leu Ser Thr Ser Asn Pro Leu Gly Phe Phe Pro Asp
    50                  55                  60

His Gln Leu Asp Pro Ala Phe Arg Ala Asn Thr Ala Asn Pro Asp Trp
65                  70                  75                  80

Asp Phe Asn Pro Asn Lys Asp Thr Trp Pro Asp Ala Asn Lys Val Gly
                85                  90                  95

Ser Arg Ser Glu Ser Lys Lys Asn Arg Gly Gly Arg Glu Glu Ile Leu
            100                 105                 110

Glu Gln Trp Val Gly Ala Arg Lys Lys Leu Glu Glu Leu Glu Arg Asp
        115                 120                 125

Leu Arg Lys Ile Lys Lys Lys Ile Lys Lys Leu Glu Glu Asn Pro
    130                 135                 140

Trp Leu Gly Asn Ile Lys Gly Ile Leu Gly Lys Lys Asp Arg Glu Gly
145                 150                 155                 160

Glu Gly Ala Pro Pro Ala Lys Arg Ala Arg Ala Asp Gln Met Glu Val
                165                 170                 175

Asp Ser Gly Pro Arg Lys Arg Pro Phe Arg Gly Glu Phe Thr Asp Lys
            180                 185                 190

Glu Arg Arg Asp His Arg Arg Lys Ala Leu Glu Asn Lys Arg Lys
        195                 200                 205

Gln Leu Ser Ser Gly Gly Lys Ser Leu Ser Lys Glu Glu Glu Glu Glu
    210                 215                 220

Leu Arg Lys Leu Thr Glu Glu Asp Glu Arg Arg Glu Arg Arg Val Ala
225                 230                 235                 240
```

```
Gly Pro Arg Val Gly Val Asn Pro Leu Glu Gly Thr Arg Gly
            245                 250                 255

Ala Pro Gly Gly Gly Phe Val Pro Ser Met Gln Gly Val Pro Glu Ser
        260                 265                 270

Pro Phe Ala Arg Thr Gly Glu Gly Leu Asp Val Arg Gly Asn Gln Gly
            275                 280                 285

Phe Pro Trp Asp Ile Leu Phe Pro Ala Asp Pro Pro Phe Ser Pro Gln
290                 295                 300

Ser Cys Arg Pro Gln Ser Arg Ser Glu Ser Lys Lys Asn Arg Gly Gly
305                 310                 315                 320

Arg Glu Glu Val Leu Glu Gln Trp Val Asn Gly Arg Lys Lys Leu Glu
                325                 330                 335

Glu Leu Glu Arg Glu Leu Arg Arg Ala Arg Lys Lys Ile Lys Lys Leu
                340                 345                 350

Glu Asp Asp Asn Pro Trp Leu Gly Asn Val Lys Gly Ile Leu Gly Lys
            355                 360                 365

Lys Asp Lys Asp Gly Glu Gly Ala Pro Pro Ala Lys Arg Ala Arg Thr
            370                 375                 380

Asp Gln Met Glu Ile Asp Ser Gly Pro Arg Lys Arg Pro Leu Arg Gly
385                 390                 395                 400

Gly Phe Thr Asp Arg Glu Arg Gln Asp His Arg Arg Lys Ala Leu
                405                 410                 415

Lys Asn Lys Lys Lys Gln Leu Ser Ala Gly Gly Lys Ser Leu Ser Lys
                420                 425                 430

Glu Glu Glu Glu Leu Lys Arg Leu Thr Arg Glu Asp Glu Glu Arg
            435                 440                 445

Lys Lys Glu Glu His Gly Pro Ser Arg Leu Gly Val Asn Pro Ser Glu
        450                 455                 460

Gly Gly Pro Arg Gly Ala Pro Gly Gly Phe Val Pro Ser Met Gln
465                 470                 475                 480

Gly Ile Pro Glu Ser Arg Phe Thr Arg Thr Gly Glu Gly Leu Asp Val
                485                 490                 495

Arg Gly Ser Arg Gly Phe Pro Gln Asp Ile Leu Phe Pro Ser Asp Pro
            500                 505                 510

Pro Phe Ser Pro Gln Ser Cys Arg Pro Gln Gly Ser Gly Ala Thr Asn
            515                 520                 525

Phe Ser Leu Leu Lys Gln Ala Gly Asp Val Glu Glu Asn Pro Gly Pro
        530                 535                 540

Met Gly Thr Asn Leu Ser Thr Ser Asn Pro Leu Gly Phe Phe Pro Asp
545                 550                 555                 560

His Gln Leu Asp Pro Ala Phe Arg Ala Asn Ser Ala Asn Pro Asp Trp
            565                 570                 575

Asp Phe Asn Pro Asn Lys Asp Thr Trp Pro Asp Ala Asn Lys Val Gly
            580                 585                 590

Gly Gln Asn Leu Ser Thr Ser Asn Pro Leu Gly Phe Phe Pro Asp His
                595                 600                 605

Gln Leu Asp Pro Ala Phe Arg Ala Asn Thr Ala Asn Pro Asp Trp Asp
            610                 615                 620

Phe Asn Pro Asn Lys Asp Thr Trp Pro Asp Ala Asn Lys Val Gly Ser
625                 630                 635                 640

Gln Ser Glu Thr Arg Arg Gly Arg Arg Gly Thr Arg Glu Glu Thr Leu
                645                 650                 655
```

```
Glu Lys Trp Ile Thr Ala Arg Lys Ala Glu Leu Glu Lys Asp
            660                 665                 670

Leu Arg Lys Thr Arg Lys Thr Ile Lys Lys Leu Glu Glu Asn Pro
            675                 680                 685

Trp Leu Gly Asn Ile Val Gly Ile Ile Arg Lys Gly Lys Asp Gly Glu
            690                 695                 700

Gly Ala Pro Pro Ala Lys Arg Pro Arg Thr Asp Gln Met Glu Val Asp
705                 710                 715                 720

Ser Gly Pro Gly Lys Arg Pro His Lys Ser Gly Phe Thr Asp Lys Glu
                725                 730                 735

Arg Glu Asp His Arg Arg Lys Ala Leu Glu Asn Lys Lys Lys Gln
            740                 745                 750

Leu Ser Ala Gly Gly Lys Ile Leu Ser Lys Glu Glu Glu Glu Leu
            755                 760                 765

Arg Arg Leu Thr Asp Glu Asp Glu Glu Arg Lys Arg Arg Val Ala Gly
            770                 775                 780

Pro Arg Val Gly Asp Val Asn Pro Ser Arg Gly Gly Pro Arg Gly Ala
785                 790                 795                 800

Pro Gly Gly Gly Phe Val Pro Gln Met Ala Gly Val Pro Glu Ser Pro
                805                 810                 815

Phe Ser Arg Thr Gly Glu Gly Leu Asp Ile Arg Gly Thr Gln Gly Phe
                820                 825                 830

Pro Trp Val Ser Pro Ser Pro Gln Gln Arg Leu Pro Leu Leu Glu
            835                 840                 845

Cys Thr Pro Gln Ser Gln Ser Glu Ser Lys Lys Asn Arg Arg Gly Gly
850                 855                 860

Arg Glu Asp Ile Leu Glu Lys Trp Ile Thr Thr Arg Arg Lys Ala Glu
865                 870                 875                 880

Glu Leu Glu Lys Asp Leu Arg Lys Ala Arg Lys Thr Ile Lys Lys Leu
                885                 890                 895

Glu Asp Glu Asn Pro Trp Leu Gly Asn Ile Ile Gly Ile Ile Arg Lys
                900                 905                 910

Gly Lys Asp Gly Glu Gly Ala Pro Pro Ala Lys Arg Pro Arg Thr Asp
            915                 920                 925

Gln Met Glu Ile Asp Ser Gly Thr Gly Lys Arg Pro His Lys Ser Gly
930                 935                 940

Phe Thr Asp Lys Glu Arg Glu Asp His Arg Arg Lys Ala Leu Glu
945                 950                 955                 960

Asn Lys Lys Lys Gln Leu Ser Ser Gly Lys Asn Leu Ser Arg Glu
            965                 970                 975

Glu Glu Glu Glu Leu Gly Arg Leu Thr Val Glu Asp Glu Glu Arg Arg
                980                 985                 990

Arg Arg Val Ala Gly Pro Arg Thr Gly Asp Val Asn Leu Ser Gly Gly
            995                 1000                1005

Gly Pro Arg Gly Ala Pro Gly Gly Phe Val Pro Arg Met Glu Gly
            1010                1015                1020

Val Pro Glu Ser Pro Phe Thr Arg Thr Gly Glu Gly Leu Asp Ile Arg
1025                1030                1035                1040

Gly Asn Gln Gly Phe Pro Trp Val Arg Pro Ser Pro Gln Gln Arg
            1045                1050                1055

Leu Pro Leu Leu Glu Cys Thr Pro Gln
            1060                1065
```

```
<210> SEQ ID NO 20
<211> LENGTH: 3753
<212> TYPE: DNA
<213> ORGANISM: Artificial Sequence
<220> FEATURE:
<223> OTHER INFORMATION: Delta 3 wt

<400> SEQUENCE: 20
```

| | | | | |
|---|---|---|---|---|
| ggcaccaacc | tgagcaccag | caacccgctg | gcttttttc | cggatcatca | gctggatccg | 60 |
| gcgtttcgcg | cgaacagcgc | gaacccggat | tgggatttta | acccgaacaa | agatacctgg | 120 |
| ccggatgcga | acaaagtggg | cggccagaac | ctgagcacca | gcaacccgct | gggctttttt | 180 |
| ccggatcatc | agctggatcc | ggcgtttcgc | gcgaacaccg | cgaacccgga | ttgggatttt | 240 |
| aacccgaaca | aagatacctg | ccggatgcg | aacaaagtgg | gcagccgcag | cgaaagcaaa | 300 |
| aaaaaccgcg | cgcgccgcga | agaaattctg | aacagtgggt | gggcgcgcg | caaaaaactg | 360 |
| gaagaactgg | aacgcgatct | gcgcaaaatt | aaaaaaaaaa | ttaaaaaact | ggaagaagaa | 420 |
| aacccgtggc | tgggcaacat | taaaggcatt | ctgggcaaaa | aagatcgcga | aggcgaaggc | 480 |
| gcgccgccgg | cgaaacgcgc | gcgcgcggat | cagatggaag | tggatagcgg | cccgcgcaaa | 540 |
| cgcccgtttc | gcggcgaatt | taccgataaa | gaacgccgcg | atcatcgccg | ccgcaaagcg | 600 |
| ctggaaaaca | aacgcaaaca | gctgagcagc | ggcggcaaaa | gcctgagcaa | agaagaagaa | 660 |
| gaagaactgc | gcaaactgac | cgaagaagat | gaacgccgcg | aacgccgcgt | ggcgggcccg | 720 |
| cgcgtgggcg | gcgtgaaccc | gctggaaggc | ggcacccgcg | gcgcgccggg | cggcggcttt | 780 |
| gtgccgagca | tgcagggcgt | gccggaaagc | ccgtttgcgc | gcaccggcga | aggcctggat | 840 |
| gtgcgcggca | accagggctt | tccgtgggat | attctgtttc | cggcggatcc | gccgtttagc | 900 |
| ccgcagagct | gccgcccgca | gagccgcagc | gaaagcaaaa | aaaaccgcgg | cggccgcgaa | 960 |
| gaagtgctgg | aacagtgggt | gaacggccgc | aaaaaactgg | aagaactgga | acgcgaactg | 1020 |
| cgccgcgcgc | gcaaaaaaat | taaaaaactg | gaagatgata | accgtggct | gggcaacgtg | 1080 |
| aaaggcattc | tgggcaaaaa | agataaagat | ggcgaaggcg | cgccgccggc | gaaacgcgcg | 1140 |
| cgcaccgatc | agatggaaat | tgatagcggc | ccgcgcaaac | gcccgctgcg | cggcggcttt | 1200 |
| accgatcgcg | aacgccagga | tcatcgccgc | cgcaaagcgc | tgaaaaacaa | aaaaaaacag | 1260 |
| ctgagcgcgg | gcggcaaaag | cctgagcaaa | gaagaagaag | aagaactgaa | acgcctgacc | 1320 |
| cgcgaagatg | aagaacgcaa | aaagaagaa | catggcccga | ccgcctgggg | cgtgaacccg | 1380 |
| agcgaaggcg | gcccgcgcgg | cgcgccgggc | ggcggctttg | tgccgagcat | gcagggcatt | 1440 |
| ccggaaagcc | gctttacccg | caccggcgaa | ggcctggatg | tgcgcggcag | ccgcggcttt | 1500 |
| ccgcaggata | ttctgtttcc | gagcgatccg | ccgtttagcc | cgcagagctg | ccgcccgcag | 1560 |
| ggcaccaacc | tgagcaccag | caacccgctg | gcttttttc | cggatcatca | gctggatccg | 1620 |
| gcgtttcgcg | cgaacagcgc | gaacccggat | tgggatttta | acccgaacaa | agatacctgg | 1680 |
| ccggatgcga | acaaagtggg | cggccagaac | ctgagcacca | gcaacccgct | gggctttttt | 1740 |
| ccggatcatc | agctggatcc | ggcgtttcgc | gcgaacaccg | cgaacccgga | ttgggatttt | 1800 |
| aacccgaaca | aagatacctg | ccggatgcg | aacaaagtgg | gcggaagcgg | agctactaac | 1860 |
| ttcagcctgc | tgaagcaggc | tggagacgtg | gaggagaacc | ctggacctat | gggcaccaac | 1920 |
| ctgagcacca | gcaacccgct | gggctttttt | ccggatcatc | agctggatcc | ggcgtttcgc | 1980 |
| gcgaacagcg | cgaacccgga | ttgggatttt | aacccgaaca | aagatacctg | gccggatgcg | 2040 |
| aacaaagtgg | gcggccagaa | cctgagcacc | agcaacccgc | tgggcttttt | tccggatcat | 2100 |

| | |
|---|---|
| cagctggatc cggcgtttcg cgcgaacacc gcgaacccgg attgggattt taacccgaac | 2160 |
| aaagatacct ggccggatgc gaacaaagtg ggcagccaga gcgaaacccg ccgcggccgc | 2220 |
| cgcggcaccc gcgaagaaac cctggaaaaa tggattaccg cgcgcaaaaa agcggaagaa | 2280 |
| ctggaaaaag atctgcgcaa aacccgcaaa accattaaaa aactggaaga agaaaacccg | 2340 |
| tggctgggca acattgtggg cattattcgc aaaggcaaag atggcgaagg cgcgccgccg | 2400 |
| gcgaaacgcc cgcgcaccga tcagatgaaa gtggatagcg gcccgggcaa acgcccgcat | 2460 |
| aaaagcggct ttaccgataa agaacgcgaa gatcatcgcc gccgcaaagc gctggaaaac | 2520 |
| aaaaaaaaac agctgagcgc gggcggcaaa attctgagca agaagaagaa agaagaactg | 2580 |
| cgccgcctga ccgatgaaga tgaagaacgc aaacgccgcg tggcgggccc gcgcgtgggc | 2640 |
| gatgtgaacc cgagccgcgg cggcccgcgc ggcgcgccgg gcggcggctt tgtgccgcag | 2700 |
| atggcgggcg tgccggaaag cccgtttagc cgcaccggcg aaggcctgga tattcgcggc | 2760 |
| acccagggct ttccgtgggt gagcccgagc ccgccgcagc agcgcctgcc gctgctggaa | 2820 |
| tgcaccccgc agagccagag cgaaagcaaa aaaaaccgcc gcggcggccg cgaagatatt | 2880 |
| ctggaaaaat ggattaccac ccgccgcaaa gcggaagaac tggaaaaaga tctgcgcaaa | 2940 |
| gcgcgcaaaa ccattaaaaa actggaagat gaaacccgt ggctgggcaa cattattggc | 3000 |
| attattcgca aaggcaaaga tggcgaaggc gcgccgccgg cgaaacgccc gcgcaccgat | 3060 |
| cagatgaaa ttgatagcgg caccggcaaa cgcccgcata aaagcggctt taccgataaa | 3120 |
| gaacgcgaag atcatcgccg ccgcaaagcg ctggaaaaca aaaaaaaaca gctgagcagc | 3180 |
| ggcggcaaaa acctgagccg cgaagaagaa gaagaactgg ccgcctgac cgtggaagat | 3240 |
| gaagaacgcc gccgccgcgt ggcgggcccg cgcaccggcg atgtgaacct gagcggcggc | 3300 |
| ggcccgcgcg gcgcgccggg cggcggcttt gtgccgcgca tggaaggcgt gccggaaagc | 3360 |
| ccgtttaccc gcaccggcga aggcctggat attcgcggca ccagggcttt ccgtgggtg | 3420 |
| cgcccgagcc cgccgcagca gcgcctgccg ctgctggaat gcaccccgca gggcaccaac | 3480 |
| ctgagcacca gcaacccgct gggcttttttt ccggatcatc agctggatcc ggcgtttcgc | 3540 |
| gcgaacagcg cgaacccgga ttgggatttt aacccgaaca aagataccctg gccggatgcg | 3600 |
| aacaaagtgg gcggccagaa cctgagcacc agcaacccgc tgggcttttt tccggatcat | 3660 |
| cagctggatc cggcgtttcg cgcgaacacc gcgaacccgg attgggattt taacccgaac | 3720 |
| aaagatacct ggccggatgc gaacaaagtg ggc | 3753 |

<210> SEQ ID NO 21
<211> LENGTH: 3785
<212> TYPE: DNA
<213> ORGANISM: Artificial Sequence
<220> FEATURE:
<223> OTHER INFORMATION: Delta 3 wt + with restriction sites (HindIII /EcoRI)

<400> SEQUENCE: 21

| | |
|---|---|
| aagcttgcac catggccggc accaacctga gcaccagcaa cccgctgggc ttttttccgg | 60 |
| atcatcagct ggatccggcg tttcgcgcga acagcgcgaa cccggattgg gattttaacc | 120 |
| cgaacaaaga tacctggccg gatgcgaaca aagtgggcgg ccagaacctg agcaccagca | 180 |
| acccgctggg cttttttccg gatcatcagc tggatccggc gtttcgcgcg aacaccgcga | 240 |
| acccggattg ggattttaac ccgaacaaag atacctggcc ggatgcgaac aaagtgggca | 300 |
| gccgcagcga aagcaaaaaa aaccgcgcg gccgcgaaga aattctggaa cagtgggtgg | 360 |

-continued

```
gcgcgcgcaa aaaactggaa gaactggaac gcgatctgcg caaaattaaa aaaaaaatta      420
aaaaactgga agaagaaaac ccgtggctgg gcaacattaa aggcattctg gcaaaaaaag      480
atcgcgaagg cgaaggcgcg ccgccggcga aacgcgcgcg cgcggatcag atggaagtgg      540
atagcggccc gcgcaaacgc ccgtttcgcg gcgaatttac cgataaagaa cgccgcgatc      600
atcgccgccg caaagcgctg gaaaacaaac gcaaacagct gagcagcggc ggcaaaagcc      660
tgagcaaaga agaagaagaa gaactgcgca aactgaccga agaagatgaa cgccgcgaac      720
gccgcgtggc gggcccgcgc gtgggcggcg tgaacccgct ggaaggcggc acccgcggcg      780
cgccgggcgg cggctttgtg ccgagcatgc agggcgtgcc ggaaagcccg tttgcgcgca      840
ccggcgaagg cctggatgtg cgcggcaacc agggctttcc gtgggatatt ctgtttccgg      900
cggatccgcc gtttagcccg cagagctgcc gcccgcagag ccgcagcgaa agcaaaaaaa      960
accgcggcgg ccgcgaagaa gtgctggaac agtgggtgaa cggccgcaaa aaactggaag     1020
aactggaacg cgaactgcgc cgcgcgcgca aaaaattaa aaaactggaa gatgataacc     1080
cgtggctggg caacgtgaaa ggcattctgg gcaaaaaaga taaagatggc gaaggcgcgc     1140
cgccggcgaa acgcgcgcgc accgatcaga tggaaattga tagcggcccg cgcaaacgcc     1200
cgctgcgcgg cggcttttacc gatcgcgaac gccaggatca tcgccgccgc aaagcgctga     1260
aaaacaaaaa aaaacagctg agcgcgggcg gcaaaagcct gagcaaagaa gaagaagaag     1320
aactgaaacg cctgacccgc gaagatgaag aacgcaaaaa agaagaacat ggcccgagcc     1380 gcctggcgt gaacccgagc gaaggcggcc cgcgcggcgc gccgggcggc ggctttgtgc     1440
cgagcatgca gggcattccg gaaagccgct ttacccgcac cggcgaaggc ctggatgtgc     1500
gcggcagccg cggctttccg caggatattc tgtttccgag cgatccgccg tttagcccgc     1560
agagctgccg cccgcagggc accaacctga gcaccagcaa cccgctgggc tttttttccgg     1620 atcatcagct ggatccggcg tttcgcgcga acagcgcgaa cccggattgg gattttaacc     1680
cgaacaaaga tacctggccg gatgcgaaca aagtgggcgg ccagaacctg agcaccagca     1740
acccgctggg cttttttccg gatcatcagc tggatccggc gtttcgcgcg aacaccgcga     1800
acccggattg ggattttaac ccgaacaaag atacctggcc ggatgcgaac aaagtgggcg     1860
gaagcggagc tactaacttc agcctgctga agcaggctgg agacgtggag gagaaccctg     1920
gacctatggg caccaacctg agcaccagca acccgctggg cttttttccg gatcatcagc     1980
tggatccggc gtttcgcgcg aacagcgcga acccggattg ggattttaac ccgaacaaag     2040
atacctggcc ggatgcgaac aaagtgggcg gccagaacct gagcaccagc aacccgctgg     2100
gcttttttcc ggatcatcag ctggatccgg cgtttcgcgc gaacaccgcg aacccggatt     2160
gggattttaa cccgaacaaa gatacctggc cggatgcgaa caaagtgggc agccagagcg     2220
aaacccgccg cggccgccgc ggcacccgcg aagaaaccct ggaaaatgg attaccgcgc     2280 gcaaaaaagc ggaagaactg aaaaagatc tgcgcaaaac ccgcaaaacc attaaaaaac     2340
tggaagaaga aaacccgtgg ctgggcaaca ttgtgggcat tattcgcaaa ggcaaagatg     2400
gcgaaggcgc gccgccggcg aaacgcccgc gcaccgatca gatggaagtg gatagcggcc     2460
cgggcaaacg cccgcataaa agcggcttta ccgataaaga acgcgaagat catcgccgcc     2520
gcaaagcgct ggaaaacaaa aaaaacagct gagcgcggg cggcaaaatt ctgagcaaag     2580
aagaagaaga gaactgcgc cgcctgaccg atgaagatga agaacgcaaa cgccgcgtgg     2640
cgggcccgcg cgtgggcgat gtgaacccga gccgcgcgg cccgcgcggc gcgccgggcg     2700
gcggctttgt gccgcagatg gcgggcgtgc cggaaagccc gtttagccgc accggcgaag     2760
```

```
gcctggatat tcgcggcacc cagggctttc cgtgggtgag cccgagcccg ccgcagcagc    2820
gcctgccgct gctggaatgc accccgcaga gccagagcga agcaaaaaa aaccgccgcg    2880 gcggccgcga agatattctg gaaaaatgga ttaccacccg ccgcaaagcg aagaactgg    2940 aaaaagatct gcgcaaagcg cgcaaaacca ttaaaaaact ggaagatgaa acccgtggc    3000 tgggcaacat tattggcatt attcgcaaag gcaaagatgg cgaaggcgcg ccgccggcga    3060
aacgcccgcg caccgatcag atggaaattg atagcggcac cggcaaacgc cgcataaaa    3120 gcggctttac cgataaagaa cgcgaagatc atcgccgccg caaagcgctg aaaacaaaa    3180 aaaaacagct gagcagcggc ggcaaaaacc tgagccgcga agaagaagaa gaactgggcc    3240
gcctgaccgt ggaagatgaa aacgccgcc gccgcgtggc gggcccgcgc accggcgatg    3300
tgaacctgag cggcggcggc ccgcgcggcg cgccgggcgg cggctttgtg ccgcgcatgg    3360
aaggcgtgcc ggaaagcccg tttacccgca ccggcgaagg cctggatatt cgcggcaacc    3420
agggctttcc gtgggtgcgc ccgagcccgc cgcagcagcg cctgccgctg ctggaatgca    3480
ccccgcaggg caccaacctg agcaccagca acccgctggg cttttttccg gatcatcagc    3540
tggatccggc gtttcgcgcg aacagcgcga acccggattg ggattttaac ccgaacaaag    3600
atacctggcc ggatgcgaac aaagtgggcg ccagaacct gagcaccagc aacccgctgg    3660
gcttttttcc ggatcatcag ctggatccgg cgtttcgcgc gaacaccgcg aacccggatt    3720 gggatttta cccgaacaaa gatacctggc cggatgcgaa caaagtgggc tgatgagaat    3780
tccgt                                                               3785

<210> SEQ ID NO 22
<211> LENGTH: 3756
<212> TYPE: DNA
<213> ORGANISM: Artificial Sequence
<220> FEATURE:
<223> OTHER INFORMATION: Delta 3 optimized

<400> SEQUENCE: 22
gccggcacca atctgtctac ctcaaatccc ctgggcttct tccccgatca tcagctggac      60
cctgccttcc gagcaaattc cgctaatcct gattgggatt caacccaaa taaggacaca     120 tgccagatg ccaacaaggt cggcggccag aacctgtcca cctctaatcc tctgggcttc     180
tttccagacc accagctgga tccgcccttc agggccaaca cagccaatcc cgactgggac    240
ttcaacccta ataaggacac ctggcctgac gccaacaagg tcggcagcag gtccgagtct    300
aagaagaata ggggaggaag ggaggagatc ctggagcagt gggtgggagc acgcaagaag    360
ctggaggagc tggagcggga cctgagaaag atcaagaaga agatcaagaa gctggaggag    420
gagaacccct ggctgggcaa tatcaaggg atcctgggca agaaggatcg ggagggagag    480
ggagcaccac ctgcaaagag ggccagagcc gaccagatgg aggtggattc cggaccaagg    540
aagcgccctt tcagaggaga gtttacagac aaggagcgga gagatcacag cgccggaag    600 gccctggaga acaagcggaa gcagctgagc tccggcggca gagcctgtc caaggaggag    660 gaggaggagc tgaaaagct gaccgaggag gacgagagaa gggagaggag ggtggccggc    720
cccagggtgg gcgcgtgaa ccctctggag ggaggaacaa ggggagcacc aggaggaggc    780
ttcgtgcctt ccatgcaggg cgtgcccgag tctcctttg ccaggaccgg agagggcctg    840
gacgtgcgcg gcaatcaggg cttccccatg gacatcctgt ttcccgccga tccacccttc    900 tctcccccaga gctgcaggcc tcagtctcgc agcgagtcca agaagaacag aggcggaagg    960
```

```
gaggaggtgc tggagcagtg ggtgaatggc aggaagaagc tggaagaact ggagagggag    1020
ctgagaaggg cccgcaagaa gatcaagaag ctggaagacg ataatccttg gctgggcaat    1080
gtgaaaggca tcctgggcaa gaaggacaag gatggagagg gagcacctcc agcaaagagg    1140
gcaagaacag accagatgga gatcgattct ggaccaagga agcgcccct gaggggaggc    1200
ttcaccgacc gggagagaca ggatcaccgc cggagaaagg ccctgaagaa caagaagaag    1260
cagctgagcg ccggcggcaa gtctctgagt aaagaagaag aggaggagct gaagcggctg    1320
accagagagg acgaggagcg gaagaaggag gagcacggcc caagcagact gggagtgaat    1380
ccatccgagg gaggacctag aggcgcccct ggcggcggct tcgtgccttc tatgcagggc    1440
atcccagaga gcaggtttac caggacaggc gaaggcctgg acgtgcgggg ctccagaggc    1500
tttccccagg acatcctgtt cccttctgat ccccctttt ccccacagtc ttgtaggccc     1560
cagggcacca acctgtccac atctaaccca ctgggcttct ttcctgatca ccagctggat    1620
ccagccttcc gcgccaactc cgccaatcca gactgggact tcaacccaa taaggacaca     1680
tggcctgatg ctaacaaggt cggaggccag aacctgagcc cctccaatcc cctgggcttc    1740
tttcctgacc accagctgga tcctgccttc gcgccaaca cagctaaccc tgattgggac     1800
ttcaacccaa ataaggatac ctggcctgat gcaaacaagg tcggaggaag cggagctact    1860
aacttcagcc tgctgaagca ggctggagac gtggaggaga accctggacc tatgggcacc    1920
aacctgtcta caagcaatcc actgggcttc tttcccgacc atcagctgga cccagccttc    1980
agggccaaca gcgccaaccc tgactgggac ttcaacccaa ataaggacac gtggcctgat    2040
gccaacaagg tcggaggaca aaacctgtcc acctctaacc ccctgggctt ctttcccgat    2100
catcaattag acccagcctt ccgcgctaac actgctaacc ctgactggga cttcaacccg    2160
aataaggata cttggcctga tgccaataag gtcggcagcc agtccgagac aaggaggggc    2220
cggagaggaa ccagggagga gacactggag aagtggatca ccgccagaaa gaaggccgag    2280
gagctggaga aggacctgag gaagacccgc aagacaatca gaagctggaa gaagagaac     2340
ccttggctgg gcaatatcgt gggcatcatc agaaagggca aggacggcga gggagcacca    2400
ccagccaaga ggccacgcac agatcagatg gaagtggata gcggaccagg caagaggcct    2460
cacaagtccg gcttcaccga caaggagagg gaggaccata ggcgccggaa ggccctggaa    2520
aacaagaaga agcaattatc cgccggcggc aagatcctgt ctaaagaaga ggaagaagag    2580
ctgagaaggc tgaccgacga ggatgaggag aggaagagga gggtggcagg acctagagtg    2640
ggcgacgtga tccatccag gggaggacca agaggagcac caggaggcgg cttcgtgcca    2700
cagatggcag gagtgccaga gagccccttt tccaggacag gagagggcct ggatatcagg    2760
ggaacccagg gcttttccttg ggtgtctcca agccctccac agcagcggct gccactgctg    2820
gagtgcacac cccagtccca gtctgagagc aagaagaaca gaaggggcgg cagagaggac    2880
atcctggaaa atggatcac cacacgcaga aaagctgaag aactgaaaaa ggacctgcgg     2940
aaggccagaa agaccatcaa gaagctggag gatgaaaatc catggctggg aaatatcatc    3000
ggcatcatcc ggaagggcaa ggacggggaa ggcgcaccac ctgcaaagcg gcccaggacc    3060
gatcagatgg aaatcgattc tggaaccggc aagcggcctc acaagagtgg cttcaccgat    3120
aaggagagag aggatcacag aaggcgcaag gccctggaga caagaagaa gcaattaagc    3180
agcggcggca gaatctgtc cagagaagag gaagaggagc tggcagagct gacagtggag    3240
gacgaggagc ggaagaaggcg cgtggcagga ccaagaaccg cgatgtgaa cctgtccgga    3300
ggaggaccaa ggggagcacc tgggggaggc ttcgtgccaa ggatggaggg agtgcctgag    3360
```

```
tcccccttca ccagaaccgg cgaaggcctg gacatcaggg gcaatcaggg attcccatgg    3420
gtgcggccct ccccacccca gcagagactg cctctgctgg agtgtacccc acagggcact    3480
aacctgtcca cctctaaccc gttaggcttc tttcctgacc atcaattaga tcccgccttc    3540
cgggccaaca gcgccaatcc tgattgggac ttcaacccga ataaggacac ctggcccgac    3600
gcaaacaagg tcggagggca aaacctgagc acctccaacc ctttaggctt ctttccagat    3660
catcagctgg atccagcctt tagagccaat accgccaacc tgactgggga tttcaaccct    3720
aacaaagata cctggcccga cgctaacaaa gtggga                              3756
```

<210> SEQ ID NO 23
<211> LENGTH: 3785
<212> TYPE: DNA
<213> ORGANISM: Artificial Sequence
<220> FEATURE:
<223> OTHER INFORMATION: Delta 3 codon optimized with restriction sites (HindIII/EcoR1)

<400> SEQUENCE: 23

```
aagcttgcac catggccggc accaatctgt ctacctcaaa tcccctgggc ttcttccccg      60
atcatcagct ggaccctgcc ttccgagcaa attccgctaa tcctgattgg gatttcaacc     120
caaataagga cacatggcca gatgccaaca aggtcggcgg ccagaacctg tccacctcta    180
atcctctggg cttcttttcca gaccaccagc tggatcccgc cttcagggcc aacacagcca    240
atcccgactg ggacttcaac cctaataagg acacctggcc tgacgccaac aaggtcggca    300
gcaggtccga gtctaagaag aatagggagg aagggaggag gatcctggag cagtgggtgg    360
gagcacgcaa gaagctggag gagctggagc gggacctgag aaagatcaag aagaagatca    420
agaagctgga ggaggagaac ccctggctgg gcaatatcaa gggcatcctg gcaagaaggg    480
atcgggaggg agagggagca ccacctgcaa agagggccag agccgaccag atggaggtgg    540
attccggacc aaggaagcgc cctttcagag gagagtttac agacaaggag cggagagatc    600
acaggcgccg gaaggccctg gagaacaagc ggaagcagct gagctccggc ggcaagagcc    660
tgtccaagga ggaggaggag gagctgagaa agctgaccga ggaggacgag agaagggaga    720
ggagggtggc cggccccagg gtgggcggcg tgaaccctct ggagggagga acaagggggag   780 caccaggagg aggcttcgtg ccttccatgc agggcgtgcc cgagtctcct tttgccagga    840
ccggagaggg cctggacgtg cgcggcaatc agggcttccc atgggacatc ctgtttcccg    900
ccgatccacc cttctctccc cagagctgca ggcctcagtc tcgcagcgag tccaagaaga    960
acagaggcgg aagggaggag gtgctggagc agtgggtgaa tggcaggaag aagctggaag   1020
aactggagag ggagctgaga agggcccgca agaagatcaa gaagctggaa gacgataatc   1080
cttggctggg caatgtgaaa ggcatcctgg gcaagaagga caaggatgga gagggagcac   1140
ctccagcaaa gagggcaaga acagaccaga tggagatcga ttctggacca aggaagcgcc   1200
ccctgagggg aggcttcacc gaccgggaga gacaggatca ccgccggaga aaggccctga   1260
agaacaagaa gaagcagctg agcgccggcg gcaagtctct gagtaaagaa gaagaggagg   1320
agctgaagcg gctgaccaga gaggacgagg agcggaagaa ggaggagcac ggcccaagca   1380
gactgggagt gaatccatcc gagggaggac ctagaggcgc ccctggcggc ggcttcgtgc   1440
cttctatgca gggcatccca gagagcaggt ttaccaggac aggcgaaggc ctggacgtgc   1500
ggggctccag aggctttccc caggacatcc tgttcccttc tgatccccct tttttcccac   1560
agtcttgtag gccccagggc accaacctgt ccacatctaa cccactgggc ttctttcctg   1620
```

```
atcaccagct ggatccagcc ttccgcgcca actccgccaa tccagactgg gacttcaacc    1680
ccaataagga cacatggcct gatgctaaca aggtcggagg ccagaacctg agcacctcca    1740
atccctgggg cttctttcct gaccaccagc tggatcctgc cttccgcgcc aacacagcta    1800
accctgattg ggacttcaac ccaaataagg atacctggcc tgatgcaaac aaggtcggag    1860
gaagcggagc tactaacttc agcctgctga agcaggctgg agacgtggag gagaaccctg    1920
gacctatggg caccaacctg tctacaagca atccactggg cttctttccc gaccatcagc    1980
tggacccagc cttcagggcc aacagcgcca accctgactg ggacttcaac ccaaataagg    2040
acacgtggcc tgatgccaac aaggtcggag gacaaaacct gtccacctct aaccccctgg    2100
gcttctttcc cgatcatcaa ttagacccag ccttccgcgc taacactgct aaccctgact    2160
gggacttcaa cccgaataag gatacttggc ctgatgccaa taaggtcggc agccagtccg    2220
agacaaggag gggccggaga ggaaccaggg aggagacact ggagaagtgg atcaccgcca    2280
gaaagaaggc cgaggagctg gagaaggacc tgaggaagac ccgcaagaca atcaagaagc    2340
tggaagaaga gaacccttgg ctgggcaata tcgtgggcat catcagaaag ggcaaggacg    2400
gcgagggagc accaccagcc aagaggccac gcacagatca gatggaagtg gatagcggac    2460
caggcaagag gcctcacaag tccggcttca ccgacaagga gagggaggac cataggcgcc    2520
ggaaggccct ggaaaacaag aagaagcaat tatccgccgg cggcaagatc ctgtctaaag    2580
aagaggaaga agagctgaga aggctgaccg acgaggatga ggagaggaag aggagggtgg    2640
caggacctag agtgggcgac gtgaatccat ccaggggagg accaagagga gcaccaggag    2700
gcggcttcgt gccacagatg gcaggagtgc cagagagccc cttttccagg acaggagagg    2760
gcctggatat caggggaacc cagggcttc cttgggtgtc tccaagccct ccacagcagc    2820
ggctgccact gctggagtgc acaccccagt cccagtctga gagcaagaag aacagaaggg    2880
gcggcagaga ggacatcctg gaaaaatgga tcaccacacg cagaaaagct gaagaactgg    2940
aaaaggacct gcggaaggcc agaaagacca tcaagaagct ggaggatgaa atccatggc    3000
tgggaaatat catcggcatc atccggaagg gcaaggacgg ggaaggcgca ccacctgcaa    3060
agcggcccag gaccgatcag atggaaatcg attctggaac cggcaagcgg cctcacaaga    3120
gtggcttcac cgataaggag agagaggatc acagaaggcg caaggccctg gagaacaaga    3180
agaagcaatt aagcagcggc ggcaagaatc tgtccagaga gaggaagag gagctgggca    3240
gactgacagt ggaggacgag gagcggagaa ggcgcgtggc aggaccaaga accggcgatg    3300
tgaacctgtc cggaggagga ccaaggggag cacctgggg aggcttcgtg ccaaggatgg    3360
agggagtgcc tgagtccccc ttcaccagaa ccggcgaagg cctggacatc aggggcaatc    3420
agggattccc atgggtgcgg ccctccccac ccagcagag actgcctctg ctggagtgta    3480
ccccacaggg cactaacctg tccacctcta acccgttagg cttctttcct gaccatcaat    3540
tagatcccgc cttccgggcc aacagcgcca atcctgattg ggacttcaac ccgaataagg    3600
acacctggcc cgacgcaaac aaggtcggag gcaaaacct gagcacctcc aaccctttag    3660
gcttctttcc agatcatcag ctggatccag ccttttagagc caataccgcc aaccctgact    3720
gggatttcaa ccctaacaaa gatacctggc ccgacgctaa caaagtggga tgatgagaat    3780
tccgt                                                               3785

<210> SEQ ID NO 24
<211> LENGTH: 1253
<212> TYPE: PRT
```

<213> ORGANISM: Artificial Sequence
<220> FEATURE:
<223> OTHER INFORMATION: Delta 3 protein

<400> SEQUENCE: 24

```
Met Ala Gly Thr Asn Leu Ser Thr Ser Asn Pro Leu Gly Phe Phe Pro
1               5                   10                  15

Asp His Gln Leu Asp Pro Ala Phe Arg Ala Asn Ser Ala Asn Pro Asp
            20                  25                  30

Trp Asp Phe Asn Pro Asn Lys Asp Thr Trp Pro Asp Ala Asn Lys Val
        35                  40                  45

Gly Gly Gln Asn Leu Ser Thr Ser Asn Pro Leu Gly Phe Phe Pro Asp
    50                  55                  60

His Gln Leu Asp Pro Ala Phe Arg Ala Asn Thr Ala Asn Pro Asp Trp
65                  70                  75                  80

Asp Phe Asn Pro Asn Lys Asp Thr Trp Pro Asp Ala Asn Lys Val Gly
                85                  90                  95

Ser Arg Ser Glu Ser Lys Asn Arg Gly Arg Glu Glu Ile Leu
            100                 105                 110

Glu Gln Trp Val Gly Ala Arg Lys Lys Leu Glu Glu Leu Glu Arg Asp
            115                 120                 125

Leu Arg Lys Ile Lys Lys Lys Ile Lys Leu Glu Glu Asn Pro
        130                 135                 140

Trp Leu Gly Asn Ile Lys Gly Ile Leu Gly Lys Lys Asp Arg Glu Gly
145                 150                 155                 160

Glu Gly Ala Pro Pro Ala Lys Arg Ala Arg Ala Asp Gln Met Glu Val
                165                 170                 175

Asp Ser Gly Pro Arg Lys Arg Pro Phe Arg Gly Glu Phe Thr Asp Lys
            180                 185                 190

Glu Arg Arg Asp His Arg Arg Lys Ala Leu Glu Asn Lys Arg Lys
        195                 200                 205

Gln Leu Ser Ser Gly Gly Lys Ser Leu Ser Lys Glu Glu Glu Glu Glu
    210                 215                 220

Leu Arg Lys Leu Thr Glu Glu Asp Glu Arg Arg Glu Arg Arg Val Ala
225                 230                 235                 240

Gly Pro Arg Val Gly Gly Val Asn Pro Leu Glu Gly Gly Thr Arg Gly
                245                 250                 255

Ala Pro Gly Gly Gly Phe Val Pro Ser Met Gln Gly Val Pro Glu Ser
            260                 265                 270

Pro Phe Ala Arg Thr Gly Glu Gly Leu Asp Val Arg Gly Asn Gln Gly
        275                 280                 285

Phe Pro Trp Asp Ile Leu Phe Pro Ala Asp Pro Pro Phe Ser Pro Gln
290                 295                 300

Ser Cys Arg Pro Gln Ser Arg Ser Glu Ser Lys Lys Asn Arg Gly Gly
305                 310                 315                 320

Arg Glu Glu Val Leu Glu Gln Trp Val Asn Gly Arg Lys Lys Leu Glu
                325                 330                 335

Glu Leu Glu Arg Glu Leu Arg Arg Ala Arg Lys Lys Ile Lys Lys Leu
            340                 345                 350

Glu Asp Asp Asn Pro Trp Leu Gly Asn Val Lys Gly Ile Leu Gly Lys
        355                 360                 365

Lys Asp Lys Asp Gly Glu Gly Ala Pro Pro Ala Lys Arg Ala Arg Thr
370                 375                 380

Asp Gln Met Glu Ile Asp Ser Gly Pro Arg Lys Arg Pro Leu Arg Gly
```

```
              385                 390                 395                 400
Gly Phe Thr Asp Arg Glu Arg Gln Asp His Arg Arg Lys Ala Leu
                405                 410                 415
Lys Asn Lys Lys Lys Gln Leu Ser Ala Gly Lys Ser Leu Ser Lys
                420                 425                 430
Glu Glu Glu Glu Glu Leu Lys Arg Leu Thr Arg Glu Asp Glu Arg
                435                 440                 445
Lys Lys Glu Glu His Gly Pro Ser Arg Leu Gly Val Asn Pro Ser Glu
            450                 455                 460
Gly Gly Pro Arg Gly Ala Pro Gly Gly Phe Val Pro Ser Met Gln
465                 470                 475                 480
Gly Ile Pro Glu Ser Arg Phe Thr Arg Thr Gly Glu Gly Leu Asp Val
                485                 490                 495
Arg Gly Ser Arg Gly Phe Pro Gln Asp Ile Leu Phe Pro Ser Asp Pro
                500                 505                 510
Pro Phe Ser Pro Gln Ser Cys Arg Pro Gln Gly Thr Asn Leu Ser Thr
                515                 520                 525
Ser Asn Pro Leu Gly Phe Phe Pro Asp His Gln Leu Asp Pro Ala Phe
            530                 535                 540
Arg Ala Asn Ser Ala Asn Pro Asp Trp Asp Phe Asn Pro Asn Lys Asp
545                 550                 555                 560
Thr Trp Pro Asp Ala Asn Lys Val Gly Gly Gln Asn Leu Ser Thr Ser
                565                 570                 575
Asn Pro Leu Gly Phe Phe Pro Asp His Gln Leu Asp Pro Ala Phe Arg
            580                 585                 590
Ala Asn Thr Ala Asn Pro Asp Trp Asp Phe Asn Pro Asn Lys Asp Thr
            595                 600                 605
Trp Pro Asp Ala Asn Lys Val Gly Gly Ser Gly Ala Thr Asn Phe Ser
        610                 615                 620
Leu Leu Lys Gln Ala Gly Asp Val Glu Glu Asn Pro Gly Pro Met Gly
625                 630                 635                 640
Thr Asn Leu Ser Thr Ser Asn Pro Leu Gly Phe Phe Pro Asp His Gln
                645                 650                 655
Leu Asp Pro Ala Phe Arg Ala Asn Ser Ala Asn Pro Asp Trp Asp Phe
                660                 665                 670
Asn Pro Asn Lys Asp Thr Trp Pro Asp Ala Asn Lys Val Gly Gly Gln
            675                 680                 685
Asn Leu Ser Thr Ser Asn Pro Leu Gly Phe Phe Pro Asp His Gln Leu
        690                 695                 700
Asp Pro Ala Phe Arg Ala Asn Thr Ala Asn Pro Asp Trp Asp Phe Asn
705                 710                 715                 720
Pro Asn Lys Asp Thr Trp Pro Asp Ala Asn Lys Val Gly Ser Gln Ser
                725                 730                 735
Glu Thr Arg Arg Gly Arg Arg Gly Thr Arg Glu Glu Thr Leu Glu Lys
                740                 745                 750
Trp Ile Thr Ala Arg Lys Lys Ala Glu Glu Leu Glu Lys Asp Leu Arg
                755                 760                 765
Lys Thr Arg Lys Thr Ile Lys Lys Leu Glu Glu Asn Pro Trp Leu
                770                 775                 780
Gly Asn Ile Val Gly Ile Ile Arg Lys Gly Lys Asp Gly Glu Gly Ala
785                 790                 795                 800
Pro Pro Ala Lys Arg Pro Arg Thr Asp Gln Met Glu Val Asp Ser Gly
                805                 810                 815
```

```
Pro Gly Lys Arg Pro His Lys Ser Gly Phe Thr Asp Lys Glu Arg Glu
        820                 825                 830

Asp His Arg Arg Arg Lys Ala Leu Glu Asn Lys Lys Lys Gln Leu Ser
        835                 840                 845

Ala Gly Gly Lys Ile Leu Ser Lys Glu Glu Glu Glu Leu Arg Arg
        850                 855                 860

Leu Thr Asp Glu Asp Glu Glu Arg Lys Arg Arg Val Ala Gly Pro Arg
865                 870                 875                 880

Val Gly Asp Val Asn Pro Ser Arg Gly Pro Arg Gly Ala Pro Gly
                885                 890                 895

Gly Gly Phe Val Pro Gln Met Ala Gly Val Pro Glu Ser Pro Phe Ser
            900                 905                 910

Arg Thr Gly Glu Gly Leu Asp Ile Arg Gly Thr Gln Gly Phe Pro Trp
            915                 920                 925

Val Ser Pro Ser Pro Pro Gln Gln Arg Leu Pro Leu Leu Glu Cys Thr
        930                 935                 940

Pro Gln Ser Gln Ser Glu Ser Lys Lys Asn Arg Arg Gly Gly Arg Glu
945                 950                 955                 960

Asp Ile Leu Glu Lys Trp Ile Thr Thr Arg Arg Lys Ala Glu Glu Leu
                965                 970                 975

Glu Lys Asp Leu Arg Lys Ala Arg Lys Thr Ile Lys Lys Leu Glu Asp
            980                 985                 990

Glu Asn Pro Trp Leu Gly Asn Ile Ile Gly Ile Ile Arg Lys Gly Lys
            995                 1000                1005

Asp Gly Glu Gly Ala Pro Pro Ala Lys Arg Pro Arg Thr Asp Gln Met
    1010                1015                1020

Glu Ile Asp Ser Gly Thr Gly Lys Arg Pro His Lys Ser Gly Phe Thr
1025                1030                1035                1040

Asp Lys Glu Arg Glu Asp His Arg Arg Lys Ala Leu Glu Asn Lys
                1045                1050                1055

Lys Lys Gln Leu Ser Ser Gly Gly Lys Asn Leu Ser Arg Glu Glu Glu
            1060                1065                1070

Glu Glu Leu Gly Arg Leu Thr Val Glu Asp Glu Arg Arg Arg
            1075                1080                1085

Val Ala Gly Pro Arg Thr Gly Asp Val Asn Leu Ser Gly Gly Gly Pro
    1090                1095                1100

Arg Gly Ala Pro Gly Gly Phe Val Pro Arg Met Glu Gly Val Pro
1105                1110                1115                1120

Glu Ser Pro Phe Thr Arg Thr Gly Glu Gly Leu Asp Ile Arg Gly Asn
            1125                1130                1135

Gln Gly Phe Pro Trp Val Arg Pro Ser Pro Gln Gln Arg Leu Pro
            1140                1145                1150

Leu Leu Glu Cys Thr Pro Gln Gly Thr Asn Leu Ser Thr Ser Asn Pro
        1155                1160                1165

Leu Gly Phe Phe Pro Asp His Gln Leu Asp Pro Ala Phe Arg Ala Asn
    1170                1175                1180

Ser Ala Asn Pro Asp Trp Asp Phe Asn Pro Asn Lys Asp Thr Trp Pro
1185                1190                1195                1200

Asp Ala Asn Lys Val Gly Gly Gln Asn Leu Ser Thr Ser Asn Pro Leu
            1205                1210                1215

Gly Phe Phe Pro Asp His Gln Leu Asp Pro Ala Phe Arg Ala Asn Thr
        1220                1225                1230
```

Ala Asn Pro Asp Trp Asp Phe Asn Pro Asn Lys Asp Thr Trp Pro Asp
           1235                1240                1245

Ala Asn Lys Val Gly
    1250

<210> SEQ ID NO 25
<211> LENGTH: 3891
<212> TYPE: DNA
<213> ORGANISM: Artificial Sequence
<220> FEATURE:
<223> OTHER INFORMATION: Delta 4 wt

<400> SEQUENCE: 25

| | | | | | |
|---|---|---|---|---|---|
| agccgcagcg | aaagcaaaaa | aaaccgcggc | ggccgcgaag | aaattctgga | acagtgggtg | 60 |
| ggcgcgcgca | aaaaactgga | agaactggaa | cgcgatctgc | gcaaaattaa | aaaaaaaatt | 120 |
| aaaaaactgg | aagaagaaaa | cccgtggctg | ggcaacatta | aaggcattct | gggcaaaaaa | 180 |
| gatcgcgaag | gcgaaggcgc | gccgccggcg | aaacgcgcgc | gcgcggatca | gatggaagtg | 240 |
| gatagcggcc | gcgcaaacg | cccgtttcgc | ggcgaattta | ccgataaaga | acgccgcgat | 300 |
| catcgccgcc | gcaaagcgct | ggaaaacaaa | cgcaaacagc | tgagcagcgg | cggcaaaagc | 360 |
| ctgagcaaag | aagaagaaga | gaactgcgc | aaactgaccg | aagaagatga | acgccgcgaa | 420 |
| cgccgcgtgg | cgggcccgcg | cgtgggcggc | gtgaacccgc | tggaaggcgg | cacccgcggc | 480 |
| gcgccgggcg | gcggctttgt | gccgagcatg | cagggcgtgc | cggaaagccc | gtttgcgcgc | 540 |
| accggcgaag | gcctggatgt | gcgcggcaac | cagggctttc | cgtgggatat | tctgtttccg | 600 |
| gcggatccgc | cgtttagccc | gcagagctgc | cgcccgcagg | caccaacct | gagcaccagc | 660 |
| aacccgctgg | gcttttttcc | ggatcatcag | ctggatccgg | cgtttcgcgc | gaacagcgcg | 720 |
| aacccggatt | gggattttaa | cccgaacaaa | gatacctggc | cggatgcgaa | caaagtgggc | 780 |
| ggccagaacc | tgagcaccag | caacccgctg | gcttttttc | cggatcatca | gctggatccg | 840 |
| gcgtttcgcg | cgaacaccgc | gaacccggat | tgggattttta | acccgaacaa | agatacctgg | 900 |
| ccggatgcga | acaaagtggg | cggaagcgga | gctactaact | tcagcctgct | gaagcaggct | 960 |
| ggagacgtgg | aggagaaccc | tggacctatg | agccgcagcg | aaagcaaaaa | aaaccgcggc | 1020 |
| ggccgcgaag | aagtgctgga | acagtgggtg | aacgccgcca | aaaaactgga | agaactggaa | 1080 |
| cgcgaactgc | gccgcgcgcg | caaaaaaatt | aaaaaactgg | aagatgataa | cccgtggctg | 1140 |
| ggcaacgtga | aaggcattct | gggcaaaaaa | gataaagatg | gcgaaggcgc | gccgccggcg | 1200 |
| aaacgcgcgc | gcaccgatca | gatggaaatt | gatagcggcc | gcgcaaacg | cccgctgcgc | 1260 |
| ggcggcttta | ccgatcgcga | acgccaggat | catcgccgcc | gcaaagcgct | gaaaaacaaa | 1320 |
| aaaaacagc | tgagcgcggg | cggcaaaagc | ctgagcaaag | aagaagaaga | gaactgaaa | 1380 |
| cgcctgaccc | gcgaagatga | agaacgcaaa | aaagaagaac | atggcccgag | ccgcctgggc | 1440 |
| gtgaacccga | gcgaaggcgg | cccgcgcggc | gcgccgggcg | gcggctttgt | gccgagcatg | 1500 |
| cagggcattc | cggaaagccg | ctttacccgc | accggcgaag | gcctggatgt | gcgcggcagc | 1560 |
| cgcggctttc | cgcaggatat | tctgtttccg | agcgatccgc | cgtttagccc | gcagagctgc | 1620 |
| cgcccgcagg | caccaacct | gagcaccagc | aacccgctgg | cttttttcc | ggatcatcag | 1680 |
| ctggatccgg | cgtttcgcgc | gaacagcgcg | aacccggatt | gggattttaa | cccgaacaaa | 1740 |
| gatacctggc | cggatgcgaa | caaagtgggc | ggccagaacc | tgagcaccag | caacccgctg | 1800 |
| gcttttttc | cggatcatca | gctggatccg | gcgtttcgcg | cgaacaccgc | gaacccggat | 1860 |
| tgggatttta | acccgaacaa | agatacctgg | ccggatgcga | acaaagtggg | cggaagcgga | 1920 |

```
gctactaact tcagcctgct gaagcaggct ggagacgtgg aggagaaccc tggacctatg    1980
agccagagcg aaacccgccg cggccgccgc ggcacccgcg aagaaccct ggaaaaatgg     2040
attaccgcgc gcaaaaaagc ggaagaactg gaaaaagatc tgcgcaaaac ccgcaaaacc   2100
attaaaaaac tggaagaaga aaacccgtgg ctgggcaaca ttgtgggcat tattcgcaaa   2160
ggcaaagatg gcgaaggcgc gccgccggcg aaacgcccgc gcaccgatca gatggaagtg   2220
gatagcggcc cgggcaaacg cccgcataaa agcggcttta ccgataaaga acgcgaagat   2280
catcgccgcc gcaaagcgct ggaaaacaaa aaaaaacagc tgagcgcggg cggcaaaatt   2340
ctgagcaaag aagaagaaga agaactgcgc cgcctgaccg atgaagatga agaacgcaaa   2400
cgccgcgtgg cgggcccgcg cgtgggcgat gtgaacccga gccgcggcgg cccgcgcggc   2460
gcgccgggcg gcggctttgt gccgcagatg gcgggcgtgc cggaaagccc gtttagccgc   2520
accggcgaag gcctggatat tcgcggcacc cagggctttc cgtgggtgag cccgagcccg   2580
ccgcagcagc gcctgccgct gctggaatgc accccgcagg gcaccaacct gagcaccagc   2640
aacccgctgg gcttttttcc ggatcatcag ctggatccgg cgtttcgcgc gaacagcgcg   2700
aacccggatt gggattttaa cccgaacaaa gatacctggc cggatgcgaa caaagtgggc   2760
ggccagaacc tgagcaccag caacccgctg gcttttttc cggatcatca gctggatccg    2820
gcgtttcgcg cgaacaccgc gaacccggat tgggattttta acccgaacaa agatacctgg   2880
ccggatgcga acaaagtggg cggaagcgga gctactaact tcagcctgct gaagcaggct   2940
ggagacgtgg aggagaaccc tggacctatg agccagagcg aaagcaaaaa aaaccgccgc   3000
ggcggccgcg aagatattct ggaaaaatgg attaccaccc gccgcaaagc ggaagaactg   3060
gaaaaagatc tgcgcaaagc gcgcaaaacc attaaaaaac tggaagatga aaacccgtgg   3120
ctgggcaaca ttattggcat tattcgcaaa ggcaaagatg gcgaaggcgc gccgccggcg   3180
aaacgcccgc gcaccgatca gatggaaatt gatagcggca ccggcaaacg cccgcataaa   3240
agcggcttta ccgataaaga acgcgaagat catcgccgcc gcaaagcgct ggaaaacaaa   3300
aaaaaacagc tgagcagcgg cggcaaaaac ctgagccgcg aagaagaaga agaactgggc   3360
cgcctgaccg tggaagatga agaacgccgc cgccgcgtgg cgggcccgcg caccggcgat   3420
gtgaacctga gcggcggcgg cccgcgcggc gcgccgggcg gcggctttgt gccgcgcatg   3480
gaaggcgtgc cggaaagccc gtttacccgc accggcgaag gcctggatat tcgcggcaac   3540
cagggctttc cgtgggtgcg cccgagcccg ccgcagcagc gcctgccgct gctggaatgc   3600
accccgcagg gcaccaacct gagcaccagc aacccgctgg cttttttcc ggatcatcag    3660
ctggatccgg cgtttcgcgc gaacagcgcg aacccggatt gggattttaa cccgaacaaa   3720
gatacctggc cggatgcgaa caaagtgggc ggccagaacc tgagcaccag caacccgctg   3780
gctttttttc cggatcatca gctggatccg gcgtttcgcg cgaacaccgc gaacccggat   3840
tgggatttta acccgaacaa agatacctgg ccggatgcga acaaagtggg c            3891
```

<210> SEQ ID NO 26
<211> LENGTH: 3923
<212> TYPE: DNA
<213> ORGANISM: Artificial Sequence
<220> FEATURE:
<223> OTHER INFORMATION: Delta 4 wt with restriction sites (HindIII/EcoR1)

<400> SEQUENCE: 26

```
aagcttgcac catggccagc cgcagcgaaa gcaaaaaaaa ccgcggcggc cgcgaagaaa     60
```

-continued

```
ttctggaaca gtgggtgggc gcgcgcaaaa aactggaaga actggaacgc gatctgcgca    120
aaattaaaaa aaaaattaaa aaactggaag aagaaaaccc gtggctgggc aacattaaag    180
gcattctggg caaaaaagat cgcgaaggcg aaggcgcgcc gccggcgaaa cgcgcgcgcg    240
cggatcagat ggaagtggat agcggcccgc gcaaacgccc gtttcgcggc gaatttaccg    300
ataaagaacg ccgcgatcat cgccgccgca aagcgctgga aaacaaacgc aaacagctga    360
gcagcggcgg caaaagcctg agcaaagaag aagaagaaga actgcgcaaa ctgaccgaag    420
aagatgaacg ccgcgaacgc cgcgtggcgg gcccgcgcgt gggcggcgtg aacccgctgg    480
aaggcggcac ccgcggcgcg ccgggcgcg gctttgtgcc gagcatgcag ggcgtgccgg    540
aaagcccgtt tgcgcgcacc ggcgaaggcc tggatgtgcg cggcaaccag ggctttccgt    600
gggatattct gtttccggcg gatccgccgt ttagcccgca gagctgccgc ccgcagggca    660
ccaacctgag caccagcaac ccgctgggct ttttttccgga tcatcagctg gatccggcgt    720
ttcgcgcgaa cagcgcgaac ccggattggg attttaaccc gaacaaagat acctggccgg    780
atgcgaacaa agtgggcggc cagaacctga gcaccagcaa cccgctgggc ttttttccgg    840
atcatcagct ggatccggcg tttcgcgcga acaccgcgaa cccggattgg gattttaacc    900
cgaacaaaga tacctggccg gatgcgaaca agtgggcgg aagcggagct actaacttca    960
gcctgctgaa gcaggctgga gacgtggagg agaaccctgg acctatgagc cgcagcgaaa   1020
gcaaaaaaaa ccgcggcggc cgcgaagaag tgctggaaca gtgggtgaac ggccgcaaaa   1080
aactggaaga actggaacgc gaactgcgcc gcgcgcgcaa aaaaattaaa aaactggaag   1140
atgataaccc gtggctgggc aacgtgaaag gcattctggg caaaaaagat aaagatggcg   1200
aaggcgcgcc gccggcgaaa cgcgcgcgca ccgatcagat ggaaattgat agcggcccgc   1260
gcaaacgccc gctgcgcggc ggctttaccg atcgcgaacg ccaggatcat cgccgccgca   1320
aagcgctgaa aaacaaaaaa aaacagctga gcgcgggcgg caaaagcctg agcaaagaag   1380
aagaagaaga actgaaacgc ctgacccgcg aagatgaaga acgcaaaaaa gaagaacatg   1440
gcccgagccg cctgggcgtg aacccgagcg aaggcggccc gcgcggcgcg ccgggcggcg   1500
gctttgtgcc gagcatgcag ggcattccgg aaagccgctt tacccgcacc ggcgaaggcc   1560
tggatgtgcg cggcagccgc ggcttttccg aggatattct gtttccgagc gatccgccgt   1620
ttagcccgca gagctgccgc ccgcagggca ccaacctgag caccagcaac ccgctgggct   1680 ttttttccgga tcatcagctg gatccggcgt ttcgcgcgaa cagcgcgaac ccggattggg   1740
attttaaccc gaacaaagat acctggccgg atgcgaacaa agtgggcggc cagaacctga   1800
gcaccagcaa cccgctgggc ttttttccgg atcatcagct ggatccggcg tttcgcgcga   1860
acaccgcgaa cccggattgg gattttaacc cgaacaaaga tacctggccg gatgcgaaca   1920
aagtgggcgg aagcggagct actaacttca gcctgctgaa gcaggctgga gacgtggagg   1980
agaaccctgg acctatgagc cagagcgaaa cccgccgcgg ccgccgcggc acccgcgaag   2040
aaaccctgga aaatggatt accgcgcgca aaaagcgga agaactggaa aaagatctgc   2100
gcaaaacccg caaaaccatt aaaaaactgg aagaagaaaa cccgtggctg gcaacattg   2160 tgggcattat tcgcaaaggc aaagatggcg aaggcgcgcc gccggcgaaa cgcccgcgca   2220
ccgatcagat ggaagtggat agcggcccgg gcaaacgccc gcataaaagc ggctttaccg   2280
ataaagaacg cgaagatcat cgccgccgca agcgctgga aacaaaaaaa aaacagctga   2340
gcgcgggcgg caaaattctg agcaaagaag aagaagaaga actgcgccgc ctgaccgatg   2400
```

```
aagatgaaga acgcaaacgc cgcgtggcgg gcccgcgcgt gggcgatgtg aacccgagcc    2460
gcggcggccc gcgcggcgcg ccgggcggcg gctttgtgcc gcagatggcg ggcgtgccgg    2520
aaagcccgtt tagccgcacc ggcgaaggcc tggatattcg cggcacccag ggctttccgt    2580
gggtgagccc gagcccgccg cagcagcgcc tgccgctgct ggaatgcacc ccgcagggca    2640
ccaacctgag caccagcaac ccgctgggct ttttccgga tcatcagctg gatccggcgt    2700
ttcgcgcgaa cagcgcgaac ccggattggg attttaaccc gaacaaagat acctggccgg    2760
atgcgaacaa agtgggcggc cagaacctga gcaccagcaa cccgctgggc ttttttccgg    2820
atcatcagct ggatccggcg tttcgcgcga acaccgcgaa cccggattgg gattttaacc    2880
cgaacaaaga tacctggccg gatgcgaaca aagtgggcgg aagcggagct actaacttca    2940
gcctgctgaa gcaggctgga gacgtggagg agaaccctgg acctatgagc cagagcgaaa    3000
gcaaaaaaaa ccgccgcggc ggccgcgaag atattctgga aaaatggatt accacccgcc    3060
gcaaagcgga gaactggaa aaagatctgc gcaaagcgcg caaaaccatt aaaaaactgg    3120
aagatgaaaa cccgtggctg gcaacatta ttggcattat tcgcaaaggc aaagatggcg    3180
aaggcgcgcc gccggcgaaa cgcccgcgca ccgatcagat ggaaattgat agcggcaccg    3240
gcaaacgccc gcataaaagc ggcttttaccg ataaagaacg cgaagatcat cgccgccgca    3300
aagcgctgga aaacaaaaaa aaacagctga gcagcggcgg caaaaacctg agccgcgaag    3360
aagaagaaga actgggccgc ctgaccgtgg aagatgaaga acgccgccgc cgcgtggcgg    3420
gcccgcgcac cggcgatgtg aacctgagcg gcggcggccc gcgcggcgcg ccgggcggcg    3480
gctttgtgcc gcgcatggaa ggcgtgccgg aaagcccgtt tacccgcacc ggcgaaggcc    3540
tggatattcg cggcaaccag ggctttccgt gggtgcgccc gagcccgccg cagcagcgcc    3600
tgccgctgct ggaatgcacc ccgcagggca ccaacctgag caccagcaac ccgctgggct    3660
tttttccgga tcatcagctg gatccggcgt ttcgcgcgaa cagcgcgaac ccggattggg    3720
attttaaccc gaacaaagat acctggccgg atgcgaacaa agtgggcggc cagaacctga    3780
gcaccagcaa cccgctgggc ttttttccgg atcatcagct ggatccggcg tttcgcgcga    3840
acaccgcgaa cccggattgg gattttaacc cgaacaaaga tacctggccg gatgcgaaca    3900
aagtgggctg atgagaattc cgt                                            3923
```

<210> SEQ ID NO 27
<211> LENGTH: 3894
<212> TYPE: DNA
<213> ORGANISM: Artificial Sequence
<220> FEATURE:
<223> OTHER INFORMATION: Delta 4 codon optimized

<400> SEQUENCE: 27

```
gccagtcgga gcgaatcaaa gaaaaatagg ggagggcggg aagaaatcct ggagcagtgg      60
gtcggagcac gaaagaaact ggaagaactg gagagggacc tgcgcaagat caagaagaag     120
atcaagaagc tggaggagga gaaccctgg ctgggcaata tcaagggcat cctgggcaag     180
aaggatcggg agggagaggg agcaccacct gcaaagaggg ccagagccga ccagatggag     240
gtggatagcg gccctaggaa gcgcccattc agaggcgagt ttacagacaa ggagcggaga     300
gatcacaggc gccggaaggc cctggagaac aagcggaagc agctgagctc cggcggcaag     360
tccctgtcta aggaggagga ggaggagctg agaaagctga ccgaggagga cgagagaagg     420
gagaggaggg tggcaggacc tagggtggga ggcgtgaacc cactggaggg aggaacaagg     480
ggagcacctg gaggaggatt cgtgccatcc atgcaggag tgcctgagtc tccatttgcc     540
```

| | |
|---|---|
| aggaccggag agggcctgga tgtgcgcgga aatcagggct tcccctggga catcctgttt | 600 |
| cctgccgatc cacccttctc cccacagtct tgcaggccac agggaaccaa cctgagcaca | 660 |
| tccaatcctc tgggcttctt tccagaccac cagctggatc ctgccttcag agccaactcc | 720 |
| gccaatccag actgggactt caaccccaat aaggacacat ggcctgatgc caacaaggtc | 780 |
| ggcggccaga acctgtctac cagcaatccc ctgggcttct ttcctgacca ccagctggat | 840 |
| ccagccttcc gggccaacac tgctaaccct gattgggact caaccctaa taaggatacc | 900 |
| tggccagacg ccaacaaggt cggcggaagc ggagctacta acttcagcct gctgaagcag | 960 |
| gctggagacg tggaggagaa ccctggacct atgtccaggt ctgagagcaa aagaatagg | 1020 |
| ggaggaagag aggaggtgct ggagcagtgg gtgaacggcc gcaagaagct ggaggagctg | 1080 |
| gagagggagc tgaagggc ccgcaagaag atcaagaagc tggaagacga taatccttgg | 1140 |
| ctgggcaatg tgaaaggcat cctgggcaag aaggacaagg atggagaggg agcacctcca | 1200 |
| gcaaagaggg caagaacaga ccagatggag atcgattctg gaccaaggaa gcgccctctg | 1260 |
| aggggaggct tcaccgaccg ggagagacag gatcaccgcc ggagaaaggc cctgaagaac | 1320 |
| aagaagaagc agctgtccgc cggcggcaag tccctgagca agaagagga gaggagctg | 1380 |
| aagaggctga cccgcgagga cgaggagcgg aagaaggagg agcacggacc aagcagactg | 1440 |
| ggagtgaatc cttccgaggg aggaccaaga ggagcacccg gaggaggctt cgtgccatct | 1500 |
| atgcagggca tccccgagag ccggtttacc agaacaggag agggcctgga cgtgaggggc | 1560 |
| tcccgcggct ttcctcagga catcctgttc ccatctgatc ccccttttag cccacagtcc | 1620 |
| tgtaggcccc agggcactaa cctgagcaca tccaacccac tgggcttctt tcctgatcat | 1680 |
| cagctggacc cagccttccg cgccaacagc gccaaccctg actgggactt caacccaaat | 1740 |
| aaggacacat ggccagatgc taacaaggtc ggaggacaaa acctgtctac cagcaaccct | 1800 |
| ctgggcttct ttcccgatca tcagctggac cccgccttca gggccaacac agccaatccc | 1860 |
| gactgggact caacccgaa taaggacacc tggccagatg caaacaaggt cggaggaagc | 1920 |
| ggagctacta acttcagcct gctgaagcag gctggagacg tggaggagaa ccctggacct | 1980 |
| atgagccagt ctgagacaag gaggggccgg agaggaacca gggaggagac actggagaag | 2040 |
| tggatcaccg ccagaaagaa ggccgaggag ctggagaagg acctgcggaa gaccagaaag | 2100 |
| acaatcaaga agctggaaga agagaaccca tggctgggca atatcgtggg catcatccgc | 2160 |
| aagggcaagg acggcgaggg agcaccacca gcaaagaggc cccgcacaga tcagatggaa | 2220 |
| gtggatagcg gccctggcaa gaggccacac aagtccggct tcaccgacaa ggagagggag | 2280 |
| gaccataggc gccggaaggc cctggaaaac aagaagaagc aattatccgc cggcggcaag | 2340 |
| atcctgtcca agaggaaga agaggagctg agaaggctga ccgacgagga tgaggagagg | 2400 |
| aaaagaaggg tggcaggacc aagagtgggc gacgtgaatc ccagcagagg cggaccaaga | 2460 |
| ggagcacctg gaggcggctt cgtgcccag atggccggcg tgcccgagtc tccttttagc | 2520 |
| agaactggag agggcctgga tatcagggga acacagggct ttccatgggt gagcccatcc | 2580 |
| cctccacagc agaggctgcc actgctggag tgcacccctc agggaaccaa cctgtctacc | 2640 |
| agcaacccgc tgggcttctt tcccgaccat cagctggacc ctgccttccg cgccaactcc | 2700 |
| gccaaccctg attgggactt caacccgaat aaggatacct ggcccgacgc taacaaggtc | 2760 |
| ggaggccaga acctgtccac ctctaacccc ttaggcttct ttcccgatca ccagctggat | 2820 |
| cccgccttca gagccaacac tgctaacccc gattgggact caacccgaa taaggacacg | 2880 |

| | |
|---|---|
| tggccagacg ctaacaaggt cggggggaagc ggagctacta acttcagcct gctgaagcag | 2940 |
| gctggagacg tggaggagaa ccctggacct atgtcgcagt ccgagtctaa gaagaataga | 3000 |
| aggggcggcc gggaggatat cctggaaaaa tggatcacca cacgcagaaa agctgaagaa | 3060 |
| ctggaaaagg acctgaggaa ggcccgcaag accatcaaga agctggagga tgaaaatcca | 3120 |
| tggctgggaa acatcatcgg catcatcaga aagggcaagg acggggaagg cgccccacct | 3180 |
| gcaaagcggc ctagaaccga tcagatgaaa atcgattctg cacaggcaa gcggccacac | 3240 |
| aagagtggct tcaccgataa ggagagagag gatcacagaa ggcgcaaggc cctggagaac | 3300 |
| aagaagaagc aattaagcag cggcggcaag aatctgtcca gagaagaaga ggaggagctg | 3360 |
| ggcagactga cagtggagga cgaggagcgg agaaggcgcg tggcaggacc aaggaccggc | 3420 |
| gatgtgaacc tgagcggagg aggacctagg ggagcaccag gaggcggctt cgtgcctagg | 3480 |
| atggagggag tgccagagtc ccccttttacc aggactggcg agggcctgga catcagggga | 3540 |
| aatcagggat tcccatgggt gcggcctagc ccaccacagc agagactgcc actgctggag | 3600 |
| tgtacacccc agggcacaaa cctgagcaca tccaatccgc tgggcttctt tccagatcat | 3660 |
| caattagatc cagccttcag ggccaactcc gccaatccgg attgggactt caacccgaat | 3720 |
| aaggacactt ggcccgacgc aaacaaggtc ggagggcaaa acctgtctac cagcaatcca | 3780 |
| cttggcttct ttcctgacca tcagctggat cccgcctttc gcgccaatac cgccaatcct | 3840 |
| gactgggact caatcctaa caaagacacc tggcccgacg caaacaaagt ggga | 3894 |

<210> SEQ ID NO 28
<211> LENGTH: 3923
<212> TYPE: DNA
<213> ORGANISM: Artificial Sequence
<220> FEATURE:
<223> OTHER INFORMATION: Delta 4 optimized with restriction sites
      (HindIII /EcoRI)

<400> SEQUENCE: 28

| | |
|---|---|
| aagcttgcac catggccagt cggagcgaat caaagaaaaa taggggaggg cggaagaaa | 60 |
| tcctggagca gtgggtcgga gcacgaaaga aactggaaga actggagagg gacctgcgca | 120 |
| agatcaagaa gaagatcaag aagctggagg aggaaccc ctggctgggc aatatcaagg | 180 |
| gcatcctggg caagaaggat cgggagggag agggagcacc acctgcaaag agggccagag | 240 |
| ccgaccagat ggaggtggat agcggcccta ggaagcgccc attcagaggc gagtttacag | 300 |
| acaaggagcg gagagatcac aggcgccgga aggccctgga gaacaagcgg aagcagctga | 360 |
| gctccggcgg caagtccctg tctaaggagg aggaggagga gctgagaaag ctgaccgagg | 420 |
| aggacgagag aagggagagg agggtggcag gacctagggt gggaggcgtg aacccactgg | 480 |
| agggaggaac aagggggagca cctggaggag gattcgtgcc atccatgcag ggagtgcctg | 540 |
| agtctccatt tgccaggacc ggagagggcc tggatgtgcg cggaaatcag ggcttcccct | 600 |
| gggacatcct gtttcctgcc gatccaccct tctccccaca gtcttgcagg ccacagggaa | 660 |
| ccaacctgag cacatccaat cctctgggct tctttccaga ccaccagctg gatcctgcct | 720 |
| tcagagccaa ctccgccaat ccagactggg acttcaaccc caataaggac acatggcctg | 780 |
| atgccaacaa ggtcggcggc cagaacctgt ctaccagcaa tccctggggc ttctttcctg | 840 |
| accaccagct ggatccagcc ttccgggcca acactgctaa ccctgattgg gacttcaacc | 900 |
| ctaataagga tacctggcca gacgccaaca aggtcggcgg aagcggagct actaacttca | 960 |
| gcctgctgaa gcaggctgga gacgtggagg agaaccctgg acctatgtcc aggtctgaga | 1020 |

-continued

```
gcaagaagaa tagggagga agagaggagg tgctggagca gtgggtgaac ggccgcaaga     1080
agctggagga gctggagagg gagctgagaa gggcccgcaa gaagatcaag aagctggaag     1140
acgataatcc ttggctgggc aatgtgaaag gcatcctggg caagaaggac aaggatggag     1200
agggagcacc tccagcaaag agggcaagaa cagaccagat ggagatcgat tctggaccaa     1260
ggaagcgccc tctgagggga ggcttcaccg accgggagag acaggatcac cgccggagaa     1320
aggccctgaa gaacaagaag aagcagctgt ccgccggcgg caagtccctg agcaaagaag     1380
aggaagagga gctgaagagg ctgacccgcg aggacgagga gcggaagaag gaggagcacg     1440
gaccaagcag actgggagtg aatccttccg agggaggacc aagaggagca cccggaggag     1500
gcttcgtgcc atctatgcag ggcatccccg agagccggtt taccagaaca ggagagggcc     1560
tggacgtgag gggctcccgc ggcttttcctc aggacatcct gttcccatct gatccccctt    1620
ttagcccaca gtcctgtagg ccccagggca ctaacctgag cacatccaac ccactgggct     1680
tctttcctga tcatcagctg acccagcct tccgcgccaa cagcgccaac cctgactggg      1740
acttcaaccc aaataaggac acatggccag atgctaacaa ggtcggagga caaaacctgt     1800
ctaccagcaa ccctctgggc ttcttttcccg atcatcagct ggaccccgcc ttcagggcca    1860
acacagccaa tcccgactgg gacttcaacc cgaataagga cacctggcca gatgcaaaca     1920
aggtcggagg aagcggagct actaacttca gcctgctgaa gcaggctgga gacgtggagg     1980
agaaccctgg acctatgagc cagtctgaga caaggagggg ccggagagga accagggagg     2040
agacactgga gaagtggatc accgccagaa agaaggccga ggagctggag aaggacctgc     2100
ggaagaccaa aaagacaatc aagaagctgg aagaagagaa cccatggctg ggcaatatcg     2160
tgggcatcat ccgcaagggc aaggacggcg agggagcacc accagcaaag aggccccgca     2220
cagatcagat ggaagtggat agcggccctg gcaagaggcc acacaagtcc ggcttcaccg     2280
acaaggagag ggaggaccat aggcgccgga aggccctgga aaacaagaag aagcaattat     2340
ccgccggcgg caagatcctg tccaaagagg aagaagagga gctgagaagg ctgaccgacg     2400
aggatgagga gaggaaaaga agggtggcag gaccaagagt gggcgacgtg aatcccagca     2460
gaggcggacc aagaggagca cctggaggcg gcttcgtgcc ccagatggcc ggcgtgcccg     2520
agtctccttt tagcagaact ggagagggcc tggatatcag gggaacacag ggcttttccat    2580 gggtgagccc atcccctcca cagcagaggc tgccactgct ggagtgcacc cctcagggaa     2640
ccaacctgtc taccagcaac ccgctgggct tctttcccga ccatcagctg gaccctgcct     2700
tccgcgccaa ctccgccaac cctgattggg acttcaaccc gaataaggat acctggcccg     2760
acgctaacaa ggtcggaggc cagaaccctgt ccacctctaa ccccttaggc ttctttcccg    2820
atcaccagct ggatcccgcc ttcagagcca acactgctaa ccccgattgg gacttcaacc     2880
cgaataagga cacgtggcca gacgctaaca aggtcggggg aagcggagct actaacttca     2940
gcctgctgaa gcaggctgga gacgtggagg agaaccctgg acctatgtcg cagtccgagt     3000
ctaagaagaa tagaaggggc ggccgggagg atatcctgga aaaatggatc accacacgca     3060
gaaaagctga gaactggaa aaggacctga ggaaggcccg caagaccatc aagaagctgg      3120
aggatgaaaa tccatggctg gaaacatca tcggcatcat cagaaagggc aaggacgggg      3180
aaggcgcccc acctgcaaag cggcctagaa ccgatcagat ggaaatcgat tctggcacag     3240
gcaagcggcc acacaagagt ggcttcaccg ataaggagag agaggatcac agaaggcgca     3300
aggccctgga gaacaagaag aagcaattaa gcagcggcgg caagatcctg tccagagaag     3360
aagaggagga gctgggcaga ctgacagtgg aggacgagga gcggagaagg cgcgtggcag     3420
```

-continued

```
gaccaaggac cggcgatgtg aacctgagcg gaggaggacc taggggagca ccaggaggcg   3480
gcttcgtgcc taggatggag ggagtgccag agtccccctt taccaggact ggcgagggcc   3540
tggacatcag gggaaatcag ggattcccat gggtgcggcc tagcccacca cagcagagac   3600
tgccactgct ggagtgtaca ccccagggca caaacctgag cacatccaat ccgctgggct   3660
tctttccaga tcatcaatta gatccagcct tcagggccaa ctccgccaat ccggattggg   3720
acttcaaccc gaataaggac acttggcccg acgcaaacaa ggtcggaggg caaaacctgt   3780
ctaccagcaa tccacttggc ttctttcctg accatcagct ggatcccgcc tttcgcgcca   3840
ataccgccaa tcctgactgg gacttcaatc ctaacaaaga cacctggccc gacgcaaaca   3900
aagtgggatg atgagaattc cgt                                           3923
```

<210> SEQ ID NO 29
<211> LENGTH: 1299
<212> TYPE: PRT
<213> ORGANISM: Artificial Sequence
<220> FEATURE:
<223> OTHER INFORMATION: Delta 4 protein

<400> SEQUENCE: 29

```
Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Lys Ala Leu Glu Asn Lys
            100                 105                 110

Arg Lys Gln Leu Ser Ser Gly Lys Ser Leu Ser Lys Glu Glu Glu
        115                 120                 125

Glu Glu Leu Arg Lys Leu Thr Glu Glu Asp Glu Arg Arg Glu Arg Arg
    130                 135                 140

Val Ala Gly Pro Arg Val Gly Val Asn Pro Leu Glu Gly Gly Thr
145                 150                 155                 160

Arg Gly Ala Pro Gly Gly Gly Phe Val Pro Ser Met Gln Gly Val Pro
                165                 170                 175

Glu Ser Pro Phe Ala Arg Thr Gly Glu Gly Leu Asp Val Arg Gly Asn
            180                 185                 190

Gln Gly Phe Pro Trp Asp Ile Leu Phe Pro Ala Asp Pro Phe Ser
        195                 200                 205

Pro Gln Ser Cys Arg Pro Gln Gly Thr Asn Leu Ser Thr Ser Asn Pro
    210                 215                 220

Leu Gly Phe Phe Pro Asp His Gln Leu Asp Pro Ala Phe Arg Ala Asn
225                 230                 235                 240

Ser Ala Asn Pro Asp Trp Asp Phe Asn Pro Asn Lys Asp Thr Trp Pro
                245                 250                 255

Asp Ala Asn Lys Val Gly Gly Gln Asn Leu Ser Thr Ser Asn Pro Leu
            260                 265                 270
```

```
Gly Phe Phe Pro Asp His Gln Leu Asp Pro Ala Phe Arg Ala Asn Thr
        275                 280                 285

Ala Asn Pro Asp Trp Asp Phe Asn Pro Asn Lys Asp Thr Trp Pro Asp
290                 295                 300

Ala Asn Lys Val Gly Gly Ser Gly Ala Thr Asn Phe Ser Leu Leu Lys
305                 310                 315                 320

Gln Ala Gly Asp Val Glu Glu Asn Pro Gly Pro Met Ser Arg Ser Glu
                325                 330                 335

Ser Lys Lys Asn Arg Gly Gly Arg Glu Glu Val Leu Glu Gln Trp Val
                340                 345                 350

Asn Gly Arg Lys Lys Leu Glu Glu Leu Glu Arg Glu Leu Arg Arg Ala
        355                 360                 365

Arg Lys Lys Ile Lys Lys Leu Glu Asp Asp Asn Pro Trp Leu Gly Asn
370                 375                 380

Val Lys Gly Ile Leu Gly Lys Lys Asp Lys Asp Gly Glu Gly Ala Pro
385                 390                 395                 400

Pro Ala Lys Arg Ala Arg Thr Asp Gln Met Glu Ile Asp Ser Gly Pro
                405                 410                 415

Arg Lys Arg Pro Leu Arg Gly Gly Phe Thr Asp Arg Glu Arg Gln Asp
                420                 425                 430

His Arg Arg Arg Lys Ala Leu Lys Asn Lys Lys Lys Gln Leu Ser Ala
        435                 440                 445

Gly Gly Lys Ser Leu Ser Lys Glu Glu Glu Glu Leu Lys Arg Leu
        450                 455                 460

Thr Arg Glu Asp Glu Glu Arg Lys Lys Glu Glu His Gly Pro Ser Arg
465                 470                 475                 480

Leu Gly Val Asn Pro Ser Glu Gly Gly Pro Arg Gly Ala Pro Gly Gly
                485                 490                 495

Gly Phe Val Pro Ser Met Gln Gly Ile Pro Glu Ser Arg Phe Thr Arg
                500                 505                 510

Thr Gly Glu Gly Leu Asp Val Arg Gly Ser Arg Gly Phe Pro Gln Asp
        515                 520                 525

Ile Leu Phe Pro Ser Asp Pro Pro Phe Ser Pro Gln Ser Cys Arg Pro
        530                 535                 540

Gln Gly Thr Asn Leu Ser Thr Ser Asn Pro Leu Gly Phe Phe Pro Asp
545                 550                 555                 560

His Gln Leu Asp Pro Ala Phe Arg Ala Asn Ser Ala Asn Pro Asp Trp
                565                 570                 575

Asp Phe Asn Pro Asn Lys Asp Thr Trp Pro Asp Ala Asn Lys Val Gly
                580                 585                 590

Gly Gln Asn Leu Ser Thr Ser Asn Pro Leu Gly Phe Phe Pro Asp His
                595                 600                 605

Gln Leu Asp Pro Ala Phe Arg Ala Asn Thr Ala Asn Pro Asp Trp Asp
        610                 615                 620

Phe Asn Pro Asn Lys Asp Thr Trp Pro Asp Ala Asn Lys Val Gly Gly
625                 630                 635                 640

Ser Gly Ala Thr Asn Phe Ser Leu Leu Lys Gln Ala Gly Asp Val Glu
                645                 650                 655

Glu Asn Pro Gly Pro Met Ser Gln Ser Glu Thr Arg Arg Gly Arg Arg
                660                 665                 670

Gly Thr Arg Glu Glu Thr Leu Glu Lys Trp Ile Thr Ala Arg Lys Lys
        675                 680                 685
```

```
Ala Glu Glu Leu Glu Lys Asp Leu Arg Lys Thr Arg Lys Thr Ile Lys
    690             695                 700

Lys Leu Glu Glu Glu Asn Pro Trp Leu Gly Asn Ile Val Gly Ile Ile
705             710                 715                 720

Arg Lys Gly Lys Asp Gly Glu Gly Ala Pro Ala Lys Arg Pro Arg
            725                 730                 735

Thr Asp Gln Met Glu Val Asp Ser Gly Pro Gly Lys Arg Pro His Lys
            740                 745                 750

Ser Gly Phe Thr Asp Lys Glu Glu Asp His Arg Arg Lys Ala
            755                 760                 765

Leu Glu Asn Lys Lys Gln Leu Ser Ala Gly Gly Lys Ile Leu Ser
770             775                 780

Lys Glu Glu Glu Glu Leu Arg Arg Leu Thr Asp Glu Asp Glu Glu
785             790                 795                 800

Arg Lys Arg Arg Val Ala Gly Pro Arg Val Gly Asp Val Asn Pro Ser
            805                 810                 815

Arg Gly Gly Pro Arg Gly Ala Pro Gly Gly Phe Val Pro Gln Met
            820                 825                 830

Ala Gly Val Pro Glu Ser Pro Phe Ser Arg Thr Gly Glu Gly Leu Asp
            835                 840                 845

Ile Arg Gly Thr Gln Gly Phe Pro Trp Val Ser Pro Ser Pro Pro Gln
850                 855                 860

Gln Arg Leu Pro Leu Leu Glu Cys Thr Pro Gln Gly Thr Asn Leu Ser
865             870                 875                 880

Thr Ser Asn Pro Leu Gly Phe Phe Pro Asp His Gln Leu Asp Pro Ala
                885                 890                 895

Phe Arg Ala Asn Ser Ala Asn Pro Asp Trp Asp Phe Asn Pro Asn Lys
            900                 905                 910

Asp Thr Trp Pro Asp Ala Asn Lys Val Gly Gly Gln Asn Leu Ser Thr
            915                 920                 925

Ser Asn Pro Leu Gly Phe Phe Pro Asp His Gln Leu Asp Pro Ala Phe
            930                 935                 940

Arg Ala Asn Thr Ala Asn Pro Asp Trp Asp Phe Asn Pro Asn Lys Asp
945                 950                 955                 960

Thr Trp Pro Asp Ala Asn Lys Val Gly Gly Ser Gly Ala Thr Asn Phe
            965                 970                 975

Ser Leu Leu Lys Gln Ala Gly Asp Val Glu Asn Pro Gly Pro Met
            980                 985                 990

Ser Gln Ser Glu Ser Lys Lys Asn Arg Arg Gly Gly Arg Glu Asp Ile
            995                 1000                1005

Leu Glu Lys Trp Ile Thr Thr Arg Arg Lys Ala Glu Glu Leu Glu Lys
1010            1015                1020

Asp Leu Arg Lys Ala Arg Lys Thr Ile Lys Lys Leu Glu Asp Glu Asn
1025            1030                1035                1040

Pro Trp Leu Gly Asn Ile Ile Gly Ile Ile Arg Lys Gly Lys Asp Gly
                1045                1050                1055

Glu Gly Ala Pro Pro Ala Lys Arg Pro Arg Thr Asp Gln Met Glu Ile
            1060                1065                1070

Asp Ser Gly Thr Gly Lys Arg Pro His Lys Ser Gly Phe Thr Asp Lys
            1075                1080                1085

Glu Arg Glu Asp His Arg Arg Lys Ala Leu Glu Asn Lys Lys Lys
            1090                1095                1100

Gln Leu Ser Ser Gly Gly Lys Asn Leu Ser Arg Glu Glu Glu Glu Glu
```

Leu Gly Arg Leu Thr Val Glu Asp Glu Glu Arg Arg Arg Val Ala
1105                1110                1115                1120

Gly Pro Arg Thr Gly Asp Val Asn Leu Ser Gly Gly Pro Arg Gly
       1125                1130                1135

Ala Pro Gly Gly Gly Phe Val Pro Arg Met Glu Gly Val Pro Glu Ser
          1140                1145                1150

Pro Phe Thr Arg Thr Gly Glu Gly Leu Asp Ile Arg Gly Asn Gln Gly
             1155                1160                1165

Phe Pro Trp Val Arg Pro Ser Pro Gln Gln Arg Leu Pro Leu Leu
1170                1175                1180

Glu Cys Thr Pro Gln Gly Thr Asn Leu Ser Thr Ser Asn Pro Leu Gly
1185                1190                1195                1200

Phe Phe Pro Asp His Gln Leu Asp Pro Ala Phe Arg Ala Asn Ser Ala
          1205                1210                1215

Asn Pro Asp Trp Asp Phe Asn Pro Asn Lys Asp Thr Trp Pro Asp Ala
             1220                1225                1230

Asn Lys Val Gly Gly Gln Asn Leu Ser Thr Ser Asn Pro Leu Gly Phe
          1235                1240                1245

Phe Pro Asp His Gln Leu Asp Pro Ala Phe Arg Ala Asn Thr Ala Asn
1250                1255                1260

Pro Asp Trp Asp Phe Asn Pro Asn Lys Asp Thr Trp Pro Asp Ala Asn
1265                1270                1275                1280

Lys Val Gly

<210> SEQ ID NO 30
<211> LENGTH: 2625
<212> TYPE: DNA
<213> ORGANISM: Artificial Sequence
<220> FEATURE:
<223> OTHER INFORMATION: Delta 5 wt

<400> SEQUENCE: 30

```
agccgcagcg aaagcaaaaa aaaccgcggc ggccgcgaag aaattctgga acagtgggtg    60
ggcgcgcgca aaaaactgga agaactggaa cgcgatctgc gcaaaattaa aaaaaaaatt   120
aaaaaactgg aagaagaaaa cccgtggctg gcaacatta aaggcattct gggcaaaaaa    180
gatcgcgaag gcgaaggcgc gccgccggcg aaacgcgcgc gcgcggatca gatggaagtg   240
gatagcggcc gcgcaaacg cccgtttcgc ggcgaattta ccgataaaga acgccgcgat    300
catcgccgcc gcaaagcgct ggaaaacaaa cgcaaacagc tgagcagcgg cggcaaaagc   360
ctgagcaaag aagaagaaga gaactgcgc aaactgaccg aagaagatga acgccgcgaa   420
cgccgcgtgg cgggcccgcg cgtgggcggc gtgaacccgc tggaaggcgg cacccgcggc   480
gcgccgggcg gcggctttgt gccgagcatg cagggcgtgc cggaaagccc gtttgcgcgc   540
accggcgaag gcctggatgt gcgcggcaac cagggcttc cgtgggatat tctgtttccg    600
gcggatccgc cgtttagccc gcagagctgc cgcccgcaga gccgcagcga aagcaaaaaa   660
aaccgcggcg gccgcgaaga agtgctgaa cagtgggtga acggccgcaa aaaactggaa    720
gaactggaac gcgaactgcg ccgcgcgcgc aaaaaaatta aaaaactgga agatgataac   780
ccgtggctgg caacgtgaa aggcattctg ggcaaaaaag ataaagatgg cgaaggcgcg   840
ccgccggcga aacgcgcgcg caccgatcag atggaaattg atagcggccc gcgcaaacgc   900
ccgctgcgcg gcggctttac cgatcgcgaa cgccaggatc atcgccgccg caaagcgctg   960
```

```
aaaaacaaaa aaaaacagct gagcgcgggc ggcaaaagcc tgagcaaaga agaagaagaa      1020
gaactgaaac gcctgacccg cgaagatgaa gaacgcaaaa aagaagaaca tggcccgagc      1080
cgcctgggcg tgaacccgag cgaaggcggc ccgcgcggcg cgccgggcgg cggctttgtg      1140
ccgagcatgc agggcattcc ggaaagccgc tttacccgca ccggcgaagg cctggatgtg      1200
cgcggcagcc gcggctttcc gcaggatatt ctgtttccga gcgatccgcc gtttagcccg      1260
cagagctgcc gcccgcaggg aagcggagct actaacttca gcctgctgaa gcaggctgga      1320
gacgtggagg agaaccctgg acctatgagc cagagcgaaa cccgccgcgg ccgccgcggc      1380
acccgcgaag aaaccctgga aaatggatt  ccgcgcgcga aaaagcgga  agaactggaa      1440
aaagatctgc gcaaaacccg caaaaccatt aaaaaactgg aagaagaaaa cccgtggctg      1500
ggcaacattg tgggcattat tcgcaaaggc aaagatggcg aaggcgcgcc gccggcgaaa      1560
cgccccgcgca ccgatcagat ggaagtggat agcggcccgg gcaaacgccc gcataaaagc      1620
ggctttaccg ataaagaacg cgaagatcat cgccgccgca aagcgctgga aaacaaaaaa      1680
aaacagctga gcgcgggcgg caaaattctg agcaaagaag aagaagaaga actgcgccgc      1740
ctgaccgatg aagatgaaga acgcaaacgc gcgtggcgg  gcccgcgcgt gggcgatgtg      1800
aacccgagcc gcgcggcccc gcgcggccgc ccgggcggcg gctttgtgcc gcagatggcg      1860
ggcgtgccgg aaagcccgtt tagccgcacc ggcgaaggcc tggatattcg cggcacccag      1920
ggctttccgt gggtgagccc gagcccgccc agcagcgcc  tgccgctgct ggaatgcacc      1980
ccgcagagcc agagcgaaag caaaaaaaac cgccgcggcg ccgcgaaga  tattctggaa      2040
aaatggatta ccacccgccg caaagcgaa  gaactggaaa aagatctgcg caaagcgcgc      2100
aaaaccatta aaaactgga  agatgaaaac ccgtggctgg gcaacattat tggcattatt      2160
cgcaaaggca aagatggcga aggcgcgccc ccggcgaaac gcccgcgcac cgatcagatg      2220
gaaattgata gcggcaccgg caaacgcccg cataaaagcg gctttaccga taaagaacgc      2280
gaagatcatc gccgccgcaa agcgctggaa aacaaaaaaa aacagctgag cagcggcggc      2340
aaaaacctga gccgcgaaga agaagaagaa ctgggccgcc tgaccgtgga agatgaagaa      2400
cgccgccgcc gcgtggcggg cccgcgcacc ggcgatgtga acctgagcgg cggcggcccg      2460
cgcggcgcgc cgggcggcgg ctttgtgccg cgcatggaag cgtgccgga  aagcccgttt      2520
acccgcaccg cgaaggcct  ggatattcgc ggcaaccagg gctttccgtg ggtgcgcccg      2580
agcccgccgc agcagcgcct gccgctgctg gaatgcaccc cgcag                     2625
```

<210> SEQ ID NO 31
<211> LENGTH: 2657
<212> TYPE: DNA
<213> ORGANISM: Artificial Sequence
<220> FEATURE:
<223> OTHER INFORMATION: Delta 5 wt with restriction sites (HindIII
      /EcoRI)

<400> SEQUENCE: 31

```
aagcttgcac catggccagc cgcagcgaaa gcaaaaaaaa ccgcggcggc gcgaagaaa       60
ttctggaaca gtgggtgggc gcgcgcaaaa actggaaga  actggaacgc gatctgcgca      120
aaattaaaaa aaaattaaa  aaactggaag aagaaaccc  gtggctgggc aacattaaag      180
gcattctggg caaaaaagat cgcgaaggcg aaggcgcgcc gccggcgaaa cgcgcgcgcg      240
cggatcagat ggaagtggat agcggcccgc gcaaacgccc gtttcgcggc gaatttaccg      300
ataaagaacg ccgcgatcat cgccgccgca aagcgctgga aaacaaacgc aaacagctga      360
```

```
gcagcggcgg caaaagccctg agcaaagaag aagaagaaga actgcgcaaa ctgaccgaag    420
aagatgaacg ccgcgaacgc cgcgtggcgg gcccgcgcgt gggcggcgtg aacccgctgg    480
aaggcggcac ccgcggcgcg ccgggcggcg gctttgtgcc gagcatgcag ggcgtgccgg    540
aaagcccgtt tgcgcgcacc ggcgaaggcc tggatgtgcg cggcaaccag ggctttccgt    600
gggatattct gtttccggcg gatccgccgt ttagcccgca gagctgccgc ccgcagagcc    660
gcagcgaaag caaaaaaaac cgcggcgcc gcgaagaagt gctggaacag tgggtgaacg    720
gccgcaaaaa actggaagaa ctggaacgcg aactgcgccg cgcgcgcaaa aaaattaaaa    780
aactggaaga tgataacccg tggctgggca cgtgaaagg cattctgggc aaaaaagata    840
aagatggcga aggcgcgccg ccggcgaaac gcgcgcgcac cgatcagatg gaaattgata    900
gcggcccgcg caaacgcccg ctgcgcggcg gctttaccga tcgcgaacgc caggatcatc    960
gccgccgcaa agcgctgaaa aacaaaaaaa aacagctgag cgcgggcggc aaaagcctga   1020
gcaaagaaga agaagaagaa ctgaaacgcc tgacccgcga agatgaagaa cgcaaaaaag   1080
aagaacatgg cccgagccgc ctgggcgtga acccgagcga aggcggcccg cgcggcgcgc   1140
cgggcggcgg ctttgtgccg agcatgcagg gcattccgga aagccgcttt acccgcaccg   1200
gcgaaggcct ggatgtgcgc ggcagccgcg gctttccgca ggatattctg tttccgagcg   1260
atccgccgtt tagcccgcag agctgccgcc cgcagggaag cggagctact aacttcagcc   1320
tgctgaagca ggctggagac gtggaggaga accctggacc tatgagccag agcgaaaccc   1380
gccgcggccg ccgcggcacc cgcgaagaaa ccctggaaaa atggattacc gcgcgcaaaa   1440
aagcggaaga actggaaaaa gatctgcgca aaacccgcaa aaccattaaa aaactggaag   1500
aagaaaaccc gtggctgggc aacattgtgg gcattattcg caaaggcaaa gatggcgaag   1560
gcgcgccgcc ggcgaaacgc ccgcgcaccg atcagatgga agtggatagc ggcccgggca   1620
aacgcccgca taaaagcggc tttaccgata agaacgcga agatcatcgc cgccgcaaag   1680
cgctggaaaa caaaaaaaaa cagctgagcg cgggcggcaa aattctgagc aaagaagaag   1740
aagaagaact gcgccgcctg accgatgaag atgaagaacg caaacgccgc gtggcgggcc   1800
cgcgcgtggg cgatgtgaac ccgagccgcg cggcccgcg cggcgcgccg ggcggcggct   1860 tgtgccgca gatggcgggc gtgccggaaa gcccgtttag ccgcaccggc gaaggcctgg   1920
atattcgcgg cacccagggc tttccgtggg tgagcccgag cccgccgcag cagcgcctgc   1980
cgctgctgga atgcacccg cagagccaga gcgaaagcaa aaaaaaccgc gcggcggcc   2040 gcgaagatat tctggaaaaa tggattacca cccgccgcaa agcggaagaa ctggaaaaag   2100
atctgcgcaa agcgcgcaaa accattaaaa aactggaaga tgaaacccg tggctgggca   2160 acattattgg cattattcgc aaaggcaaag atggcgaagg cgcgccgccg gcgaaacgcc   2220
cgcgcaccga tcagatggaa attgatagcg gcaccggcaa acgcccgcat aaaagcggct   2280
ttaccgataa agaacgcgaa gatcatcgcc gccgcaaagc gctggaaaac aaaaaaaaac   2340
agctgagcag cggcggcaaa aacctgagcc gcgaagaaga agaagaactg gccgccctga   2400
ccgtggaaga tgaagaacgc cgccgcgcg tggcgggccc gcgcaccggc gatgtgaacc   2460
tgagcggcgc cggcccgcgc ggcgcgccgg gcggcggctt tgtgccgcgc atggaaggcg   2520
tgccggaaag cccgtttacc cgcaccggcg aaggcctgga tattcgcggc aaccagggct   2580
ttccgtgggt gcgcccgagc ccgccgcagc agcgcctgcc gctgctggaa tgcacccgc   2640 agtgatgaga attccgt                                                   2657
```

<210> SEQ ID NO 32
<211> LENGTH: 2628
<212> TYPE: DNA
<213> ORGANISM: Artificial Sequence
<220> FEATURE:
<223> OTHER INFORMATION: Delta 5 codon optimized

<400> SEQUENCE: 32

```
gcctcacggt cagagtcaaa gaaaaatagg gggggcggg aagaaatcct ggaacagtgg      60
gtcggagcac ggaaaaaact ggaagagctg gagagggacc tgcgcaagat caagaagaag     120
atcaagaagc tggaggagga aacccctgg ctgggcaata tcaagggcat cctgggcaag     180
aaggatcggg agggagaggg agcaccacct gcaaagaggg ccagagccga ccagatggag    240
gtggatagcg gccctaggaa gcgcccattc agaggcgagt ttaccgacaa ggagcggaga    300
gatcacaggc gccggaaggc cctggagaac aagcggaagc agctgagctc cggcggcaag    360
tccctgtcta aggaggagga ggaggagctg agaaagctga cagaggagga cgagagaagg    420
gagcgccggg tggccggccc aagggtgggc ggcgtgaacc ccctggaggg aggaaccagg    480
ggagcacctg gaggaggctt cgtgccatct atgcagggcg tgcctgagag cccatttgcc    540
aggacaggag agggcctgga tgtgcgcggc aatcagggct tcccctggga catcctgttt    600
cctgccgatc caccccttcag cccacagtcc tgcaggcctc agagcagatc cgagtctaag    660
aagaacaggg gaggaagaga ggaggtgctg gagcagtggg tgaatggccg gaagaagctg    720
gaggagctgg agcgggagct gagaagggcc agaaagaaga tcaagaagct ggaagacgat    780
aatccttggc tgggcaatgt gaaaggcatc ctgggcaaga aggacaagga tggagaggga    840
gcacctccag caaagagggc aagaaccgac cagatggaga tcgatagcgg accaaggaag    900
cgccctctga ggaggcttt cacagaccgg gagagacagg atcaccgccg gagaaaggcc    960
ctgaagaaca agaagaagca gctgtccgcc ggaggcaaga gcctgtccaa gaagaggaa   1020
gaggagctga gaggctgac cgcgaggac gaggagcgga gaaggagga gcacggccct   1080
tccagactgg gcgtgaatcc atctgaggga ggaccaaggg gagcaccagg cggcggcttc   1140
gtgccaagca tgcagggcat ccccgagtcc cggtttacca gaacaggaga gggcctggac   1200
gtgaggggct ctcgcggctt tcctcaggac atcctgttcc caagcgatcc ccttttct    1260
ccacagagct gtcgccccca gggaagcgga gctactaact tcagcctgct gaagcaggct   1320
ggagacgtgg aggagaaccc tggacctatg tctcagagcg acaaggag gggccggaga   1380
ggaaccaggg aggagacact ggagaagtgg atcacagcca aaagaaggc cgaggagctg   1440
gagaaggacc tgcggaagac cagaaagaca atcaagaagc tggaagaaga aaatccatgg   1500
ctgggaaata tcgtgggcat catcaggaag ggcaaggacg gcgagggagc accaccagcc   1560
aagaggcctc gcactgatca gatggaggtg gattccggcc ctgcaagag gccacacaag   1620
tctggcttca cagacaagga gagggaggac ataggcgcc ggaaggccct ggaaaacaag   1680
aagaagcaat tatctgccgg cggcaagatc ctgagcaaag aggaagagga ggagctgaga   1740
aggctgaccg acgaggatga ggagaggaag aggagggtgg caggaccaag agtgggcgac   1800
gtgaatcccta gcagaggcgg accaagaggc gccccaggcg ggggcttcgt gccacagatg   1860
gcaggagtgc cagagtcccc ttttctagg accgagagg gcctggatat caggggaaca   1920
cagggctttc catgggtgtc cccatctcct ccacagcaga ggctgccact gctggagtgc   1980
accccctcaga gccagtccga gtctaagaag aatagaaggg gcgccggcga ggacatcctg   2040
gagaagtgga tcaccacacg cagaaaagct gaagaactgg aaaggaccct gaggaaggcc   2100
```

```
cgcaaaacaa tcaagaagct ggaggatgag aacccttggc tgggcaatat catcggaatt    2160
atcaggaagg gcaaggatgg cgaaggcgcc ccacctgcaa agcggccaag gactgatcag    2220
atggaaatcg atagcggaac aggcaagcgg ccccacaagt ccggcttcac cgacaaggag    2280
agagaggatc acagaaggcg caaggccctg gagaacaaga gaagcaatt aagcagcggc    2340 ggcaagaatc tgtccagaga agaagaggag gagctgggca gactgaccgt ggaggacgag    2400
gagcggagaa ggcgcgtggc aggacctcgc acaggcgatg tgaacctgtc cggaggagga    2460
cctaggggag caccaggagg cggcttcgtg ccacgcatgg agggcgtgcc agagtctccc    2520
tttacccgca ccggagaggg cctggacatc aggggcaatc agggcttcc ctgggtccgc    2580 ccctcccccc ctcagcagag actgcccctg ctggaatgca caccacag              2628
```

<210> SEQ ID NO 33
<211> LENGTH: 2657
<212> TYPE: DNA
<213> ORGANISM: Artificial Sequence
<220> FEATURE:
<223> OTHER INFORMATION: Delta 5 codon optimized with restriction sites
      (HindIII /EcoRI)

<400> SEQUENCE: 33

```
aagcttgcac catggcctca cggtcagagt caaagaaaaa tagggggggg cgggaagaaa      60
tcctggaaca gtgggtcgga gcacggaaaa aactggaaga gctggagagg gacctgcgca    120
agatcaagaa gaagatcaag aagctggagg aggagaaccc ctggctgggc aatatcaagg    180
gcatcctggg caagaaggat cgggaggag agggagcacc acctgcaaag agggccagag    240
ccgaccagat ggaggtggat agcggcccta ggaagcgccc attcagaggc gagtttaccg    300
acaaggagcg gagagatcac aggcgccgga aggccctgga gaacaagcgg aagcagctga    360
gctccggcgg caagtccctg tctaaggagg aggaggagga gctgagaaag ctgacagagg    420
aggacgagag aagggagcgc cgggtggccg gcccaagggt gggcggcgtg aaccccctgg    480
agggaggaac caggggagca cctggaggag gcttcgtgcc atctatgcag ggcgtgcctg    540
agagcccatt tgccaggaca ggagagggcc tggatgtgcg cggcaatcag ggcttcccct    600
gggacatcct gtttcctgcc gatccaccct tcagcccaca gtcctgcagg cctcagagca    660
gatccgagtc taagaagaac agggggaggaa gagaggaggt gctggagcag tgggtgaatg    720
gccggaagaa gctggaggag ctgagcgggg agctgagaag ggccagaaag aagatcaaga    780
agctggaaga cgataatcct tggctgggca atgtgaaagg catcctgggc aagaaggaca    840
aggatggaga gggagcacct ccagcaaaga gggcaagaac cgaccagatg gagatcgata    900
gcggaccaag gaagcgccct ctgagaggag gcttcacaga ccgggagaga caggatcacc    960 gccgagaaa ggccctgaag aacaagaaga agcagctgtc cgccgaggc aagagcctgt    1020 ccaaagaaga ggaagaggag ctgaagaggc tgacccgcga ggacgaggag cggaagaagg    1080
aggagcacgc cccttccaga ctgggcgtga atccatctga gggaggacca aggggagcac    1140
caggcggcgg cttcgtgcca agcatgcagg gcatccccga gtcccggttt accagaacag    1200
gagagggcct ggacgtgagg ggctctcgcg gctttcctca ggacatcctg ttcccaagcg    1260
atcccccttt ttctccacag agctgtcgcc cccaggggaag cggagctact aacttcagcc    1320
tgctgaagca ggctggagac gtggaggaga accctggacc tatgtctcag agcgagacaa    1380 ggagggggccg agaggaacc agggaggaga cactggagaa gtggatcaca gccagaaaga    1440
aggccgagga gctggagaag gacctgcgga agaccagaaa gacaatcaag aagctggaag    1500
```

```
aagaaaatcc atggctggga aatatcgtgg gcatcatcag gaagggcaag gacggcgagg    1560
gagcaccacc agccaagagg cctcgcactg atcagatgga ggtggattcc ggccctggca    1620
agaggccaca caagtctggc ttcacagaca aggagaggga ggaccatagg cgccggaagg    1680
ccctggaaaa caagaagaag caattatctg ccggcggcaa gatcctgagc aaagaggaag    1740
aggaggagct gagaaggctg accgacgagg atgaggagag gaagaggagg gtggcaggac    1800
caagagtggg cgacgtgaat cctagcagag gcggaccaag aggcgcccca ggcggggggct    1860 tcgtgccaca gatggcagga gtgccagagt ccccttttc taggaccgga gagggcctgg    1920
atatcagggg aacacagggc tttccatggg tgtccccatc tcctccacag cagaggctgc    1980
cactgctgga gtgcacccct cagagccagt ccgagtctaa gaagaataga aggggcggcc    2040
gcgaggacat cctggagaag tggatcacca cacgcagaaa agctgaagaa ctggaaaagg    2100
acctgaggaa ggcccgcaaa acaatcaaga agctggagga tgagaaccct tggctgggca    2160
atatcatcgg aattatcagg aagggcaagg atggcgaagg cgccccacct gcaaagcggc    2220
caaggactga tcagatggaa atcgatacg gaacaggcaa gcggcccac aagtccggct    2280 tcaccgacaa ggagagagag gatcacagaa ggcgcaaggc cctggagaac aagaagaagc    2340
aattaagcag cggcggcaag aatctgtcca gagaagaaga ggaggagctg ggcagactga    2400
ccgtggagga cgaggagcgg agaaggcgcg tggcaggacc tcgcacaggc gatgtgaacc    2460
tgtccggagg aggacctagg ggagcaccag gaggcggctt cgtgccacgc atggagggcg    2520
tgccagagtc tccctttacc cgcaccggag agggcctgga catcaggggc aatcagggct    2580
ttccctgggt ccgcccctcc ccccctcagc agagactgcc cctgctggaa tgcacaccac    2640
agtgatgaga attccgt                                                  2657
```

<210> SEQ ID NO 34
<211> LENGTH: 877
<212> TYPE: PRT
<213> ORGANISM: Artificial Sequence
<220> FEATURE:
<223> OTHER INFORMATION: Delta 5 protein

<400> SEQUENCE: 34

```
Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Ala Lys Arg Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Lys Ala Leu Glu Asn Lys
            100                 105                 110

Arg Lys Gln Leu Ser Ser Gly Gly Lys Ser Leu Ser Lys Glu Glu Glu
        115                 120                 125

Glu Glu Leu Arg Lys Leu Thr Glu Glu Asp Glu Arg Arg Glu Arg Arg
    130                 135                 140

Val Ala Gly Pro Arg Val Gly Gly Val Asn Pro Leu Glu Gly Gly Thr
145                 150                 155                 160
```

-continued

```
Arg Gly Ala Pro Gly Gly Phe Val Pro Ser Met Gln Gly Val Pro
            165                 170                 175

Glu Ser Pro Phe Ala Arg Thr Gly Glu Gly Leu Asp Val Arg Gly Asn
        180                 185                 190

Gln Gly Phe Pro Trp Asp Ile Leu Phe Pro Ala Asp Pro Pro Phe Ser
        195                 200                 205

Pro Gln Ser Cys Arg Pro Gln Ser Arg Ser Glu Ser Lys Lys Asn Arg
        210                 215                 220

Gly Gly Arg Glu Glu Val Leu Glu Gln Trp Val Asn Gly Arg Lys Lys
225                 230                 235                 240

Leu Glu Glu Leu Glu Arg Glu Leu Arg Arg Ala Arg Lys Lys Ile Lys
                245                 250                 255

Lys Leu Glu Asp Asp Asn Pro Trp Leu Gly Asn Val Lys Gly Ile Leu
            260                 265                 270

Gly Lys Lys Asp Lys Asp Gly Glu Gly Ala Pro Pro Ala Lys Arg Ala
        275                 280                 285

Arg Thr Asp Gln Met Glu Ile Asp Ser Gly Pro Arg Lys Arg Pro Leu
        290                 295                 300

Arg Gly Gly Phe Thr Asp Arg Glu Arg Gln Asp His Arg Arg Arg Lys
305                 310                 315                 320

Ala Leu Lys Asn Lys Lys Gln Leu Ser Ala Gly Lys Ser Leu
                325                 330                 335

Ser Lys Glu Glu Glu Glu Leu Lys Arg Leu Thr Arg Glu Asp Glu
            340                 345                 350

Glu Arg Lys Lys Glu Glu His Gly Pro Ser Arg Leu Gly Val Asn Pro
        355                 360                 365

Ser Glu Gly Gly Pro Arg Gly Ala Pro Gly Gly Phe Val Pro Ser
        370                 375                 380

Met Gln Gly Ile Pro Glu Ser Arg Phe Thr Arg Thr Gly Glu Gly Leu
385                 390                 395                 400

Asp Val Arg Gly Ser Arg Gly Phe Pro Gln Asp Ile Leu Phe Pro Ser
                405                 410                 415

Asp Pro Pro Phe Ser Pro Gln Ser Cys Arg Pro Gln Ser Gly Ala
            420                 425                 430

Thr Asn Phe Ser Leu Leu Lys Gln Ala Gly Asp Val Glu Glu Asn Pro
        435                 440                 445

Gly Pro Met Ser Gln Ser Glu Thr Arg Arg Gly Arg Arg Gly Thr Arg
        450                 455                 460

Glu Glu Thr Leu Glu Lys Trp Ile Thr Ala Arg Lys Lys Ala Glu Glu
465                 470                 475                 480

Leu Glu Lys Asp Leu Arg Lys Thr Arg Lys Thr Ile Lys Lys Leu Glu
                485                 490                 495

Glu Glu Asn Pro Trp Leu Gly Asn Ile Val Gly Ile Ile Arg Lys Gly
            500                 505                 510

Lys Asp Gly Glu Gly Ala Pro Pro Ala Lys Arg Pro Arg Thr Asp Gln
        515                 520                 525

Met Glu Val Asp Ser Gly Pro Gly Lys Arg Pro His Lys Ser Gly Phe
        530                 535                 540

Thr Asp Lys Glu Arg Glu Asp His Arg Arg Arg Lys Ala Leu Glu Asn
545                 550                 555                 560

Lys Lys Lys Gln Leu Ser Ala Gly Gly Lys Ile Leu Ser Lys Glu Glu
                565                 570                 575
```

```
Glu Glu Glu Leu Arg Arg Leu Thr Asp Glu Asp Glu Glu Arg Lys Arg
                575                 580                 585                 590

Arg Val Ala Gly Pro Arg Val Gly Asp Val Asn Pro Ser Arg Gly Gly
                595                 600                 605

Pro Arg Gly Ala Pro Gly Gly Gly Phe Val Pro Gln Met Ala Gly Val
                610                 615                 620

Pro Glu Ser Pro Phe Ser Arg Thr Gly Glu Gly Leu Asp Ile Arg Gly
625                 630                 635                 640

Thr Gln Gly Phe Pro Trp Val Ser Pro Ser Pro Gln Gln Arg Leu
                645                 650                 655

Pro Leu Leu Glu Cys Thr Pro Gln Ser Gln Ser Glu Ser Lys Lys Asn
                660                 665                 670

Arg Arg Gly Gly Arg Glu Asp Ile Leu Glu Lys Trp Ile Thr Thr Arg
                675                 680                 685

Arg Lys Ala Glu Glu Leu Glu Lys Asp Leu Arg Lys Ala Arg Lys Thr
                690                 695                 700

Ile Lys Lys Leu Glu Asp Glu Asn Pro Trp Leu Gly Asn Ile Ile Gly
705                 710                 715                 720

Ile Ile Arg Lys Gly Lys Asp Gly Glu Gly Ala Pro Ala Lys Arg
                725                 730                 735

Pro Arg Thr Asp Gln Met Glu Ile Asp Ser Gly Thr Gly Lys Arg Pro
                740                 745                 750

His Lys Ser Gly Phe Thr Asp Lys Glu Arg Glu Asp His Arg Arg Arg
                755                 760                 765

Lys Ala Leu Glu Asn Lys Lys Lys Gln Leu Ser Ser Gly Gly Lys Asn
                770                 775                 780

Leu Ser Arg Glu Glu Glu Glu Leu Gly Arg Leu Thr Val Glu Asp
785                 790                 795                 800

Glu Glu Arg Arg Arg Val Ala Gly Pro Arg Thr Gly Asp Val Asn
                805                 810                 815

Leu Ser Gly Gly Gly Pro Arg Gly Ala Pro Gly Gly Phe Val Pro
                820                 825                 830

Arg Met Glu Gly Val Pro Glu Ser Pro Phe Thr Arg Thr Gly Glu Gly
                835                 840                 845

Leu Asp Ile Arg Gly Asn Gln Gly Phe Pro Trp Val Arg Pro Ser Pro
850                 855                 860

Pro Gln Gln Arg Leu Pro Leu Leu Glu Cys Thr Pro Gln
865                 870                 875
```

<210> SEQ ID NO 35
<211> LENGTH: 2763
<212> TYPE: DNA
<213> ORGANISM: Artificial Sequence
<220> FEATURE:
<223> OTHER INFORMATION: Delta 6 wt

<400> SEQUENCE: 35

```
agccgcagcg aaagcaaaaa aaaccgcggc ggccgcgaag aaattctgga acagtgggtg      60
ggcgcgcgca aaaactgga agaactggaa cgcgatctgc gcaaaattaa aaaaaaaatt     120
aaaaaactgg aagaagaaaa cccgtggctg ggcaacatta aaggcattct ggcaaaaaaa     180
gatcgcgaag gcgaaggcgc gccgccggcg aaacgcgcgc gcgcggatca gatggaagtg     240
gatagcggcc gcgcaaacg cccgtttcgc ggcgaattta ccgataaaga acgccgcgat     300
catcgccgcc gcaaagcgct ggaaaacaaa cgcaaacagc tgagcagcgg cggcaaaagc     360
```

```
ctgagcaaag aagaagaaga agaactgcgc aaactgaccg aagaagatga acgccgcgaa    420
cgccgcgtgg cgggcccgcg cgtgggcggc gtgaacccgc tggaaggcgg cacccgcggc    480
gcgccgggcg gcggctttgt gccgagcatg cagggcgtgc cggaaagccc gtttgcgcgc    540
accggcgaag gcctggatgt gcgcggcaac cagggctttc cgtgggatat tctgtttccg    600
gcggatccgc cgtttagccc gcagagctgc cgcccgcagg gaagcggagc tactaacttc    660
agcctgctga gcaggctgg agacgtggag gagaaccctg gacctatgag ccgcagcgaa    720
agcaaaaaaa accgcggcgg ccgcgaagaa gtgctggaac agtgggtgaa cggccgcaaa    780
aaactggaag aactggaacg cgaactgcgc cgcgcgcgca aaaaaattaa aaaactggaa    840
gatgataacc cgtggctggg caacgtgaaa ggcattctgg gcaaaaaaga taaagatggc    900
gaaggcgcgc cgccggcgaa acgcgcgcgc accgatcaga tggaaattga tagcggcccg    960
cgcaaacgcc cgctgcgcgg cggctttacc gatcgcgaac gccaggatca tcgccgccgc   1020
aaagcgctga aaacaaaaa aaacagctg agcgcgggcg gcaaaagcct gagcaaagaa   1080
gaagaagaag aactgaaacg cctgacccgc gaagatgaag aacgcaaaaa agaagaacat   1140
ggcccgagcc gcctgggcgt gaacccgagc gaaggcggcc cgcgcggcgc gccgggcggc   1200
ggctttgtgc cgagcatgca gggcattccg gaaagccgct ttacccgcac cggcgaaggc   1260
ctggatgtgc gcggcagccg cggctttccg caggatattc tgtttccgag cgatccgccg   1320
tttagcccgc agagctgccg cccgcaggga agcggagcta ctaacttcag cctgctgaag   1380
caggctggag acgtggagga gaaccctgga cctatgagcc agagcgaaac cgccgcggc   1440
cgccgcggca cccgcgaaga aaccctggaa aatggattac cgcgcgcaa aaaagcggaa   1500
gaactggaaa aagatctgcg caaaacccgc aaaaccatta aaaactgga agaagaaaac   1560
ccgtggctgg gcaacattgt gggcattatt cgcaaaggca agatggcga aggcgcgccg   1620
ccggcgaaac gcccgcgcac cgatcagatg gaagtggata gcggcccggg caaacgcccg   1680
cataaaagcg gctttaccga taaagaacgc gaagatcatc gccgccgcaa agcgctggaa   1740
aacaaaaaaa aacagctgag cgcgggcggc aaaattctga gcaaagaaga agaagaagaa   1800
ctgcgccgcc tgaccgatga agatgaagaa cgcaaacgcc gcgtggcggg cccgcgcgtg   1860
ggcgatgtga acccgagccg cggcggcccg cgcggcgcgc cgggcggcgg ctttgtgccg   1920
cagatggcgg gcgtgccgga aagcccgttt agccgcaccg cgaaggcct ggatattcgc   1980
ggcacccagg gctttccgtg ggtgagcccg agcccgccgc agcagcgcct gccgctgctg   2040
gaatgcaccc gcagggaag cggagctact aacttcagcc tgctgaagca ggctggagac   2100
gtggaggaga accctggacc tatgagccag agcgaaagca aaaaaaaccg ccgcggcggc   2160
cgcgaagata ttctggaaaa atggattacc cccgccgca aagcggaaga actggaaaaa   2220
gatctgcgca aagcgcgcaa aaccattaaa aaactggaag atgaaaaccc gtggctgggc   2280
aacattattg gcattattcg caaaggcaaa gatggcgaag gcgcgccgcc ggcgaaacgc   2340
ccgcgcaccg atcagatgga aattgatagc ggcaccggca acgcccgca taaaagcggc   2400
tttaccgata agaacgcga agatcatcgc cgccgcaaag cgctggaaaa caaaaaaaaa   2460
cagctgagca gcgcggcaa aaacctgagc gcgaagaa aagaagaact gggccgcctg   2520
accgtggaag atgaagaacg ccgccgccgc gtggcgggcc cgcgcaccgg cgatgtgaac   2580
ctgagcggcg gcgccccgcg cggcgcgccg gcggcggct tgtgccgcg catggaaggc   2640
gtgccggaaa gcccgtttac ccgcaccggc gaaggcctgg atattcgcgg caaccagggc   2700
tttccgtggg tgcgcccgag cccgccgcag cagcgcctgc cgctgctgga atgcacccg   2760
``` cag                                                                    2763

<210> SEQ ID NO 36
<211> LENGTH: 2795
<212> TYPE: DNA
<213> ORGANISM: Artificial Sequence
<220> FEATURE:
<223> OTHER INFORMATION: Delta 6 wt with restriction sites (HindIII
      /EcoRI)

<400> SEQUENCE: 36

| | | | | | |
|---|---|---|---|---|---|
| aagcttgcac | catggccagc | cgcagcgaaa | gcaaaaaaaa | ccgcggcggc | cgcgaagaaa | 60 |
| ttctggaaca | gtgggtgggc | gcgcgcaaaa | aactggaaga | actggaacgc | gatctgcgca | 120 |
| aaattaaaaa | aaaaattaaa | aaactggaag | aagaaaaccc | gtggctgggc | aacattaaag | 180 |
| gcattctggg | caaaaaagat | cgcgaaggcg | aaggcgcgcc | gccggcgaaa | cgcgcgcgcg | 240 |
| cggatcagat | ggaagtggat | agcggcccgc | gcaaacgccc | gtttcgcggc | gaatttaccg | 300 |
| ataaagaacg | ccgcgatcat | cgccgccgca | aagcgctgga | aaacaaacgc | aaacagctga | 360 |
| gcagcggcgg | caaaagcctg | agcaaagaag | aagaagaaga | actgcgcaaa | ctgaccgaag | 420 |
| aagatgaacg | ccgcgaacgc | cgcgtggcgg | gcccgcgcgt | gggcggcgtg | aacccgctgg | 480 |
| aaggcggcac | ccgcggcgcg | ccgggcggcg | gctttgtgcc | gagcatgcag | ggcgtgccgg | 540 |
| aaagcccgtt | tgcgcgcacc | ggcgaaggcc | tggatgtgcg | cggcaaccag | ggcttttccgt | 600 |
| gggatattct | gtttccggcg | gatccgccgt | ttagcccgca | gagctgccgc | ccgcagggaa | 660 |
| gcggagctac | taacttcagc | ctgctgaagc | aggctggaga | cgtggaggag | aaccctggac | 720 |
| ctatgagccg | cagcgaaagc | aaaaaaaacc | gcggcggccg | cgaagaagtg | ctggaacagt | 780 |
| gggtgaacgg | ccgcaaaaaa | ctggaagaac | tggaacgcga | actgcgccgc | gcgcgcaaaa | 840 |
| aaattaaaaa | actggaagat | gataacccgt | ggctgggcaa | cgtgaaaggc | attctgggca | 900 |
| aaaaagataa | agatggcgaa | ggcgcgccgc | cggcgaaacg | cgcgcgcacc | gatcagatgg | 960 |
| aaattgatag | cggcccgcgc | aaacgcccgc | tgcgcggcgg | ctttaccgat | cgcgaacgcc | 1020 |
| aggatcatcg | ccgccgcaaa | gcgctgaaaa | acaaaaaaaa | acagctgagc | gcgggcggca | 1080 |
| aaagcctgag | caaagaagaa | gaagaagaac | tgaaacgcct | gacccgcgaa | gatgaagaac | 1140 |
| gcaaaaaaga | agaacatggc | ccgagccgcc | tgggcgtgaa | cccgagcgaa | ggcggccccgc | 1200 |
| gcggcgcgcc | gggcggcggc | tttgtgccga | gcatgcaggg | cattccggaa | agccgcttta | 1260 |
| cccgcaccgg | cgaaggcctg | gatgtgcgcg | gcagccgcgg | cttccgcag | gatattctgt | 1320 |
| ttccgagcga | tccgccgttt | agcccgcaga | gctgccgccc | gcagggaagc | ggagctacta | 1380 |
| acttcagcct | gctgaagcag | gctggagacg | tggaggagaa | ccctggacct | atgagccaga | 1440 |
| gcgaaacccg | ccgcggccgc | cgcggcaccc | gcgaagaaac | cctggaaaaa | tggattaccg | 1500 |
| cgcgcaaaaa | agcggaagaa | ctggaaaaag | atctgcgcaa | acccgcaaa | accattaaaa | 1560 |
| aactggaaga | agaaaacccg | tggctgggca | acattgtggg | cattattcgc | aaaggcaaag | 1620 |
| atggcgaagg | cgcgccgccg | gcgaaacgcc | cgcgcaccga | tcagatggaa | gtggatagcg | 1680 |
| gcccgggcaa | acgcccgcat | aaaagcggct | ttaccgataa | agaacgcgaa | gatcatcgcc | 1740 |
| gccgcaaagc | gctggaaaac | aaaaaaaaac | agctgagcgc | gggcggcaaa | attctgagca | 1800 |
| aagaagaaga | agaagaactg | cgccgcctga | ccgatgaaga | tgaagaacgc | aaacgccgcg | 1860 |
| tggcgggccc | gcgcgtgggc | gatgtgaacc | cgagccgcgg | cggcccgcgc | ggcgcgccgg | 1920 |
| gcggcggctt | tgtgccgcag | atggcgggcg | tgccggaaag | cccgtttagc | cgcaccggcg | 1980 |

```
aaggcctgga tattcgcggc acccagggct ttccgtgggt gagcccgagc ccgccgcagc    2040
agcgcctgcc gctgctggaa tgcacccccgc agggaagcgg agctactaac ttcagcctgc    2100
tgaagcaggc tggagacgtg gaggagaacc ctggacctat gagccagagc gaaagcaaaa    2160
aaaaccgccg cggcggccgc gaagatattc tggaaaaatg gattaccacc cgccgcaaag    2220
cggaagaact ggaaaaagat ctgcgcaaag cgcgcaaaac cattaaaaaa ctggaagatg    2280
aaaacccgtg gctgggcaac attattggca ttattcgcaa aggcaaagat ggcgaaggcg    2340
cgccgccggc gaaacgcccg cgcaccgatc agatggaaat tgatagcggc accggcaaac    2400
gcccgcataa aagcggcttt accgataaag aacgcgaaga tcatcgccgc cgcaaagcgc    2460
tggaaaacaa aaaaaaacag ctgagcagcg gcggcaaaaa cctgagccgc gaagaagaag    2520
aagaactggg ccgcctgacc gtggaagatg aagaacgccg ccgccgcgtg gcgggcccgc    2580
gcaccggcga tgtgaacctg agcggcggcg gcccgcgcgg cgcgccgggc ggcggctttg    2640
tgccgcgcat ggaaggcgtg ccggaaagcc cgtttacccg caccggcgaa ggcctggata    2700
ttcgcggcaa ccagggctttt ccgtgggtgc gcccgagccc gccgcagcag cgcctgccgc    2760
tgctggaatg cacccccgcag tgatgagaat tccgt                              2795

<210> SEQ ID NO 37
<211> LENGTH: 2766
<212> TYPE: DNA
<213> ORGANISM: Artificial Sequence
<220> FEATURE:
<223> OTHER INFORMATION: Delta 6 codon optimized

<400> SEQUENCE: 37
gcctcacggt cagagtcaaa gaagaacaga ggcggaagag aagaaatcct ggagcagtgg      60
gtcggagcac ggaaaaagct ggaagaactg gagagggacc tgcgcaagat caagaagaag     120
atcaagaagc tggaggagga gaaccccctgg ctgggcaata tcaagggcat cctgggcaag    180
aaggataggg agggagaggg agcaccacct gcaaagaggg ccagagccga ccagatggag    240
gtggatagcg gaccaaggaa gcgccccttc cgcggagagt ttaccgacaa ggagcggaga    300
gatcacaggc gccggaaggc cctggagaac aagaggaagc agctgagctc cggcggcaag    360
tccctgtcta aggaggagga ggaggagctg cgcaagctga cagaggagga cgagagaagg    420
gagaggaggg tggcaggacc aagggtggga ggagtgaatc ctctggaggg aggaaccaga    480
ggagcaccag gaggaggctt cgtgccaagc atgcagggag tgccagagtc ccccttttgcc    540 aggacaggag agggcctgga cgtgagaggc aaccagggct tccccttggga catcctgttt    600 ccagccgatc caccccttcag ccctcagtcc tgcaggccac agggaagcgg agctactaac    660
ttcagcctgc tgaagcaggc tggagacgtg gaggagaacc ctggacctat gagccggtcc    720
gagtctaaga gaataggggg aggaagagag gaggtgctgg agcagtgggt gaacggcaga    780
aagaagctgg aggagctgga gggagctg agaagggccc gcaagaagat caagaagctg    840
gaagacgata atccttggct gggcaatgtg aaaggcatcc tgggcaagaa ggacaaggat    900
ggagagggag cacctccagc aaagagggca agaaccgacc agatggagat cgatagcgga    960
cctaggaagc gcccactgag gggaggctt acagaccggg agacagga tcaccgccgg    1020 agaaaggccc tgaagaacaa gaagaagcag ctgtccgccg gaggcaagag cctgtccaaa    1080
gaagaggaag aggagctgaa gaggctgacc cgcgaggacg aggagaggaa gaaggaggag    1140
cacggaccat ctaggctggg agtgaatccc agcgagggag gaccaagggg agcacctgga    1200
```

-continued

```
ggaggcttcg tgccctccat gcagggcatc cctgagtctc ggtttaccag aaccggcgag      1260
ggcctggacg tgaggggcag ccgcggcttt ccacaggaca tcctgttccc ctccgatccc      1320
cctttttctc cccagagctg tcgccctcaa ggaagcggag ctactaactt cagcctgctg      1380
aagcaggctg gagacgtgga ggagaaccct ggacctatgt ctcagagcga gacaaggagg      1440
ggccggagag gaaccaggga ggagacactg gagaagtgga tcacagcccg caagaaggcc      1500
gaggagctgg agaaggacct gcggaagacc agaaagacaa tcaagaagct ggaagaagag      1560
aacccttggc tgggcaatat cgtgggcatc atcaggaagg caaggacgg cgagggagca      1620 ccaccagcca agaggccacg cactgatcag atggaggtgg attctggacc aggcaagcgg      1680
ccccacaaga gcggcttcac agacaaggag agagaggacc ataggcgccg aaggccctg      1740 gaaaacaaga agagcaatt aagcgccggc ggcaagatcc tgtccaaaga ggaagaggag      1800
gagctgagaa ggctgaccga cgaggatgag gagaggaaaa gaagggtggc aggacctagg      1860
gtgggcgacg tgaatccaag caggggagga cctagaggag caccaggagg cggcttcgtg      1920
ccacagatgg caggagtgcc tgagtcccca ttttctcgga ccggcgaggg cctggatatc      1980
agaggcacac agggcttccc ctgggtgtcc ccttctcctc cacagcagcg gctgcctctg      2040
ctggagtgca cccctcaggg aagcggagct actaacttca gcctgctgaa gcaggctgga      2100
gacgtggagg agaaccctgg acctatgtcg cagagcgaat ctaagaagaa tagaagggc      2160 ggcagagagg atatcctgga gaagtggatc accacacgca gaaaagctga gaactggaa      2220 aaggacctga ggaaggcccg caagaccatc aagaagctgg aggatgaaaa tccatggctg      2280
ggaaatatca tcggcatcat ccggaagggc aaggacgggg aaggcgcccc acctgcaaag      2340
cggcccagga ctgatcagat ggaaatcgat tccggcacag gcaagaggcc tcacaagtct      2400
ggcttcacag ataaagagcg cgaggatcac agaaggcgca aggccctgga gaacaagaag      2460
aagcaattat ctagcggcgg caagaatctg tccagagaag aagaggagga gctgggccgc      2520
ctgaccgtgg aggacgagga gcggagaagg cgcgtggcag accaagaac aggcgatgtg      2580 aacctgtctg gaggcggccc aaggggcgcc ccggcggag gcttcgtgcc aagaatggaa      2640
ggcgtgccag agtccccttt tacccggaca ggggaaggcc tggacattag aggcaatcag      2700
ggctttccct gggtgcgacc aagccccct cagcagcgac tgcctctgct ggagtgtacc      2760
cctcag                                                                2766
```

<210> SEQ ID NO 38
<211> LENGTH: 2795
<212> TYPE: DNA
<213> ORGANISM: Artificial Sequence
<220> FEATURE:
<223> OTHER INFORMATION: Delta 6 codon optimized with restriction sites
      (HindIII /EcoRI)

<400> SEQUENCE: 38

```
aagcttgcac catggcctca cggtcagagt caaagaagaa cagaggcgga agagaagaaa        60
tcctggagca gtgggtcgga gcacggaaaa agctggaaga actggagagg gacctgcgca       120
agatcaagaa gaagatcaag aagctggagg aggagaaccc ctggctgggc aatatcaagg       180
gcatcctggg caagaaggat agggaggag agggagcacc acctgcaaag agggccagag       240
ccgaccagat ggaggtggat agcggaccaa ggaagcgccc cttccgcgga gagtttaccg       300
acaaggagcg gagagatcac aggcgccgga aggccctgga gaacaagagg aagcagctga       360
gctccggcgg caagtccctg tctaaggagg aggaggagga gctgcgcaag ctgacagagg       420
```

-continued

```
aggacgagag aagggagagg agggtggcag gaccaagggt gggaggagtg aatcctctgg    480
agggaggaac cagaggagca ccaggaggag gcttcgtgcc aagcatgcag ggagtgccag    540
agtccccctt tgccaggaca ggagagggcc tggacgtgag aggcaaccag ggcttccctt    600
gggacatcct gtttccagcc gatccaccct tcagccctca gtcctgcagg ccacagggaa    660
gcggagctac taacttcagc ctgctgaagc aggctggaga cgtggaggag aaccctggac    720
ctatgagccg gtccgagtct aagaagaata ggggaggaag agaggaggtg ctggagcagt    780
gggtgaacgg cagaaagaag ctggaggagc tggagaggga gctgagaagg gcccgcaaga    840
agatcaagaa gctggaagac gataatcctt ggctgggcaa tgtgaaaggc atcctgggca    900
agaaggacaa ggatggagag ggagcacctc cagcaaagag ggcaagaacc gaccagatgg    960
agatcgatag cggacctagg aagcgcccac tgagggagg ctttacagac cgggagagac   1020
aggatcaccg ccggagaaag gccctgaaga acaagaagaa gcagctgtcc gccggaggca   1080
agagcctgtc caaagaagag gaagaggagc tgaagaggct gacccgcgag gacgaggaga   1140
ggaagaagga ggagcacgga ccatctaggc tgggagtgaa tcccagcgag ggaggaccaa   1200
ggggagcacc tggaggaggc ttcgtgccct ccatgcaggg catccctgag tctcggttta   1260
ccagaaccgc gagggcctg gacgtgaggg gcagccgcgg cttccacag gacatcctgt    1320 tcccctccga tccccctttt tctccccaga gctgtcgccc tcaaggaagc ggagctacta   1380
acttcagcct gctgaagcag gctggagacg tggaggagaa ccctggacct atgtctcaga   1440
gcgagacaag gaggggccgg agaggaacca gggaggagac actggagaag tggatcacag   1500
cccgcaagaa ggccgaggag ctggagaagg acctgcggaa gaccagaaag acaatcaaga   1560
agctggaaga agagaaccct tggctgggca atatcgtggg catcatcagg aagggcaagg   1620
acggcgaggg agcaccacca gccaagaggc cacgcactga tcagatggag gtggattctg   1680
gaccaggcaa gcggccccac aagagcggct tcacagacaa ggagagagag gaccataggc   1740 gccgaaggc cctggaaaac aagaagaagc aattaagcgc cggcggcaag atcctgtcca   1800 agaggaaga ggaggagctg agaaggctga ccgacgagga tgaggagagg aaaagaaggg   1860
tggcaggacc tagggtgggc gacgtgaatc caagcagggg aggacctaga ggagcaccag   1920
gaggcggctt cgtgccacag atggcaggag tgcctgagtc cccattttct cggaccggcg   1980
agggcctgga tatcagaggc acacaggct tcccctgggt gtcccttct cctccacagc    2040 agcggctgcc tctgctggag tgcacccctc agggaagcgg agctactaac ttcagcctgc   2100
tgaagcaggc tggagacgtg gaggagaacc ctggacctat gtcgcagagc gaatctaaga   2160
agaatagaag gggcggcaga gaggatatcc tggagaagtg gatcaccaca cgcagaaaag   2220
ctgaagaact ggaaaaggac ctgaggaagg cccgcaagac catcaagaag ctggaggatg   2280
aaaatccatg gctgggaaat atcatcggca tcatccggaa gggcaaggac ggggaaggcg   2340
ccccacctgc aaagcggccc aggactgatc agatggaaat cgattccggc acaggcaaga   2400
ggcctcacaa gtctggcttc acagataaag agcgcgagga tcacagaagg cgcaaggccc   2460
tggagaacaa gaagaagcaa ttatctagcg gcggcaagaa tctgtccaga gaagaagagg   2520
aggagctggg ccgcctgacc gtggaggacg aggagcggaa aagcgcgtg gcaggaccaa   2580 gaacaggcga tgtgaacctg tctggaggcg gcccaagggg cgcccccggc ggaggcttcg   2640
tgccaagaat ggaaggcgtg ccagagtccc ttttacccg gacaggggaa ggcctggaca   2700
ttagaggcaa tcagggcttt ccctgggtgc gaccaagccc cctcagcag cgactgcctc   2760 tgctggagtg taccccctcag tgatgagaat tccgt                            2795
```

<210> SEQ ID NO 39
<211> LENGTH: 923
<212> TYPE: PRT
<213> ORGANISM: Artificial Sequence
<220> FEATURE:
<223> OTHER INFORMATION: Delta 6 protein

<400> SEQUENCE: 39

```
Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Arg Lys Ala Leu Glu Asn Lys
            100                 105                 110

Arg Lys Gln Leu Ser Ser Gly Gly Lys Ser Leu Ser Lys Glu Glu
        115                 120                 125

Glu Glu Leu Arg Lys Leu Thr Glu Gly Asp Glu Arg Arg Glu Arg Arg
130                 135                 140

Val Ala Gly Pro Arg Val Gly Val Asn Pro Leu Glu Gly Gly Thr
145                 150                 155                 160

Arg Gly Ala Pro Gly Gly Phe Val Pro Ser Met Gln Gly Val Pro
                165                 170                 175

Glu Ser Pro Phe Ala Arg Thr Gly Glu Gly Leu Asp Val Arg Gly Asn
            180                 185                 190

Gln Gly Phe Pro Trp Asp Ile Leu Phe Pro Ala Asp Pro Pro Phe Ser
        195                 200                 205

Pro Gln Ser Cys Arg Pro Gln Gly Ser Gly Ala Thr Asn Phe Ser Leu
    210                 215                 220

Leu Lys Gln Ala Gly Asp Val Glu Glu Asn Pro Gly Pro Met Ser Arg
225                 230                 235                 240

Ser Glu Ser Lys Lys Asn Arg Gly Gly Arg Glu Glu Val Leu Glu Gln
                245                 250                 255

Trp Val Asn Gly Arg Lys Lys Leu Glu Glu Leu Glu Arg Glu Leu Arg
            260                 265                 270

Arg Ala Arg Lys Lys Ile Lys Lys Leu Glu Asp Asp Asn Pro Trp Leu
        275                 280                 285

Gly Asn Val Lys Gly Ile Leu Gly Lys Lys Asp Lys Asp Gly Glu Gly
    290                 295                 300

Ala Pro Pro Ala Lys Arg Ala Arg Thr Asp Gln Met Glu Ile Asp Ser
305                 310                 315                 320

Gly Pro Arg Lys Arg Pro Leu Arg Gly Gly Phe Thr Asp Arg Glu Arg
                325                 330                 335

Gln Asp His Arg Arg Arg Lys Ala Leu Lys Asn Lys Lys Gln Leu
            340                 345                 350

Ser Ala Gly Gly Lys Ser Leu Ser Lys Glu Glu Glu Glu Leu Lys
        355                 360                 365
```

Arg Leu Thr Arg Glu Asp Glu Glu Arg Lys Glu Glu His Gly Pro
    370                 375                 380

Ser Arg Leu Gly Val Asn Pro Ser Glu Gly Pro Arg Gly Ala Pro
385                 390                 395                 400

Gly Gly Gly Phe Val Pro Ser Met Gln Gly Ile Pro Glu Ser Arg Phe
                405                 410                 415

Thr Arg Thr Gly Glu Gly Leu Asp Val Arg Gly Ser Arg Gly Phe Pro
            420                 425                 430

Gln Asp Ile Leu Phe Pro Ser Asp Pro Phe Ser Pro Gln Ser Cys
        435                 440                 445

Arg Pro Gln Gly Ser Gly Ala Thr Asn Phe Ser Leu Leu Lys Gln Ala
    450                 455                 460

Gly Asp Val Glu Glu Asn Pro Gly Pro Met Ser Gln Ser Glu Thr Arg
465                 470                 475                 480

Arg Gly Arg Arg Gly Thr Arg Glu Glu Thr Leu Glu Lys Trp Ile Thr
                485                 490                 495

Ala Arg Lys Lys Ala Glu Glu Leu Glu Lys Asp Leu Arg Lys Thr Arg
                500                 505                 510

Lys Thr Ile Lys Lys Leu Glu Glu Glu Asn Pro Trp Leu Gly Asn Ile
            515                 520                 525

Val Gly Ile Ile Arg Lys Gly Lys Asp Gly Glu Gly Ala Pro Pro Ala
530                 535                 540

Lys Arg Pro Arg Thr Asp Gln Met Glu Val Asp Ser Gly Pro Gly Lys
545                 550                 555                 560

Arg Pro His Lys Ser Gly Phe Thr Asp Lys Glu Arg Glu Asp His Arg
                565                 570                 575

Arg Arg Lys Ala Leu Glu Asn Lys Lys Lys Gln Leu Ser Ala Gly Gly
            580                 585                 590

Lys Ile Leu Ser Lys Glu Glu Glu Glu Leu Arg Arg Leu Thr Asp
        595                 600                 605

Glu Asp Glu Glu Arg Lys Arg Arg Val Ala Gly Pro Arg Val Gly Asp
610                 615                 620

Val Asn Pro Ser Arg Gly Gly Pro Arg Gly Ala Pro Gly Gly Gly Phe
625                 630                 635                 640

Val Pro Gln Met Ala Gly Val Pro Glu Ser Pro Phe Ser Arg Thr Gly
                645                 650                 655

Glu Gly Leu Asp Ile Arg Gly Thr Gln Gly Phe Pro Trp Val Ser Pro
            660                 665                 670

Ser Pro Pro Gln Gln Arg Leu Pro Leu Leu Glu Cys Thr Pro Gln Gly
        675                 680                 685

Ser Gly Ala Thr Asn Phe Ser Leu Leu Lys Gln Ala Gly Asp Val Glu
        690                 695                 700

Glu Asn Pro Gly Pro Met Ser Gln Ser Glu Ser Lys Lys Asn Arg Arg
705                 710                 715                 720

Gly Gly Arg Glu Asp Ile Leu Glu Lys Trp Ile Thr Thr Arg Arg Lys
                725                 730                 735

Ala Glu Glu Leu Glu Lys Asp Leu Arg Lys Ala Arg Lys Thr Ile Lys
                740                 745                 750

Lys Leu Glu Asp Glu Asn Pro Trp Leu Gly Asn Ile Ile Gly Ile Ile
            755                 760                 765

Arg Lys Gly Lys Asp Gly Glu Gly Ala Pro Pro Ala Lys Arg Pro Arg
    770                 775                 780

| | | | | | | | | | | | | |
|---|---|---|---|---|---|---|---|---|---|---|---|---|
|Thr|Asp|Gln|Met|Glu|Ile|Asp|Ser|Gly|Thr|Gly|Lys|Arg|Pro|His|Lys|
|785| | | | |790| | | | |795| | | | |800|

Ser Gly Phe Thr Asp Lys Glu Arg Glu Asp His Arg Arg Lys Ala
            805                 810                 815

Leu Glu Asn Lys Lys Lys Gln Leu Ser Ser Gly Gly Lys Asn Leu Ser
            820                 825                 830

Arg Glu Glu Glu Glu Leu Gly Arg Leu Thr Val Glu Asp Glu Glu
            835                 840                 845

Arg Arg Arg Arg Val Ala Gly Pro Arg Thr Gly Asp Val Asn Leu Ser
        850                 855                 860

Gly Gly Gly Pro Arg Gly Ala Pro Gly Gly Gly Phe Val Pro Arg Met
865                 870                 875                 880

Glu Gly Val Pro Glu Ser Pro Phe Thr Arg Thr Gly Glu Gly Leu Asp
            885                 890                 895

Ile Arg Gly Asn Gln Gly Phe Pro Trp Val Arg Pro Ser Pro Pro Gln
            900                 905                 910

Gln Arg Leu Pro Leu Leu Glu Cys Thr Pro Gln
            915                 920

```
<210> SEQ ID NO 40
<211> LENGTH: 1560
<212> TYPE: DNA
<213> ORGANISM: Artificial Sequence
<220> FEATURE:
<223> OTHER INFORMATION: Delta 7 wt

<400> SEQUENCE: 40
agccgcagcg aaagcaaaaa aaaccgcggc ggccgcgaag aaattctgga acagtgggtg      60
ggcgcgcgca aaaaactgga agaactgaaa cgcgatctgc gcaaaattaa aaaaaaaatt     120
aaaaaactgg aagaagaaaa cccgtggctg gcaacattaa aaggcattct gggcaaaaaa     180
gatcgcgaag gcgaaggcgc gccgccggcg aaacgcgcgc gcgcggatca gatggaagtg     240
gatagcggcc gcgcaaacg cccgtttcgc ggcgaattta ccgataaaga acgccgcgat      300
catcgccgcc gcaaagcgct ggaaaacaaa cgcaaacagc tgagcagcgg cggcaaaagc     360
ctgagcaaag aagaagaaga agaactgcgc aaactgaccg aagaagatga acgccgcgaa     420
cgccgcgtgg cgggcccgcg cgtgggcggc gtgaacccgc tggaaggcgg caccgcggc      480 gcgccgggcg gcggctttgt gccgagcatg cagggcgtgc cggaaagccc gtttgcgcgc    540
accggcgaag gcctggatgt gcgcggcaac cagggctttc cgtgggatat tctgtttccg    600
gcggatccgc cgtttagccc gcagagctgc cgcccgcaga gccgcagcga aagcaaaaaa    660
aaccgcggcg gccgcgaaga agtgctggaa cagtgggtga acggccgcaa aaaactggaa    720
gaactggaac gcgaactgcg ccgcgcgcgc aaaaaaatta aaaaactgga agatgataac    780
ccgtggctgg gcaacgtgaa aggcattctg ggcaaaaaag ataaagatgg cgaaggcgcg    840
ccgccggcga aacgcgcgcg caccgatcag atggaaattg atagcggccc gcgcaaacgc    900
ccgctgcgcg gcggctttac cgatcgcgaa cgccaggatc atcgccgccg caaagcgctg    960
aaaaacaaaa aaaaacagct gagcgcgggc ggcaaaagcc tgagcaaaga agaagaagaa   1020
gaactgaaac gcctgacccg cgaagatgaa gaacgcaaaa aagaagaaca tggcccgagc   1080
cgcctgggcg tgaacccgag cgaaggcggc ccgcgcggcg cgccgggcgg cggctttgtg   1140
ccgagcatgc agggcattcc ggaaagccgc tttacccgca ccggcgaagg cctggatgtg   1200
cgcggcagcc gcggctttcc gcaggatatt ctgtttccga gcgatccgcc gtttagcccg   1260
```

```
cagagctgcc gcccgcaggg caccaacctg agcaccagca acccgctggg cttttttccg    1320
gatcatcagc tggatccggc gtttcgcgcg aacagcgcga acccggattg ggattttaac    1380
ccgaacaaag atacctggcc ggatgcgaac aaagtgggcg ccagaacct gagcaccagc    1440 aacccgctgg gctttttcc ggatcatcag ctggatccgg cgtttcgcgc gaacaccgcg    1500
aacccggatt gggattttaa cccgaacaaa gatacctggc cggatgcgaa caaagtgggc    1560
```

<210> SEQ ID NO 41
<211> LENGTH: 1592
<212> TYPE: DNA
<213> ORGANISM: Artificial Sequence
<220> FEATURE:
<223> OTHER INFORMATION: Delta 7 wt with restriction sites (HindIII
      /EcoRI)

<400> SEQUENCE: 41

```
aagcttgcac catggccagc cgcagcgaaa gcaaaaaaaa ccgcggcggc cgcgaagaaa      60
ttctggaaca gtgggtgggc gcgcgcaaaa aactggaaga actggaacgc gatctgcgca    120
aaattaaaaa aaaaattaaa aaactggaag aagaaaaccc gtggctgggc aacattaaag    180
gcattctggg caaaaaagat cgcgaaggcg aaggcgcgcc gccggcgaaa cgcgcgcgcg    240
cggatcagat ggaagtggat agcggcccgc gcaaacgccc gtttcgcggc gaatttaccg    300
ataaagaacg ccgcgatcat cgccgccgca agcgctgga aaacaaacgc aaacagctga    360
gcagcggcgg caaaagcctg agcaaagaag aagaagaaga actgcgcaaa ctgaccgaag    420
aagatgaacg ccgcgaacgc cgcgtggcgg gcccgcgcgt gggcggcgtg aacccgctgg    480
aaggcggcac ccgcggcgcg ccgggcggcg gctttgtgcc gagcatgcag ggcgtgccgg    540
aaagcccgtt tgcgcgcacc ggcgaaggcc tggatgtgcg cggcaaccag ggctttccgt    600
gggatattct gtttccggcg gatccgccgt ttagcccgca gagctgccgc ccgcagagcc    660
gcagcgaaag caaaaaaaac cgcggcgcc gcgaagaagt gctggaacag tgggtgaacg    720
gccgcaaaaa actggaagaa ctggaacgcg aactgcgccg cgcgcgcaaa aaaattaaaa    780
aactggaaga tgataacccg tggctgggca acgtgaaagg cattctgggc aaaaaagata    840
aagatggcga aggcgcgccg ccggcgaaac gcgcgcgcac cgatcagatg gaaattgata    900
gcggcccgcg caaacgcccg ctgcgcggcg gctttaccga tcgcgaacgc caggatcatc    960
gccgccgcaa agcgctgaaa acaaaaaaa acagctgag cgcgggcggc aaaagcctga   1020
gcaaagaaga agaagaagaa ctgaaacgcc tgacccgcga agatgaagaa cgcaaaaaag   1080
aagaacatgg cccgagccgc ctgggcgtga acccgagcga aggcggcccg cgcggcgcgc   1140
cgggcggcgg ctttgtgccg agcatgcagg gcattccgga aagccgcttt acccgcaccg   1200
gcgaaggcct ggatgtgcgc ggcagccgcg gctttccgca ggatattctg tttccgagcg   1260
atccgccgtt tagcccgcag agctgccgcc cgcagggcac caacctgagc accagcaacc   1320 cgctggctt ttttccggat catcagctgg atccggcgtt tcgcgcgaac agcgcgaacc   1380
cggattggga ttttaacccg aacaaagata cctggccgga tgcgaacaaa gtgggcggcc   1440
agaacctgag caccagcaac ccgctgggct ttttccgga tcatcagctg gatccggcgt   1500
ttcgcgcgaa caccgcgaac ccggattggg attttaaccc gaacaaagat acctggccgg   1560
atgcgaacaa agtgggctga tgagaattcc gt                                1592
```

<210> SEQ ID NO 42
<211> LENGTH: 1563
<212> TYPE: DNA

<213> ORGANISM: Artificial Sequence
<220> FEATURE:
<223> OTHER INFORMATION: Delta 7 codon optimized

<400> SEQUENCE: 42

```
gcctcacggt ctgagtcaaa gaagaatcgg gggggaagag aagaaatcct ggaacagtgg      60
gtcggcgcac ggaaaaaact ggaagaactg gagcgggacc tgagaaagat caagaagaag     120
atcaagaagc tggaggaaga gaaccccctgg ctgggcaata tcaagggcat cctgggcaag    180
aaggatcggg agggcgaggg agcaccacct gcaaagaggg caagggcaga ccagatggag    240
gtggattccg gacctaggaa gcggcccttc cggggagagt ttaccgacaa ggagcggaga     300
gatcacaggc gccggaaggc cctggagaac aagcggaagc agctgagctc cggcggcaag     360
tctctgagca aggaggagga ggaggagctg agaaagctga cagaggagga cgagagaagg     420
gagcgccggg tggccggccc aagggtgggc ggcgtgaacc ccctggaggg aggaaccagg    480
ggagcaccag gaggaggctt cgtgccttct atgcagggcg tgccagagag cccctttgcc    540
aggacaggag agggcctgga tgtgcgcggc aatcaggggc tcccatggga catcctgttt     600
cccgccgatc caccccttctc ccctcagtct tgcaggccac agtcccgctc tgagagcaag     660
aagaacaggg gaggaaggga ggaggtgctg gagcagtggg tgaatggcag gaagaagctg     720
gaggagctgg agcggagct gagaaggggcc agaaagaaga tcaagaagct ggaagacgat     780
aatccttggc tgggcaatgt gaaaggcatc ctgggcaaga aggacaagga tggagaggga     840
gcacctccag caaagagggc acgcaccgac cagatggaga tcgattccgg accaaggaag     900
cggcccctga ggggaggctt cacagacagg gagcgccagg atcaccgccg agaaaaggcc     960
ctgaagaaca agaagaagca gctgtctgcc ggcggcaagt ccctgtctaa gaagaggag    1020
gaggagctga gcggctgac cagagaggac gaggagcgga gaaggagga gcacggccct    1080
tccagactgg gcgtgaatcc atctgaggga ggaccaagag gcgcccctgg cggaggcttc    1140
gtgcctagca tgcagggcat cccagagtcc aggtttacca gaaccggaga gggcctggac    1200
gtgcggggct ctagaggctt tccccaggac atcctgttcc ctagcgatcc ccttttagc    1260
ccccagtcct gtaggcctca gggcaccaac ctgagcacat ccaatccact gggcttcttt    1320
ccagaccacc agctggatcc agccttccgc gccaacagcg ccaatccaga ctgggacttc    1380
aaccccaata aggacacctg gcctgatgcc aacaaggtcg gcggccagaa cctgtctaca    1440
agcaatcctc tgggcttctt tcctgatcac cagctggatc ctgcctttcg ggccaataca    1500
gccaaccctg actgggactt caatcctaac aaagacactt ggcccgatgc taataaggtc    1560
ggc                                                                 1563
```

<210> SEQ ID NO 43
<211> LENGTH: 1592
<212> TYPE: DNA
<213> ORGANISM: Artificial Sequence
<220> FEATURE:
<223> OTHER INFORMATION: Delta 7 codon optimized with restriction sites
      (HindIII /EcoRI)

<400> SEQUENCE: 43

```
aagcttgcac catggcctca cggtctgagt caaagaagaa tcgggggga agagaagaaa      60
tcctggaaca gtgggtcggc gcacggaaaa aactggaaga actggagcgg gacctgagaa    120
agatcaagaa gaagatcaag aagctggagg aagagaaccc ctggctgggc aatatcaagg    180
gcatcctggg caagaaggat cgggagggcg agggagcacc acctgcaaag agggcaaggg    240
```

```
cagaccagat ggaggtggat tccggaccta ggaagcggcc cttccgggga gagtttaccg    300
acaaggagcg gagagatcac aggcgccgga aggccctgga gaacaagcgg aagcagctga    360
gctccggcgg caagtctctg agcaaggagg aggaggagga gctgagaaag ctgacagagg    420
aggacgagag aagggagcgc cgggtggccg gcccaagggt gggcggcgtg aaccccctgg    480
agggaggaac caggggagca ccaggaggag gcttcgtgcc ttctatgcag ggcgtgccag    540
agagccccct tgccaggaca ggagagggcc tggatgtgcg cggcaatcag ggcttcccat    600
gggacatcct gtttcccgcc gatccaccct tctcccctca gtcttgcagg ccacagtccc    660
gctctgagag caagaagaac aggggaggaa gggaggaggt gctggagcag tgggtgaatg    720
gcaggaagaa gctggaggag ctggagcggg agctgagaag ggccagaaag aagatcaaga    780
agctggaaga cgataatcct tggctgggca atgtgaaagg catcctgggc aagaaggaca    840
aggatggaga gggagcacct ccagcaaaga gggcacgcac cgaccagatg agatcgatt    900 ccggaccaag gaagcggccc ctgagggag gcttcacaga cagggagcgc caggatcacc    960
gccggagaaa ggccctgaag aacaagaaga agcagctgtc tgccggcggc aagtccctgt   1020
ctaaagaaga ggaggaggag ctgaagcggc tgaccagaga ggacgaggag cggaagaagg   1080
aggagcacgg cccttccaga ctgggcgtga atccatctga gggaggacca agaggcgccc   1140
ctggcggagg cttcgtgcct agcatgcagg catcccaga gtccaggttt accagaaccg   1200
gagagggcct ggacgtgcgg ggctctagag gcttctcccca ggacatcctg ttccctagcg   1260 atccccttt tagcccccag tcctgtaggc ctcagggcac caacctgagc acatccaatc   1320
cactgggctt ctttccagac caccagctgg atccagcctt ccgcgccaac agcgccaatc   1380
cagactggga cttcaacccc aataaggaca cctggcctga tgccaacaag gtcggcggcc   1440
agaacctgtc tacaagcaat cctctgggct tctttcctga tcaccagctg gatcctgcct   1500
ttcgggccaa tacagccaac cctgactggg acttcaatcc taacaaagac acttggcccg   1560
atgctaataa ggtcggctga tgagaattcc gt                                  1592
```

<210> SEQ ID NO 44
<211> LENGTH: 522
<212> TYPE: PRT
<213> ORGANISM: Artificial Sequence
<220> FEATURE:
<223> OTHER INFORMATION: Delta 7 protein

<400> SEQUENCE: 44

```
Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Arg Lys Ala Leu Glu Asn Lys
            100                 105                 110

Arg Lys Gln Leu Ser Ser Gly Gly Lys Ser Leu Ser Lys Glu Glu Glu
        115                 120                 125
```

Glu Glu Leu Arg Lys Leu Thr Glu Glu Asp Glu Arg Arg Glu Arg Arg
            130                 135                 140

Val Ala Gly Pro Arg Val Gly Gly Val Asn Pro Leu Glu Gly Gly Thr
145                 150                 155                 160

Arg Gly Ala Pro Gly Gly Gly Phe Val Pro Ser Met Gln Gly Val Pro
                165                 170                 175

Glu Ser Pro Phe Ala Arg Thr Gly Glu Gly Leu Asp Val Arg Gly Asn
            180                 185                 190

Gln Gly Phe Pro Trp Asp Ile Leu Phe Pro Ala Asp Pro Pro Phe Ser
        195                 200                 205

Pro Gln Ser Cys Arg Pro Gln Ser Arg Ser Glu Ser Lys Lys Asn Arg
    210                 215                 220

Gly Gly Arg Glu Glu Val Leu Glu Gln Trp Val Asn Gly Arg Lys Lys
225                 230                 235                 240

Leu Glu Glu Leu Glu Arg Glu Leu Arg Arg Ala Arg Lys Lys Ile Lys
                245                 250                 255

Lys Leu Glu Asp Asp Asn Pro Trp Leu Gly Asn Val Lys Gly Ile Leu
                260                 265                 270

Gly Lys Lys Asp Lys Asp Gly Glu Gly Ala Pro Pro Ala Lys Arg Ala
        275                 280                 285

Arg Thr Asp Gln Met Glu Ile Asp Ser Gly Pro Arg Lys Arg Pro Leu
    290                 295                 300

Arg Gly Gly Phe Thr Asp Arg Glu Arg Gln Asp His Arg Arg Arg Lys
305                 310                 315                 320

Ala Leu Lys Asn Lys Lys Gln Leu Ser Ala Gly Lys Ser Leu
                325                 330                 335

Ser Lys Glu Glu Glu Glu Leu Lys Arg Leu Thr Arg Glu Asp Glu
            340                 345                 350

Glu Arg Lys Lys Glu Glu His Gly Pro Ser Arg Leu Gly Val Asn Pro
        355                 360                 365

Ser Glu Gly Gly Pro Arg Gly Ala Pro Gly Gly Phe Val Pro Ser
    370                 375                 380

Met Gln Gly Ile Pro Glu Ser Arg Phe Thr Arg Thr Gly Glu Gly Leu
385                 390                 395                 400

Asp Val Arg Gly Ser Arg Gly Phe Pro Gln Asp Ile Leu Phe Pro Ser
                405                 410                 415

Asp Pro Pro Phe Ser Pro Gln Ser Cys Arg Pro Gln Gly Thr Asn Leu
                420                 425                 430

Ser Thr Ser Asn Pro Leu Gly Phe Phe Pro Asp His Gln Leu Asp Pro
        435                 440                 445

Ala Phe Arg Ala Asn Ser Ala Asn Pro Asp Trp Asp Phe Asn Pro Asn
450                 455                 460

Lys Asp Thr Trp Pro Asp Ala Asn Lys Val Gly Gly Gln Asn Leu Ser
465                 470                 475                 480

Thr Ser Asn Pro Leu Gly Phe Phe Pro Asp His Gln Leu Asp Pro Ala
                485                 490                 495

Phe Arg Ala Asn Thr Ala Asn Pro Asp Trp Asp Phe Asn Pro Asn Lys
            500                 505                 510

Asp Thr Trp Pro Asp Ala Asn Lys Val Gly
        515                 520

<210> SEQ ID NO 45
<211> LENGTH: 1560

```
<212> TYPE: DNA
<213> ORGANISM: Artificial Sequence
<220> FEATURE:
<223> OTHER INFORMATION: Delta 8 wt

<400> SEQUENCE: 45
agccagagcg aaacccgccg cggccgccgc ggcacccgcg aagaaaccct ggaaaaatgg     60
attaccgcgc gcaaaaaagc ggaagaactg gaaaagatc  tgcgcaaaac ccgcaaaacc    120
attaaaaaac tggaagaaga aaacccgtgg ctgggcaaca ttgtgggcat tattcgcaaa    180
ggcaaagatg gcgaaggcgc gccgccggcg aaacgcccgc gcaccgatca gatggaagtg    240
gatagcggcc cgggcaaacg cccgcataaa agcggctttta ccgataaaga acgcgaagat    300
catcgccgcc gcaaagcgct ggaaaacaaa aaaaacagc  tgagcgcggg cggcaaaatt    360
ctgagcaaag aagaagaaga agaactgcgc cgcctgaccg atgaagatga agaacgcaaa    420
cgccgcgtgg cgggcccgcg cgtgggcgat gtgaacccga gccgcggcgg cccgcgcggc    480
gcgccgggcg gcggctttgt gccgcagatg gcgggcgtgc cggaaagccc gtttagccgc    540
accggcgaag gcctggatat tcgcggcacc cagggctttc cgtgggtgag cccgagcccg    600
ccgcagcagc gcctgccgct gctggaatgc accccgcaga gccagagcga aagcaaaaaa    660
aaccgccgcg gcggccgcga agatattctg gaaaaatgga ttaccacccg ccgcaaagcg    720
gaagaactgg aaaagatct  gcgcaaagcg cgcaaaacca ttaaaaaact ggaagatgaa    780
aacccgtggc tgggcaacat tattggcatt attcgcaaag gcaaagatgg cgaaggcgcg    840
ccgccggcga aacgcccgcg caccgatcag atggaaattg atagcggcac cggcaaacgc    900
ccgcataaaa gcggctttac cgataaagaa cgcgaagatc atcgccgccg caaagcgctg    960
gaaaacaaaa aaaacagct  gagcagcggc ggcaaaaacc tgagccgcga agaagaagaa   1020
gaactgggcc gcctgaccgt ggaagatgaa gaacgccgcc gcgcgtggc  gggcccgcgc   1080 accggcgatg tgaacctgag cggcggcggc ccgcgcggcg cgccgggcgg cggctttgtg   1140
ccgcgcatgg aaggcgtgcc ggaaagcccg tttacccgca ccggcgaagg cctggatatt   1200
cgcggcaacc agggctttcc gtgggtgcgc ccgagcccgc cgcagcagcg cctgccgctg   1260
ctggaatgca ccccgcaggg caccaacctg agcaccagca accgctgggg ctttttttccg   1320 gatcatcagc tggatccggc gtttcgcgcg aacagcgcga accgggattg ggattttaac   1380
ccgaacaaag atacctggcc ggatgcgaac aaagtgggcg ccagaacct  gagcaccagc   1440 aacccgctgg gctttttttcc ggatcatcag ctggatccgg cgtttcgcgc gaacaccgcg   1500
aacccggatt gggattttaa cccgaacaaa gatacctggc cggatgcgaa caaagtgggc   1560

<210> SEQ ID NO 46
<211> LENGTH: 1592
<212> TYPE: DNA
<213> ORGANISM: Artificial Sequence
<220> FEATURE:
<223> OTHER INFORMATION: Delta 8 wt with restriction sites (HindIII
      /EcoRI)

<400> SEQUENCE: 46
aagcttgcac catggccagc cagagcgaaa cccgccgcgg ccgccgcggc acccgcgaag     60
aaaccctgga aaaatggatt accgcgcgca aaaagcgga  agaactggaa aagatctgc    120 gcaaacccg  caaaaccatt aaaaaactgg aagaagaaaa cccgtggctg gcaacattg    180 tgggcattat tcgcaaaggc aaagatggcg aaggcgcgcc gccggcgaaa cgcccgcgca    240
ccgatcagat ggaagtggat agcggcccgg gcaaacgccc gcataaaagc ggctttaccg    300
```

```
ataaagaacg cgaagatcat cgccgccgca aagcgctgga aaacaaaaaa aaacagctga    360
gcgcgggcgg caaaattctg agcaaagaag aagaagaaga actgcgccgc ctgaccgatg    420
aagatgaaga acgcaaacgc cgcgtggcgg gcccgcgcgt gggcgatgtg aacccgagcc    480
gcggcggccc gcgcggcgcg ccgggcggcg ctttgtgcc gcagatggcg ggcgtgccgg     540
aaagcccgtt tagccgcacc ggcgaaggcc tggatattcg cggcacccag ggctttccgt    600
gggtgagccc gagcccgccg cagcagcgcc tgccgctgct ggaatgcacc ccgcagagcc    660
agagcgaaag caaaaaaaac cgccgcggcg gccgcgaaga tattctggaa aaatggatta    720
ccacccgccg caaagcggaa gaactggaaa aagatctgcg caaagcgcgc aaaaccatta    780
aaaaactgga agatgaaaac ccgtggctgg gcaacattat tggcattatt cgcaaaggca    840
aagatggcga aggcgcgccg ccggcgaaac gcccgcgcac cgatcagatg gaaattgata    900
gcggcaccgg caaacgcccg cataaaagcg ctttaccga taaagaacgc gaagatcatc    960
gccgccgcaa agcgctggaa aacaaaaaaa aacagctgag cagcggcggc aaaaacctga   1020
gccgcgaaga agaagaagaa ctgggccgcc tgaccgtgga agatgaagaa cgccgccgcc   1080
gcgtggcggg cccgcgcacc ggcgatgtga acctgagcgg cggcggcccg cgcggcgcgc   1140
cgggcggcgg ctttgtgccg cgcatggaag gcgtgccgga aagcccgttt acccgcaccg   1200
gcgaaggcct ggatattcgc ggcaaccagg gctttccgtg ggtgcgcccg agcccgccgc   1260
agcagcgcct gccgctgctg gaatgcaccc cgcagggcac caacctgagc accagcaacc   1320
cgctgggctt ttttccggat catcagctgg atccggcgtt tcgcgcgaac agcgcgaacc   1380
cggattggga ttttaacccg aacaaagata cctggccgga tgcgaacaaa gtgggcggcc   1440
agaacctgag caccagcaac ccgctgggct tttttccgga tcatcagctg gatccggcgt   1500
ttcgcgcgaa caccgcgaac ccggattggg atttaacccc gaacaaagat acctggccgg   1560
atgcgaacaa agtgggctga tgagaattcc gt                                 1592
```

<210> SEQ ID NO 47
<211> LENGTH: 1563
<212> TYPE: DNA
<213> ORGANISM: Artificial Sequence
<220> FEATURE:
<223> OTHER INFORMATION: Delta 8 optimized

<400> SEQUENCE: 47

```
gccagtcaga gcgagacccg cagaggacgg agaggaacac gagaagagac actggagaaa     60
tggattacag cacggaagaa ggcagaagag ctggagaagg acctgaggaa gacccgcaag    120
acaatcaaga agctggagga ggagaacccc tggctgggca atatcgtggg catcatcagg    180
aagggcaagg atggagaggg agcaccacct gccaagaggc ctcgcacaga ccagatggag    240
gtggatagcg gaccaggcaa gcggcctcac aagtccggct tcaccgacaa ggagagagag    300
gatcaccgga aggaaggcc ctggagaaca agaagaagc agctgtccgc cggcggcaag    360
atcctgtcta aggaggagga ggaggagctg cgccggctga cagacgagga tgaggagagg    420
aagagaaggg tggcaggacc aagggtgggc gacgtgaatc cttctagggg aggaccaagg    480
ggagcaccag gaggaggctt cgtgcctcag atggccggcg tgccagagtc tccctttagc    540
cggacaggcg agggcctgga tatcagaggc acccagggct ttccttgggt gtctccaagc    600
ccaccacagc agcggctgcc actgctggag tgcacacccc agtccagtc tgagagcaag    660
aagaacagga gggaggaag agaggacatc ctggagaagt ggatcaccac aagaaggaag    720
```

```
gccgaggagc tggagaagga cctgcggaag gccagaaaga ccatcaagaa gctggaggat    780
gaaaatcctt ggctgggaaa tatcatcgga attattagaa aaggcaagga cggagaggga    840
gcacctccag caaagcggcc aagaacagac cagatggaga tcgattctgg aaccggcaag    900
aggccccaca agagtggctt caccgataag gagcgcgagg atcaccgccg agaaaggcc     960 ctggaaaaca agaagaagca attaagctcc ggcggcaaga atctgagcag agaagaagag   1020
gaggagctgg ccgcctgac  agtggaggac gaggagaggc  gccggagagt ggcaggacct  1080
agaaccggcg atgtgaacct gtccggaggc ggcccaaggg gagcacctgg aggcggcttc   1140
gtgccacgca tggagggcgt gcctgagtct cccttcacca ggacaggaga gggcctggac   1200
atcagaggca atcagggatt cccatgggtg cggcccagcc cacctcagca gagactgcct   1260
ctgctggagt gtaccccaca gggcacaaac ctgtccacct ctaatcctct gggcttcttt   1320
ccagaccacc agctggatcc agccttcagg gccaactccg ccaaccctga ctgggacttc   1380
aaccctaata aggacacatg gccagatgcc aacaaggtcg gcggccagaa cctgagcacc   1440
tccaatcccc tgggcttctt tcctgaccac cagctggatc ccgcctttcg cgccaatacc   1500
gccaatcccg actgggactt caatccaaat aaggacacct ggcccgatgc taacaaagtg   1560
gga                                                                 1563
```

<210> SEQ ID NO 48
<211> LENGTH: 1592
<212> TYPE: DNA
<213> ORGANISM: Artificial Sequence
<220> FEATURE:
<223> OTHER INFORMATION: Delta 8 codon optimized with restriction sites
      (HindIII /EcoRI)

<400> SEQUENCE: 48

```
aagcttgcac catggccagt cagagcgaga cccgcagagg acggagagga acacgagaag     60
agacactgga gaaatggatt acagcacgga agaaggcaga agagctggag aaggacctga   120
ggaagacccg caagacaatc aagaagctgg aggaggagaa ccccctggctg ggcaatatcg   180 tgggcatcat caggaagggc aaggatggag agggagcacc acctgccaag aggcctcgca   240
cagaccagat ggaggtggat agcggaccag gcaagcggcc tcacaagtcc ggcttcaccg   300
acaaggagag agaggatcac cggagaagga aggccctgga gaacaagaag aagcagctgt   360
ccgccggcgg caagatcctg tctaaggagg aggaggagga gctgcgccgg ctgacagacg   420
aggatgagga gaggaagaga agggtggcag gaccaagggt gggcgacgtg aatccttcta   480
ggggaggacc aaggggagca ccaggaggag gcttcgtgcc tcagatgcc  ggcgtgccag    540 agtctcccctt tagccggaca ggcgagggcc tggatatcag aggcacccag ggctttcctt   600
gggtgtctcc aagcccacca cagcagcggc tgccactgct ggagtgcaca ccccagtccc   660
agtctgagag caagaagaac aggaggggag aagagagga  catcctggag aagtggatca   720
ccacaagaag gaaggccgag gagctggaga aggacctgcg gaaggccaga aagaccatca   780
agaagctgga ggatgaaaat ccttggctgg gaaatatcat cggaattatt agaaaggca   840 aggacggaga gggagcacct ccagcaaagc ggccaagaac agaccagatg gagatcgatt   900
ctggaaccgg caagaggccc cacaagagtg gcttcaccga taaggagcgc gaggatcacc   960
gccggagaaa ggccctggaa aacaagaaga gcaattaag  ctccggcggc aagaatctga  1020
gcagagaaga agaggaggag ctgggccgcc tgacagtgga ggacgaggag aggcgccgga  1080
gagtggcagg acctagaacc ggcgatgtga acctgtccgg aggcggccca aggggagcac  1140
```

```
ctggaggcgg cttcgtgcca cgcatggagg gcgtgcctga gtctcccttc accaggacag    1200
gagagggcct ggacatcaga ggcaatcagg gattcccatg ggtgcggccc agcccacctc    1260
agcagagact gcctctgctg gagtgtaccc cacagggcac aaacctgtcc acctctaatc    1320
ctctgggctt ctttccagac caccagctgg atccagcctt cagggccaac tccgccaacc    1380
ctgactggga cttcaaccct aataaggaca catggccaga tgccaacaag gtcggcggcc    1440
agaacctgag cacctccaat cccctgggct tctttcctga ccaccagctg gatcccgcct    1500
ttcgcgccaa taccgccaat cccgactggg acttcaatcc aaataaggac acctggcccg    1560
atgctaacaa agtgggatga tgagaattcc gt                                  1592
```

<210> SEQ ID NO 49
<211> LENGTH: 522
<212> TYPE: PRT
<213> ORGANISM: Artificial Sequence
<220> FEATURE:
<223> OTHER INFORMATION: Delta 8 protein

<400> SEQUENCE: 49

```
Met Ala Ser Gln Ser Glu Thr Arg Arg Gly Arg Arg Gly Thr Arg Glu
1               5                   10                  15

Glu Thr Leu Glu Lys Trp Ile Thr Ala Arg Lys Lys Ala Glu Glu Leu
            20                  25                  30

Glu Lys Asp Leu Arg Lys Thr Arg Lys Thr Ile Lys Lys Leu Glu Glu
        35                  40                  45

Glu Asn Pro Trp Leu Gly Asn Ile Val Gly Ile Ile Arg Lys Gly Lys
    50                  55                  60

Asp Gly Glu Gly Ala Pro Pro Ala Lys Arg Pro Arg Thr Asp Gln Met
65                  70                  75                  80

Glu Val Asp Ser Gly Pro Gly Lys Arg Pro His Lys Ser Gly Phe Thr
                85                  90                  95

Asp Lys Glu Arg Glu Asp His Arg Arg Arg Lys Ala Leu Glu Asn Lys
            100                 105                 110

Lys Lys Gln Leu Ser Ala Gly Gly Lys Ile Leu Ser Lys Glu Glu Glu
        115                 120                 125

Glu Glu Leu Arg Arg Leu Thr Asp Glu Asp Glu Glu Arg Lys Arg Arg
    130                 135                 140

Val Ala Gly Pro Arg Val Gly Asp Val Asn Pro Ser Arg Gly Gly Pro
145                 150                 155                 160

Arg Gly Ala Pro Gly Gly Gly Phe Val Pro Gln Met Ala Gly Val Pro
                165                 170                 175

Glu Ser Pro Phe Ser Arg Thr Gly Glu Gly Leu Asp Ile Arg Gly Thr
            180                 185                 190

Gln Gly Phe Pro Trp Val Ser Pro Ser Pro Gln Gln Arg Leu Pro
        195                 200                 205

Leu Leu Glu Cys Thr Pro Gln Ser Gln Ser Ser Lys Lys Asn Arg
    210                 215                 220

Arg Gly Gly Arg Glu Asp Ile Leu Glu Lys Trp Ile Thr Thr Arg Arg
225                 230                 235                 240

Lys Ala Glu Glu Leu Glu Lys Asp Leu Arg Lys Ala Arg Lys Thr Ile
                245                 250                 255

Lys Lys Leu Glu Asp Glu Asn Pro Trp Leu Gly Asn Ile Ile Gly Ile
            260                 265                 270

Ile Arg Lys Gly Lys Asp Gly Glu Gly Ala Pro Pro Ala Lys Arg Pro
        275                 280                 285
```

Arg Thr Asp Gln Met Glu Ile Asp Ser Gly Thr Gly Lys Arg Pro His
            290                 295                 300

Lys Ser Gly Phe Thr Asp Lys Glu Arg Glu Asp His Arg Arg Arg Lys
305                 310                 315                 320

Ala Leu Glu Asn Lys Lys Gln Leu Ser Ser Gly Gly Lys Asn Leu
            325                 330                 335

Ser Arg Glu Glu Glu Glu Leu Gly Arg Leu Thr Val Glu Asp Glu
            340                 345                 350

Glu Arg Arg Arg Val Ala Gly Pro Arg Thr Gly Asp Val Asn Leu
            355                 360                 365

Ser Gly Gly Gly Pro Arg Gly Ala Pro Gly Gly Phe Val Pro Arg
            370                 375                 380

Met Glu Gly Val Pro Glu Ser Pro Phe Thr Arg Thr Gly Glu Gly Leu
385                 390                 395                 400

Asp Ile Arg Gly Asn Gln Gly Phe Pro Trp Val Arg Pro Ser Pro Pro
            405                 410                 415

Gln Gln Arg Leu Pro Leu Leu Glu Cys Thr Pro Gln Gly Thr Asn Leu
            420                 425                 430

Ser Thr Ser Asn Pro Leu Gly Phe Phe Pro Asp His Gln Leu Asp Pro
            435                 440                 445

Ala Phe Arg Ala Asn Ser Ala Asn Pro Asp Trp Asp Phe Asn Pro Asn
450                 455                 460

Lys Asp Thr Trp Pro Asp Ala Asn Lys Val Gly Gly Gln Asn Leu Ser
465                 470                 475                 480

Thr Ser Asn Pro Leu Gly Phe Phe Pro Asp His Gln Leu Asp Pro Ala
            485                 490                 495

Phe Arg Ala Asn Thr Ala Asn Pro Asp Trp Asp Phe Asn Pro Asn Lys
            500                 505                 510

Asp Thr Trp Pro Asp Ala Asn Lys Val Gly
            515                 520

<210> SEQ ID NO 50
<211> LENGTH: 1278
<212> TYPE: DNA
<213> ORGANISM: Artificial Sequence
<220> FEATURE:
<223> OTHER INFORMATION: Delta 9 wt

<400> SEQUENCE: 50
agccgcagcg aaagcaaaaa aaaccgcggc ggccgcgaag aaattctgga acagtgggtg      60
ggcgcgcgca aaaactgga agaactggaa cgcgatctgc gcaaaattaa aaaaaaaatt     120
aaaaaactgg aagaagaaaa cccgtggctg ggcaacatta aaggcattct gggcaaaaaa     180
gatcgcgaag gcgaaggcgc gccgccggcg aaacgcgcgc gcgcggatca gatggaagtg     240
gatagcggcc gcgcaaaacg cccgtttcgc ggcgaattta ccgataaaga acgccgcgat     300
catcgccgcc gcaaagcgct ggaaaacaaa cgcaaacagc tgagcagcgg cggcaaaagc     360
ctgagcaaag aagaagaaga gaactgcgc aaactgaccg aagaagatga acgccgcgaa     420
cgccgcgtgg cgggccccgcg cgtgggcggc gtgaacccgc tggaaggcgg cacccgcggc     480
gcgccgggcg gcggctttgt gccgagcatg cagggcgtgc cggaaagccc gtttgcgcgc     540
accggcgaag gcctggatgt gcgcggcaac cagggctttc cgtgggatat tctgtttccg     600
gcggatccgc cgtttagccc gcagagctgc cgcccgcaga gccgcagcga aagcaaaaaa     660
aaccgcggcg gccgcgaaga agtgctggaa cagtgggtga acggccgcaa aaaactggaa     720

```
gaactggaac gcgaactgcg ccgcgcgcgc aaaaaaatta aaaaactgga agatgataac      780
ccgtggctgg gcaacgtgaa aggcattctg ggcaaaaaag ataaagatgg cgaaggcgcg      840
ccgccggcga aacgcgcgcg caccgatcag atggaaattg atagcggccc gcgcaaacgc      900
ccgctgcgcg gcggctttac cgatcgcgaa cgccaggatc atcgccgccg caaagcgctg      960
aaaaacaaaa aaaaacagct gagcgcgggc ggcaaaagcc tgagcaaaga agaagaagaa     1020
gaactgaaac gcctgacccg cgaagatgaa gaacgcaaaa aagaagaaca tggcccgagc     1080
cgcctgggcg tgaacccgag cgaaggcggc ccgcgcggcg cgccgggcgg cggctttgtg     1140
ccgagcatgc agggcattcc ggaaagccgc tttacccgca ccggcgaagg cctggatgtg     1200
cgcggcagcc gcggctttcc gcaggatatt ctgtttccga gcgatccgcc gtttagcccg     1260
cagagctgcc gcccgcag                                                   1278
```

<210> SEQ ID NO 51
<211> LENGTH: 1310
<212> TYPE: DNA
<213> ORGANISM: Artificial Sequence
<220> FEATURE:
<223> OTHER INFORMATION: Delta 9 wt with restriction sites (HindIII
      /EcoRI)

<400> SEQUENCE: 51

```
aagcttgcac catggccagc cgcagcgaaa gcaaaaaaaa ccgcggcggc cgcgaagaaa       60
ttctggaaca gtgggtgggc gcgcgcaaaa aactggaaga actggaacgc gatctgcgca      120
aaattaaaaa aaaaattaaa aaactggaag aagaaacccc gtggctgggc aacattaaag      180
gcattctggg caaaaaagat cgcgaaggcg aaggcgcgcc gccggcgaaa cgcgcgcgcg      240
cggatcagat ggaagtggat agcggcccgc gcaaacgccc gtttcgcggc gaatttaccg      300
ataaagaacg ccgcgatcat cgccgccgca aagcgctgga aaacaaacgc aaacagctga      360
gcagcggcgg caaaagcctg agcaaagaag aagaagaaga actgcgcaaa ctgaccgaag      420
aagatgaacg ccgcgaacgc gcgtggcgg gcccgcgcgt gggcggcgtg aacccgctgg      480
aaggcggcac ccgcggcgcg ccgggcgcg ctttgtgcc gagcatgcag ggcgtgccgg      540
aaagcccgtt tgcgcgcacc ggcgaaggcc tggatgtgcg cggcaaccag ggctttccgt      600
gggatattct gtttccggcg gatccgccgt ttagcccgca gagctgccgc ccgcagagcc      660
gcagcgaaag caaaaaaaac cgcggcggcc gcgaagaagt gctggaacag tgggtgaacg      720
gccgcaaaaa actggaagaa ctggaacgcg aactgcgccg cgcgcgcaaa aaattaaaa      780 aactggaaga tgataacccg tggctgggca acgtgaaagg cattctgggc aaaaaagata      840
aagatggcga aggcgcgccg ccggcgaaac gcgcgcgcac cgatcagatg gaaattgata      900
gcggcccgcg caaacgcccg ctgcgcggcg ctttaccga tcgcgaacgc caggatcatc      960
gccgccgcaa agcgctgaaa aacaaaaaaa aacagctgag cgcgggcggc aaaagcctga     1020
gcaaagaaga agaagaagaa ctgaaacgcc tgacccgcga agatgaagaa cgcaaaaaag     1080
aagaacatgg cccgagccgc ctgggcgtga acccgagcga aggcggcccg cgcggcgcgc     1140
cgggcggcgg ctttgtgccg agcatgcagg gcattccgga aagccgcttt acccgcaccg     1200
gcgaaggcct ggatgtgcgc ggcagccgcg gctttccgca ggatattctg tttccgagcg     1260
atccgccgtt tagcccgcag agctgccgcc cgcagtgatg agaattccgt                1310
```

<210> SEQ ID NO 52
<211> LENGTH: 1281

```
<212> TYPE: DNA
<213> ORGANISM: Artificial Sequence
<220> FEATURE:
<223> OTHER INFORMATION: Delta 9 codon optimized

<400> SEQUENCE: 52
gccagtcgga gcgaatcaaa gaaaaataga gggggaagag aagaaatcct ggagcagtgg      60
gtcggggcac ggaaaaaact ggaagaactg gagcgggacc tgagaaagat caagaagaag     120
atcaagaagc tggaggaaga gaaccccctgg ctgggcaata tcaagggcat cctgggcaag    180
aaggataggg agggcgaggg agcaccacct gcaaagaggg caagggcaga ccagatggag     240
gtggattccg gaccaaggaa gcggcccttc cggggagagt ttaccgacaa ggagcggaga     300
gatcacaggc gccggaaggc cctggagaac aagcggaagc agctgagctc cggcggcaag     360
tctctgagca aggaggagga ggaggagctg agaaagctga cagaggagga cgagagaagg     420
gagaggaggg tggcaggacc tagggtggga ggcgtgaacc cactggaggg aggaaccagg     480
ggagcacctg gaggaggctt tgtgccatct atgcagggag tgccagagag cccttttcgcc    540 aggacaggag agggcctgga tgtgcgcggc aatcagggct tcccctggga catcctgttt     600
cctgccgatc caccccttcag cccacagtcc tgcaggccac agtcccgctc tgagagcaag    660
aagaacaggg gaggaaggga ggaggtgctg gagcagtggg tgaatggccg gaagaagctg     720
gaggagctgg agcgggagct gagaagggcc agaaagaaga tcaagaagct ggaagacgat     780
aatccttggc tgggcaatgt gaaaggcatc ctgggcaaga ggacaagga tggagaggga    840 gcacctccag caaagagggc acgcaccgac cagatgagca tcgattctgg acctaggaag     900
cggcccctga gggaggctt tacagacagg agcgccagg atcaccgccg agaaaggcc      960 ctgaagaaca agaagaagca gctgagcgcc ggcggcaagt ccctgtctaa gaagaggag    1020 gaggagctga gcggctgac cagagaggac gaggagcgga gaaggagga gcacggacca    1080 tccagactgg gagtgaatcc ttctgaggga ggaccaagag gcgccccagg cggcggcttt    1140
gtgccaagca tgcagggcat ccccgagtcc aggttcacca gaaccggcga aggcctggat    1200 gtgcgggggca gcagaggctt ccccaggat attctgtttc cctccgaccc cccctcagt    1260 ccccagtctt gccgacctca g                                              1281

<210> SEQ ID NO 53
<211> LENGTH: 1310
<212> TYPE: DNA
<213> ORGANISM: Artificial Sequence
<220> FEATURE:
<223> OTHER INFORMATION: Delta 9 codon optimized with restriction sites
      (HindIII /EcoRI)

<400> SEQUENCE: 53
aagcttgcac catggccagt cggagcgaat caaagaaaaa tagagggggga agagaagaaa    60 tcctggagca gtgggtcggg gcacggaaaa actggaagag actggagcgg gacctgagaa   120
agatcaagaa gaagatcaag aagctggagg aagagaaccc ctggctgggc aatatcaagg   180
gcatcctggg caagaaggat agggagggcg agggagcacc acctgcaaag agggcaaggg   240
cagaccagat ggaggtggat tccgaccaa ggaagcggcc cttccgggga gagtttaccg    300
acaaggagcg agagatcac aggcgccgga aggccctgga gaacaagcgg aagcagctga   360
gctccggcgg caagtctctg agcaaggagg aggaggagga gctgagaaag ctgacagagg   420
aggacgagag aagggagagg agggtggcag gacctagggt gggaggcgtg aacccactgg   480
agggaggaac caggggagca cctggaggag gctttgtgcc atctatgcag ggagtgccag   540
```

```
agagcccttt cgccaggaca ggagagggcc tggatgtgcg cggcaatcag ggcttcccct    600
gggacatcct gtttcctgcc gatccaccct tcagcccaca gtcctgcagg ccacagtccc    660
gctctgagag caagaagaac aggggaggaa ggggaggaggt gctggagcag tgggtgaatg   720
gccggaagaa gctggaggag ctggagcggg agctgagaag ggccagaaag aagatcaaga    780
agctggaaga cgataatcct tggctgggca atgtgaaagg catcctgggc aagaaggaca    840
aggatggaga gggagcacct ccagcaaaga gggcacgcac cgaccagatg gagatcgatt    900
ctggacctag gaagcggccc ctgagaggag gctttacaga cagggagcgc caggatcacc    960
gccggagaaa ggccctgaag aacaagaaga agcagctgag cgccggcggc aagtccctgt   1020
ctaaagaaga ggaggaggag ctgaagcggc tgaccagaga ggacgaggag cggaagaagg   1080
aggagcacgg accatccaga ctgggagtga atccttctga gggaggacca agaggcgccc   1140
caggcggcgg ctttgtgcca agcatgcagg gcatccccga gtccaggttc accagaaccg   1200
gcgaaggcct ggatgtgcgg ggcagcagag gcttcccccca ggatattctg tttccctccg   1260 acccccccttt cagtccccag tcttgccgac ctcagtgatg agaattccgt            1310
```

<210> SEQ ID NO 54
<211> LENGTH: 428
<212> TYPE: PRT
<213> ORGANISM: Artificial Sequence
<220> FEATURE:
<223> OTHER INFORMATION: Delta 9 protein

<400> SEQUENCE: 54

```
Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Lys Ala Leu Glu Asn Lys
            100                 105                 110

Arg Lys Gln Leu Ser Ser Gly Lys Ser Leu Ser Lys Glu Glu Glu
        115                 120                 125

Glu Glu Leu Arg Lys Leu Thr Glu Glu Asp Arg Arg Glu Arg Arg
    130                 135                 140

Val Ala Gly Pro Arg Val Gly Val Asn Pro Leu Glu Gly Gly Thr
145                 150                 155                 160

Arg Gly Ala Pro Gly Gly Gly Phe Val Pro Ser Met Gln Gly Val Pro
                165                 170                 175

Glu Ser Pro Phe Ala Arg Thr Gly Glu Gly Leu Asp Val Arg Gly Asn
            180                 185                 190

Gln Gly Phe Pro Trp Asp Ile Leu Phe Pro Ala Asp Pro Pro Phe Ser
        195                 200                 205

Pro Gln Ser Cys Arg Pro Gln Ser Arg Ser Glu Ser Lys Lys Asn Arg
    210                 215                 220
```

Gly Gly Arg Glu Glu Val Leu Glu Gln Trp Val Asn Gly Arg Lys Lys
225                 230                 235                 240

Leu Glu Glu Leu Glu Arg Glu Leu Arg Arg Ala Arg Lys Lys Ile Lys
            245                 250                 255

Lys Leu Glu Asp Asp Asn Pro Trp Leu Gly Asn Val Lys Gly Ile Leu
        260                 265                 270

Gly Lys Lys Asp Lys Asp Gly Glu Gly Ala Pro Pro Ala Lys Arg Ala
    275                 280                 285

Arg Thr Asp Gln Met Glu Ile Asp Ser Gly Pro Arg Lys Arg Pro Leu
290                 295                 300

Arg Gly Gly Phe Thr Asp Arg Glu Arg Gln Asp His Arg Arg Arg Lys
305                 310                 315                 320

Ala Leu Lys Asn Lys Lys Gln Leu Ser Ala Gly Gly Lys Ser Leu
            325                 330                 335

Ser Lys Glu Glu Glu Glu Leu Lys Arg Leu Thr Arg Glu Asp Glu
        340                 345                 350

Glu Arg Lys Lys Glu Glu His Gly Pro Ser Arg Leu Gly Val Asn Pro
        355                 360                 365

Ser Glu Gly Gly Pro Arg Gly Ala Pro Gly Gly Gly Phe Val Pro Ser
370                 375                 380

Met Gln Gly Ile Pro Glu Ser Arg Phe Thr Arg Thr Gly Glu Gly Leu
385                 390                 395                 400

Asp Val Arg Gly Ser Arg Gly Phe Pro Gln Asp Ile Leu Phe Pro Ser
            405                 410                 415

Asp Pro Pro Phe Ser Pro Gln Ser Cys Arg Pro Gln
            420                 425

<210> SEQ ID NO 55
<211> LENGTH: 1278
<212> TYPE: DNA
<213> ORGANISM: Artificial Sequence
<220> FEATURE:
<223> OTHER INFORMATION: Delta 10 wt

<400> SEQUENCE: 55
agccagagcg aaacccgccg cggccgccgc ggcacccgcg aagaaaccct ggaaaatgg      60 attaccgcgc gcaaaaaagc ggaagaactg gaaaagatc tgcgcaaaac ccgcaaaacc    120
attaaaaaac tggaagaaga aaacccgtgg ctgggcaaca ttgtgggcat tattcgcaaa    180
ggcaaagatg gcgaaggcgc gccgccggcg aaacgcccgc gcaccgatca gatggaagtg    240
gatagcggcc cgggcaaacg cccgcataaa gcggcttta ccgataaaga acgcgaagat    300
catcgccgcc gcaaagcgct ggaaaacaaa aaaaacagc tgagcgcggg cggcaaaatt    360
ctgagcaaag aagaagaaga agaactgcgc cgcctgaccg atgaagatga agaacgcaaa    420
cgccgcgtgg cgggcccgcg cgtgggcgat gtgaacccga gccgcggcgg cccgcgcggc    480
gcgccgggcg gcggctttgt gccgcagatg gcgggcgtgc cggaaagccc gtttagccgc    540
accggcgaag gcctggatat cgcggcacc cagggctttc cgtgggtgag cccgagcccg    600
ccgcagcagc gcctgccgct gctggaatgc accccgcaga gccagagcga aagcaaaaaa    660
aaccgccgcg gcggccgcga agatattctg gaaaatgga ttaccacccg ccgcaaagcg    720
gaagaactgg aaaaagatct gcgcaaagcg cgcaaaacca ttaaaaaact ggaagatgaa    780
aacccgtggc tgggcaacat tattggcatt attcgcaaag gcaaagatgg cgaaggcgcg    840
ccgccggcga aacccgcg caccgatcag atggaaattg atagcggcac cggcaaacgc    900

```
ccgcataaaa gcggctttac cgataaagaa cgcgaagatc atcgccgccg caaagcgctg    960
gaaaacaaaa aaaaacagct gagcagcggc ggcaaaaacc tgagccgcga agaagaagaa   1020
gaactgggcc gcctgaccgt ggaagatgaa gaacgccgcc gccgcgtggc gggcccgcgc   1080
accggcgatg tgaacctgag cggcggcggc cgcgcggcg cgccgggcgg cggctttgtg   1140
ccgcgcatgg aaggcgtgcc ggaaagcccg tttacccgca ccggcgaagg cctggatatt   1200
cgcggcaacc agggctttcc gtgggtgcgc ccgagcccgc cgcagcagcg cctgccgctg   1260
ctggaatgca ccccgcag                                                 1278
```

<210> SEQ ID NO 56  
<211> LENGTH: 1310  
<212> TYPE: DNA  
<213> ORGANISM: Artificial Sequence  
<220> FEATURE:  
<223> OTHER INFORMATION: Delta 10 wt with restriction sites (HindIII /EcoRI)

<400> SEQUENCE: 56

```
aagcttgcac catggccagc cagagcgaaa cccgccgcgg ccgccgcggc acccgcgaag     60
aaaccctgga aaatggatt accgcgcgca aaaaagcgga agaactggaa aaagatctgc    120
gcaaaacccg caaaccatt aaaaaactgg aagaagaaaa cccgtggctg gcaacattg    180 tgggcattat tcgcaaaggc aaagatggcg aaggcgcgcc gccggcgaaa cgcccgcgca    240
ccgatcagat ggaagtggat agcggcccgg gcaaacgccc gcataaaagc ggctttaccg    300
ataaagaacg cgaagatcat cgccgccgca agcgctggaa aaacaaaaaa aaacagctga    360
gcgcgggcgg caaaattctg agcaaagaag aagaagaaga actgcgccgc ctgaccgatg    420
aagatgaaga acgcaaacgc cgcgtggcgg gcccgcgcgt gggcgatgtg aacccgagcc    480
gcggcggccc gcgcggcgcg ccgggcggcg ctttgtgcc gcagatggcg ggcgtgccgg    540
aaagcccgtt tagccgcacc ggcgaaggcc tggatattcg cggcacccag ggctttccgt    600
gggtgagccc gagcccgccg cagcagcgcc tgccgctgct ggaatgcacc ccgcagagcc    660
agagcgaaag caaaaaaaac cgccgcggcg ccgcgaaga tattctggaa aaatggatta    720 ccaccccgccg caaagcggaa gaactggaaa aagatctgcg caaagcgcgc aaaaccatta    780
aaaaactgga agatgaaaac ccgtggctgg gcaacattat tggcattatt cgcaaaggca    840
aagatggcga aggcgcgccg ccggcgaaac gcccgcgcac cgatcagatg gaaattgata    900
gcggcaccgg caaacgcccg cataaaagcg gctttaccga taaagaacgc gaagatcatc    960
gccgccgcaa agcgctggaa aacaaaaaaa acagctgag cagcggcggc aaaaacctga   1020
gccgcgaaga agaagaagaa ctgggccgcc tgaccgtgga agatgaagaa cgccgccgcc   1080
gcgtggcggg cccgcgcacc ggcgatgtga acctgagcgg cggcggcccg cgcggcgcgc   1140
cgggcggcgg ctttgtgccg cgcatggaag gcgtgccgga aagcccgttt acccgcaccg   1200
gcgaaggcct ggatattcgc ggcaaccagg gctttccgtg ggtgcgcccg agcccgccgc   1260
agcagcgcct gccgctgctg gaatgcaccc cgcagtgatg agaattccgt              1310
```

<210> SEQ ID NO 57  
<211> LENGTH: 1281  
<212> TYPE: DNA  
<213> ORGANISM: Artificial Sequence  
<220> FEATURE:  
<223> OTHER INFORMATION: Delta 10 codon optimized

<400> SEQUENCE: 57

```
gcctcacaga gcgaaacacg gcgggggcgg aggggaacta gagaggaaac actggaaaaa      60
tggattacag cacggaaaaa ggcagaggaa ctggagaagg acctgaggaa gacccgcaag     120
acaatcaaga agctggagga ggagaaccca tggctgggca atatcgtggg catcatccgg     180
aagggcaagg atggagaggg agcaccacct gcaaagaggc cccgcaccga ccagatggag     240
gtggattctg gccctggcaa gaggccacac aagagcggct tcacagacaa ggagcgcgag     300
gatcaccgga gaaggaaggc cctggagaac aagaagaagc agctgagcgc cggcggcaag     360
atcctgtcca aggaggagga ggaggagctg cgccggctga ccgacgagga tgaggagcgg     420
aagagaaggg tggcaggacc aagagtgggc gacgtgaatc cctctagggg aggaccaagg     480
ggagcacctg gaggaggctt cgtgcctcag atggcaggag tgccagagtc ccctttttct     540
aggaccggag agggcctgga tatcagggga acacagggct ttccatgggt gtctccaagc     600
ccaccacagc agaggctgcc actgctggag tgcacccctc agtcccagtc tgagagcaag     660
aagaacagga ggggaggaag ggaggacatc ctggagaagt ggatcaccac aagaaggaag     720
gccgaggagc tggagaagga cctgcggaag gccagaaaaa caatcaagaa gctggaagat     780
gagaacccct ggctgggcaa tatcatcggc atcatcagaa aaggcaagga cggcgaggga     840
gcacctccag caaagcggcc tagaaccgac cagatggaga tcgattccgg cacaggcaag     900
cggccacaca gtctggcttt caccgacaag gagagagagg atcaccgccg gagaaaggcc     960
ctggaaaaca agaagaagca attaagctcc ggcggcaaga atctgagcag agaagaagag    1020
gaggagctgg gcagactgac cgtggaggac gaggagaggc cggagagt ggcaggaccc    1080 agaacaggcg atgtgaacct gagcggagga ggacctaggg gagcaccagg aggcggcttc    1140
gtgcctagaa tggagggcgt gccagagtcc ccctttacca ggacaggaga gggcctggac    1200
atcaggggca atcagggctt tccctgggtc cgccttcac caccacagca gagactgccc    1260
ctgctggaat gcacaccaca g                                             1281

<210> SEQ ID NO 58
<211> LENGTH: 1310
<212> TYPE: DNA
<213> ORGANISM: Artificial Sequence
<220> FEATURE:
<223> OTHER INFORMATION: Delta 10 codon optimized with restriction sites
      (HindIII /EcoRI)

<400> SEQUENCE: 58
aagcttgcac catggcctca cagagcgaaa cacggcgggg gcggagggga actagagagg      60
aaacactgga aaatggatt acagcacgga aaaaggcaga ggaactggag aaggacctga     120
ggaagacccg caagacaatc aagaagctgg aggaggagaa cccatggctg gcaatatcg     180 tgggcatcat ccggaaggc aaggatggag agggagcacc acctgcaaag aggccccgca     240
ccgaccagat ggaggtggat tctggccctg gcaagaggcc acacaagagc ggcttcacag     300
acaaggagcg cgaggatcac cggagaagga aggccctgga gaacaagaag aagcagctga     360
gcgccggcgg caagatcctg tccaaggagg aggaggagga gctgcgccgg ctgaccgacg     420
aggatgagga gcggaagaga agggtggcag gaccaagagt gggcgacgtg aatccctcta     480
ggggaggacc aaggggagca cctggaggag gcttcgtgcc tcagatggca ggagtgccag     540
agtccccttt ttctaggacc ggagagggcc tggatatcag gggaacacag gctttccat     600 gggtgtctcc aagcccacca cagcagaggc tgccactgct ggagtgcacc ctcagtccc     660 agtctgagag caagaagaac aggagggag gaagggagga catcctggag aagtggatca     720
```

```
ccacaagaag gaaggccgag gagctggaga aggacctgcg gaaggccaga aaaacaatca    780
agaagctgga agatgagaac ccctggctgg gcaatatcat cggcatcatc agaaaaggca    840
aggacggcga gggagcacct ccagcaaagc ggcctagaac cgaccagatg gagatcgatt    900
ccggcacagg caagcggcca cacaagtctg gcttcaccga caaggagaga gaggatcacc    960
gccggagaaa ggccctggaa aacaagaaga agcaattaag ctccggcggc aagaatctga   1020
gcagagaaga agaggaggag ctgggcagac tgaccgtgga ggacgaggag aggcgccgga   1080
gagtggcagg acccagaaca ggcgatgtga acctgagcgg aggaggacct aggggagcac   1140
caggaggcgg cttcgtgcct agaatggagg gcgtgccaga gtccccctttt accaggacag   1200 gagagggcct ggacatcagg ggcaatcagg gctttccctg ggtccgccct tcaccaccac   1260
agcagagact gccctgctg gaatgcacac cacagtgatg agaattccgt                1310
```

```
<210> SEQ ID NO 59
<211> LENGTH: 428
<212> TYPE: PRT
<213> ORGANISM: Artificial Sequence
<220> FEATURE:
<223> OTHER INFORMATION: Delta 10 protein

<400> SEQUENCE: 59

Met Ala Ser Gln Ser Glu Thr Arg Arg Gly Arg Arg Gly Thr Arg Glu
1               5                   10                  15

Glu Thr Leu Glu Lys Trp Ile Thr Ala Arg Lys Lys Ala Glu Glu Leu
            20                  25                  30

Glu Lys Asp Leu Arg Lys Thr Arg Lys Thr Ile Lys Lys Leu Glu Glu
        35                  40                  45

Glu Asn Pro Trp Leu Gly Asn Ile Val Gly Ile Ile Arg Lys Gly Lys
    50                  55                  60

Asp Gly Glu Gly Ala Pro Pro Ala Lys Arg Pro Arg Thr Asp Gln Met
65                  70                  75                  80

Glu Val Asp Ser Gly Pro Gly Lys Arg Pro His Lys Ser Gly Phe Thr
                85                  90                  95

Asp Lys Glu Arg Glu Asp His Arg Arg Arg Lys Ala Leu Glu Asn Lys
            100                 105                 110

Lys Lys Gln Leu Ser Ala Gly Gly Lys Ile Leu Ser Lys Glu Glu Glu
        115                 120                 125

Glu Glu Leu Arg Arg Leu Thr Asp Glu Asp Glu Glu Arg Lys Arg Arg
    130                 135                 140

Val Ala Gly Pro Arg Val Gly Asp Val Asn Pro Ser Arg Gly Gly Pro
145                 150                 155                 160

Arg Gly Ala Pro Gly Gly Gly Phe Val Pro Gln Met Ala Gly Val Pro
                165                 170                 175

Glu Ser Pro Phe Ser Arg Thr Gly Glu Gly Leu Asp Ile Arg Gly Thr
            180                 185                 190

Gln Gly Phe Pro Trp Val Ser Pro Ser Pro Gln Gln Arg Leu Pro
        195                 200                 205

Leu Leu Glu Cys Thr Pro Gln Ser Gln Ser Glu Ser Lys Lys Asn Arg
    210                 215                 220

Arg Gly Gly Arg Glu Asp Ile Leu Glu Lys Trp Ile Thr Thr Arg Arg
225                 230                 235                 240

Lys Ala Glu Glu Leu Glu Lys Asp Leu Arg Lys Ala Arg Lys Thr Ile
                245                 250                 255

Lys Lys Leu Glu Asp Glu Asn Pro Trp Leu Gly Asn Ile Ile Gly Ile
```

```
                    260                 265                 270
Ile Arg Lys Gly Lys Asp Gly Glu Gly Ala Pro Pro Ala Lys Arg Pro
            275                 280                 285

Arg Thr Asp Gln Met Glu Ile Asp Ser Gly Thr Gly Lys Arg Pro His
        290                 295                 300

Lys Ser Gly Phe Thr Asp Lys Glu Arg Glu Asp His Arg Arg Arg Lys
305                 310                 315                 320

Ala Leu Glu Asn Lys Lys Lys Gln Leu Ser Ser Gly Gly Lys Asn Leu
                325                 330                 335

Ser Arg Glu Glu Glu Glu Leu Gly Arg Leu Thr Val Glu Asp Glu
            340                 345                 350

Glu Arg Arg Arg Val Ala Gly Pro Arg Thr Gly Asp Val Asn Leu
        355                 360                 365

Ser Gly Gly Pro Arg Gly Ala Pro Gly Gly Phe Val Pro Arg
    370                 375                 380

Met Glu Gly Val Pro Glu Ser Pro Phe Thr Arg Thr Gly Glu Gly Leu
385                 390                 395                 400

Asp Ile Arg Gly Asn Gln Gly Phe Pro Trp Val Arg Ser Pro Pro
                405                 410                 415

Gln Gln Arg Leu Pro Leu Leu Glu Cys Thr Pro Gln
            420                 425

<210> SEQ ID NO 60
<211> LENGTH: 546
<212> TYPE: DNA
<213> ORGANISM: Artificial Sequence
<220> FEATURE:
<223> OTHER INFORMATION: Core 1 wt (C-gt-H)

<400> SEQUENCE: 60
gatattgatc cgtataaaga atttggcgcg agcgtggaac tgctgagctt tctgccgagc      60 gattttttc cgagcgtgcg cgatctgctg ataccgcga gcgcgctgta tcgcgatgcg      120
ctggaaagcc cggaacattg caccccgaac cataccgcgc tgcgccaggc gattctgtgc      180
tggggcgaac tgatgaccct ggcgagctgg gtgggcaaca acctggaaga tccggcggcg      240
cgcgatctgg tggtgaacta tgtgaacacc aacatgggcc tgaaaattcg ccagctgctg      300
tggtttcata ttagctgcct gacctttggc cgcgaaaccg tgctggaata tctggtgagc      360
tttggcgtgt ggattcgcac cccgccggcg tatcgcccgc gaacgcgcc gattctgagc      420 accctgccgg aaaccaccgt ggtgcgccag cgcggccgcg cgccgcgccg ccgcaccccg      480
agcccgcgcc gccgccgcag ccagagcccg cgccgccgcc gcagccagag cccggcgagc      540
cagtgc                                                                 546

<210> SEQ ID NO 61
<211> LENGTH: 575
<212> TYPE: DNA
<213> ORGANISM: Artificial Sequence
<220> FEATURE:
<223> OTHER INFORMATION: Core 1 wt with restriction sites (HindIII
      /EcoRI)

<400> SEQUENCE: 61
aagcttgcac catggatatt gatccgtata agaatttgg cgcgagcgtg gaactgctga      60
gctttctgcc gagcgatttt ttccgagcg tgcgcgatct gctggatacc gcgagcgcgc      120
tgtatcgcga tgcgctggaa agcccggaac attgcacccc gaaccatacc gcgctgcgcc      180
```

```
aggcgattct gtgctggggc gaactgatga ccctggcgag ctgggtgggc aacaacctgg    240
aagatccggc ggcgcgcgat ctggtggtga actatgtgaa caccaacatg ggcctgaaaa    300
ttcgccagct gctgtggttt catattagct gcctgacctt tggccgcgaa accgtgctgg    360
aatatctggt gagctttggc gtgtggattc gcaccccgcc ggcgtatcgc ccgccgaacg    420
cgccgattct gagcaccctg ccggaaacca ccgtggtgcg ccagcgcggc cgcgcgccgc    480
gccgccgcac cccgagcccg cgccgccgcc gcagccagag cccgcgccgc cgccgcagcc    540
agagcccggc gagccagtgc tgatgagaat tccgt                              575
```

<210> SEQ ID NO 62
<211> LENGTH: 546
<212> TYPE: DNA
<213> ORGANISM: Artificial Sequence
<220> FEATURE:
<223> OTHER INFORMATION: Core 1 codon optimized

<400> SEQUENCE: 62

```
gatattgatc cctataagga gtttggagcc tctgtggagc tgctgagttt tctgccatcc     60
gatttctttc ccagtgtccg agacctgctg acaccgcaa gcgccctgta cagggatgca    120
ctggagtccc cagagcactg caccctaac cacacagccc tgaggcaggc aatcctgtgc    180
tggggagagc tgatgaccct ggcaagctgg gtgggcaaca atctggagga ccctgcagca    240
cgggatctgg tggtgaatta tgtgaacaca atatgggcc tgaagatccg gcagctgctg    300
tggttccaca tctcttgcct gacctttggc agagagacag tgctggagta cctggtgagc    360
ttcggcgtgt ggatcaggac cccacctgca tataggccac aaacgcacc aatcctgtcc    420 acactgccag agacaacagt ggtgcgccag aggggaagag caccacggag aaggacacct    480
tctccaagac gaaggcgaag ccagagcccc aggcgaagac gaagccagtc cccagcaagc    540
cagtgc                                                              546
```

<210> SEQ ID NO 63
<211> LENGTH: 575
<212> TYPE: DNA
<213> ORGANISM: Artificial Sequence
<220> FEATURE:
<223> OTHER INFORMATION: Core 1 codon optimized with restriction sites
      (HindIII /EcoRI)

<400> SEQUENCE: 63

```
aagcttgcac catggatatt gatccctata aggagtttgg agcctctgtg agctgctga     60 gttttctgcc atccgatttc tttcccagtg tccgagacct gctggacacc gcaagcgccc    120
tgtacaggga tgcactggag tccccagagc actgcacccc taaccacaca gccctgaggc    180
aggcaatcct gtgctgggga gagctgatga ccctggcaag ctgggtgggc aacaatctgg    240
aggaccctgc agcacgggat ctggtggtga attatgtgaa cacaaatatg ggcctgaaga    300
tccggcagct gctgtggttc acatctctt gcctgacctt tggcagagag acagtgctgg    360
agtacctggt gagcttcggc gtgtggatca ggaccccacc tgcatatagg ccaccaaacg    420
caccaatcct gtccacactg ccagagacaa cagtggtgcg ccagagggga agagcaccac    480
ggagaaggac accttctcca agacgaaggc gaagccagag ccccaggcga agacgaagcc    540
agtccccagc aagccagtgc tgatgagaat tccgt                              575
```

<210> SEQ ID NO 64
<211> LENGTH: 183
<212> TYPE: PRT

<213> ORGANISM: Artificial Sequence
<220> FEATURE:
<223> OTHER INFORMATION: Core 1 protein

<400> SEQUENCE: 64

```
Met Asp Ile Asp Pro Tyr Lys Glu Phe Gly Ala Ser Val Glu Leu Leu
1               5                  10                  15
Ser Phe Leu Pro Ser Asp Phe Phe Pro Ser Val Arg Asp Leu Leu Asp
            20                  25                  30
Thr Ala Ser Ala Leu Tyr Arg Asp Ala Leu Glu Ser Pro Glu His Cys
        35                  40                  45
Thr Pro Asn His Thr Ala Leu Arg Gln Ala Ile Leu Cys Trp Gly Glu
    50                  55                  60
Leu Met Thr Leu Ala Ser Trp Val Gly Asn Asn Leu Glu Asp Pro Ala
65                  70                  75                  80
Ala Arg Asp Leu Val Val Asn Tyr Val Asn Thr Asn Met Gly Leu Lys
                85                  90                  95
Ile Arg Gln Leu Leu Trp Phe His Ile Ser Cys Leu Thr Phe Gly Arg
            100                 105                 110
Glu Thr Val Leu Glu Tyr Leu Val Ser Phe Gly Val Trp Ile Arg Thr
        115                 120                 125
Pro Pro Ala Tyr Arg Pro Pro Asn Ala Pro Ile Leu Ser Thr Leu Pro
    130                 135                 140
Glu Thr Thr Val Val Arg Gln Arg Gly Arg Ala Pro Arg Arg Arg Thr
145                 150                 155                 160
Pro Ser Pro Arg Arg Arg Arg Ser Gln Ser Pro Arg Arg Arg Arg Ser
                165                 170                 175
Gln Ser Pro Ala Ser Gln Cys
            180
```

<210> SEQ ID NO 65
<211> LENGTH: 633
<212> TYPE: DNA
<213> ORGANISM: Artificial Sequence
<220> FEATURE:
<223> OTHER INFORMATION: Pre-C-gt-H wt

<400> SEQUENCE: 65

```
cagctgtttc atctgtgcct gattattttt tgcagctgcc cgaccgtgca ggcgagcaaa    60
ctgtgcctgg gctggctgtg gggcatggat attgatccgt ataaagaatt tggcgcgagc   120
gtggaactgc tgagctttct gccgagcgat ttttttccga gcgtgcgcga tctgctggat   180
accgcgagcg cgctgtatcg cgatgcgctg gaaagcccgg aacattgcac cccgaaccat   240
accgcgctgc gccaggcgat tctgtgctgg ggcgaactga tgaccctggc gagctgggtg   300
ggcaacaacc tggaagatcc ggcggcgcgc gatctggtgg tgaactatgt gaacaccaac   360
atgggcctga aaattcgcca gctgctgtgg tttcatatta gctgcctgac ctttggccgc   420
gaaaccgtgc tggaatatct ggtgagcttt ggcgtgtgga ttcgcacccc gccggcgtat   480
cgcccgccga acgcgccgat tctgagcacc ctgccggaaa ccaccgtggt gcgccagcgc   540
ggccgcgcgc cgcgccgccg caccccgagc ccgcgccgcc gccgcagcca gagcccgcgc   600
cgccgccgca gccagagccc ggcgagccag tgc                                633
```

<210> SEQ ID NO 66
<211> LENGTH: 665
<212> TYPE: DNA
<213> ORGANISM: Artificial Sequence
<220> FEATURE:
<223> OTHER INFORMATION: Pre-C-gt-H wt with restriction sites (HindIII /EcoRI)

<400> SEQUENCE: 66

```
aagcttgcac catggcccag ctgtttcatc tgtgcctgat tattttttgc agctgcccga      60
ccgtgcaggc gagcaaactg tgcctgggct ggctgtgggg catggatatt gatccgtata     120
aagaatttgg cgcgagcgtg gaactgctga gctttctgcc gagcgatttt tttccgagcg     180
tgcgcgatct gctggatacc gcgagcgcgc tgtatcgcga tgcgctggaa agcccggaac     240
attgcacccc gaaccatacc gcgctgcgcc aggcgattct gtgctggggc gaactgatga     300
ccctggcgag ctgggtgggc aacaacctgg aagatccggc ggcgcgcgat ctggtggtga     360
actatgtgaa caccaacatg ggcctgaaaa ttcgccagct gctgtggttt catattagct     420
gcctgacctt tggccgcgaa accgtgctgg aatatctggt gagctttggc gtgtggattc     480
gcaccccgcc ggcgtatcgc ccgccgaacg cgccgattct gagcaccctg ccggaaacca     540
ccgtggtgcg ccagcgcggc cgcgcgccgc gccgccgcac cccgagcccg cgccgccgcc     600
gcagccagag cccgcgccgc cgccgcagcc agagcccggc gagccagtgc tgatgagaat     660
tccgt                                                                 665
```

<210> SEQ ID NO 67
<211> LENGTH: 636
<212> TYPE: DNA
<213> ORGANISM: Artificial Sequence
<220> FEATURE:
<223> OTHER INFORMATION: Pre-C-gt-H codon optimized

<400> SEQUENCE: 67

```
gcccagctgt tcatctgtgt cctgattatt ttctgttcat gccctaccgt ccaggcttct      60
aaactgtgcc tggggtggct gtggggaatg gacatcgatc cctacaagga gttcggcgcc     120
agcgtggagc tgctgagctt tctgccctcc gacttctttc cttctgtgcg ggacctgctg     180
gataccgcaa gcgccctgta tagagatgca ctggagtccc agagcactg caccccaaac     240
cacacagccc tgaggcaggc aatcctgtgc tggggagagc tgatgaccct ggcatcctgg     300
gtgggcaaca atctggagga ccctgccgcc agagatctgg tggtgaatta cgtgaacaca     360
aatatgggcc tgaagatcag gcagctgctg tggttccaca tctcttgcct gacctttggc     420
cgcgagacag tgctggagta cctggtgagc ttcggcgtgt ggatcaggac cccacctgca     480
tataggccac caaacgcacc tatcctgtcc acactgccag agacaacagt ggtgcgccag     540
aggggaagag caccacggag aaggacacct tctccaagga ggagaagaag ccagtcccca     600
cgaagaagac gaagccagag cccagccagc cagtgt                              636
```

<210> SEQ ID NO 68
<211> LENGTH: 665
<212> TYPE: DNA
<213> ORGANISM: Artificial Sequence
<220> FEATURE:
<223> OTHER INFORMATION: Pre-C-gt-H codon optimized with restriction sites (HindIII /EcoRI)

<400> SEQUENCE: 68

```
aagcttgcac catggcccag ctgtttcatc tgtgcctgat tattttctgt tcatgcccta      60
ccgtccaggc ttctaaactg tgcctggggt ggctgtgggg aatggacatc gatccctaca     120
aggagttcgg cgccagcgtg gagctgctga gctttctgcc ctccgacttc tttccttctg     180
```

```
tgcgggacct gctggatacc gcaagcgccc tgtatagaga tgcactggag tccccagagc    240
actgcacccc aaaccacaca gccctgaggc aggcaatcct gtgctgggga gagctgatga    300
ccctggcatc ctgggtgggc aacaatctgg aggaccctgc cgccagagat ctggtggtga    360
attacgtgaa cacaaatatg ggcctgaaga tcaggcagct gctgtggttc cacatctctt    420
gcctgacctt tggccgcgag acagtgctgg agtacctggt gagcttcggc gtgtggatca    480 ggacccacc tgcatatagg ccaccaaacg cacctatcct gtccacactg ccagagacaa    540
cagtggtgcg ccagagggga agagcaccac ggagaaggac accttctcca aggaggagaa    600
gaagccagtc cccacgaaga agacgaagcc agagcccagc cagccagtgt tgatgagaat    660
tccgt                                                                665
```

```
<210> SEQ ID NO 69
<211> LENGTH: 213
<212> TYPE: PRT
<213> ORGANISM: Artificial Sequence
<220> FEATURE:
<223> OTHER INFORMATION: Pre-C-gt-H protein

<400> SEQUENCE: 69

Met Ala Gln Leu Phe His Leu Cys Leu Ile Ile Phe Cys Ser Cys Pro
1               5                   10                  15

Thr Val Gln Ala Ser Lys Leu Cys Leu Gly Trp Leu Trp Gly Met Asp
            20                  25                  30

Ile Asp Pro Tyr Lys Glu Phe Gly Ala Ser Val Glu Leu Leu Ser Phe
        35                  40                  45

Leu Pro Ser Asp Phe Phe Pro Ser Val Arg Asp Leu Leu Asp Thr Ala
    50                  55                  60

Ser Ala Leu Tyr Arg Asp Ala Leu Glu Ser Pro Glu His Cys Thr Pro
65                  70                  75                  80

Asn His Thr Ala Leu Arg Gln Ala Ile Leu Cys Trp Gly Glu Leu Met
                85                  90                  95

Thr Leu Ala Ser Trp Val Gly Asn Asn Leu Glu Asp Pro Ala Ala Arg
            100                 105                 110

Asp Leu Val Val Asn Tyr Val Asn Thr Asn Met Gly Leu Lys Ile Arg
        115                 120                 125

Gln Leu Leu Trp Phe His Ile Ser Cys Leu Thr Phe Gly Arg Glu Thr
    130                 135                 140

Val Leu Glu Tyr Leu Val Ser Phe Gly Val Trp Ile Arg Thr Pro Pro
145                 150                 155                 160

Ala Tyr Arg Pro Pro Asn Ala Pro Ile Leu Ser Thr Leu Pro Glu Thr
                165                 170                 175

Thr Val Val Arg Gln Arg Gly Arg Ala Pro Arg Arg Thr Pro Ser
            180                 185                 190

Pro Arg Arg Arg Arg Ser Gln Ser Pro Arg Arg Arg Ser Gln Ser
        195                 200                 205

Pro Ala Ser Gln Cys
    210

<210> SEQ ID NO 70
<211> LENGTH: 633
<212> TYPE: DNA
<213> ORGANISM: Artificial Sequence
<220> FEATURE:
<223> OTHER INFORMATION: PreC-C-Mut-gt-H wt

<400> SEQUENCE: 70
```

```
cagctgtttc atctgtgcct gattattttt tgcagctgcc cgacctttca gtttccgaaa    60
ctgtgcctgg gctggctgtg gggcatggat attgatccgt ataaagaatt tggcgcgagc   120
gtggaactgc tgagctttct gccgagcgat tttttccga gcgtgcgcga tctgctggat    180
accgcgagcg cgctgtatcg cgatgcgctg gaaagcccgg aacattgcac cccgaaccat   240
accgcgctgc gccaggcgat tctgtgctgg ggcgaactga tgaccctggc gagctgggtg   300
ggcaacaacc tggaagatcc ggcggcgcgc gatctggtgg tgaactatgt gaacaccaac   360
atgggcctga aaattcgcca gctgctgtgg tttcatatta gctgcctgac ctttggccgc   420
gaaaccgtgc tggaatatct ggtgagcttt ggcgtgtgga ttcgcacccc gccggcgtat   480
cgcccgccga acgcgccgat tctgagcacc ctgccggaaa ccaccgtggt gcgccagcgc   540
ggccgcgcgc cgccgccgcc cacccccgagc ccgcgccgcc gccgcagcca gagcccgcgc   600
cgccgccgca gccagagccc ggcgagccag tgc                                 633

<210> SEQ ID NO 71
<211> LENGTH: 665
<212> TYPE: DNA
<213> ORGANISM: Artificial Sequence
<220> FEATURE:
<223> OTHER INFORMATION: PreC-C-Mut-gt-H wt with restriction sites
      (HindIII /EcoRI)

<400> SEQUENCE: 71
aagcttgcac catggcccag ctgtttcatc tgtgcctgat tatttttgc agctgcccga     60 cctttcagtt tccgaaactg tgcctgggct ggctgtgggg catggatatt gatccgtata   120
aagaatttgg cgcgagcgtg gaactgctga gctttctgcc gagcgatttt tttccgagcg   180
tgcgcgatct gctggatacc gcgagcgcgc tgtatcgcga tgcgctggaa agcccggaac   240
attgcacccc gaaccatacc gcgctgcgcc aggcgattct gtgctggggc gaactgatga   300
ccctggcgag ctgggtgggc aacaacctgg aagatccggc ggcgcgcgat ctggtggtga   360
actatgtgaa caccaacatg ggcctgaaaa ttcgccagct gctgtggttt catattagct   420
gcctgacctt tggccgcgaa accgtgctgg aatatctggt gagctttggc gtgtggattc   480
gcaccccgcc ggcgtatcgc ccgccgaacg cgccgattct gagcaccctg ccggaaacca   540
ccgtggtgcg ccagcgcggc cgcgcgccg ccgccgccg ccgccgcac cccgagcccg cgccgccgcc   600
gcagccagag cccgcgccgc cgccgcagcc agagcccggc gagccagtgc tgatgagaat   660
tccgt                                                                665

<210> SEQ ID NO 72
<211> LENGTH: 636
<212> TYPE: DNA
<213> ORGANISM: Artificial Sequence
<220> FEATURE:
<223> OTHER INFORMATION: PreC-C-Mut-gt-H codon optimized

<400> SEQUENCE: 72
gcccagctgt tcatctgtg cctgattatt ttctgttcat gccctacctt ccagttcccc     60
aaactgtgcc tggggtggct gtggggaatg gacatcgatc cctacaagga gttcggcgcc   120
agcgtggagc tgctgagctt tctgccctcc gacttctttc cttctgtgcg ggacctgctg   180
gataccgcaa gcgccctgta tagagatgca ctggagtccc cagagcactg caccccaaac   240
cacacagccc tgaggcaggc aatcctgtgc tgggagagc tgatgaccct ggcatcctgg   300
gtgggcaaca atctggagga ccctgccgcc agagatctgg tggtgaatta cgtgaacaca   360
```

```
aatatgggcc tgaagatcag gcagctgctg tggttccaca tctcttgcct gacctttggc      420
cgcgagacag tgctggagta cctggtgagc ttcggcgtgt ggatcaggac cccacctgca      480
tataggccac caaacgcacc tatcctgtcc acactgccag agacaacagt ggtgcgccag      540
aggggaagag caccacggag aaggacacct tctccaagga ggagaagaag ccagtcccca      600
cgaagaagac gaagccagag cccagccagc cagtgt                                636
```

<210> SEQ ID NO 73
<211> LENGTH: 665
<212> TYPE: DNA
<213> ORGANISM: Artificial Sequence
<220> FEATURE:
<223> OTHER INFORMATION: PreC-C-Mut-gt-H codon optimized with
      restriction sites (HindIII /EcoRI)

<400> SEQUENCE: 73

```
aagcttgcac catggcccag ctgtttcatc tgtgcctgat tatttttctgt tcatgcccta      60 ccttccagtt ccccaaactg tgcctggggt ggctgtgggg aatggacatc gatccctaca     120
aggagttcgg cgccagcgtg gagctgctga gctttctgcc ctccgacttc tttccttctg     180
tgcgggacct gctggatacc gcaagcgccc tgtatagaga tgcactggag tccccagagc     240
actgcacccc aaaccacaca gccctgaggc aggcaatcct gtgctgggga gagctgatga     300
ccctggcatc ctgggtgggc aacaatctgg aggaccctgc cgccagagat ctggtggtga     360
attacgtgaa cacaaatatg ggcctgaaga tcaggcagct gctgtggttc cacatctctt     420
gcctgacctt tggccgcgag acagtgctgg agtacctggt gagcttcggc gtgtggatca     480 ggacccccacc tgcatatagg ccaccaaacg cacctatcct gtccacactg ccagagacaa     540
cagtggtgcg ccagagggga agagcaccac ggagaaggac accttctcca aggaggagaa     600
gaagccagtc ccacgaaga gacgaagcc agagcccagc cagccagtgt tgatgagaat       660
tccgt                                                                  665
```

<210> SEQ ID NO 74
<211> LENGTH: 213
<212> TYPE: PRT
<213> ORGANISM: Artificial Sequence
<220> FEATURE:
<223> OTHER INFORMATION: PreC-C-Mut-gt-H protein

<400> SEQUENCE: 74

```
Met Ala Gln Leu Phe His Leu Cys Leu Ile Ile Phe Cys Ser Cys Pro
  1               5                  10                  15

Thr Phe Gln Phe Pro Lys Leu Cys Leu Gly Trp Leu Trp Gly Met Asp
                 20                  25                  30

Ile Asp Pro Tyr Lys Glu Phe Gly Ala Ser Val Glu Leu Leu Ser Phe
             35                  40                  45

Leu Pro Ser Asp Phe Phe Pro Ser Val Arg Asp Leu Leu Asp Thr Ala
         50                  55                  60

Ser Ala Leu Tyr Arg Asp Ala Leu Glu Ser Pro Glu His Cys Thr Pro
 65                  70                  75                  80

Asn His Thr Ala Leu Arg Gln Ala Ile Leu Cys Trp Gly Glu Leu Met
                 85                  90                  95

Thr Leu Ala Ser Trp Val Gly Asn Asn Leu Glu Asp Pro Ala Ala Arg
                100                 105                 110

Asp Leu Val Val Asn Tyr Val Asn Thr Asn Met Gly Leu Lys Ile Arg
            115                 120                 125
```

```
Gln Leu Leu Trp Phe His Ile Ser Cys Leu Thr Phe Gly Arg Glu Thr
    130                 135                 140

Val Leu Glu Tyr Leu Val Ser Phe Gly Val Trp Ile Arg Thr Pro Pro
145                 150                 155                 160

Ala Tyr Arg Pro Pro Asn Ala Pro Ile Leu Ser Thr Leu Pro Glu Thr
                165                 170                 175

Thr Val Val Arg Gln Arg Gly Arg Ala Pro Arg Arg Arg Thr Pro Ser
            180                 185                 190

Pro Arg Arg Arg Arg Ser Gln Ser Pro Arg Arg Arg Arg Ser Gln Ser
        195                 200                 205

Pro Ala Ser Gln Cys
    210

<210> SEQ ID NO 75
<211> LENGTH: 20
<212> TYPE: PRT
<213> ORGANISM: Artificial Sequence
<220> FEATURE:
<223> OTHER INFORMATION: L-HDAg-gt1-#1

<400> SEQUENCE: 75

Met Gly Arg Ser Glu Ser Lys Arg Asn Arg Asp Gly Arg Glu Gly Ile
1               5                   10                  15

Leu Glu Gln Trp
            20

<210> SEQ ID NO 76
<211> LENGTH: 20
<212> TYPE: PRT
<213> ORGANISM: Artificial Sequence
<220> FEATURE:
<223> OTHER INFORMATION: L-HDAg-gt1-#2

<400> SEQUENCE: 76

Asp Gly Arg Glu Gly Ile Leu Glu Gln Trp Val Asn Gly Arg Lys Lys
1               5                   10                  15

Leu Glu Asp Leu
            20

<210> SEQ ID NO 77
<211> LENGTH: 20
<212> TYPE: PRT
<213> ORGANISM: Artificial Sequence
<220> FEATURE:
<223> OTHER INFORMATION: L-HDAg-gt1-#3

<400> SEQUENCE: 77

Val Asn Gly Arg Lys Lys Leu Glu Asp Leu Glu Arg Glu Ala Arg Lys
1               5                   10                  15

Ile Lys Lys Lys
            20

<210> SEQ ID NO 78
<211> LENGTH: 20
<212> TYPE: PRT
<213> ORGANISM: Artificial Sequence
<220> FEATURE:
<223> OTHER INFORMATION: L-HDAg-gt1-#4

<400> SEQUENCE: 78

Glu Arg Glu Ala Arg Lys Ile Lys Lys Lys Ile Lys Lys Leu Glu Asp
1               5                   10                  15
```

Glu Asn Pro Trp
          20

<210> SEQ ID NO 79
<211> LENGTH: 20
<212> TYPE: PRT
<213> ORGANISM: Artificial Sequence
<220> FEATURE:
<223> OTHER INFORMATION: L-HDAg-gt1-#5

<400> SEQUENCE: 79

Ile Lys Lys Leu Glu Asp Glu Asn Pro Trp Leu Gly Asn Ile Lys Gly
1               5                   10                  15

Ile Leu Gly Lys
          20

<210> SEQ ID NO 80
<211> LENGTH: 20
<212> TYPE: PRT
<213> ORGANISM: Artificial Sequence
<220> FEATURE:
<223> OTHER INFORMATION: L-HDAg-gt1-#6

<400> SEQUENCE: 80

Leu Gly Asn Ile Lys Gly Ile Leu Gly Lys Arg Asp Lys Asp Gly Glu
1               5                   10                  15

Gly Ala Pro Pro
          20

<210> SEQ ID NO 81
<211> LENGTH: 20
<212> TYPE: PRT
<213> ORGANISM: Artificial Sequence
<220> FEATURE:
<223> OTHER INFORMATION: L-HDAg-gt1-#7

<400> SEQUENCE: 81

Arg Asp Lys Asp Gly Glu Gly Ala Pro Pro Ala Lys Arg Ala Arg Thr
1               5                   10                  15

Asp Gln Met Glu
          20

<210> SEQ ID NO 82
<211> LENGTH: 20
<212> TYPE: PRT
<213> ORGANISM: Artificial Sequence
<220> FEATURE:
<223> OTHER INFORMATION: L-HDAg-gt1-#8

<400> SEQUENCE: 82

Ala Lys Arg Ala Arg Thr Asp Gln Met Glu Ile Asp Ser Gly Pro Gly
1               5                   10                  15

Lys Arg Pro Leu
          20

<210> SEQ ID NO 83
<211> LENGTH: 20
<212> TYPE: PRT
<213> ORGANISM: Artificial Sequence
<220> FEATURE:
<223> OTHER INFORMATION: L-HDAg-gt1-#9

<400> SEQUENCE: 83

Ile Asp Ser Gly Pro Gly Lys Arg Pro Leu Arg Gly Gly Phe Ser Asp

```
                1               5                  10                 15
Lys Glu Arg Gln
            20

<210> SEQ ID NO 84
<211> LENGTH: 20
<212> TYPE: PRT
<213> ORGANISM: Artificial Sequence
<220> FEATURE:
<223> OTHER INFORMATION: L-HDAg-gt1-#10

<400> SEQUENCE: 84

Arg Gly Gly Phe Ser Asp Lys Glu Arg Gln Asp His Arg Arg Arg Lys
1               5                   10                  15

Ala Leu Glu Asn
            20

<210> SEQ ID NO 85
<211> LENGTH: 20
<212> TYPE: PRT
<213> ORGANISM: Artificial Sequence
<220> FEATURE:
<223> OTHER INFORMATION: L-HDAg-gt1-#11

<400> SEQUENCE: 85

Asp His Arg Arg Arg Lys Ala Leu Glu Asn Lys Arg Lys Gln Leu Ala
1               5                   10                  15

Ala Gly Gly Lys
            20

<210> SEQ ID NO 86
<211> LENGTH: 20
<212> TYPE: PRT
<213> ORGANISM: Artificial Sequence
<220> FEATURE:
<223> OTHER INFORMATION: L-HDAg-gt1-#12

<400> SEQUENCE: 86

Lys Arg Lys Gln Leu Ala Ala Gly Gly Lys His Leu Ser Lys Glu Glu
1               5                   10                  15

Glu Glu Glu Leu
            20

<210> SEQ ID NO 87
<211> LENGTH: 20
<212> TYPE: PRT
<213> ORGANISM: Artificial Sequence
<220> FEATURE:
<223> OTHER INFORMATION: L-HDAg-gt1-#13

<400> SEQUENCE: 87

His Leu Ser Lys Glu Glu Glu Glu Leu Lys Arg Leu Thr Glu Glu
1               5                   10                  15

Asp Glu Arg Arg
            20

<210> SEQ ID NO 88
<211> LENGTH: 20
<212> TYPE: PRT
<213> ORGANISM: Artificial Sequence
<220> FEATURE:
<223> OTHER INFORMATION: L-HDAg-gt1-#14

<400> SEQUENCE: 88
```

```
Lys Arg Leu Thr Glu Glu Asp Glu Arg Arg Glu Arg Arg Thr Ala Gly
1               5                   10                  15

Pro Ser Val Gly
            20

<210> SEQ ID NO 89
<211> LENGTH: 20
<212> TYPE: PRT
<213> ORGANISM: Artificial Sequence
<220> FEATURE:
<223> OTHER INFORMATION: L-HDAg-gt1-#15

<400> SEQUENCE: 89

Glu Arg Arg Thr Ala Gly Pro Ser Val Gly Gly Val Asn Pro Leu Glu
1               5                   10                  15

Gly Gly Ser Arg
            20

<210> SEQ ID NO 90
<211> LENGTH: 20
<212> TYPE: PRT
<213> ORGANISM: Artificial Sequence
<220> FEATURE:
<223> OTHER INFORMATION: L-HDAg-gt1-#16

<400> SEQUENCE: 90

Gly Val Asn Pro Leu Glu Gly Gly Ser Arg Gly Ala Pro Gly Gly Gly
1               5                   10                  15

Phe Val Pro Asn
            20

<210> SEQ ID NO 91
<211> LENGTH: 20
<212> TYPE: PRT
<213> ORGANISM: Artificial Sequence
<220> FEATURE:
<223> OTHER INFORMATION: L-HDAg-gt1-#17

<400> SEQUENCE: 91

Gly Ala Pro Gly Gly Gly Phe Val Pro Asn Met Leu Ser Val Pro Glu
1               5                   10                  15

Ser Pro Phe Ser
            20

<210> SEQ ID NO 92
<211> LENGTH: 20
<212> TYPE: PRT
<213> ORGANISM: Artificial Sequence
<220> FEATURE:
<223> OTHER INFORMATION: L-HDAg-gt1-#18

<400> SEQUENCE: 92

Met Leu Ser Val Pro Glu Ser Pro Phe Ser Arg Thr Gly Glu Gly Leu
1               5                   10                  15

Asp Val Arg Gly
            20

<210> SEQ ID NO 93
<211> LENGTH: 20
<212> TYPE: PRT
<213> ORGANISM: Artificial Sequence
<220> FEATURE:
<223> OTHER INFORMATION: L-HDAg-gt1-#19

<400> SEQUENCE: 93
```

```
Arg Thr Gly Glu Gly Leu Asp Val Arg Gly Asn Gln Gly Phe Pro Trp
1               5                   10                  15

Asp Ile Leu Phe
            20

<210> SEQ ID NO 94
<211> LENGTH: 20
<212> TYPE: PRT
<213> ORGANISM: Artificial Sequence
<220> FEATURE:
<223> OTHER INFORMATION: L-HDAg-gt1-#20

<400> SEQUENCE: 94

Asn Gln Gly Phe Pro Trp Asp Ile Leu Phe Pro Ala Asp Pro Pro Phe
1               5                   10                  15

Ser Pro Gln Ser
            20

<210> SEQ ID NO 95
<211> LENGTH: 14
<212> TYPE: PRT
<213> ORGANISM: Artificial Sequence
<220> FEATURE:
<223> OTHER INFORMATION: L-HDAg-gt1-#21

<400> SEQUENCE: 95

Pro Ala Asp Pro Pro Phe Ser Pro Gln Ser Cys Arg Pro Gln
1               5                   10

<210> SEQ ID NO 96
<211> LENGTH: 20
<212> TYPE: PRT
<213> ORGANISM: Artificial Sequence
<220> FEATURE:
<223> OTHER INFORMATION: L-HDAg-gt2-#1

<400> SEQUENCE: 96

Met Gly Gln Pro Asp Ser Arg Arg Pro Arg Arg Gly Arg Glu Glu Ser
1               5                   10                  15

Leu Gly Lys Trp
            20

<210> SEQ ID NO 97
<211> LENGTH: 20
<212> TYPE: PRT
<213> ORGANISM: Artificial Sequence
<220> FEATURE:
<223> OTHER INFORMATION: L-HDAg-gt2-#2

<400> SEQUENCE: 97

Arg Gly Arg Glu Glu Ser Leu Gly Lys Trp Ile Asp Ala Arg Arg Arg
1               5                   10                  15

Lys Glu Glu Leu
            20

<210> SEQ ID NO 98
<211> LENGTH: 20
<212> TYPE: PRT
<213> ORGANISM: Artificial Sequence
<220> FEATURE:
<223> OTHER INFORMATION: L-HDAg-gt2-#3

<400> SEQUENCE: 98

Ile Asp Ala Arg Arg Arg Lys Glu Glu Leu Glu Arg Asp Leu Arg Lys
```

```
1               5                   10                  15
Val Asn Lys Thr
            20

<210> SEQ ID NO 99
<211> LENGTH: 20
<212> TYPE: PRT
<213> ORGANISM: Artificial Sequence
<220> FEATURE:
<223> OTHER INFORMATION: L-HDAg-gt2-#4

<400> SEQUENCE: 99

Glu Arg Asp Leu Arg Lys Val Asn Lys Thr Ile Lys Arg Leu Glu Glu
1               5                   10                  15
Asp Asn Pro Trp
            20

<210> SEQ ID NO 100
<211> LENGTH: 20
<212> TYPE: PRT
<213> ORGANISM: Artificial Sequence
<220> FEATURE:
<223> OTHER INFORMATION: L-HDAg-gt2-#5

<400> SEQUENCE: 100

Ile Lys Arg Leu Glu Glu Asp Asn Pro Trp Leu Gly Asn Ile Arg Gly
1               5                   10                  15
Ile Ile Gly Arg
            20

<210> SEQ ID NO 101
<211> LENGTH: 20
<212> TYPE: PRT
<213> ORGANISM: Artificial Sequence
<220> FEATURE:
<223> OTHER INFORMATION: L-HDAg-gt2-#6

<400> SEQUENCE: 101

Leu Gly Asn Ile Arg Gly Ile Ile Gly Arg Lys Asp Lys Asp Gly Glu
1               5                   10                  15
Gly Ala Pro Pro
            20

<210> SEQ ID NO 102
<211> LENGTH: 20
<212> TYPE: PRT
<213> ORGANISM: Artificial Sequence
<220> FEATURE:
<223> OTHER INFORMATION: L-HDAg-gt2-#7

<400> SEQUENCE: 102

Lys Asp Lys Asp Gly Glu Gly Ala Pro Pro Ala Lys Arg Ala Arg Thr
1               5                   10                  15
Asp Gln Met Glu
            20

<210> SEQ ID NO 103
<211> LENGTH: 20
<212> TYPE: PRT
<213> ORGANISM: Artificial Sequence
<220> FEATURE:
<223> OTHER INFORMATION: L-HDAg-gt2-#8

<400> SEQUENCE: 103
```

```
Ala Lys Arg Ala Arg Thr Asp Gln Met Glu Val Asp Ser Gly Pro Arg
1               5                   10                  15

Lys Arg Lys His
            20

<210> SEQ ID NO 104
<211> LENGTH: 20
<212> TYPE: PRT
<213> ORGANISM: Artificial Sequence
<220> FEATURE:
<223> OTHER INFORMATION: L-HDAg-gt2-#9

<400> SEQUENCE: 104

Val Asp Ser Gly Pro Arg Lys Arg Lys His Pro Gly Gly Phe Thr Glu
1               5                   10                  15

Gln Glu Arg Arg
            20

<210> SEQ ID NO 105
<211> LENGTH: 20
<212> TYPE: PRT
<213> ORGANISM: Artificial Sequence
<220> FEATURE:
<223> OTHER INFORMATION: L-HDAg-gt2-#10

<400> SEQUENCE: 105

Pro Gly Gly Phe Thr Glu Gln Glu Arg Arg Asp His Arg Arg Arg Lys
1               5                   10                  15

Ala Leu Glu Asn
            20

<210> SEQ ID NO 106
<211> LENGTH: 20
<212> TYPE: PRT
<213> ORGANISM: Artificial Sequence
<220> FEATURE:
<223> OTHER INFORMATION: L-HDAg-gt2-#11

<400> SEQUENCE: 106

Asp His Arg Arg Arg Lys Ala Leu Glu Asn Lys Lys Lys Gln Leu Ser
1               5                   10                  15

Ser Gly Gly Lys
            20

<210> SEQ ID NO 107
<211> LENGTH: 20
<212> TYPE: PRT
<213> ORGANISM: Artificial Sequence
<220> FEATURE:
<223> OTHER INFORMATION: L-HDAg-gt2-#12

<400> SEQUENCE: 107

Lys Lys Lys Gln Leu Ser Ser Gly Gly Lys Asp Leu Ser Arg Glu Glu
1               5                   10                  15

Glu Glu Glu Leu
            20

<210> SEQ ID NO 108
<211> LENGTH: 20
<212> TYPE: PRT
<213> ORGANISM: Artificial Sequence
<220> FEATURE:
<223> OTHER INFORMATION: L-HDAg-gt2-#13

<400> SEQUENCE: 108
```

Asp Leu Ser Arg Glu Glu Glu Glu Leu Arg Arg Leu Thr Glu Glu
1               5                   10                  15

Asp Glu Arg Arg
            20

<210> SEQ ID NO 109
<211> LENGTH: 20
<212> TYPE: PRT
<213> ORGANISM: Artificial Sequence
<220> FEATURE:
<223> OTHER INFORMATION: L-HDAg-gt2-#14

<400> SEQUENCE: 109

Arg Arg Leu Thr Glu Glu Asp Glu Arg Arg Glu Arg Arg Val Ala Gly
1               5                   10                  15

Pro Arg Val Gly
            20

<210> SEQ ID NO 110
<211> LENGTH: 20
<212> TYPE: PRT
<213> ORGANISM: Artificial Sequence
<220> FEATURE:
<223> OTHER INFORMATION: L-HDAg-gt2-#15

<400> SEQUENCE: 110

Glu Arg Arg Val Ala Gly Pro Arg Val Gly Asp Val Asn Pro Leu Asp
1               5                   10                  15

Gly Gly Pro Arg
            20

<210> SEQ ID NO 111
<211> LENGTH: 20
<212> TYPE: PRT
<213> ORGANISM: Artificial Sequence
<220> FEATURE:
<223> OTHER INFORMATION: L-HDAg-gt2-#16

<400> SEQUENCE: 111

Asp Val Asn Pro Leu Asp Gly Gly Pro Arg Gly Ala Pro Gly Gly Gly
1               5                   10                  15

Phe Val Pro Ser
            20

<210> SEQ ID NO 112
<211> LENGTH: 20
<212> TYPE: PRT
<213> ORGANISM: Artificial Sequence
<220> FEATURE:
<223> OTHER INFORMATION: L-HDAg-gt2-#17

<400> SEQUENCE: 112

Gly Ala Pro Gly Gly Gly Phe Val Pro Ser Met Gln Gly Ile Pro Glu
1               5                   10                  15

Ser Pro Phe Thr
            20

<210> SEQ ID NO 113
<211> LENGTH: 20
<212> TYPE: PRT
<213> ORGANISM: Artificial Sequence
<220> FEATURE:
<223> OTHER INFORMATION: L-HDAg-gt2-#18

-continued

<400> SEQUENCE: 113

```
Met Gln Gly Ile Pro Glu Ser Pro Phe Thr Arg Arg Gly Asp Gly Leu
1               5                   10                  15

Asp Thr Arg Gly
            20
```

<210> SEQ ID NO 114
<211> LENGTH: 20
<212> TYPE: PRT
<213> ORGANISM: Artificial Sequence
<220> FEATURE:
<223> OTHER INFORMATION: L-HDAg-gt2-#19

<400> SEQUENCE: 114

```
Arg Arg Gly Asp Gly Leu Asp Thr Arg Gly Thr Gln Glu Phe Pro Trp
1               5                   10                  15

Val Asn Pro Gln
            20
```

<210> SEQ ID NO 115
<211> LENGTH: 20
<212> TYPE: PRT
<213> ORGANISM: Artificial Sequence
<220> FEATURE:
<223> OTHER INFORMATION: L-HDAg-gt2-#20

<400> SEQUENCE: 115

```
Thr Gln Glu Phe Pro Trp Val Asn Pro Gln Pro Pro Pro Pro Arg Leu
1               5                   10                  15

Pro Leu Leu Glu
            20
```

<210> SEQ ID NO 116
<211> LENGTH: 14
<212> TYPE: PRT
<213> ORGANISM: Artificial Sequence
<220> FEATURE:
<223> OTHER INFORMATION: L-HDAg-gt2-#21

<400> SEQUENCE: 116

```
Pro Pro Pro Pro Arg Leu Pro Leu Leu Glu Cys Thr Pro Gln
1               5                   10
```